(12) United States Patent
Fang et al.

(10) Patent No.: US 10,913,749 B2
(45) Date of Patent: Feb. 9, 2021

(54) MACROCYCLIZATION REACTIONS AND INTERMEDIATES AND OTHER FRAGMENTS USEFUL IN THE SYNTHESIS OF HALICHONDRIN MACROLIDES

(71) Applicant: EISAI R&D MANAGEMENT CO., LTD., Tokyo (JP)

(72) Inventors: Francis G. Fang, Andover, MA (US); Dae-Shik Kim, Andover, MA (US); Hyeong-Wook Choi, Andover, MA (US); Charles E. Chase, Londonderry, NH (US)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 0 days.

(21) Appl. No.: 16/387,820

(22) Filed: Apr. 18, 2019

(65) Prior Publication Data

US 2019/0308992 A1 Oct. 10, 2019

Related U.S. Application Data

(62) Division of application No. 15/571,921, filed as application No. PCT/US2016/031546 on May 9, 2016, now Pat. No. 10,308,661.

(60) Provisional application No. 62/291,918, filed on Feb. 5, 2016, provisional application No. 62/158,506, filed on May 7, 2015.

(51) Int. Cl.
 *C07D 493/22* (2006.01)
 *C07F 9/655* (2006.01)

(52) U.S. Cl.
 CPC .......... *C07D 493/22* (2013.01); *C07F 9/6552* (2013.01)

(58) Field of Classification Search
 CPC ...................... C07D 493/22; C07F 9/6552
 See application file for complete search history.

(56) References Cited

U.S. PATENT DOCUMENTS

| | | | |
|---|---|---|---|
| 5,338,865 A | 8/1994 | Kishi et al. |
| 5,436,238 A | 7/1995 | Kishi et al. |
| 5,451,573 A | 9/1995 | Hemmerle et al. |
| 6,194,586 B1 | 2/2001 | Martinelli et al. |
| 6,214,865 B1 | 4/2001 | Littlefield et al. |
| 6,365,759 B1 | 4/2002 | Littlefield et al. |
| 6,469,182 B1 | 10/2002 | Littlefield et al. |
| 6,653,341 B1 | 11/2003 | Littlefield et al. |
| 7,470,720 B2 | 12/2008 | Littlefield et al. |
| 7,982,060 B2 | 7/2011 | Austad et al. |
| 8,093,410 B2 | 1/2012 | Chase et al. |
| 8,097,648 B2 | 1/2012 | Littlefield et al. |
| 8,148,554 B2 | 4/2012 | Seletsky et al. |
| 8,203,010 B2 | 6/2012 | Endo et al. |
| 8,350,067 B2 | 1/2013 | Endo et al. |
| 8,445,701 B2 | 5/2013 | Austad et al. |
| 8,598,373 B2 | 12/2013 | Hu |
| 8,618,313 B2 | 12/2013 | Benayoud et al. |
| 8,884,031 B2 | 11/2014 | Chase et al. |
| RE45,324 E | 1/2015 | Austad et al. |
| 8,927,597 B2 | 1/2015 | Endo et al. |
| 8,975,422 B2 | 3/2015 | Fang et al. |
| 8,987,479 B2 | 3/2015 | Chase et al. |
| 9,206,194 B2 | 12/2015 | Hu |
| 9,303,039 B2 | 4/2016 | Zhang et al. |
| 9,303,050 B2 | 4/2016 | Benayoud et al. |
| 9,382,262 B2 | 7/2016 | Endo et al. |
| 9,469,651 B2 | 10/2016 | Hu |
| 9,604,993 B2 | 3/2017 | Chase et al. |
| 9,695,188 B2 | 7/2017 | Hu et al. |
| 9,783,549 B2 | 10/2017 | Fang et al. |
| 9,802,953 B2 | 10/2017 | Chase et al. |
| 9,856,276 B2 | 1/2018 | Endo et al. |
| RE46,965 E | 7/2018 | Austad et al. |
| 10,030,032 B2 | 7/2018 | Hu et al. |
| 10,214,539 B2 | 2/2019 | Chase et al. |
| 10,221,189 B2 | 3/2019 | Fang et al. |
| 10,308,661 B2 | 6/2019 | Fang et al. |
| 10,450,324 B2 | 10/2019 | Hu et al. |
| 10,494,388 B2 | 12/2019 | Endo et al. |
| RE47,797 E | 1/2020 | Benayoud et al. |
| 10,611,773 B2 | 4/2020 | Fang et al. |
| 10,676,481 B2 | 6/2020 | Baran et al. |
| 2002/0103387 A1 | 8/2002 | Smith et al. |
| 2004/0092581 A1 | 5/2004 | Burzlaff et al. |

(Continued)

FOREIGN PATENT DOCUMENTS

| | | |
|---|---|---|
| CN | 1312804 A | 9/2001 |
| CN | 101899026 A | 12/2010 |

(Continued)

OTHER PUBLICATIONS

U.S. Appl. No. 16/684,332, Benayoud et al.
U.S. Appl. No. 16/833,923, Fang et al.
Choi et al., "Prins reaction of homoallenyl alcohols: Access to substituted pyrans in the halichondrin series," Org Lett. 19(22): 6092-5 (2017).
Gradillas et al., "Macrocyclization by ring-closing metathesis in the total synthesis of natural products: reaction conditions and limitations," Angew Chem Int Ed Engl. 45(37): 6086-6101 (2006).
Ko, "Prins reactions and applications," http://gbdong.cm.utexas.edu/seminar/old/Prins%20reactions%20and%20Applications_Haye%20Min%20Ko.pdf, retrieved Jan. 21, 2020, dated Nov. 28, 2012 (30 pages).
Kong et al., "Total synthesis of the spirocyclic imine marine toxin (-)-gymnodimine and an unnatural C4-epimer," J Am Chem Soc. 133(49): 19844-56 (2011).

(Continued)

*Primary Examiner* — Timothy R Rozof
(74) *Attorney, Agent, or Firm* — Clark & Elbing LLP

(57) ABSTRACT

The invention provides methods for the synthesis of a halichondrin macrolides through a macrocyclization strategy. The macrocyclization strategy of the present invention involves subjecting a non-macrocyclic intermediate to a carbon-carbon bond-forming reaction (e.g., an olefination reaction (e.g., Horner-Wadsworth-Emmons olefination), catalytic Ring-Closing Olefin Metathesis, or Nozaki-Hiyama-Kishi reaction) to afford a macrocyclic macrolide. The invention also provides compounds useful as intermediates in the synthesis of a halichondrin macrolides and methods for preparing the same.

21 Claims, 6 Drawing Sheets

(56) References Cited

U.S. PATENT DOCUMENTS

| | | |
|---|---|---|
| 2006/0045846 A1 | 3/2006 | Horstmann et al. |
| 2009/0093649 A1 | 4/2009 | Nobis |
| 2009/0104285 A1 | 4/2009 | Littlefield et al. |
| 2009/0203771 A1 | 8/2009 | Inanaga et al. |
| 2010/0184860 A1 | 7/2010 | Yoshimura et al. |
| 2012/0029213 A1 | 2/2012 | Austad et al. |
| 2012/0309988 A1 | 12/2012 | Austad et al. |
| 2015/0065733 A1 | 3/2015 | Souza et al. |
| 2016/0152631 A1 | 6/2016 | Souza et al. |
| 2017/0298078 A1 | 10/2017 | Hu et al. |
| 2018/0002342 A1 | 1/2018 | Fang et al. |
| 2018/0037588 A1 | 2/2018 | Chase et al. |
| 2018/0162885 A1 | 6/2018 | Endo et al. |
| 2019/0010166 A1 | 1/2019 | Hu et al. |
| 2019/0144463 A1 | 5/2019 | Fang et al. |
| 2019/0161495 A1 | 5/2019 | Chase et al. |
| 2019/0263826 A1 | 8/2019 | Chase et al. |

FOREIGN PATENT DOCUMENTS

| | | |
|---|---|---|
| CN | 102803254 A | 11/2012 |
| CN | 104334562 A | 2/2015 |
| EP | 0572109 A1 | 12/1993 |
| EP | 2277873 A1 | 1/2011 |
| JP | H07-504664 A | 5/1995 |
| JP | 2002-518384 A | 6/2002 |
| JP | 2008-501715 A | 1/2008 |
| JP | 2010-168320 A | 8/2010 |
| JP | 2011-516493 A | 5/2011 |
| JP | 2015-512897 A | 4/2015 |
| RU | 2112773 C1 | 6/1998 |
| RU | 2517167 C2 | 5/2014 |
| SU | 652800 A1 | 3/1979 |
| WO | WO-93/17690 A1 | 9/1993 |
| WO | WO-98/09942 A1 | 3/1998 |
| WO | WO-99/65894 A1 | 12/1999 |
| WO | WO-2005/118565 A1 | 12/2005 |
| WO | WO-2006/076100 A2 | 7/2006 |
| WO | WO-2008/010776 A1 | 1/2008 |
| WO | WO-2009/064029 A1 | 5/2009 |
| WO | WO-2009/124237 A1 | 10/2009 |
| WO | WO-2011/094339 A1 | 8/2011 |
| WO | WO-2012/147900 A1 | 11/2012 |
| WO | WO-2013/078559 A1 | 6/2013 |
| WO | WO-2013/142999 A1 | 10/2013 |
| WO | WO-2015/000070 A1 | 1/2015 |
| WO | WO-2015/066729 A1 | 5/2015 |
| WO | WO-2016/038624 A1 | 3/2016 |
| WO | WO-2017/139664 A1 | 8/2017 |
| WO | WO-2018/006031 A1 | 1/2018 |
| WO | WO-2018/217894 A1 | 11/2018 |
| WO | WO-2019/136145 A1 | 7/2019 |

OTHER PUBLICATIONS

Namba et al., "A simple but remarkably effective device for forming the C8-C14 polycyclic ring system of halichondrin B," J Am Chem Soc. 126(25): 7770-1 (2004) (10 pages).
Search Report for Chinese Patent Application No. 2016800400158, dated Nov. 4, 2019 (5 pages).
Search Report for Russian Patent Application No. 2017142100, dated Dec. 26, 2019 (4 pages).
Ward et al., "Catalytic enantioselective diels-alder reaction by self-assembly of the components on a Lewis acid template," Org Lett. 7(16):3533-6 (2005) (Abstract only) (2 pages).
U.S. Appl. No. 15/944,480, Benayoud et al.
U.S. Appl. No. 16/076,028, Baran et al.
U.S. Appl. No. 16/284,405, Chase et al.
Aicher et al., "Synthetic studies towards halichondrins: synthesis of the C.27-C.38 segment," Tetrahedron Lett. 33(12):1549-52 (1992).
Aicher et al., "Total synthesis of halichondrin B and norhalichondrin B," J Am Chem Soc. 114(8):3162-4 (1992).
Aicher, Thesis, Chapter 4, "Synthetic studies towards halichondrin B," Doctor of Philosophy in Chemistry, Harvard University, 35-54, 1989 (26 pages).
AkzoNobel Polymer Chemicals, "Diisobutylaluminum hydride (DIBAL-H) and other isobutyl aluminum Alkyls (DIBAL-BOT, TIBAL) as specialty organic synthesis reagents," The AkzoNobel Technical Bulletin, 1-14 (2006).
Alley et al. "Comparison of the relative efficacies and toxicities of Halichondrin B analogues," Proceedings of the AACR-NCI-EORTC Conference on Molecular Targets and Cancer Therapeutics. C230:257 (2005).
Anderson, "Developing processes for crystallization-induced asymmetric transformation," Org Process Res Dev. 9:800-13 (2005).
Ando et al., "Z-selective intramolecular Horner-Wadsworth-Emmons reaction for the synthesis of macrocyclic lactones," Org Lett. 12(7):1460-3 (2010).
Austad et al. (2005): STN International HCAPLUS database, Columbus (OH), accession No. 2005: 1313925.
Austad et al., "Commercial manufacture of Halaven®: chemoselective transformations en route to structurally complex macrocyclic ketones," Synlett. 24 (2013). Supporting Information, (13 pages).
Austad et al., "Commercial manufacture of Halaven®: chemoselective transformations en route to structurally complex macrocyclic ketones," Synlett. 24(3):333-7 (2013).
Austad et al., "Process development of Halaven®: synthesis of the C14-C35 fragment via iterative Nozaki-Hiyama-Kishi reaction—Williamson ether cyclization," Synlett. 24(3):327-32 (2013).
Bai et al., "Halichondrin B and Homohalichondrin B, marine natural products binding in the vinca domain of tubulin. Discovery of tubulin-based mechanism of action by analysis of differential cytotoxicity data," J Biol Chem. 266(24):15882-9 (1991).
Bernet et al., "Carbocyclische verbindungen aus monosacchariden. I. Umsetzungen in der glucosereihe," Helv Chim Acta. 62(6):1990-2016 (1979).
Blanchette et al., "Horner-Wadsworth-Emmons reaction: use of lithium chloride and an amine for base-sensitive compounds," Tetrahedron Lett. 25(21):2183-6 (1984).
Burke et al., "Enantioselective synthesis of a Halichondrin B C(20)→C(36) precursor," Tetrahedron Lett. 36(39):7023-6 (1995).
Burke et al., "Synthesis of a C(22)-C(34) Halichondrin B precursor via ring opening-double ring closing metathesis," J Org Chem. 63:8626-7 (1998).
Burke et al., "Synthesis of a C(22)→C(34) Halichondrin precursor via a double dioxanone-to-dihydropyran rearrangement," Tetrahedron Lett. 32(32):3961-4 (1991).
Burke et al., "Synthetic studies toward complex polyether macrolides of marine origin," Spec Publ R Soc Chem. 198:(Anti-Infectives) 73-85 (1997).
Carruthers et al., Main-group chemistry. *Modern Methods of Organic Synthesis, Fourth Edition*. Cambridge University Press, 65 (2004).
Chase et al., "Process development of Halaven®: Synthesis of the C1-C13 fragment from D-(−)-Gulono-1, 4-lactone," Synlett. 24(3):323-6 (2013).
Chen et al., "Ni(II)/Cr(II)-mediated coupling reaction: An asymmetric process," J Org Chem. 60(17):5386-7 (1995).
Choi et al., "Asymmetric Ni(II)/Cr(II)-mediated coupling reaction: catalytic process," Org Lett. 4(25):4435-8 (2002).
Choi et al., "Supporting information for asymmetric Ni(II)/Cr(II)-mediated coupling reaction: catalytic process," Org Lett. 4(25) (2002) (8 pages).
Choi et al., "Synthetic studies on the marine natural product Halichondrins," Pure Appl Chem. 75(1):1-17 (2003).
Cooper et al., "Total Synthesis of Halichondrin B from common sugars: an F-ring intermediate from D-glucose and efficient construction of the Cl to C21 segment," Tetrahedron Lett. 34(51):8193-6 (1993).
Cunningham et al., "The influence of pH on the kinetic constants of alpha-chymotrypsin-catalyzed esterolysis," J Biol Chem. 221(1):287-99 (1956).
Dabydeen et al. "Comparison of the activities of the truncated Halichondrin B analog NSC 707389 (E7389) with those of the parent compound and a proposed binding site on tubulin," Mol Pharmacol. 70(6):1866-75 (2006).

(56) References Cited

OTHER PUBLICATIONS

Del Valle et al., "Total synthesis of (+)-trienomycins A and F via C-C bond-forming hydrogenation and transfer hydrogenation," J Am Chem Soc. 135(30):10986-89 (2013).
Dong et al. "New syntheses of E7389 C14-C35 and halichondrin C14-C38 building blocks: reductive cyclization and oxy-michael cyclization approaches," J Am Chem Soc. 131(43):15642-6 (2009).
Duan et al., "Synthetic studies on halichondrins: a new practical synthesis of the C.1-C.12 segment," Tetrahedron Lett. 34(47):7541-4 (1993).
English Translation of "Chemistry Handbook, Applied Chemistry, 6th Edition," Maruzen Publishing Co., Ltd. p. 178 (2003), received Oct. 6, 2014 (3 pages).
Fleming et al., "Nitrile anion cyclizations," Tetrahedron. 58(1):1-23 (2002).
Gesinski et al., "Symmetric macrocycles by a Prins dimerization and macrocyclization strategy," available in PMC Nov. 1, 2010, published in final edited form as: Org Lett. 11(22):5342-5 (2009) (13 pages).
Greene et al. *Protective Groups in Organic Synthesis, Third Edition.* John Wiley & Sons, Inc., 24, 127, 128, 134, 142, 170, 207, 209, 215, and 216 (1999).
Greene et al., *Protective Groups in Organic Synthesis, Third Edition.* John Wiley & Sons, Inc., 133-9 (1999).
Guo et al., "Toolbox approach to the search for effective ligands for catalytic asymmetric Cr-mediated coupling reactions," J Am Chem Soc. 131(42):15387-93 (2009).
Hirata et al., "Halichondrins—antitumor polyether macrolides from a marine sponge," Pure Appl Chem. 58(5):701-10 (1986).
Hori et al., "Efficient synthesis of 2,3-trans-tetrahydropyrans and oxepanes: rearrangement-ring expansion of cyclic ethers having a chloromethanesulfonate," Tetrahedron Lett. 40(11):2145-8 (1999).
Horita et al., "Research on anti-tumor active site of marine source natural product, Halichondrin B.," International Congress Series, 1157 (Towards Natural Medicine Research in the 21st Century), 327-336 (1998).
Horita et al., "Synthetic studies of halichondrin B, an antitumor polyether macrolide isolated from a marine sponge. 2. Efficient synthesis of C16-C26 fragments via construction of the D ring by a highly stereocontrolled iodoetherification," Synlett. 40-43 (1994).
Horita et al., "Synthetic studies of Halichondrin B, an antitumor polyether macrolide isolated from a marine sponge. 3. Synthesis of C27-C36 subunit via completely stereoselective C-glycosylation to the F ring," Synlett. 43-45 (1994).
Horita et al., "Synthetic studies of Halichondrin B, an antitumor polyether macrolide isolated from a marine sponge. 7. Synthesis of two C27-C36 units via construction of the F ring and completely stereoselective C-glycosylation using mixed Lewis acids," Chem Pharm Bull. 45(10):1558-72 (1997).
Horita et al., "Synthetic studies of Halichondrin B, an antitumor polyether macrolide isolated from a marine sponge. 8. Synthesis of the lactone part (C1-C36) via Horner-Emmons coupling between C1-C15 and C16-C36 fragments and yamaguchi lactonization," Tetrahedron Lett. 38(52):8965-8 (1997).
Horita et al., "Synthetic studies on Halichondrin B, an antitumor polyether macrolide isolated from a marine sponge. 9. Synthesis of the C16-C36 unit via stereoselective construction of the D and E rings," Chem Pharm Bull. 46(8):1199-216 (1998).
Horita et al., Synthetic study of a highly antitumorigenic marine phytochemical, Halichondrin B. *Phytochemicals and Phytopharmaceuticals.* Fereidoon Shahidi and Chi-Tang Ho, 386-397 (2000).
International Search Report and Written Opinion for International Application No. PCT/US2016/031546, dated Aug. 18, 2016 (28 pages).
Jackson et al., "A total synthesis of norhalichondrin B," Angew Chem Int Ed. 48(13):2346-50 (2009).
Jackson et al., "The halichondrins and E7389," Chem Rev. 109(7):3044-79 (2009).
Jiang et al. "A novel route to the F-ring of Halichondrin B. Diastereoselection in Pd(0)-mediated meso and C2 diol desymmetrization," Org Lett. 4(20):3411-4 (2002).
Jiang et al., "A practical synthesis of the F-ring of halichondrin B via ozonolytic desymmetrization of a C(2)-symmetric dihydroxycyclohexene," J Org Chem. 68(3):1150-3 (2003).
Kawaguchi et al., "Drug and crystal polymorphism," Journal of Human Environmental Engineering. 4(2):310-7 (2002) (10 pages).
Kim et al., "New syntheses of E7389 C14-C35 and Halichondrin C14-C38 building blocks: double-inversion approach," J Am Chem Soc. 131(43):15636-41 (2009).
Kurosu et al., "Fe/Cr- and Co/Cr-mediated catalytic asymmetric 2-Haloallylations of aldehydes," J Am Chem Soc. 126(39):12248-9 (2004).
Kurosu et al., "Supporting information for Fe/Cr- and Co/Cr-mediated catalytic asymmetric 2-haloallylations of aldehydes," J Am Chem Soc. 126(39) (2004) (31 pages).
March. *Advanced Organic Chemistry, Fourth Edition.* John Wiley & Sons, 386-388 (1992).
March. *Advanced Organic Chemistry, Fourth Edition.* John Wiley and Sons, 348-357 (1992).
Mattocks, "371. Novel reactions of some alpha-acyloxy acid chlorides," J Chem Soc. Resumed. 1918-30 (1964).
Mattocks, "932. Novel reactions of some alpha-acyloxy-acid halides," J Chem Soc. 4840-5 (1964).
Mitsunobu, "The use of diethyl azodicarboxylate and triphenylphosphine in synthesis and transformation of natural products," Synthesis. 1-28 (1981).
Namba et al., "New catalytic cycle for couplings of aldehydes with organochromium reagents," Org Lett. 6(26):5031-3 (2004).
Newman, "Drug evaluation: eribulin, a simplified ketone analog of the tubulin inhibitor Halichondrin B, for the potential treatment of cancer," Curr Opin Invest Drugs. 8(12):1057-66 (2007).
Nicolaou et al., "Total synthesis of brevetoxin A: Part 3: construction of GHIJ and BCDE ring systems," Chem Eur J. 5(2):628-45 (1999).
Nicolaou et al., "Total synthesis of the CP molecules CP-263,114 and CP-225,917—Part 1: synthesis of key intermediates and intelligence gathering," Angew Chem Int Ed. 38(11):1669-75 (1999).
Ritter, "Synthetic transformations of vinyl and aryl triflates," Synthesis: Reviews. 8:735-62 (1993).
Sakamoto et al., "Stereoselective ring expansion via bicyclooxonium ion. A novel approach to oxocanes," Org Lett. 4(5):675-8 (2002).
Schreiber, "Hydrogen transfer from tertiary amines to trifluoroacetic anhydride," Tetrahedron Lett. 21(11):1027-30 (1980).
Seletsky et al. "Structurally simplified macrolactone analogues of halichondrin B," Bioorg Med Chem Lett. 14(22):5547-50 (2004).
Stamos et al., "A mild preparation of vinyliodides from vinylsilanes," Tetrahedron Lett. 37(48): 8647-50 (1996).
Stamos et al., "New synthetic route to the C.14-C.38 segment of Halichondrins," J Org Chem. 62(22):7552-3 (1997).
Stamos et al., "Ni(II)/Cr(II)-mediated coupling reaction: beneficial effects of 4-tert-butylpyridine as an additive and development of new and improved workup procedures," Tetrahedron Lett. 38(36):6355-8 (1997).
Stamos et al., "Synthetic studies on Halichondrins: a practical synthesis of the C.1-C.13 segment," Tetrahedron Lett. 37(48):8643-6 (1996).
Sutherland et al., "The synthesis of 6alpha- and 6beta-fluoroshikimic acids," J Chem Soc Chem Commun. 18:1386-7 (1989).
Takai et al., "Reactions of alkenylchromium reagents prepared from alkenyl trifluoromethanesulfonates (triflates) with chromium(II) chloride under nickel catalysis" J Am Chem Soc. 108(19):6048-50 (1986).
Tokunaga et al., "Asymmetric catalysis with water: efficient kinetic resolution of terminal epoxides by means of catalytic hydrolysis," Science. 277(5328):936-8 (1997).
Towle et al. "In vitro and in vivo anticancer activities of synthetic macrocyclic ketone analogues of Halichondrin B," Cancer Res. 61(3):1013-21 (2001).
Towle et al., "Halichondrin B macrocyclic ketone analog E7389: medicinal chemistry repair of lactone ester instability generated

(56) References Cited

OTHER PUBLICATIONS during structural simplification to clinical Candidate," Annual Meeting of the American Association for Cancer Research, Apr. 6-10, 2002, 5721 (3 pages).
Uemura et al., "Norhalichondrin A: an antitumor polyether macrolide from a marine sponge," J Am Chem Soc. 107(16):4796-8 (1985).
Vandat et al., "Phase II study of eribulin mesylate, a Halichondrin B analog, in patients with metastatic breast cancer previously treated with an anthracycline and a taxane," J Clin Oncol. 27(18):2954-61 (2009).
Varseev et al, "Enantioselective total synthesis of (+)-neosymbioimine," Org Lett. 9(8):1461-4 (2007).
Wan et al., "Asymmetric Ni(II)/Cr(II)-mediated coupling reaction: Stoichiometric process," Org Lett. 4(25):4431-4 (2002) Supporting Information, 8 pages.
Wan et al., "Asymmetric Ni(II)/Cr(II)-mediated coupling reaction: Stoichiometric process," Org Lett. 4(25):4431-4 (2002).
Wang et al., "Facile preparation of peracetates and per-3-bromobenzoates of alpha-mono- and disaccharides," Molecules. 10(10):1325-34 (2005).
Wang et al., "Structure-activity relationships of halichondrin B analogues: modifications at C.30-C.38" Bioorg Med Chem Lett. 10(10):1029-32 (2000).
Xie et al., "Synthesis of the C20-C26 building block of Halichondrins via a regiospecific and stereoselective SN2' reaction," Org Lett. 4(25): 4427-9 (2002).
Yamamoto et al., "Total synthesis of halichondrin C," J Am Chem Soc. 134(2):893-6 (2012).
Yang et al., "Second generation synthesis of C27-C35 building block of E7389, a synthetic Halichondrin analogue," Org Lett. 11(20): 4516-9 (2009).
Youssefyeh, "Acylations of ketals and enol ethers," J Am Chem Soc. 85(23):3901-2 (1963).
Yu et al., "Atom-based enumeration: new eribulin analogues with low susceptibility to P-glycoprotein-mediated drug efflux," Bioorg Med Chem Lett. 22(24):7363-6 (2012).
Yu et al., "From micrograms to grams: scale-up synthesis of eribulin mesylate," Nat Prod Rep. 30(9):1158-64 (2013).
Yu et al., "Macrocyclic drugs and synthetic methodologies toward macrocycles," Molecules 18(6):6230-68 (2013).
Yu et al., "New synthetic route to the C.14-C.21 fragment of Halichondrin B," Book of Abstracts. 219th ACS National Meeting, San Francisco, CA, Mar. 26-30, 2000 (1 page).
Yu et al., Discovery of E7389 a fully synthetic macrocyclic ketone analog of Halichondrin B. *Anticancer Agents from Natural Products*. CRC Press, 241-265 (2005) (27 pages).
Zheng et al., "Macrocyclic ketone analogues of halichondrin B," Bioorg Med Chem Lett. 14(22): 5551-4 (2004).
Zheng et al., "Synthetic macrocyclic ketone analogs of halichondrin B: structure-activity relationships" Proceedings of the American Association for Cancer Research, 41:301, Abstract #1915 (2000).

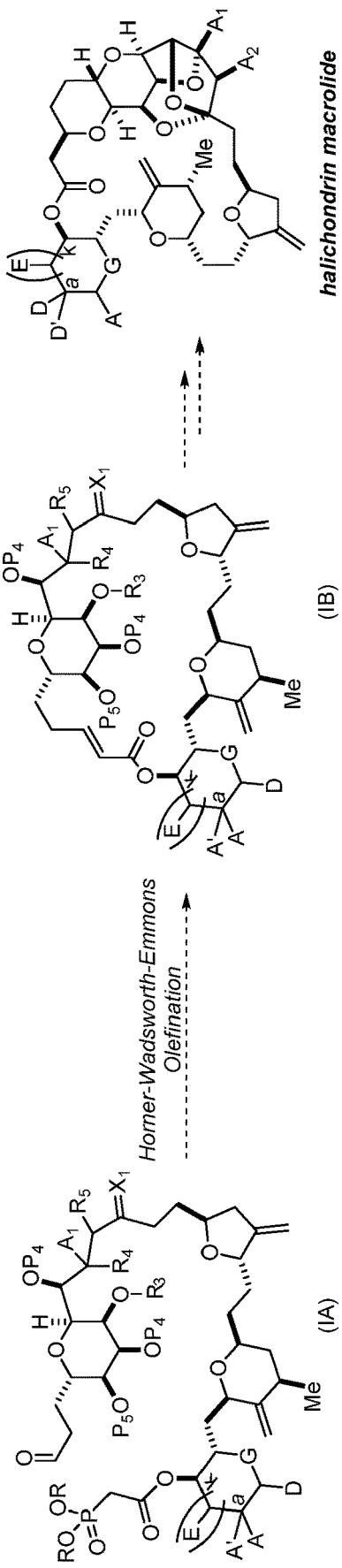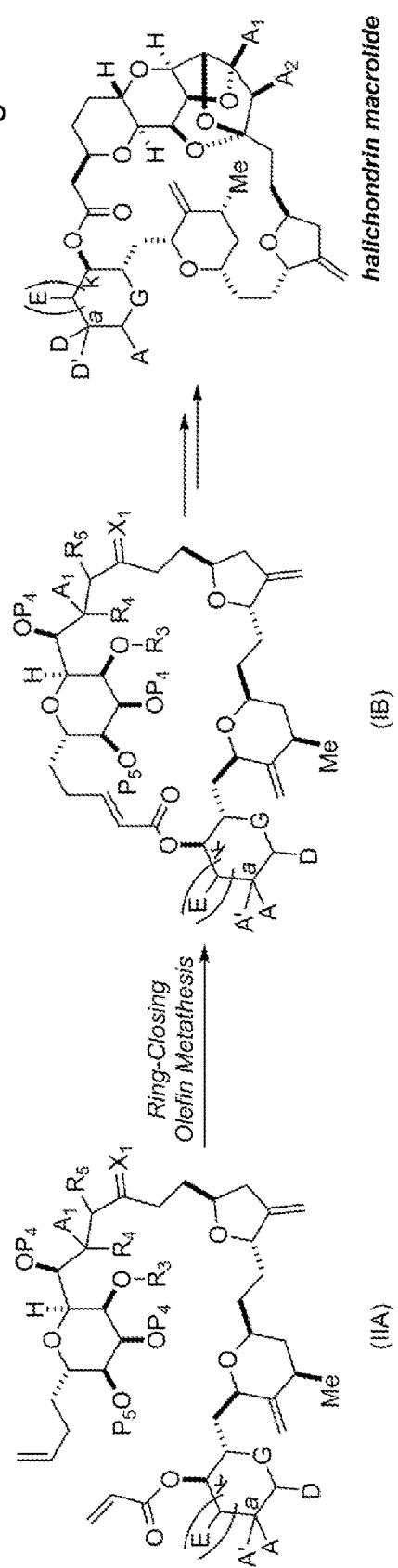

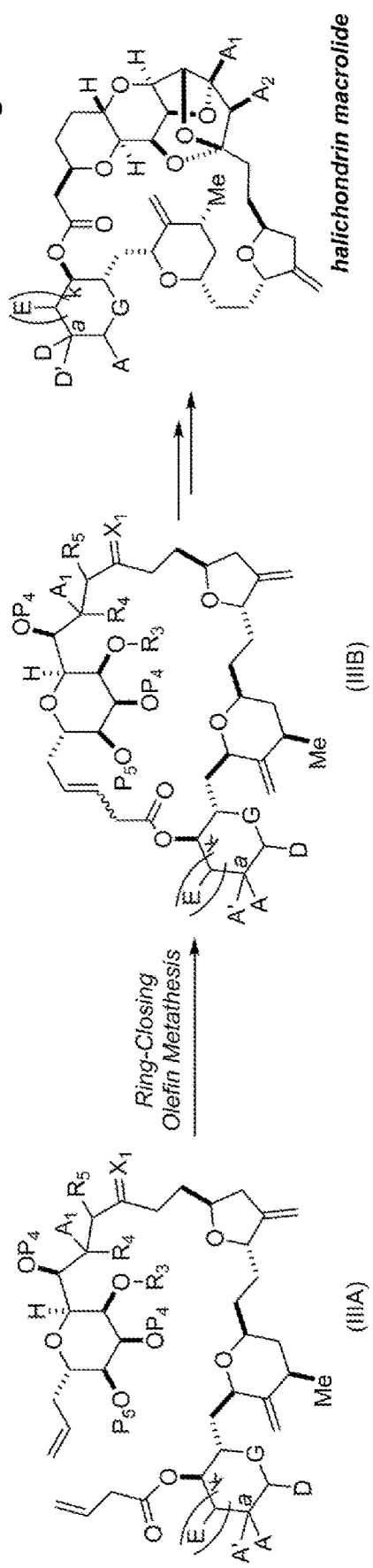

MACROCYCLIZATION REACTIONS AND INTERMEDIATES AND OTHER FRAGMENTS USEFUL IN THE SYNTHESIS OF HALICHONDRIN MACROLIDES

BACKGROUND

The invention relates to intermediates useful in the synthesis of pharmaceutically active macrolide compounds and methods of synthesizing macrolide compounds. Halichondrin B is a potent anticancer agent originally isolated from the marine sponge *Halichondria okadai*, and subsequently found in *Axinella* sp., *Phakellia carteri*, and *Lissodendoryx* sp. A total synthesis of halichondrin B was published in 1992 (Aicher, T. D. et al., J. Am. Chem. Soc. 114:3162-3164). Further synthetic and structure-activity relationship studies have been discloses in U.S. Pat. Nos. 5,338,865 and 5,436,238 and in Towle et al., *Annual Meeting of the American Association for Cancer Research*, Apr. 6-10, 2002, 5721 and Wang et al., *Bioorg. Med. Chem. Lett.*, 10:1029-1032, 2000. Methods and intermediates for the synthesis of certain halichondrin B analogs and intermediates are described in International Publication Nos. WO 2005/118565, WO 2009/046308, WO 2009/064029, and WO 2009/124237; U.S. Pat. No. 6,214,865; Austad et al., Synlett 24(3):333-337, 2013; Austad et al., Synlett. 24(3):327-332, 2013; and Chase et al., Synlett 24(3):323-326, 2013. New methods for the synthesis of halichondrin B and its analogs (e.g., macrolide analogs) are desirable.

SUMMARY OF THE INVENTION

In general, the present invention provides methods for macrocyclization of intermediates in the synthesis of a halichondrin macrolide. The invention also provides intermediates that can be employed in the macrocyclization reactions described herein.

In a first aspect, the invention provides a method of preparing a macrocyclic intermediate in the synthesis of a halichondrin macrolide, the method involving performing a macrocyclization reaction on a non-macrocyclic intermediate, the macrocyclization reaction producing the macrocyclic intermediate by forming C.2-C.3, C.3-C.4, C.12-C.13, C.15-C.16, C.19-C.20, or C.26-C.27 bond in the structure of the halichondrin macrolide.

In some embodiments of the first aspect, performing the macrocyclization reaction involves contacting the non-macrocyclic intermediate (e.g., a compound of formula (IA)) with an organic base (e.g., DBU or triethylamine) and a Lewis acid (e.g., a salt of Li or Zn). The non-macrocyclic intermediate can be a compound of formula (IA):

(IA)

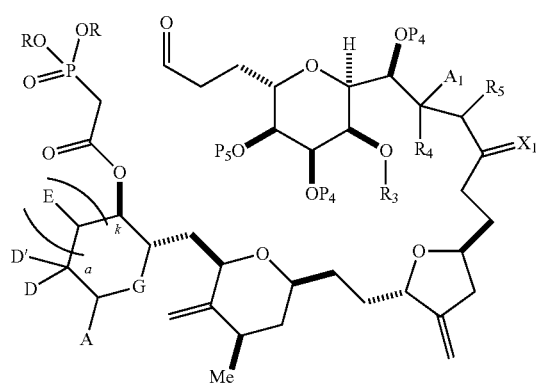

or a salt or a tautomer thereof, where
each R is independently optionally substituted alkyl or optionally substituted aryl;
each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

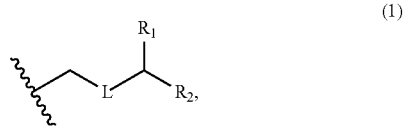

(1)

where
L is —(CH($OP_2$))—, —(C(OH)($OP_2$))—, or —C(O)—;
$R_1$ is H, or $R_1$ and $P_1$ combine to form a bond;
$R_2$ is H or —(CH$_2$)$_n$OP$_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

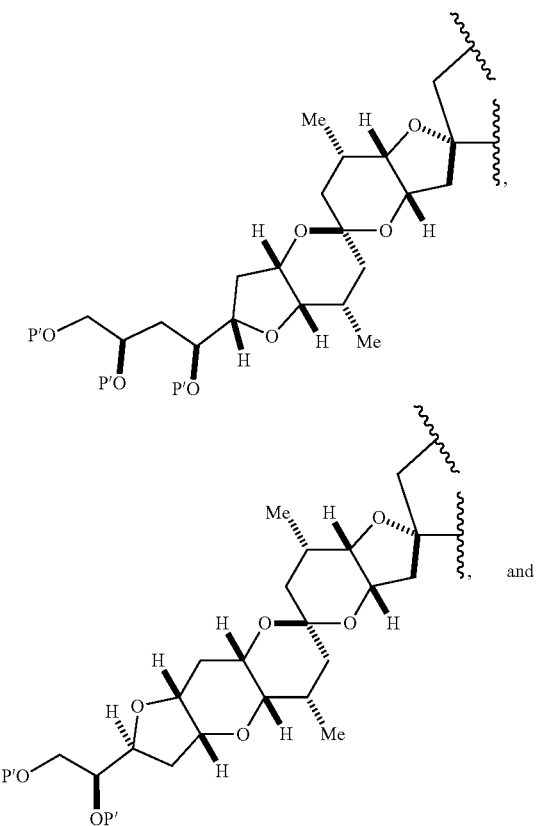

-continued

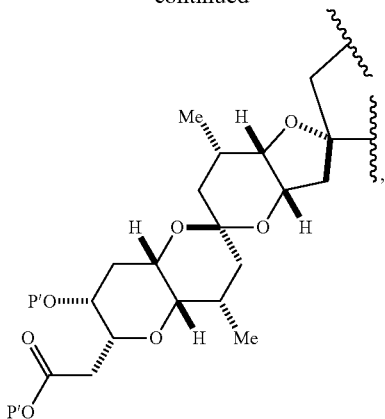

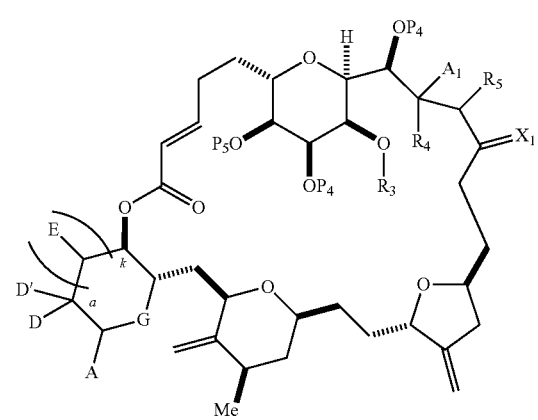

or a salt or a tautomer thereof.

In formula (IA) or (IB), each R can be optionally substituted $C_{1-6}$ alkyl. In formula (IA) or (IB), both $P_4$ groups and $X_1$, together with the atoms to which each is attached, can combine to form ketal. In formula (IA) or (IB), $X_1$, together with the carbon atom to which it is attached, can be —(CH(OP$_Y$))—, where P$_Y$ is H or a hydroxyl protecting group. In formula (IA) or (IB), $P_5$ can be a hydroxyl protecting group. In formula (IA) or (IB), $R_3$ and $R_4$ can combine to form a bond, and $R_5$ can be H.

In particular embodiments of the first aspect, performing the macrocyclization reaction involves contacting the non-macrocyclic intermediate (e.g., a compound of formula (IIA), formula (IIIA), formula (IVA), or formula (VA)) with an olefin metathesis catalyst (e.g., a ruthenium-carbene complex).

The non-macrocyclic intermediate can be a compound of formula (IIA):

where each P' is independently H or a hydroxyl protecting group;

E is optionally substituted alkyl or optionally substituted alkoxy;

G is O, S, CH$_2$, or NR$_N$, where R$_N$ is H, an N-protecting group, or optionally substituted alkyl;

each $Q_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2;

A$_1$ and R$_4$ combine to form oxo, R$_3$ is H or a hydroxyl protecting group, and R$_5$ is H;

or

A$_1$ is H or OP''', where P''' is H or a hydroxyl protecting group, and:

(i) R$_3$ is H or a hydroxyl protecting group, and R$_4$ and R$_5$ combine to form a double bond;

or (ii) R$_3$ and R$_4$ combine to form a bond, and R$_5$ is H or OP''';

each $P_4$ is independently H or a hydroxyl protecting group, and $X_1$ is oxo or $X_1$, together with the carbon atom to which it is attached, is —(CH(OP$_Y$))—, wherein P$_Y$ is H or a hydroxyl protecting group; or both $P_4$ groups and $X_1$, together with the atoms to which each is attached, combine to form ketal; and $P_5$ is H or a hydroxyl protecting group; and the macrocyclic intermediate in the synthesis of a halichondrin macrolide is a compound of formula (IB):

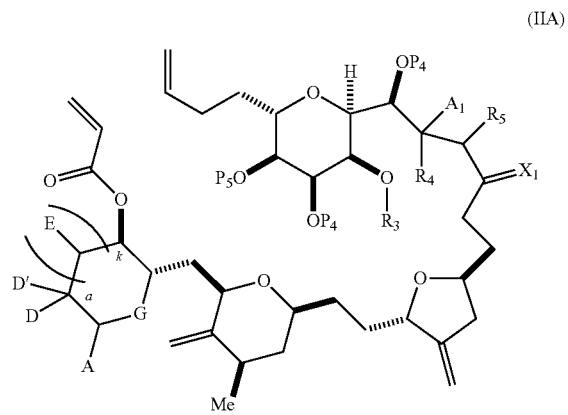

or a salt or a tautomer thereof, where each of D and D' is independently H, optionally substituted alkyl, or OP$_1$, provided that only one of D and D' is OP$_1$, where P$_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

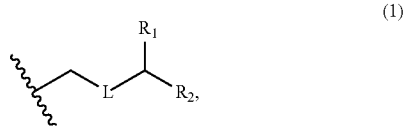

where

L is —(CH(OP$_2$))—, —(C(OH)(OP$_2$))—, or —C(O)—;

R$_1$ is H, or R$_1$ and P$_1$ combine to form a bond;

R$_2$ is H or —(CH$_2$)$_n$OP$_3$, and each of P$_2$ and P$_3$ is independently H, optionally substituted alkyl, or a hydroxyl protecting group, or P$_2$ and P$_3$, together with the atoms to which each is attached, combine to form a ketal, a cyclic carbonate, a dicarbonyl-dioxo, or silylene-dioxo; or R$_2$ and P$_2$ combine to form an optionally substituted ethylene or a structure selected from the group consisting of:

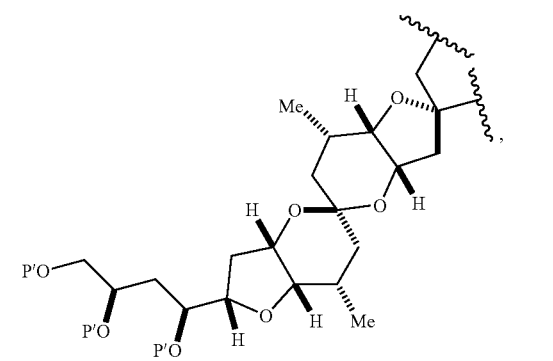

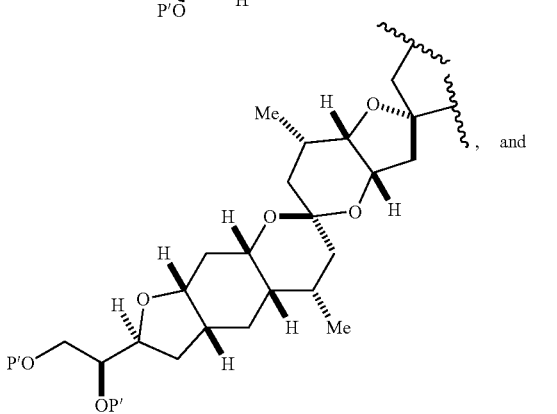

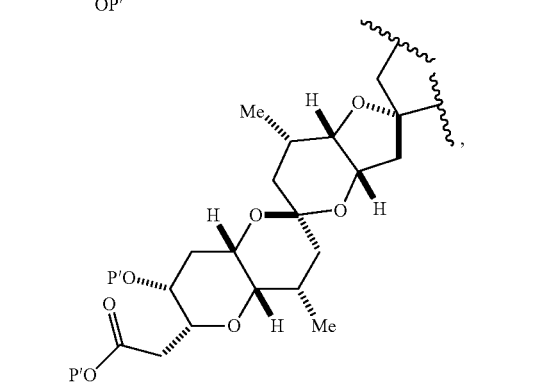

where each P' is independently H or a hydroxyl protecting group;

E is optionally substituted alkyl or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2;

A$_1$ and R$_4$ combine to form oxo, R$_3$ is H or a hydroxyl protecting group, and R$_5$ is H;

or

A$_1$ is H or OP''', where P''' is H or a hydroxyl protecting group, and:

(i) R$_3$ is H or a hydroxyl protecting group, and R$_4$ and R$_5$ combine to form a double bond;

or (ii) R$_3$ and R$_4$ combine to form a bond, and R$_5$ is H or OP''';

each P$_4$ is independently H or a hydroxyl protecting group, and X$_1$ is oxo or X$_1$, together with the carbon atom to which it is attached, is —(CH(OP$_Y$))—, wherein P$_Y$ is H or a hydroxyl protecting group; or both P$_4$ groups and X$_1$, together with the atoms to which each is attached, combine to form ketal; and P$_5$ is H or a hydroxyl protecting group; and where the macrocyclic intermediate in the synthesis of a halichondrin macrolide is a compound of formula (IB):

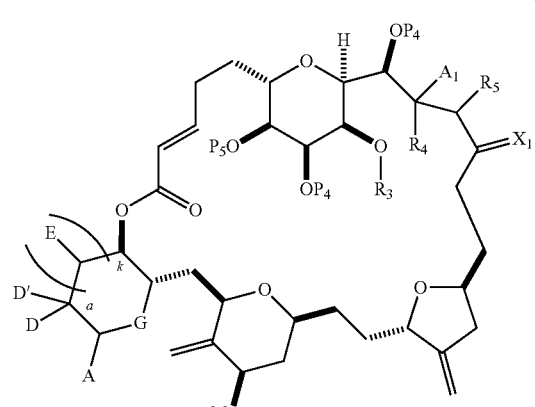

or a salt or a tautomer thereof.

The non-macrocyclic intermediate can be a compound of formula (IIIA):

(IIIA)

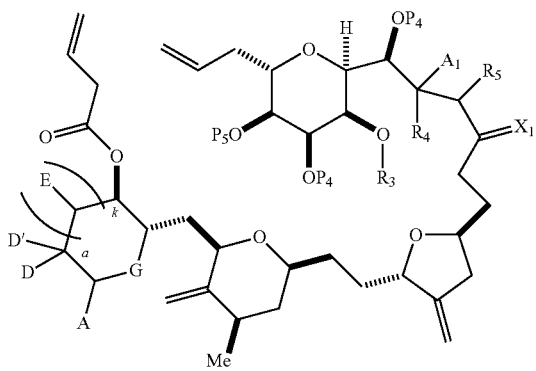

or a salt or a tautomer thereof,
where
each of D and D' is independently H, optionally substituted alkyl, or OP$_1$, provided that only one of D and D' is OP$_1$, where P$_1$ is H, alkyl, or a hydroxyl protecting group; A is a group of formula (1) or a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, the group of formula (1) having the structure:

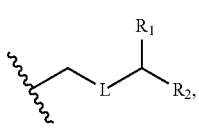
(1)

where
L is —(CH(OP$_2$))—, —(C(OH)(OP$_2$))—, or —C(O)—;
R$_1$ is H, or R$_1$ and P$_1$ combine to form a bond;
R$_2$ is H or —(CH$_2$)$_n$OP$_3$, and each of P$_2$ and P$_3$ is independently H, optionally substituted alkyl, or a hydroxyl protecting group, or P$_2$ and P$_3$, together with the atoms to which each is attached, combine to form a ketal, a cyclic carbonate, a dicarbonyl-dioxo, or silylene-dioxo; or R$_2$ and P$_2$ combine to form an optionally substituted ethylene or a structure selected from the group consisting of:

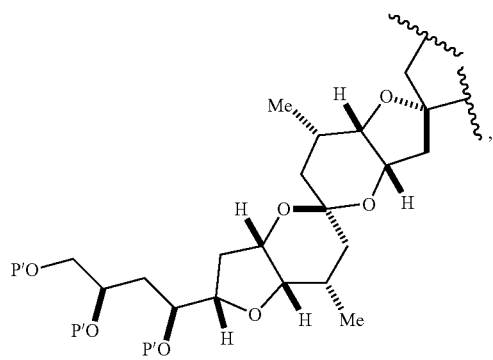

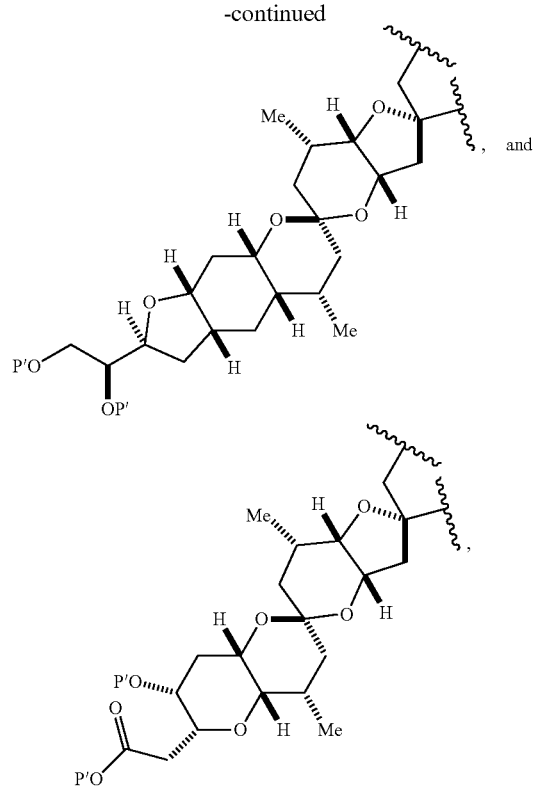

where each P' is independently H or a hydroxyl protecting group;
E is optionally substituted alkyl or optionally substituted alkoxy;
G is O, S, CH$_2$, or NR$_N$, where R$_N$ is H, an N-protecting group, or optionally substituted alkyl;
each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
k is 0 or 1;
n is 0, 1, or 2;
A$_1$ and R$_4$ combine to form oxo, R$_3$ is H or a hydroxyl protecting group, and R$_5$ is H;
or
A$_1$ is H or OP''', where P''' is H or a hydroxyl protecting group, and:
(i) R$_3$ is H or a hydroxyl protecting group, and R$_4$ and R$_5$ combine to form a double bond;
or
(ii) R$_3$ and R$_4$ combine to form a bond, and R$_5$ is H or OP''';
each P$_4$ is independently H or a hydroxyl protecting group, and X$_1$ is oxo or X$_1$, together with the carbon atom to which it is attached, is —(CH(OP$_Y$))—, wherein P$_Y$ is H or a hydroxyl protecting group; or both P₄ groups and X₁, together with the atoms to which each is attached, combine to form ketal; and
P₅ is H or a hydroxyl protecting group; and
where the macrocyclic intermediate in the synthesis of a halichondrin macrolide is a compound of formula (IIIB):

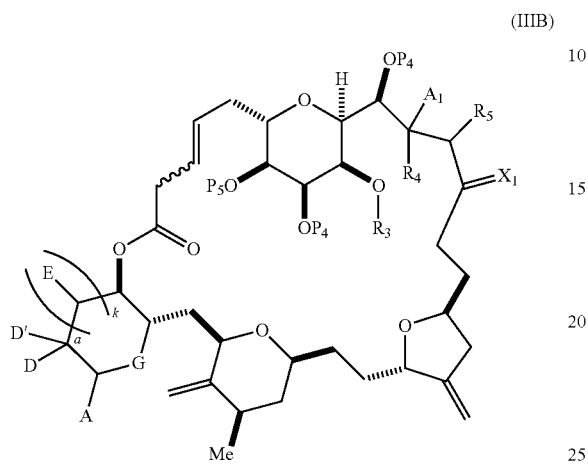

(IIIB)

or a salt or a tautomer thereof.

In formula (IIA), (IIB), (IIIA), or (IIIB), both P₄ groups and X₁, together with the atoms to which each is attached, can combine to form ketal. In formula (IIA), (IIB), (IIIA), or (IIIB), P₅ can be a hydroxyl protecting group. In formula (IIA), (IIB), (IIIA), or (IIIB), X₁, together with the carbon atom to which it is attached, can be —(CH(OP$_Y$))—, where P$_Y$ is H. In formula (IIA), (IIB), (IIIA), or (IIIB), X₁ can be oxo.

the non-macrocyclic intermediate is a compound of formula (IVA):

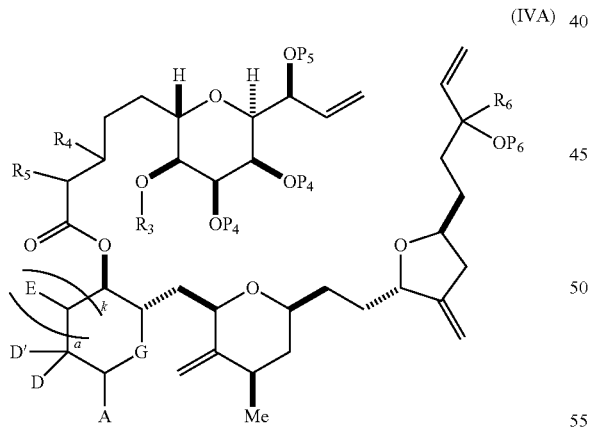

(IVA)

or a salt thereof,
where
each of D and D' is independently H, optionally substituted alkyl, or OP₁, provided that only one of D and D' is OP₁, where P₁ is H, alkyl, or a hydroxyl protecting group; A is a group of formula (1) or a C₁₋₆ saturated or C₂₋₆ unsaturated hydrocarbon skeleton, the skeleton being unsubstituted or having from 1 to 10 substituents independently selected from the group consisting of cyano, halo, azido, oxo, and Q₁, the group of formula (1) having the structure:

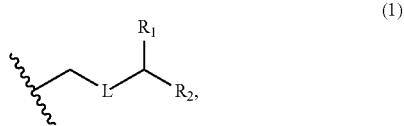

(1)

where
L is —(CH(OP₂))—, —(C(OH)(OP₂))—, or —C(O)—;

R₁ is H, or R₁ and P₁ combine to form a bond;

R₂ is H or —(CH₂)$_n$OP₃, and each of P₂ and P₃ is independently H, optionally substituted alkyl, or a hydroxyl protecting group, or P₂ and P₃, together with the atoms to which each is attached, combine to form a ketal, a cyclic carbonate, a dicarbonyl-dioxo, or silylene-dioxo; or R₂ and P₂ combine to form an optionally substituted ethylene or a structure selected from the group consisting of:

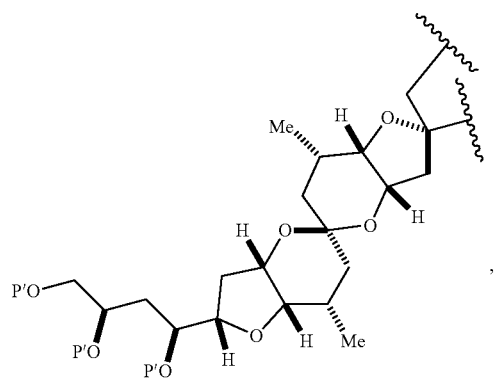

,

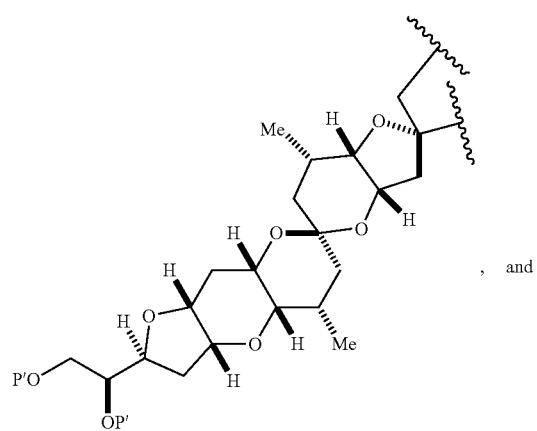

, and

-continued

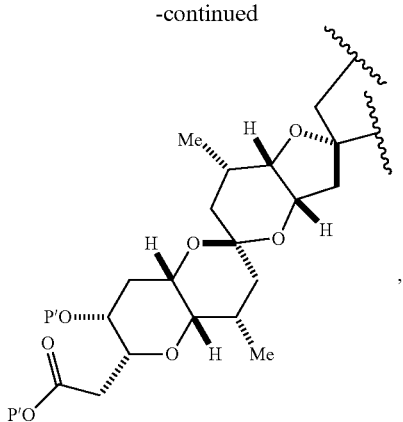

where each P' is independently H or a hydroxyl protecting group;
  E is optionally substituted alkyl or optionally substituted alkoxy;
  G is O, S, $CH_2$, or $NR_N$, where $R_N$ is H, an N-protecting group, or optionally substituted alkyl;
  each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
  k is 0 or 1;
  n is 0, 1, or 2;
  (i) $R_3$ is H or a hydroxyl protecting group, $R_4$ is alkyl ether, and $R_5$ is H;
  (ii) $R_3$ is H or a hydroxyl protecting group, and $R_4$ and $R_5$ combine to form a double bond;
  or
  (iii) $R_3$ and $R_4$ combine to form a bond, and $R_5$ is H;
  each $P_4$ and $P_5$ is independently H or a hydroxyl protecting group;
  $R_6$ is H, and $P_6$ is H or a hydroxyl protecting group; or $R_6$ and $P_6$ combine to form a double bond; and
  where the macrocyclic intermediate in the synthesis of a halichondrin macrolide is a compound of formula (IVB):

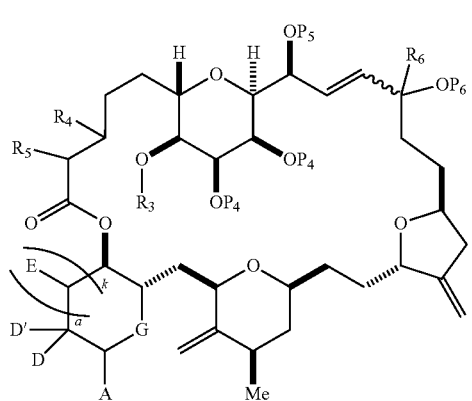

or a salt thereof.

In formula (IVA) or (IVB), at least one of $P_4$ and $P_5$ can be H. In formula (IVA) or (IVB), $R_6$ and $P_6$ can combine to form a double bond.

The non-macrocyclic intermediate can be a compound of formula (VA):

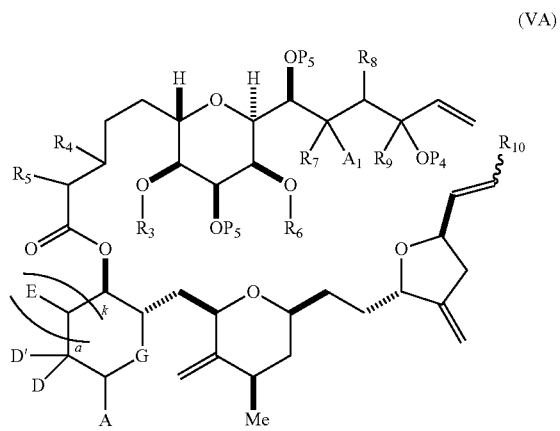

or a salt or a tautomer thereof,
where
each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

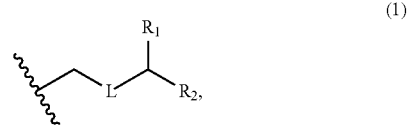

where
  L is —(CH($OP_2$))—, —(C(OH)($OP_2$))—, or —C(O)—;
  $R_1$ is H, or $R_1$ and $P_1$ combine to form a bond;
  $R_2$ is H or —$(CH_2)_nOP_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

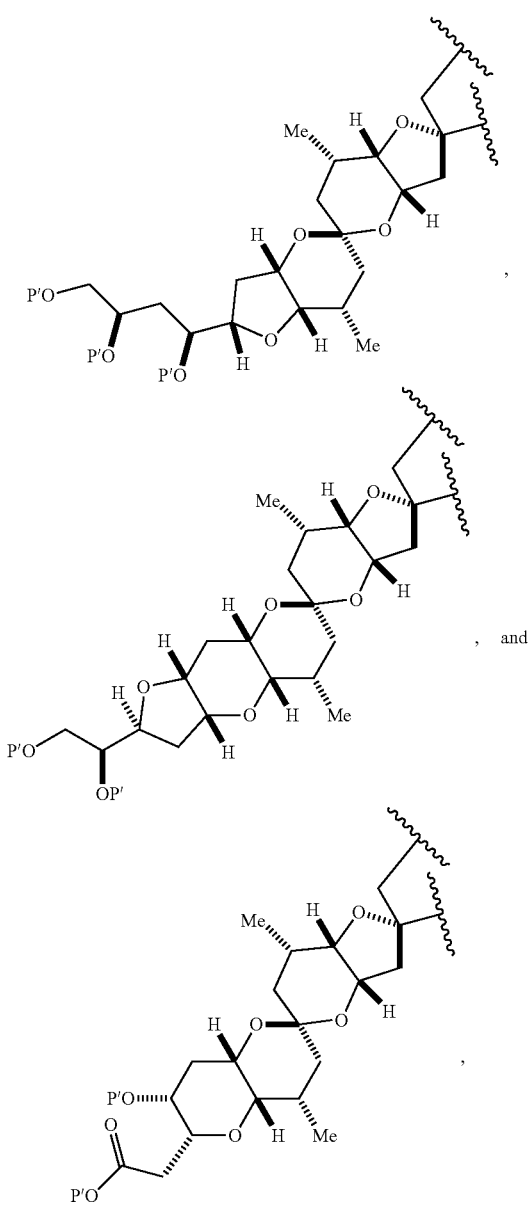

, and

, where each P' is independently H or a hydroxyl protecting group;
E is optionally substituted alkyl or optionally substituted alkoxy;
G is O, S, CH$_2$, or NR$_N$, where R$_N$ is H, an N-protecting group, or optionally substituted alkyl;
each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
k is 0 or 1;
n is 0, 1, or 2;
(a1) R$_3$ is H or a hydroxyl protecting group, R$_4$ is alkyl ether, and R$_5$ is H;
(a2) R$_3$ is H or a hydroxyl protecting group, and R$_4$ and R$_5$ combine to form a double bond;
or
(a3) R$_3$ and R$_4$ combine to form a bond, and R$_5$ is H;
(b1) A$_1$ and R$_7$ combine to form oxo, R$_6$ is H or a hydroxyl protecting group, and R$_8$ is H;
or
(b2) A$_1$ is H or OP'', where P'' is H or a hydroxyl protecting group, and:
 (i) R$_6$ is H or a hydroxyl protecting group, and R$_7$ and R$_8$ combine to form a double bond;
 or
 (ii) R$_6$ and R$_7$ combine to form a bond, and R$_8$ is H or OP'';
(c1) R$_9$ is H, and P$_4$ is H or a hydroxyl protecting group;
or
(c2) R$_9$ and P$_4$ combine to form a double bond;
R$_{10}$ is H or —CH$_2$X$_1$CH$_2$CH=CH$_2$, where X$_1$ is O, —C(R$_{11}$)$_2$—, or NP$_6$, and where each R$_{11}$ is independently H or —COOR$_{12}$, P$_6$ is an N-protecting group, and R$_{12}$ is alkyl;
each P$_5$ is independently H or a hydroxyl protecting group; and
where the macrocyclic intermediate in the synthesis of a halichondrin macrolide is a compound of formula (VB):

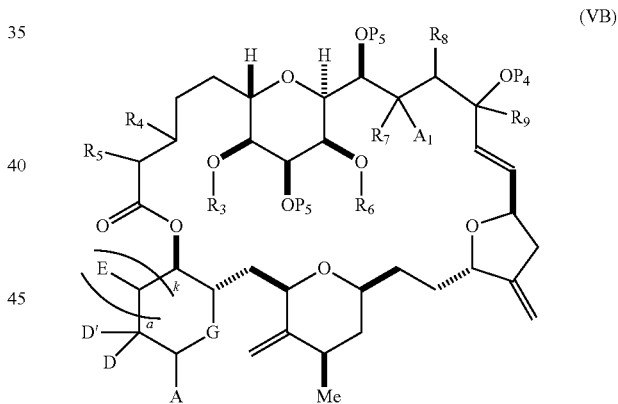

(VB)

or a salt or a tautomer thereof.

In formula (VA) or (VB), R$_9$ can be H, and P$_4$ can be H. In formula (VA) or (VB), R$_{10}$ can be —CH$_2$X$_1$CH$_2$CH=CH$_2$, and X$_1$ can be O. In formula (VA) or (VB), R$_6$ and R$_7$ can combine to form a bond, and R$_8$ can be H. In formula (VA) or (VB), each P$_5$ can be independently a hydroxyl protecting group. In formula (VA) or (VB), at least one P$_5$ can be H. In formula (VA) or (VB), R$_3$ and R$_4$ can combine to form a bond, and R$_5$ can be H.

In certain embodiments of the first aspect, performing the macrocyclization reaction involves contacting the non-macrocyclic intermediate (e.g., a compound of formula (VIA) or (VIIA)) with a Cr(II) salt and a Ni(II) salt.

The non-macrocyclic intermediate can be a compound of formula (VIA):

(VIA)

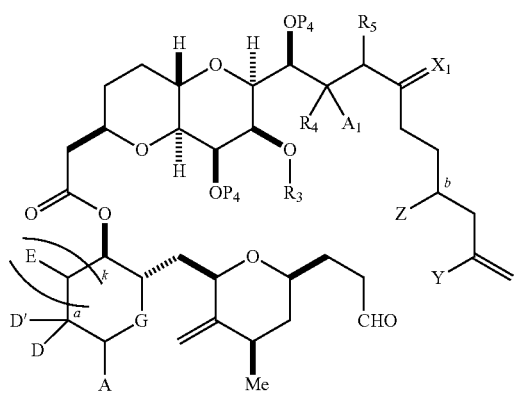

or a salt or a tautomer thereof,
where
Y is iodide, bromide, or trifluoromethanesulfonate;
b designates (R)-stereogenic center, and Z is a sulfonate, chloride, bromide, or iodide; or b designates (S)-stereogenic center, and Z is $OR_6$, where $R_6$ is a hydroxyl protecting group;
each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

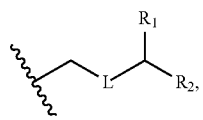

(1)

where
L is —(CH($OP_2$))—, —(C(OH)($OP_2$))—, or —C(O)—;
$R_1$ is H, or $R_1$ and $P_1$ combine to form a bond;
$R_2$ is H or —(CH$_2$)$_n$OP$_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

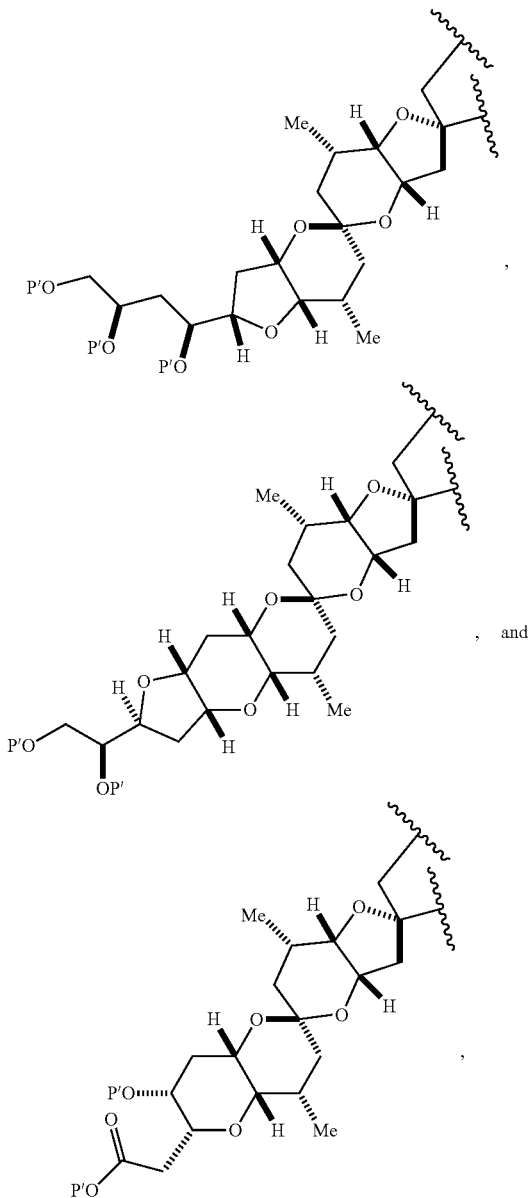

where each P' is independently H or a hydroxyl protecting group;
E is optionally substituted alkyl or optionally substituted alkoxy;
G is O, S, CH$_2$, or NR$_N$, where R$_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
k is 0 or 1;
n is 0, 1, or 2;
$A_1$ and $R_4$ combine to form oxo, $R_3$ is H or a hydroxyl protecting group, and $R_5$ is H;

or

A₁ is H or OP''', where P''' is H or a hydroxyl protecting group, and:
  (i) R₃ is H or a hydroxyl protecting group, and R₄ and R₅ combine to form a double bond;
  or
  (ii) R₃ and R₄ combine to form a bond, and R₅ is H or OP''';

each P₄ is independently H or a hydroxyl protecting group, and X₁ is oxo; or both P₄ groups and X₁, together with the atoms to which each is attached, combine to form ketal; and where the macrocyclic intermediate in the synthesis of a halichondrin macrolide is a compound of formula (IVB):

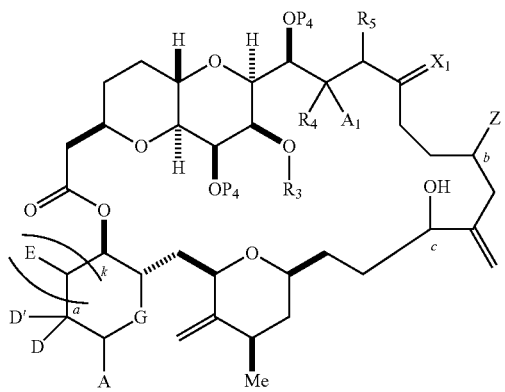
(VIB)

or a salt or a tautomer thereof,
where
  b designates (R)-stereogenic center, c designates (S)-stereogenic center, and Z is a sulfonate, chloride, bromide, or iodide;
or
  b designates (S)-stereogenic center, c designates (R)-stereogenic center, and Z is OR₆, where R₆ is a hydroxyl protecting group.

In formula (VIA) or (VIB), Y can be bromide. In formula (VIA) or (VIB), R₃ and R₄ can combine to form a bond, and R₅ can be H. In formula (VIA) or (VIB), both P₄ groups and X₁, together with the atoms to which each is attached, can combine to form ketal. In formula (VIA) or (VIB), Z can be a sulfonate. In formula (VIA) or (VIB), Z can be OR₆, where R₆ is a hydroxyl protecting group. In formula (VIA) or (VIB), Z can be an ester, carbonate, or carbamate.

The non-macrocyclic intermediate can be a compound of formula (VIIA):

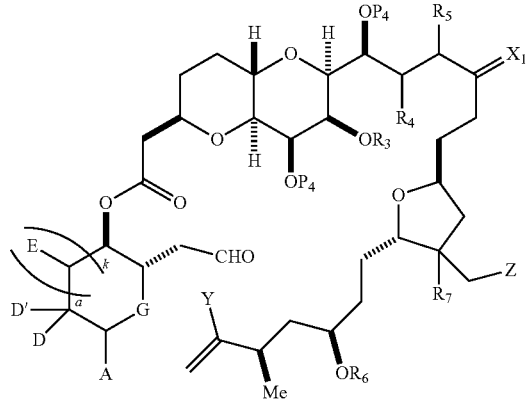
(VIIA)

or a salt thereof,
where
Y is iodide, bromide, or trifluoromethanesulfonate;
each of D and D' is independently H, optionally substituted alkyl, or OP₁, provided that only one of D and D' is OP₁, where P₁ is H, alkyl, or a hydroxyl protecting group; A is a group of formula (1) or a C₁₋₆ saturated or C₂₋₆ unsaturated hydrocarbon skeleton, the skeleton being unsubstituted or having from 1 to 10 substituents independently selected from the group consisting of cyano, halo, azido, oxo, and Q₁, the group of formula (1) having the structure:

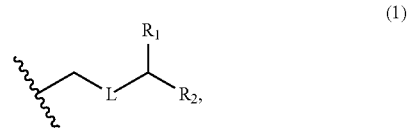
(1)

where
L is —(CH(OP₂))—, —(C(OH)(OP₂))—, or —C(O)—;
R₁ is H, or R₁ and P₁ combine to form a bond;
R₂ is H or —(CH₂)ₙOP₃, and each of P₂ and P₃ is independently H, optionally substituted alkyl, or a hydroxyl protecting group, or P₂ and P₃, together with the atoms to which each is attached, combine to form a ketal, a cyclic carbonate, a dicarbonyl-dioxo, or silylene-dioxo; or R₂ and P₂ combine to form an optionally substituted ethylene or a structure selected from the group consisting of:

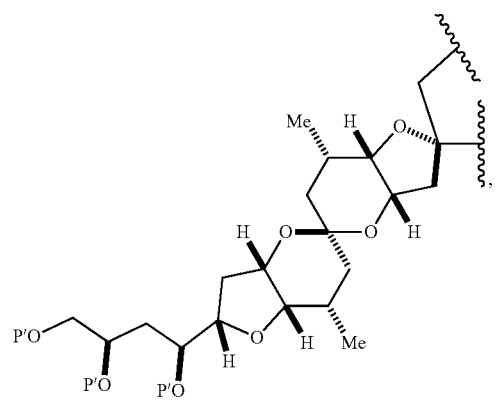

-continued

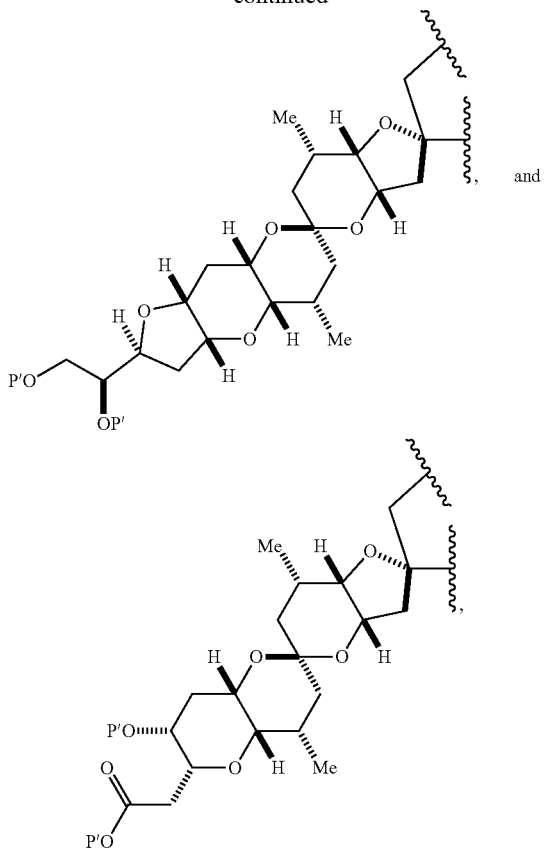

where each P' is independently H or a hydroxyl protecting group;
E is optionally substituted alkyl or optionally substituted alkoxy;
G is O, S, $CH_2$, or $NR_N$, where $R_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
k is 0 or 1;
n is 0, 1, or 2;
(a1) $R_3$ is H or a hydroxyl protecting group, $R_4$ and $R_5$ combine to form a double bond, each $P_4$ is independently H or a hydroxyl protecting group, and $X_1$, together with the carbon to which is attached, forms a carbonyl or —(CH($OR_8$))—, where $R_8$ is H or a hydroxyl protecting group;
or
(a2) $R_3$ and $R_4$ combine to form a bond, $R_5$ is H, and each $P_4$ is independently H or a hydroxyl protecting group, and $X_1$, together with the carbon to which it is attached, forms a carbonyl or —(CH($OR_8$))—;
or
both $P_4$ groups and $X_1$, together with the atoms to which each is attached, combine to form ketal;
(b1) Z is chloride, bromide, or iodide, and $R_6$ and $R_7$ combine to form a bond;

or
(b2) Z and $R_7$ combine to form a double bond, and $R_6$ is a hydroxyl protecting group;
and
where the macrocyclic intermediate in the synthesis of a halichondrin macrolide is a compound of formula (VIIB):

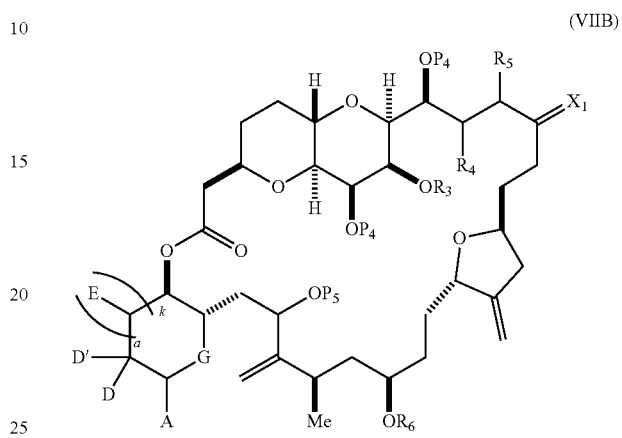

or a salt thereof,
where each of $P_5$ and $R_6$ is independently H or a hydroxyl protecting group.
In formula (VIIA), Z can be iodide. In formula (VIIA) or (VIIB), Y can be trifluoromethanesulfonate. In formula (VIIA) or (VIIB), $R_3$ can be H or a hydroxyl protecting group, $R_4$ and $R_5$ can combine to form a double bond, each $P_4$ can independently be H or a hydroxyl protecting group, and $X_1$, together with the carbon to which it is attached, can form —(CH($OR_8$))—, where $R_8$ is H or a hydroxyl protecting group. In formula (VIIA) or (VIIB), at least one of $P_3$, $P_4$, and $R_6$ can be a hydroxyl protecting group. In formula (VIIA), Z can be chloride, bromide, or iodide, and $R_6$ and $R_7$ combine to form a bond.
In a second aspect, the invention provides a method of preparing:

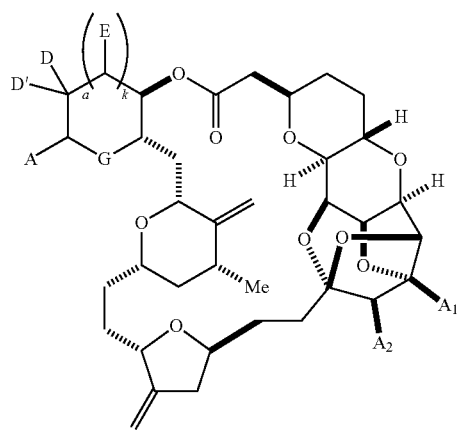

halichondrin macrolide or a salt thereof,
where
each of $A_1$ and $A_2$ is independently H or OP''', where each P''' is independently H or a hydroxyl protecting group;

each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

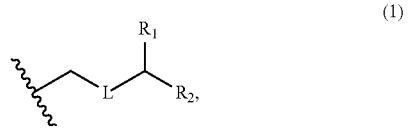

(1)

where

L is —(CH($OP_2$))—, —(C(OH)($OP_2$))—, or —C(O)—;

$R_1$ is H, or $R_1$ and $P_1$ combine to form a bond;

$R_2$ is H or —(CH$_2$)$_n$OP$_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

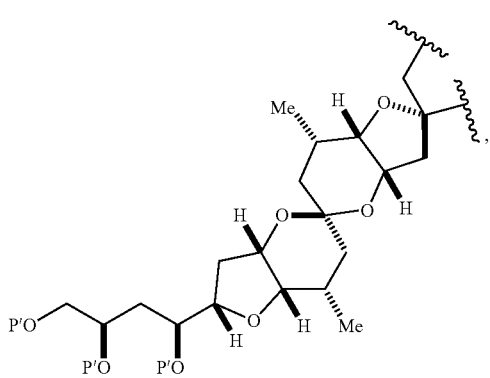

and

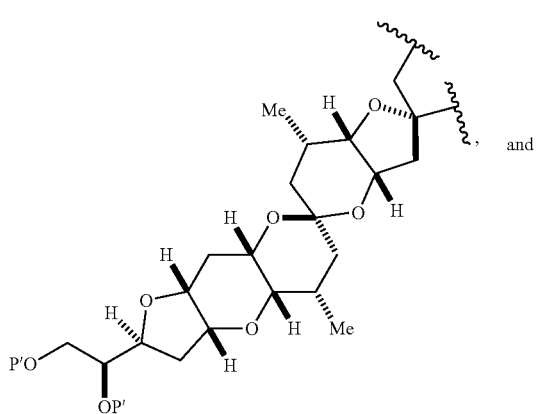

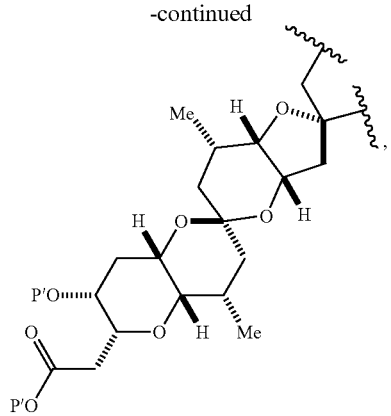

where each P' is independently H or a hydroxyl protecting group;

E is optionally substituted alkyl or optionally substituted alkoxy;

G is O, S, CH$_2$, or NR$_N$, where $R_N$ is H, an N-protecting group, or optionally substituted alkyl;

each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2;

the method involving:

(A) producing a compound of formula (IB) from a compound of formula (IA), the compound of formula (IA) having the following structure:

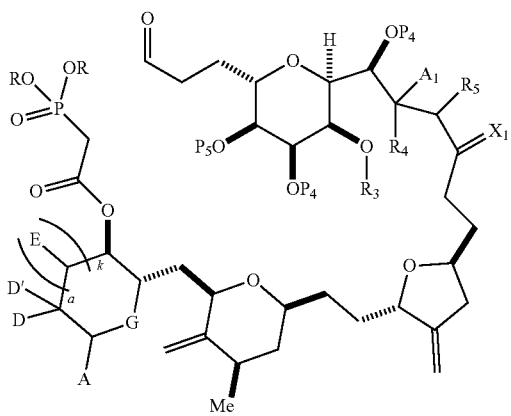

(IA)

or a salt or a tautomer thereof, wherein each R is independently optionally substituted alkyl or optionally substituted aryl;

$A_1$ and $R_4$ combine to form oxo, $R_3$ is H or a hydroxyl protecting group, and $R_5$ is H;

or
A₁ is H or OP‴, where P‴ is H or a hydroxyl protecting group, and:
(i) R₃ is H or a hydroxyl protecting group, and R₄ and R₅ combine to form a double bond;
or
(ii) R₃ and R₄ combine to form a bond, and R₅ is H or OP‴;

each P₄ is independently H or a hydroxyl protecting group, and X₁ is oxo or X₁, together with the carbon atom to which it is attached, is —(CH(OP$_Y$))—, wherein P$_Y$ is H or a hydroxyl protecting group; or both P₄ groups and X₁, together with the atoms to which each is attached, combine to form ketal; and P₅ is H or a hydroxyl protecting group; and
the compound of formula (IB) having the following structure:

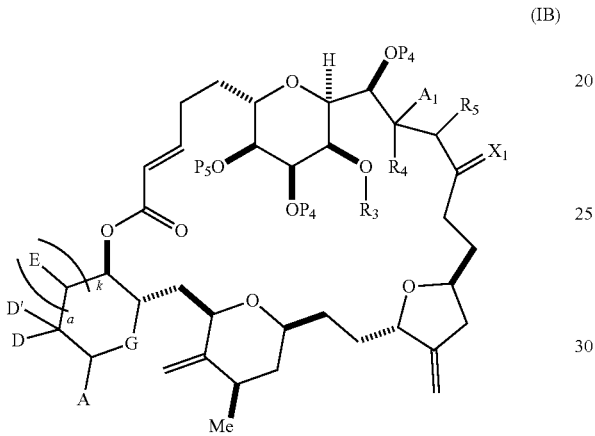

(IB)

or a salt or a tautomer thereof;
and
(B) producing the halichondrin macrolide from compound (IB).

In some embodiments of the second aspect, the producing the compound of formula (IB) involves reacting the compound of formula (IA) with an organic base and a Lewis acid. In certain embodiments of the second aspect, the producing the halichondrin macrolide involves reacting the compound of formula (IB) with a hydroxyl protecting group removing agent. In particular embodiments of the second aspect, each R is optionally substituted alkyl.

In a third aspect, the invention provides a method of preparing:

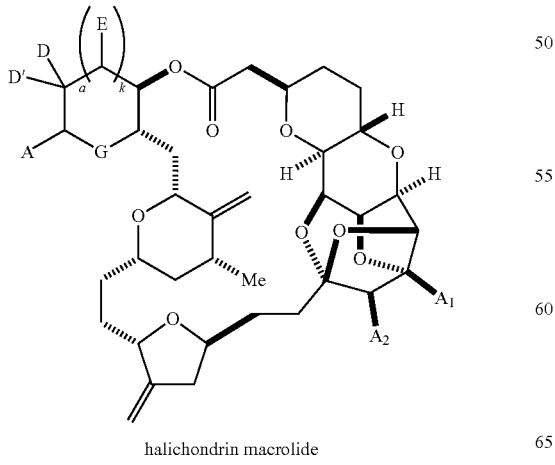

halichondrin macrolide or a salt thereof, where
each of A₁ and A₂ is independently H or OP‴, where each P‴ is independently H or a hydroxyl protecting group;
each of D and D' is independently H, optionally substituted alkyl, or OP₁, provided that only one of D and D' is OP₁, where P₁ is H, alkyl, or a hydroxyl protecting group; A is a group of formula (1) or a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q₁, the group of formula (1) having the structure:

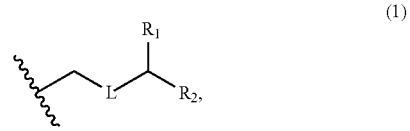

(1)

where
L is —(CH(OP₂))—, —(C(OH)(OP₂))—, or —C(O)—;
R₁ is H, or R₁ and P₁ combine to form a bond;
R₂ is H or —(CH₂)$_n$OP₃, and each of P₂ and P₃ is independently H, optionally substituted alkyl, or a hydroxyl protecting group, or P₂ and P₃, together with the atoms to which each is attached, combine to form a ketal, a cyclic carbonate, a dicarbonyl-dioxo, or silylene-dioxo; or R₂ and P₂ combine to form an optionally substituted ethylene or a structure selected from the group consisting of:

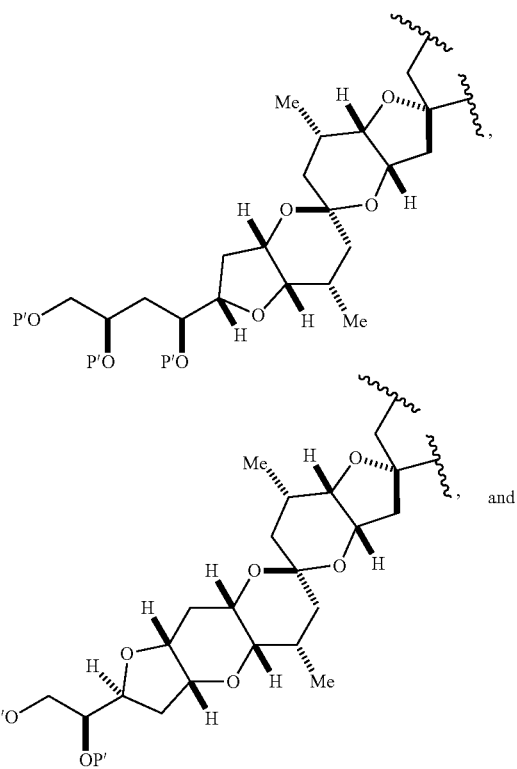

-continued

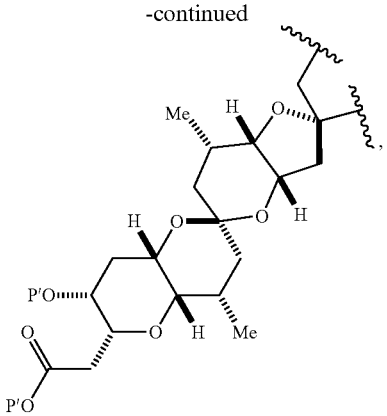

where each P' is independently H or a hydroxyl protecting group;
E is optionally substituted alkyl or optionally substituted alkoxy;
G is O, S, $CH_2$, or $NR_N$, where $R_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
k is 0 or 1;
n is 0, 1, or 2;
the method involving:
(A) producing a compound of formula (IB) from a compound of formula (IIA), the compound of formula (IIA) having the following structure:

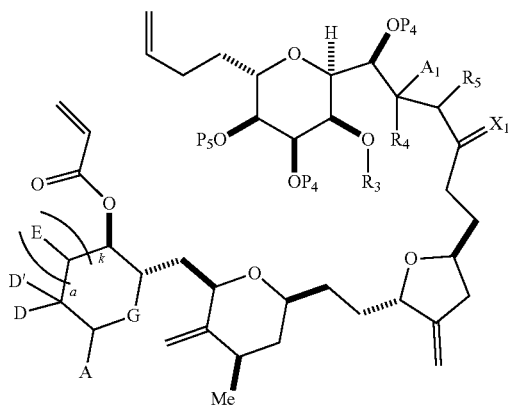

(IIA)

or a salt or a tautomer thereof,
wherein
$A_1$ and $R_4$ combine to form oxo, $R_3$ is H or a hydroxyl protecting group, and $R_5$ is H; or
$A_1$ is H or OP''', where P''' is H or a hydroxyl protecting group, and:
(i) $R_3$ is H or a hydroxyl protecting group, and $R_4$ and $R_5$ combine to form a double bond;

or
(ii) $R_3$ and $R_4$ combine to form a bond, and $R_5$ is H or OP''';
each $P_4$ is independently H or a hydroxyl protecting group, and $X_1$ is oxo or $X_1$, together with the carbon atom to which it is attached, is —(CH($OP_Y$))—, wherein $P_Y$ is H or a hydroxyl protecting group; or both $P_4$ groups and $X_1$, together with the atoms to which each is attached, combine to form ketal; and
$P_5$ is H or a hydroxyl protecting group; and
the compound of formula (IB) having the following structure:

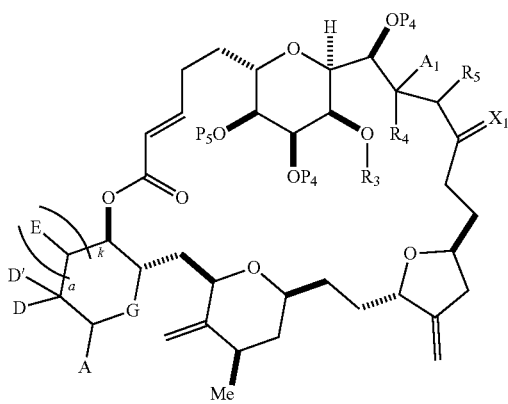

(IB)

or a salt or a tautomer thereof;
and
(B) producing the halichondrin macrolide from compound (IB).

In some embodiments of the third aspect, the producing the compound of formula (IB) involves reacting the compound of formula (IIA) with an olefin metathesis catalyst (e.g., a ruthenium-carbene complex). In some embodiments of the third aspect, the producing the halichondrin macrolide involves reacting the compound of formula (IB) with a hydroxyl protecting group removing agent.

In a fourth aspect, the invention provides a method of preparing:

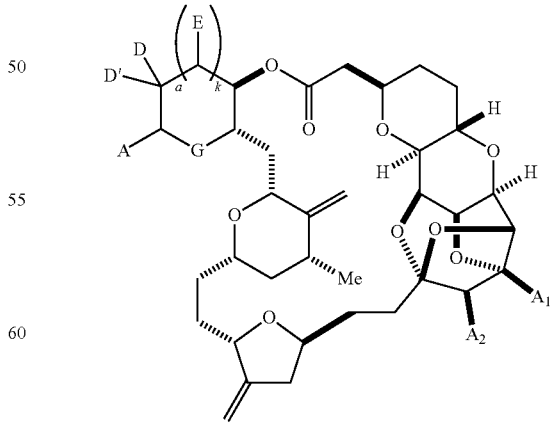

halichondrin macrolide or a salt thereof, wherein each of $A_1$ and $A_2$ is independently H or OP''', where each P''' is independently H or a hydroxyl protecting group;

each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

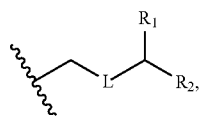
(1)

where

L is $-(CH(OP_2))-$, $-(C(OH)(OP_2))-$, or $-C(O)-$;

$R_1$ is H, or $R_1$ and $P_1$ combine to form a bond;

$R_2$ is H or $-(CH_2)_nOP_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

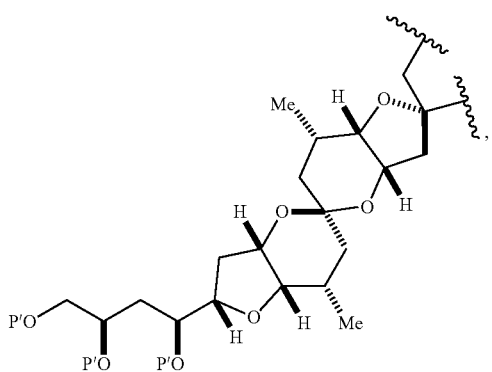

and

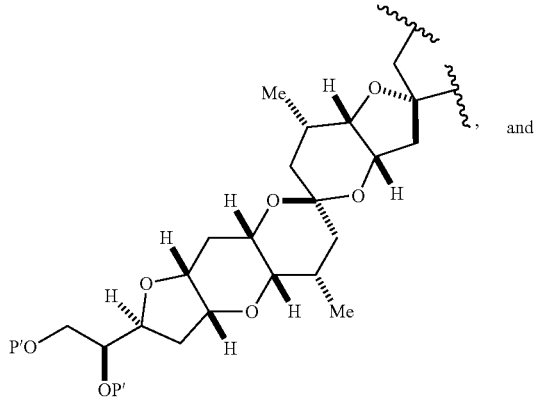

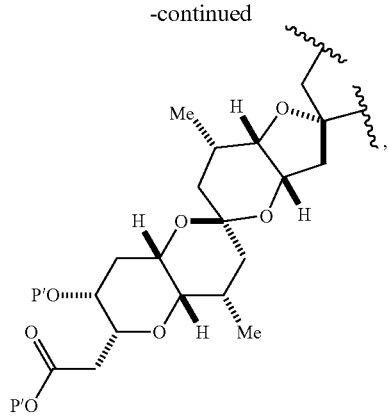

where each P' is independently H or a hydroxyl protecting group;

E is optionally substituted alkyl or optionally substituted alkoxy;

G is O, S, $CH_2$, or $NR_N$, where $R_N$ is H, an N-protecting group, or optionally substituted alkyl;

each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2;

the method involving:

(A) producing a compound of formula (IIIB) from a compound of formula (IIIA), the compound of formula (IIIA) having the following structure:

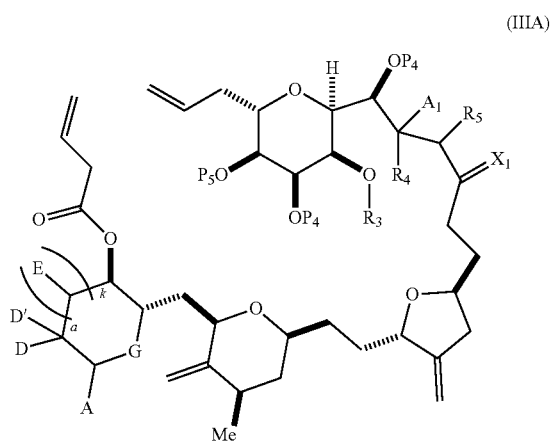
(IIIA)

or a salt or a tautomer thereof, wherein $A_1$ and $R_4$ combine to form oxo, $R_3$ is H or a hydroxyl protecting group, and $R_5$ is H;

or $A_1$ is H or OP''', where P''' is H or a hydroxyl protecting group, and:

(i) $R_3$ is H or a hydroxyl protecting group, and $R_4$ and $R_5$ combine to form a double bond;

or (ii) $R_3$ and $R_4$ combine to form a bond, and $R_5$ is H or OP''';

each $P_4$ is independently H or a hydroxyl protecting group, and $X_1$ is oxo or $X_1$, together with the carbon atom to which it is attached, is —(CH(OP$_Y$))—, wherein $P_Y$ is H or a hydroxyl protecting group; or both $P_4$ groups and $X_1$, together with the atoms to which each is attached, combine to form ketal; and $P_5$ is H or a hydroxyl protecting group; and the compound of formula (IIIB) having the following structure:

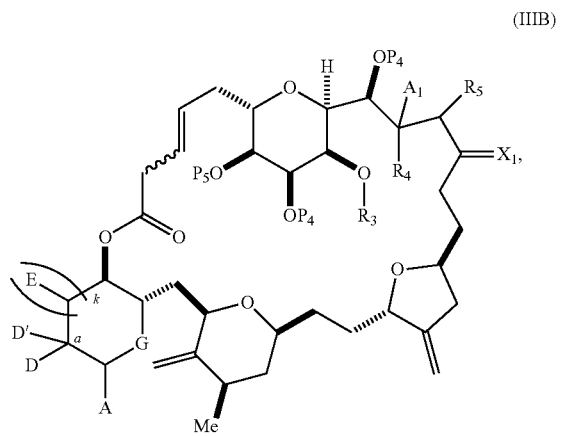

(IIIB)

or a salt or a tautomer thereof;

and (B) producing the halichondrin macrolide from the compound of formula (IIIB).

In some embodiments of the fourth aspect, the producing the compound of formula (IIIB) involves reacting the compound of formula (IIIA) with an olefin metathesis catalyst. In certain embodiments of the fourth aspect, the producing the halichondrin macrolide involves reacting the compound of formula (IIIB) with a hydroxyl protecting group removing agent. In particular embodiments of the fourth aspect, both $P_4$ groups and $X_1$, together with the atoms to which each is attached, combine to form ketal. In further embodiments of the fourth aspect, $P_5$ is a hydroxyl protecting group.

In a fifth aspect, the invention provides a method of preparing:

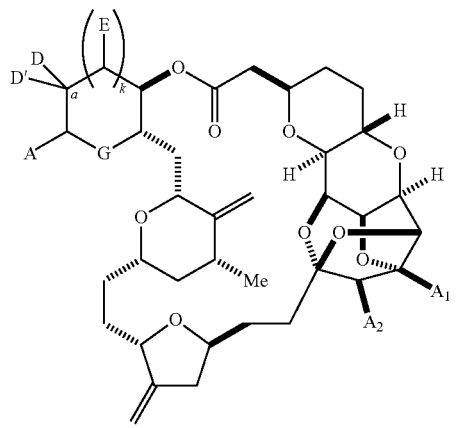

halichondrin macrolide or a salt thereof, where each of $A_1$ and $A_2$ is independently H or OP''', where each P''' is independently H or a hydroxyl protecting group;

each of D and D' is independently H, optionally substituted alkyl, or OP$_1$, provided that only one of D and D' is OP$_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

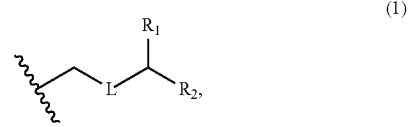

(1)

where

L is —(CH(OP$_2$))—, —(C(OH)(OP$_2$))—, or —C(O)—;

$R_1$ is H, or $R_1$ and $P_1$ combine to form a bond;

$R_2$ is H or —(CH$_2$)$_n$OP$_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

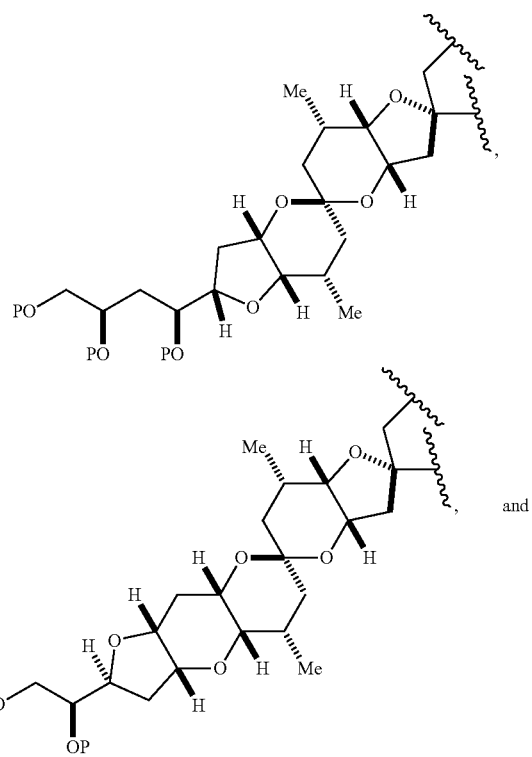

-continued

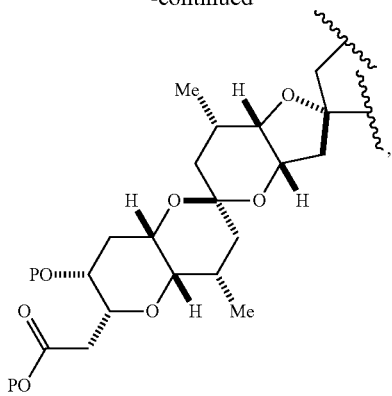

where each P' is independently H or a hydroxyl protecting group;
E is optionally substituted alkyl or optionally substituted alkoxy;
G is O, S, CH$_2$, or NR$_N$, where R$_N$ is H, an N-protecting group, or optionally substituted alkyl;
each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
k is 0 or 1;
n is 0, 1, or 2;
the method involving:
(A) producing a compound of formula (IVB) from a compound of formula (IVA), the compound of formula (IVA) having the following structure:

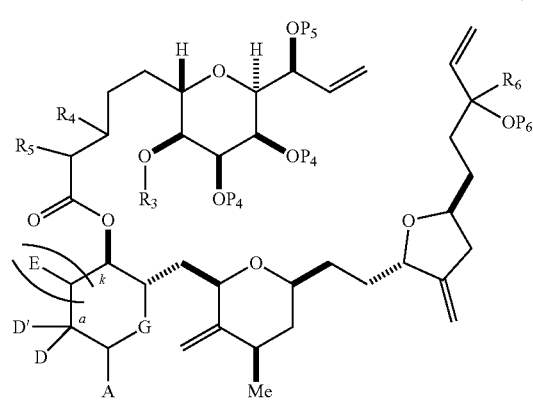

(IVA)

or a salt thereof,
where
(i) R$_3$ is H or a hydroxyl protecting group, R$_4$ is alkyl ether, and R$_5$ is H;
(ii) R$_3$ is H or a hydroxyl protecting group, and R$_4$ and R$_5$ combine to form a double bond;
or
(iii) R$_3$ and R$_4$ combine to form a bond, and R$_5$ is H;

each P$_4$ and P$_5$ is independently H or a hydroxyl protecting group;
R$_6$ is H, and P$_6$ is H or a hydroxyl protecting group; or R$_6$ and P$_6$ combine to form a double bond; and
the compound of formula (IVB) having the following structure:

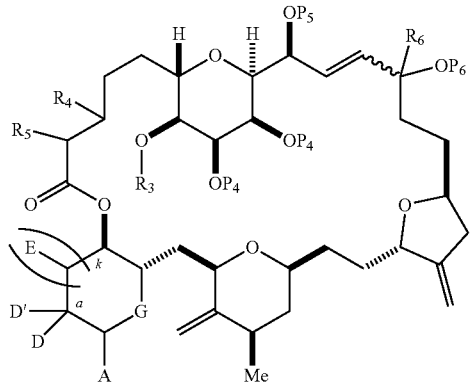

(IVB)

or a salt thereof;
and
(B) producing the halichondrin macrolide from the compound of formula (IVB).
In some embodiments of the fifth aspect, the producing the compound of formula (IVB) involves reacting the compound of formula (IVA) with an olefin metathesis catalyst. In certain embodiments of the fifth aspect, the producing the halichondrin macrolide from the compound of formula (IVB) involves reacting the compound of formula (IVB) with a Brønsted acid. In other embodiments of the fifth aspect, the producing the halichondrin macrolide involves producing the compound of formula (IVC), the compound of formula (IVC) having the following structure:

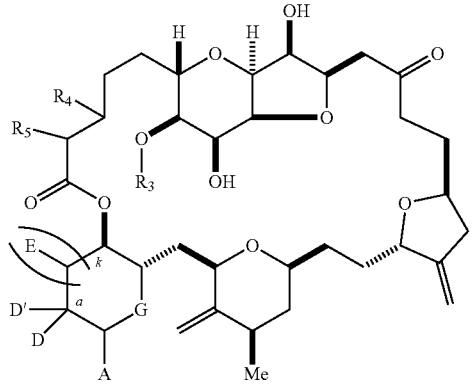

(IVC)

or a salt thereof;
and producing the halichondrin macrolide from the compound of formula (IVC).
In yet other embodiments of the fifth aspect, the producing the compound of formula (IVC) involves reacting the compound of formula (IVB) with a hydroxyl protecting group removing agent. In still other embodiments of the fifth aspect, the producing the halichondrin macrolide from the compound of formula (IVC) involves reacting the compound of formula (IVC) with a Brønsted acid. In particular embodiments of the fifth aspect, at least one of $P_4$ and $P_5$ is H.

In a sixth aspect, the invention provides a method of preparing:

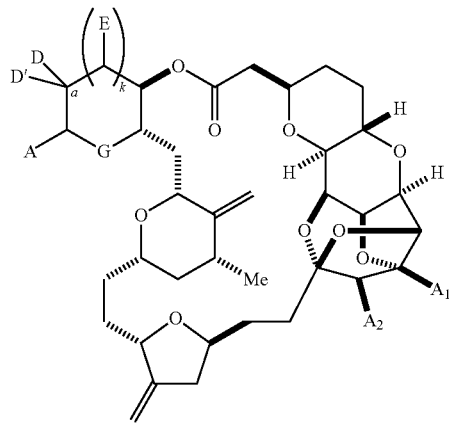

halichondrin macrolide or a salt thereof,
where
each of $A_1$ and $A_2$ is independently H or OP''', where each P''' is independently H or a hydroxyl protecting group;
each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

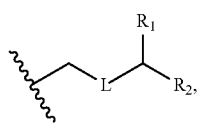 (1)

where
L is —(CH(OP$_2$))—, —(C(OH)(OP$_2$))—, or —C(O)—;
$R_1$ is H, or $R_1$ and $P_1$ combine to form a bond;
$R_2$ is H or —(CH$_2$)$_n$OP$_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

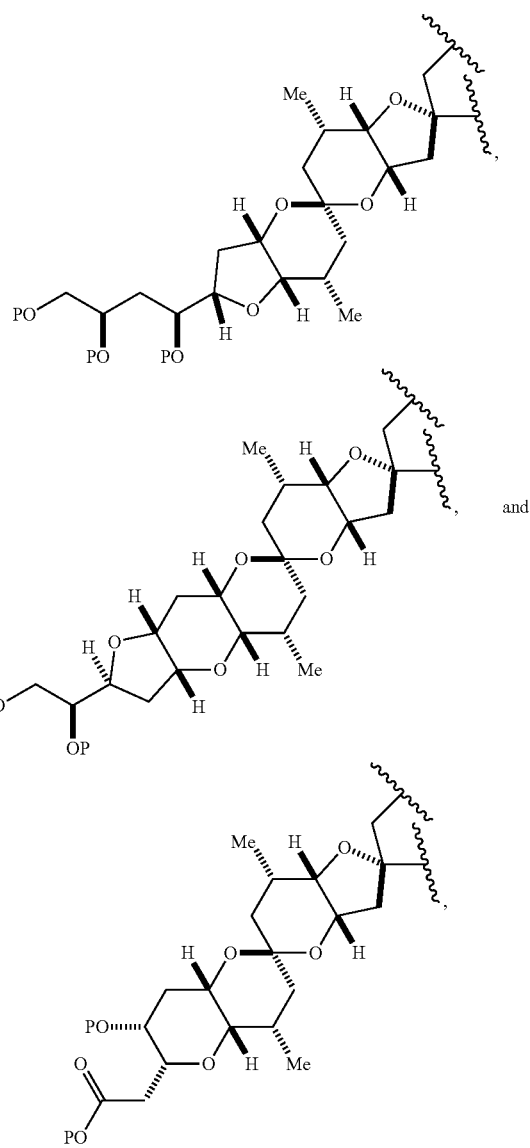

where each P' is independently H or a hydroxyl protecting group;
E is optionally substituted alkyl or optionally substituted alkoxy;
G is O, S, CH$_2$, or NR$_N$, where R$_N$ is H, an N-protecting group, or optionally substituted alkyl;
each $Q_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
k is 0 or 1;
n is 0, 1, or 2;
the method involving:
(A) producing a compound of formula (VB) from a compound of formula (VA), the compound of formula (VA) having the following structure:

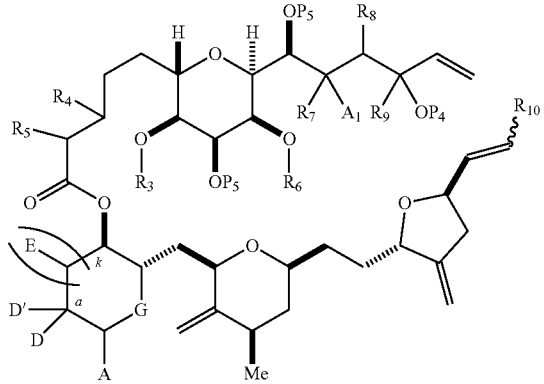

(VA)

or a salt or a tautomer thereof,
where
- (a1) $R_3$ is H or a hydroxyl protecting group, $R_4$ is alkyl ether, and $R_5$ is H;
- (a2) $R_3$ is H or a hydroxyl protecting group, and $R_4$ and $R_5$ combine to form a double bond; or
- (a3) $R_3$ and $R_4$ combine to form a bond, and $R_5$ is H;
- (b1) $A_1$ and $R_7$ combine to form oxo, $R_6$ is H or a hydroxyl protecting group, and $R_8$ is H; or
- (b2) $A_1$ is H or OP''', where P''' is H or a hydroxyl protecting group, and:
  - (i) $R_6$ is H or a hydroxyl protecting group, and $R_7$ and $R_8$ combine to form a double bond; or
  - (ii) $R_6$ and $R_7$ combine to form a bond, and $R_8$ is H or OP''';
- (c1) $R_9$ is H, and $P_4$ is H or a hydroxyl protecting group; or
- (c2) $R_9$ and $P_4$ combine to form a double bond;

$R_{10}$ is H or $-CH_2X_1CH_2CH=CH_2$, where $X_1$ is O, $-C(R_{11})_2-$, or $NP_6$, and where each $R_{11}$ is independently H or $-COOR_{12}$, $P_6$ is an N-protecting group, and $R_{12}$ is alkyl;

each $P_5$ is independently H or a hydroxyl protecting group; and where the macrocyclic intermediate in the synthesis of a halichondrin macrolide is a compound of formula (VB):

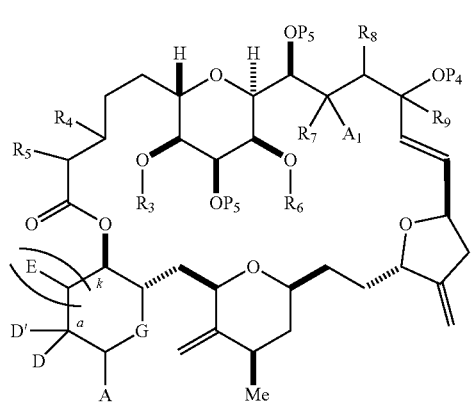

(VB)

or a salt or a tautomer thereof;

(B) producing a compound of formula (VC) from the compound of formula (VB), the compound of formula (VC) having the following structure:

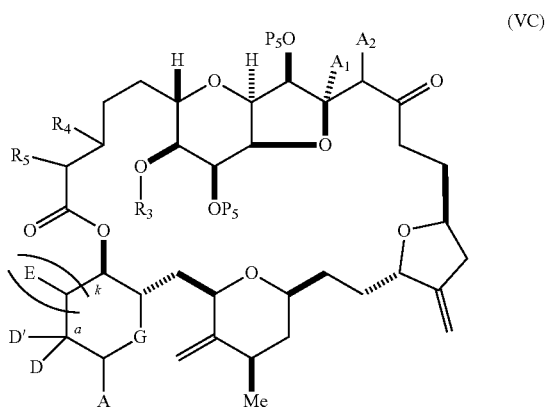

(VC)

or a salt thereof, where each of $A_1$ and $A_2$ is independently H or OP''';

(C) producing a compound of formula (IVC) from the compound of formula (VC), the compound of formula (IVC) having the following structure:

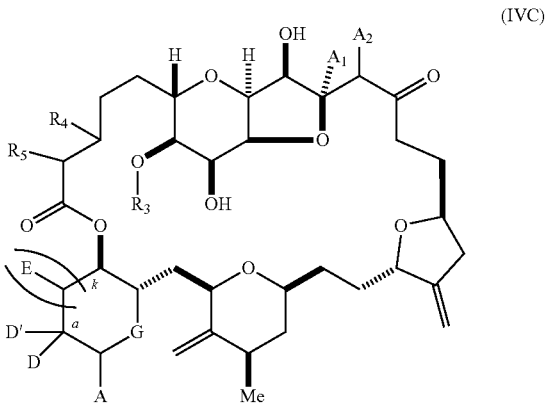

(IVC)

or a salt thereof, where each of $A_1$ and $A_2$ is independently H or OP'''; and (D) producing the halichondrin macrolide from the compound of formula (IVC).

In some embodiments of the sixth aspect, the producing the compound of formula (VB) involves contacting the compound of formula (VA) with an olefin metathesis catalyst. In certain embodiments of the sixth aspect, $P_4$ is H, $R_9$ is H, and the producing the compound of formula (VC) involves oxidizing the compound of formula (VB) to produce a compound of formula (VBa):

(VBa)

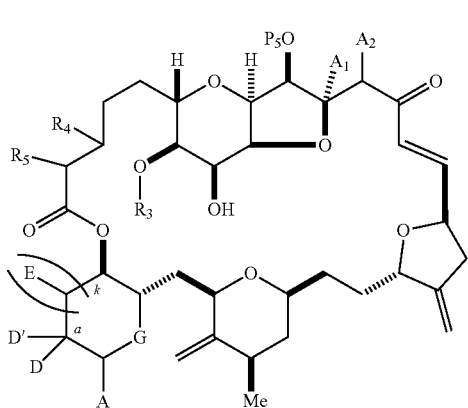

or a salt thereof;
where each of $A_1$ and $A_2$ is independently H or OP'''
and reacting the compound of formula (VBa) with a 1,4-reducing agent to produce the compound of formula (VC).

In particular embodiments of the sixth aspect, the producing the compound of formula (IVC) involves contacting the compound of formula (VC) with a hydroxyl protecting group removing agent. In further embodiments of the sixth aspect, the producing the halichondrin macrolide involves contacting the compound of formula (IVC) with a Brønsted acid.

In a seventh aspect, the invention provides a method of preparing:

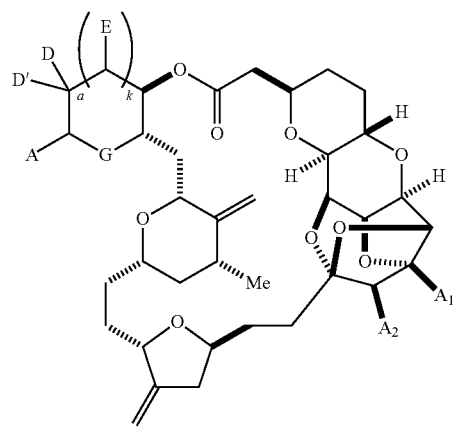

halichondrin macrolide or a salt thereof,
where
each of $A_1$ and $A_2$ is independently H or OP''', where each P''' is independently H or a hydroxyl protecting group;
each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

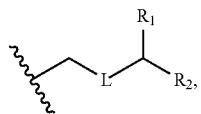

where
L is $-(CH(OP_2))-$, $-(C(OH)(OP_2))-$, or $-C(O)-$;
$R_1$ is H, or $R_1$ and $P_1$ combine to form a bond;
$R_2$ is H or $-(CH_2)_nOP_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

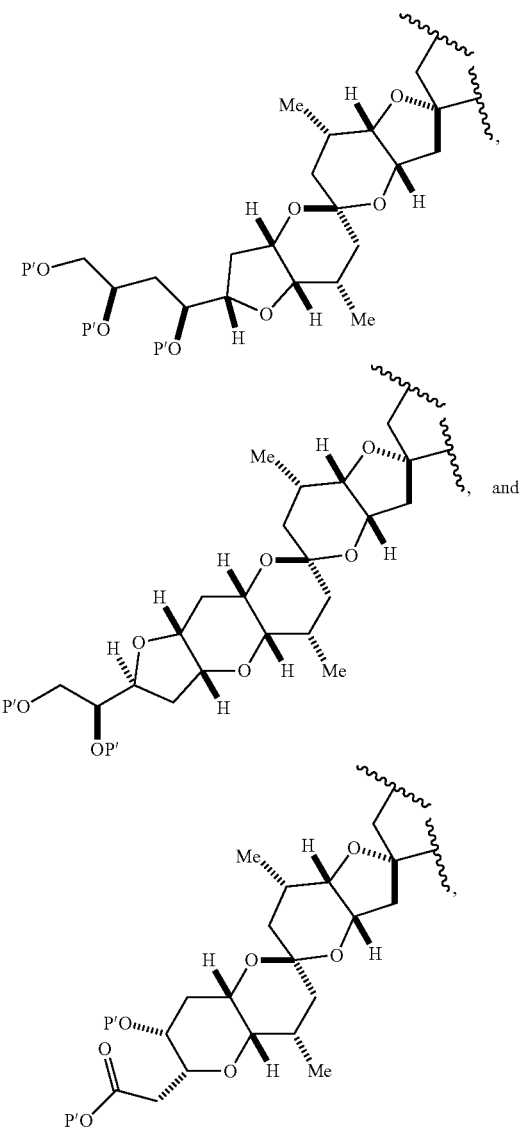

where each P' is independently H or a hydroxyl protecting group;

E is optionally substituted alkyl or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2;

the method involving:

(A) producing a compound of formula (VIB) from a compound of formula (VIA), the compound of formula (VIA) having the following structure:

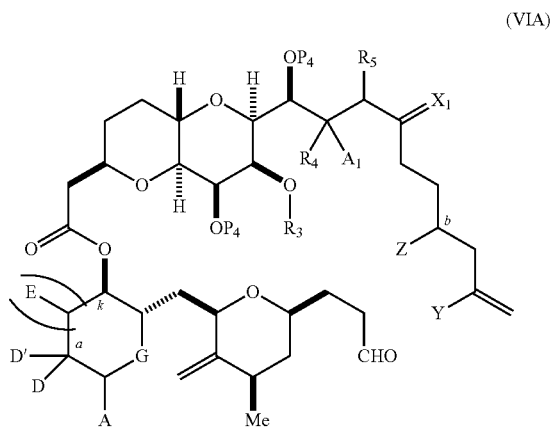

(VIA)

or a salt or a tautomer thereof, where

Y is iodide, bromide, or trifluoromethanesulfonate;

b designates (R)-stereogenic center, and Z is a sulfonate, chloride, bromide, or iodide; or b designates (S)-stereogenic center, and Z is OR$_6$, where R$_6$ is a hydroxyl protecting group;

A$_1$ and R$_4$ combine to form oxo, R$_3$ is H or a hydroxyl protecting group, and R$_5$ is H;

or

A$_1$ is H or OP''', where P''' is H or a hydroxyl protecting group, and:

(i) R$_3$ is H or a hydroxyl protecting group, and R$_4$ and R$_5$ combine to form a double bond;

or (ii) R$_3$ and R$_4$ combine to form a bond, and R$_5$ is H or OP''';

each P$_4$ is independently H or a hydroxyl protecting group, and X$_1$ is oxo; or both P$_4$ groups and X$_1$, together with the atoms to which each is attached, combine to form ketal;

the compound of formula (VIB) having the following structure:

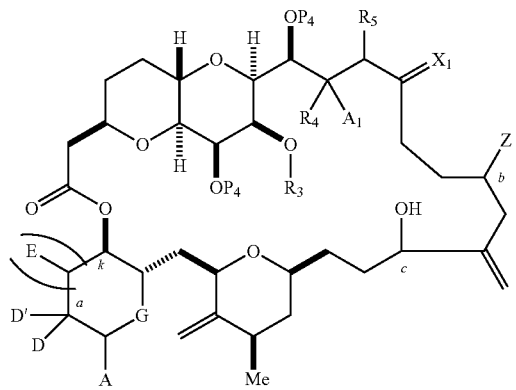

(VIB)

or a salt or a tautomer thereof, where b designates (R)-stereogenic center, c designates (S)-stereogenic center, and Z is a sulfonate, chloride, bromide, or iodide;

or b designates (S)-stereogenic center, c designates (R)-stereogenic center, and Z is OR$_6$, where R$_6$ is a hydroxyl protecting group;

(B) producing the halichondrin macrolide from the compound of formula (VIB).

In some embodiments of the seventh aspect, the producing the compound of formula (VIB) involves reacting the compound of formula (VIA) with a Cr(II) salt and a Ni(II) salt. In particular embodiments of the seventh aspect, the producing the halichondrin macrolide involves the step of nucleophilic ring-closing of the compound of formula (VIB). In certain embodiments of the seventh aspect, both P$_4$ groups and X$_1$, together with the atoms to which each is attached, combine to form ketal. In further embodiments of the seventh aspect, R$_3$ and R$_4$ combine to form a bond, and R$_5$ is H.

In an eighth aspect, the invention provides a method of preparing:

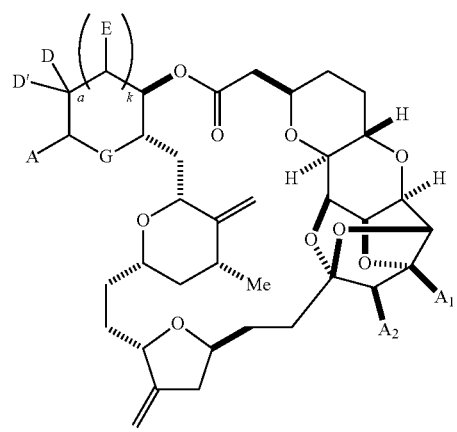

halichondrin macrolide or a salt thereof, where each of A$_1$ and A$_2$ is independently H or OP''', where each P''' is independently H or a hydroxyl protecting group;

each of D and D' is independently H, optionally substituted alkyl, or OP$_1$, provided that only one of D and D' is OP$_1$, where P$_1$ is H, alkyl, or a hydroxyl protecting group; A is a group of formula (1) or a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, the group of formula (1) having the structure:

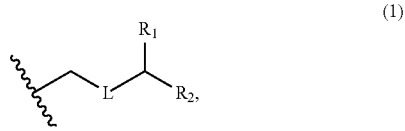
(1)

where

L is —(CH(OP$_2$))—, —(C(OH)(OP$_2$))—, or —C(O)—;

R$_1$ is H, or R$_1$ and P$_1$ combine to form a bond;

R$_2$ is H or —(CH$_2$)$_n$OP$_3$, and each of P$_2$ and P$_3$ is independently H, optionally substituted alkyl, or a hydroxyl protecting group, or P$_2$ and P$_3$, together with the atoms to which each is attached, combine to form a ketal, a cyclic carbonate, a dicarbonyl-dioxo, or silylene-dioxo; or R$_2$ and P$_2$ combine to form an optionally substituted ethylene or a structure selected from the group consisting of:

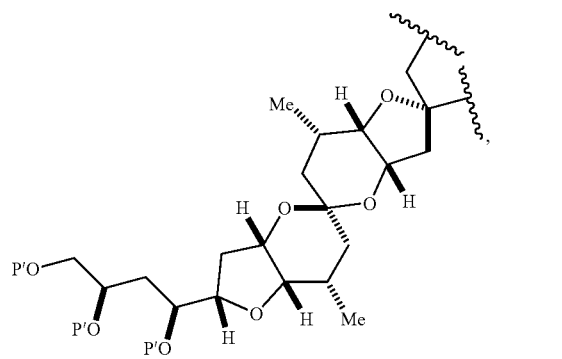
,

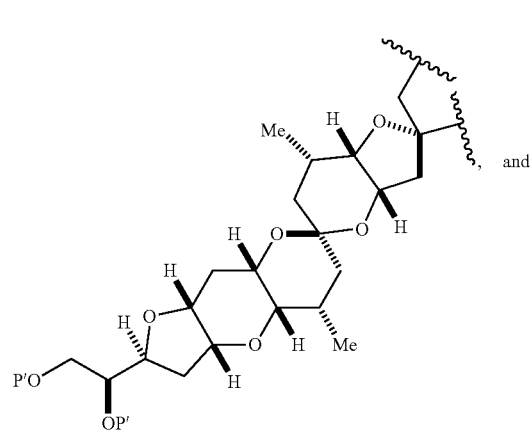
, and

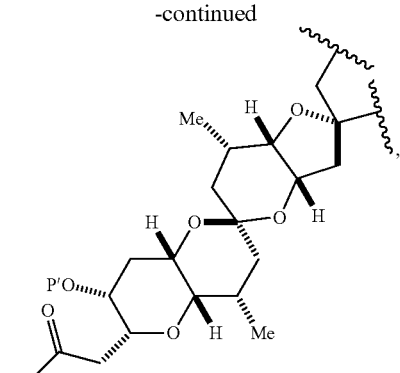
, where each P' is independently H or a hydroxyl protecting group;

E is optionally substituted alkyl or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO) NR$_B$R$_A$, NR$_B$(CO)OR$_A$, (CO)OR$_A$, O(CO)R$_A$, (CO) NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2;

the method involving:

(A) producing a compound of formula (VIIB) from a compound of formula (VIIA), the compound of formula (VIIA) having the following structure:

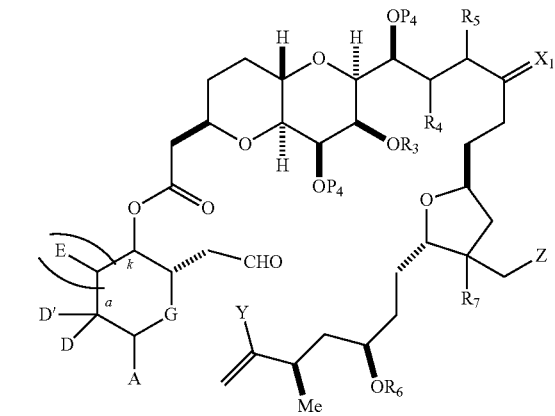
(VIIA)

or a salt thereof, where

Y is iodide, bromide, or trifluoromethanesulfonate;

(a1) R$_3$ is H or a hydroxyl protecting group, R$_4$ and R$_5$ combine to form a double bond, each P$_4$ is independently H or a hydroxyl protecting group, and X$_1$, together with the carbon to which it is attached, forms a carbonyl or —(CH(OR$_8$))—;

or
(a2) $R_3$ and $R_4$ combine to form a bond, $R_5$ is H, and each $P_4$ is independently H or a hydroxyl protecting group, and $X_1$, together with the carbon to which it is attached, forms a carbonyl or —(CH(OR$_8$))—;
or
both $P_4$ groups and $X_1$, together with the atoms to which each is attached, combine to form ketal;
(b1) Z is chloride, bromide, or iodide, and $R_6$ and $R_7$ combine to form a bond;
or
(b2) Z and $R_7$ combine to form a double bond, and $R_6$ is a hydroxyl protecting group;
and
where $R_8$ is H or a hydroxyl protecting group;
and
the compound of formula (VIIB) having the following structure:

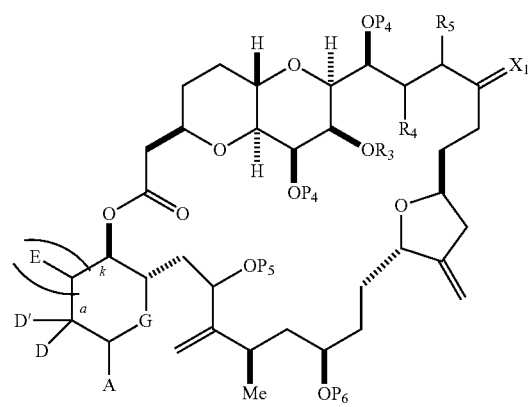

(VIIB)

or a salt thereof,
where each of $P_5$ and $R_6$ is independently H or a hydroxyl protecting group;
(B) producing a compound of formula (VIIC) from the compound of formula (VIIB), the compound of formula (VIIC) having the following structure:

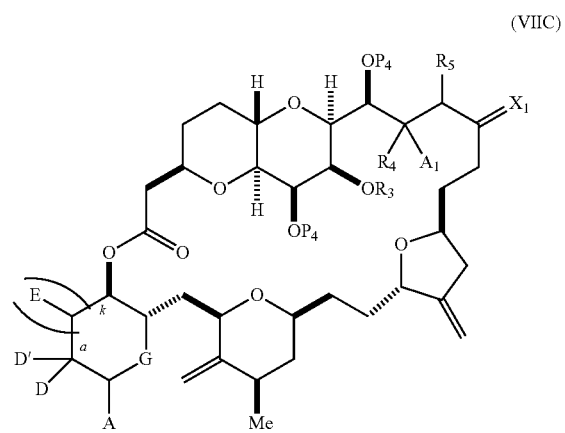

(VIIC)

or a salt or a tautomer thereof,
where
$A_1$ and $R_4$ combine to form oxo, $R_3$ is H or a hydroxyl protecting group, and $R_5$ is H;

or
$A_1$ is H or OP''', where P''' is H or a hydroxyl protecting group, and:
(i) $R_3$ is H or a hydroxyl protecting group, and $R_4$ and $R_5$ combine to form a double bond;
or
(ii) $R_3$ and $R_4$ combine to form a bond, and $R_5$ is H or OP''';
(C) producing a compound of formula (VIID) from the compound of formula (VIIC), the compound of formula (VIID) having the following structure:

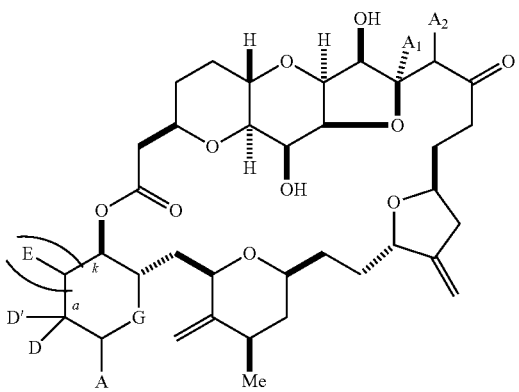

(VIID)

or a salt thereof,
where each of $A_1$ and $A_2$ is independently H or OP'''; and
(D) producing the halichondrin macrolide from the compound of formula (VIID).

In some embodiments of the eighth aspect, the producing the compound of formula (VIIB) involves reacting the compound of formula (VIIA) with a Cr(II) salt and a Ni(II) salt. In certain embodiments of the eighth aspect, the producing the compound of formula (VIIC) involves the step of nucleophilic ring-closing of the compound of formula (VIIB). In particular embodiments of the eighth aspect, the producing the compound of formula (VIID) involves reacting the compound of formula (VIIC) with a hydroxyl protecting group removing agent. In further embodiments of the eighth aspect, the producing the halichondrin macrolide involves reacting the compound of formula (VIID) with a Brønsted acid. In other embodiments of the eighth aspect, Z is iodide. In yet other embodiments of the eighth aspect, Y is trifluoromethanesulfonate. In still embodiments of the eighth aspect, $R_3$ is H or a hydroxyl protecting group, and $R_4$ and $R_5$ combine to form a double bond. In some embodiments of the eighth aspect, each $P_4$ is independently H or a hydroxyl protecting group, and $X_1$, together with the carbon to which it is attached, forms —(CH(OR$_8$))—, where $R_8$ is H or a hydroxyl protecting group. In particular embodiments of the eighth aspect, $P_5$ is H. In certain embodiments of the eighth aspect, Z is chloride, bromide, or iodide, and $R_6$ and $R_7$ combine to form a bond.

In some embodiments of any aspect, a designates (S)-stereogenic center. In certain embodiments of any aspect, one and only one of D and D' is optionally substituted alkyl or OP$_1$. In particular embodiments of any aspect, one and only one of D and D' is OP$_1$, where P$_1$ is H, alkyl, or a hydroxyl protecting group. In further embodiments of any aspect, A is a group of formula (1). In certain embodiments of any aspect, L is —(CH(OP$_2$))—. In other embodiments of any aspect, R$_1$ and P$_1$ combine to form a bond. In yet other embodiments of any aspect, G is O. In still other embodiments of any aspect, E is optionally substituted alkyl. In some embodiments of any aspect, k is 1. In certain embodiments of any aspect, R$_2$ is —(CH$_2$)$_n$OP$_3$. In particular embodiments of any aspect, at least one of P$_2$ and P$_3$ is a hydroxyl protecting group. In certain embodiments of any aspect, A$_1$ is H. In some embodiments of any aspect, A$_2$ is H.

In a ninth aspect, the invention provides a method of preparing an intermediate in the synthesis of a halichondrin macrolide. The method involves performing an allene-Prins reaction by contacting a compound of formula (VIIIA) with a compound of formula (VIIIB) and R$_4$OH, where R$_4$ is an optionally substituted acyl;

where the compound of formula (VIIIA) has the following structure:

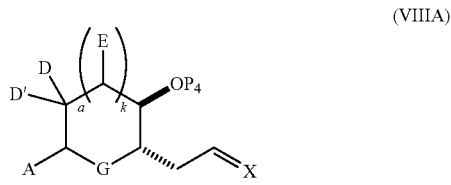

(VIIIA)

or a salt thereof, where each of D and D' is independently H, optionally substituted alkyl, or OP$_1$, provided that only one of D and D' is OP$_1$, where P$_1$ is H, alkyl, or a hydroxyl protecting group; A is a group of formula (1) or a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, the group of formula (1) having the structure:

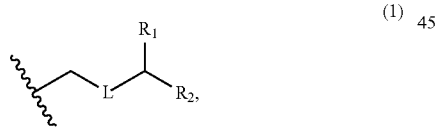

(1)

where

L is —(CH(OP$_2$))—, —(C(OH)(OP$_2$))—, or —C(O)—;

R$_1$ is H, or R$_1$ and P$_1$ combine to form a bond;

R$_2$ is H or —(CH$_2$)$_n$OP$_3$, and each of P$_2$ and P$_3$ is independently H, optionally substituted alkyl, or a hydroxyl protecting group, or P$_2$ and P$_3$, together with the atoms to which each is attached, combine to form a ketal, a cyclic carbonate, a dicarbonyl-dioxo, or silylene-dioxo; or R$_2$ and P$_2$ combine to form an optionally substituted ethylene or a structure selected from the group consisting of:

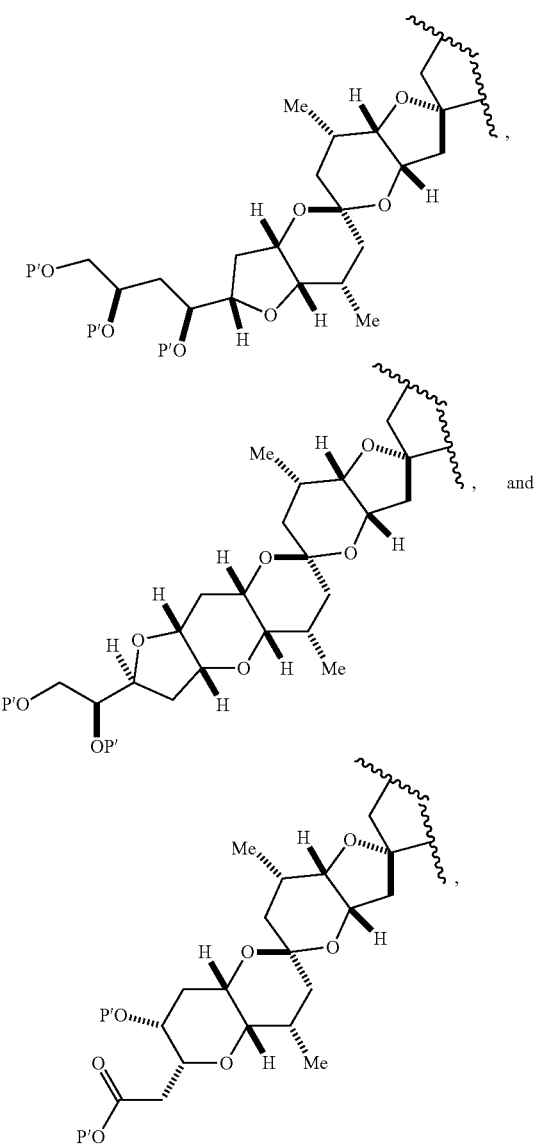

where each P' is independently H or a hydroxyl protecting group;

E is optionally substituted alkyl or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2;

X is O, or X, together with the carbon atom to which it is attached, forms —(C(OP$_Z$)$_2$)—, wherein each P$_Z$ is independently optionally substituted alkyl or optionally substituted aryl, or both $P_Z$ combine to form optionally substituted alkylene or optionally substituted arylene; and $P_4$ is H or a hydroxyl protecting group;

where the compound of formula (VIIIB) has the following structure:

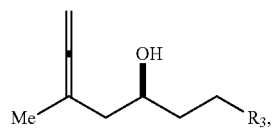
(VIIIB)

where $R_3$ is —$CH_2$—$OP_5$, —CH=$CH_2$,

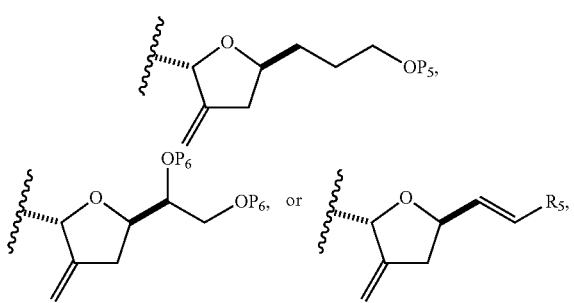

where $P_5$ is H or a hydroxyl protecting group; each $P_6$ is independently a hydroxyl protecting group, or both $P_6$ groups, together with the atoms to which each is attached, combine to form a cyclic protected diol; and $R_5$ is H or —$CH_2X_1CH_2CH$=$CH_2$, where $X_1$ is O, —$CH_2$—, or $NP_7$, where $P_7$ is a sulfonyl; and where the intermediate is a compound of formula (VIIIC):

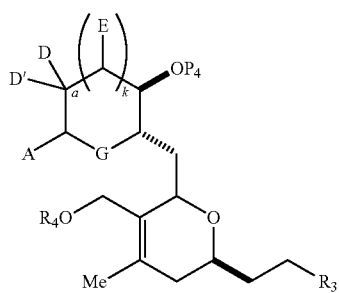
(VIIIC)

or a salt thereof, where $a$ designates (R)-stereogenic center or (S)-stereogenic center.

In some embodiments of the ninth aspect, the performing a Prins reaction involves reacting the compound of formula (VIIIA) with a Lewis acid. In certain embodiments of the ninth aspect, k is 1.

In a tenth aspect, the invention provides a compound of formula (IA) or formula (IB),

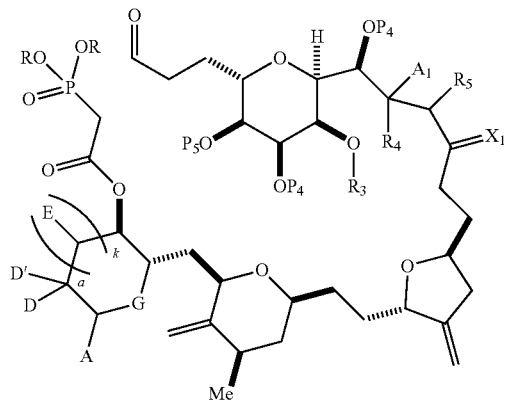
(IA)

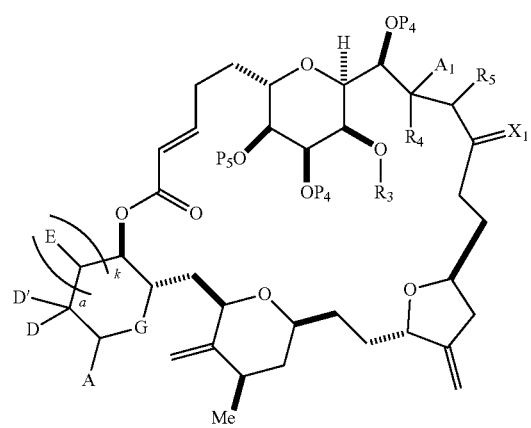
(IB)

or a salt or a tautomer thereof, where each R is independently optionally substituted alkyl or optionally substituted aryl;

each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

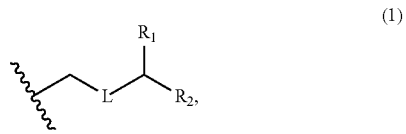
(1)

where

L is —(CH($OP_2$))—, —(C(OH)($OP_2$))—, or —C(O)—;

$R_1$ is H, or $R_1$ and $P_1$ combine to form a bond;

$R_2$ is H or —($CH_2$)$_n OP_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

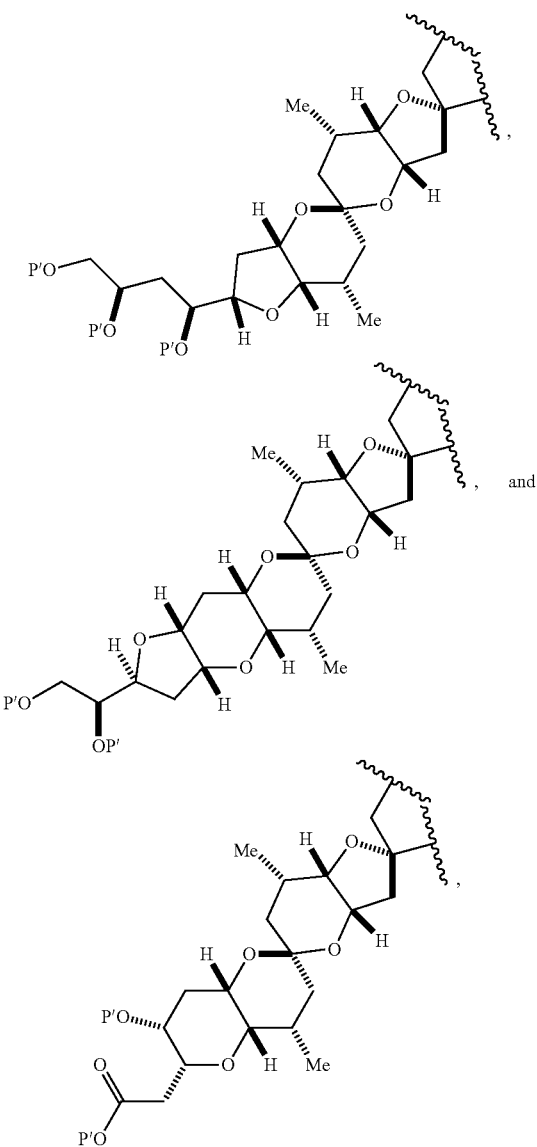

where each P' is independently H or a hydroxyl protecting group;

E is optionally substituted alkyl or optionally substituted alkoxy;

G is O, S, $CH_2$, or $NR_N$, where $R_N$ is H, an N-protecting group, or optionally substituted alkyl;

each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2;

$A_1$ and $R_4$ combine to form oxo, $R_3$ is H or a hydroxyl protecting group, and $R_5$ is H;

or $A_1$ is H or OP''', where P''' is H or a hydroxyl protecting group, and:

(i) $R_3$ is H or a hydroxyl protecting group, and $R_4$ and $R_5$ combine to form a double bond;

or (ii) $R_3$ and $R_4$ combine to form a bond, and $R_5$ is H or OP''';

each $P_4$ is independently H or a hydroxyl protecting group, and $X_1$ is oxo or $X_1$, together with the carbon atom to which it is attached, is —(CH($OP_Y$))—, wherein $P_Y$ is H or a hydroxyl protecting group; or both $P_4$ groups and $X_1$, together with the atoms to which each is attached, combine to form ketal; and $P_5$ is H or a hydroxyl protecting group.

In an eleventh aspect, the invention provides a compound of formula (IIA), formula (IIIA), or formula (IIIB):

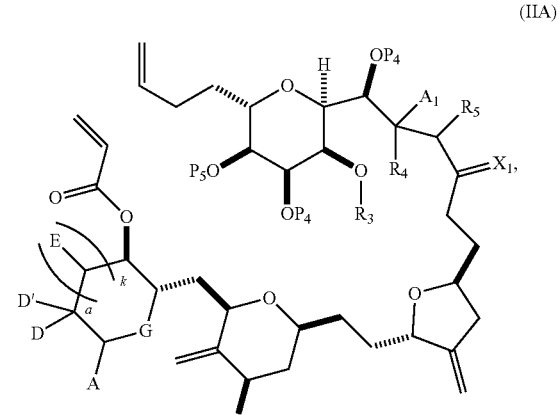
(IIA)

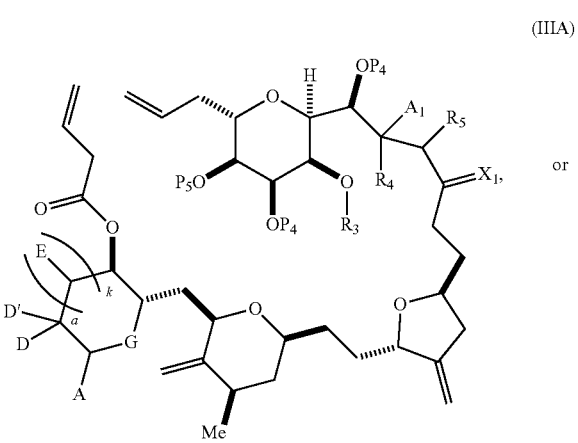
(IIIA)

or

-continued (IIIB)

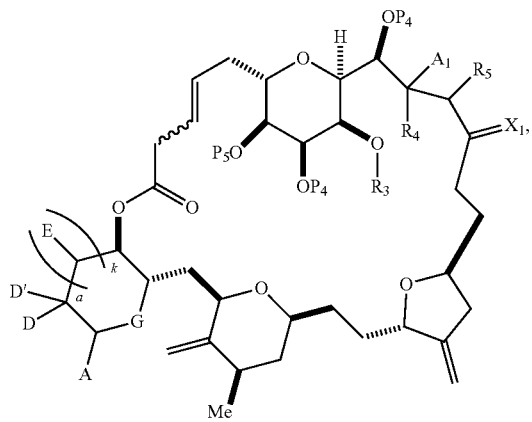

or a salt or a tautomer thereof,
where
each of D and D' is independently H, optionally substituted alkyl, or OP$_1$, provided that only one of D and D' is OP$_1$, where P$_1$ is H, alkyl, or a hydroxyl protecting group; A is a group of formula (1) or a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, the group of formula (1) having the structure:

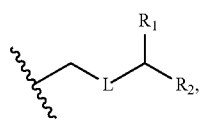
(1)

where
L is —(CH(OP$_2$))—, —(C(OH)(OP$_2$))—, or —C(O)—;
R$_1$ is H, or R$_1$ and P$_1$ combine to form a bond;
R$_2$ is H or —(CH$_2$)$_n$OP$_3$, and each of P$_2$ and P$_3$ is independently H, optionally substituted alkyl, or a hydroxyl protecting group, or P$_2$ and P$_3$, together with the atoms to which each is attached, combine to form a ketal, a cyclic carbonate, a dicarbonyl-dioxo, or silylene-dioxo; or R$_2$ and P$_2$ combine to form an optionally substituted ethylene or a structure selected from the group consisting of:

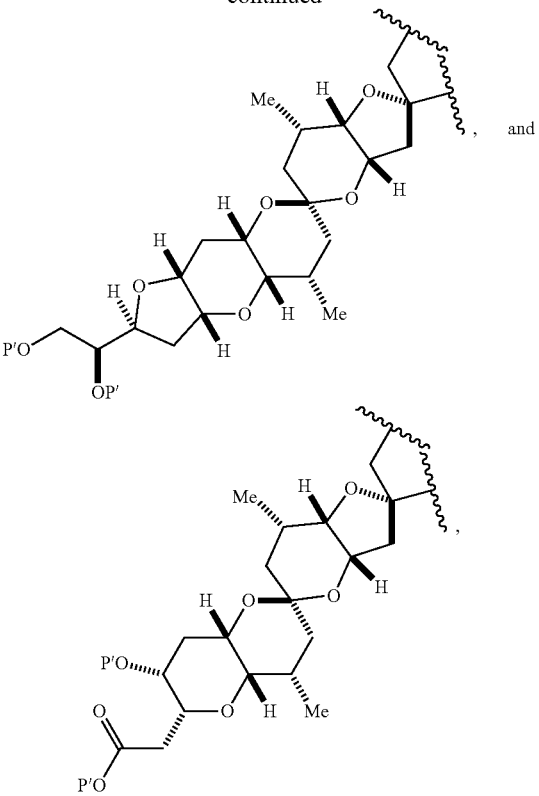

where each P' is independently H or a hydroxyl protecting group;
E is optionally substituted alkyl or optionally substituted alkoxy;
G is O, S, CH$_2$, or NR$_N$, where R$_N$ is H, an N-protecting group, or optionally substituted alkyl;
each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
k is 0 or 1;
n is 0, 1, or 2;
A$_1$ and R$_4$ combine to form oxo, R$_3$ is H or a hydroxyl protecting group, and R$_5$ is H;
or
A$_1$ is H or OP''', where P''' is H or a hydroxyl protecting group, and:
(i) R$_3$ is H or a hydroxyl protecting group, and R$_4$ and R$_5$ combine to form a double bond;
or
(ii) R$_3$ and R$_4$ combine to form a bond, and R$_5$ is H or OP''';
each P$_4$ is independently H or a hydroxyl protecting group, and X$_1$ is oxo or X$_1$, together with the carbon atom to which it is attached, is —(CH(OP$_Y$))—, wherein P$_Y$ is H or a hydroxyl protecting group; or both P$_4$ groups and X$_1$, together with the atoms to which each is attached, combine to form ketal; and
P$_5$ is H or a hydroxyl protecting group.

In a twelfth aspect, the invention provides a compound of formula (IVA), formula (IVB), or formula (IVC):

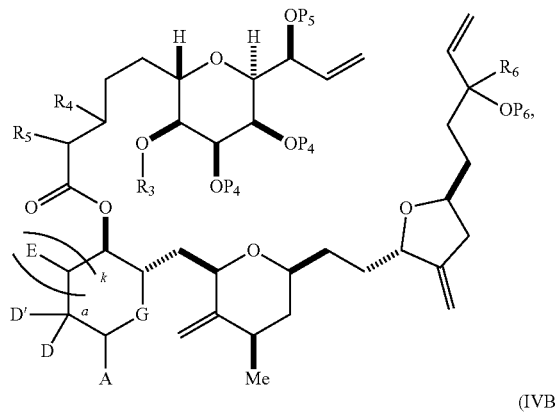
(IVA)

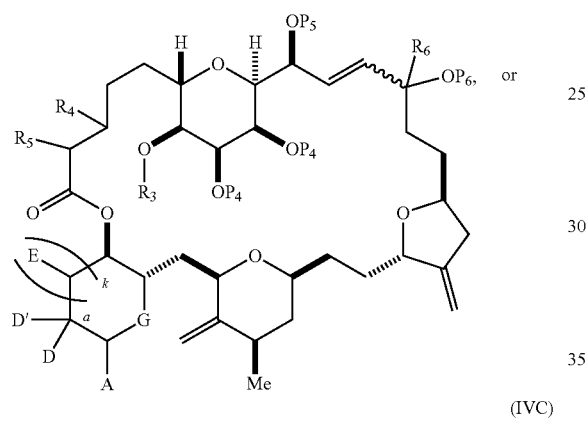
(IVB)

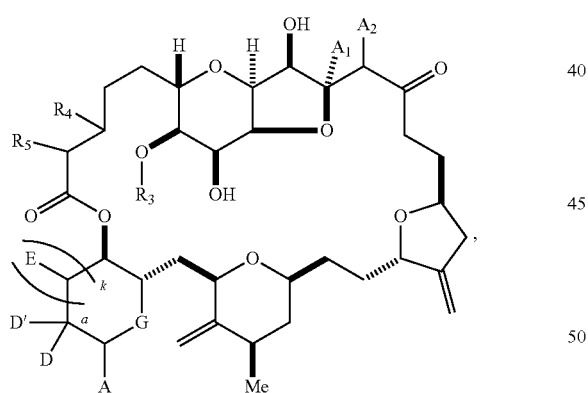
(IVC)

or a salt thereof,
where
each of $A_1$ and $A_2$ is H or OP''', where P''' is H or a hydroxyl protecting group;
each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

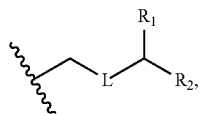
(1)

where
L is —(CH(OP$_2$))—, —(C(OH)(OP$_2$))—, or —C(O)—;
$R_1$ is H, or $R_1$ and $P_1$ combine to form a bond;
$R_2$ is H or —(CH$_2$)$_n$OP$_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

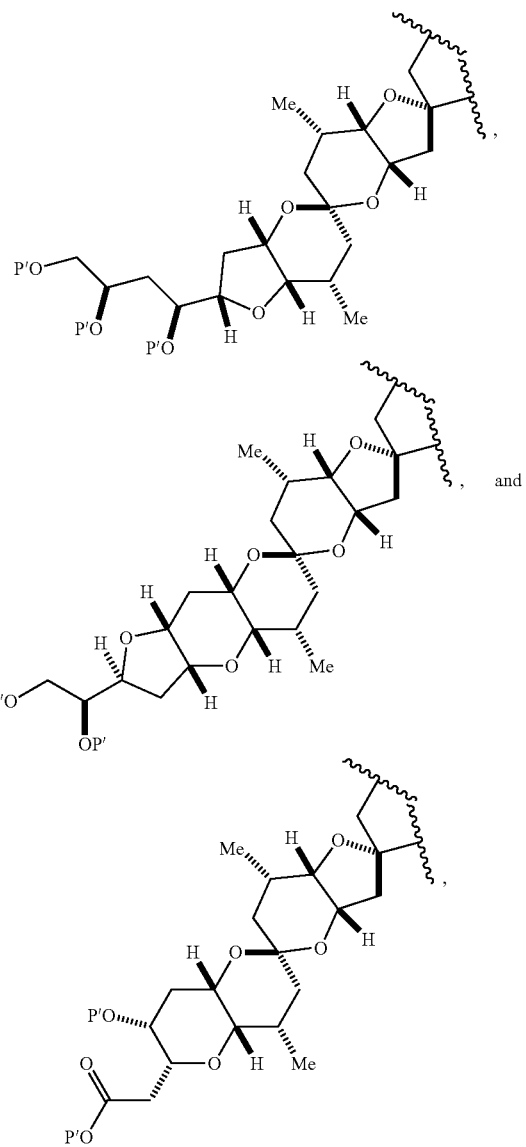

where each P' is independently H or a hydroxyl protecting group;

E is optionally substituted alkyl or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2;

(i) R$_3$ is H or a hydroxyl protecting group, R$_4$ is alkyl ether, and R$_5$ is H;

(ii) R$_3$ is H or a hydroxyl protecting group, and R$_4$ and R$_5$ combine to form a double bond;

or (iii) R$_3$ and R$_4$ combine to form a bond, and R$_5$ is H;

each P$_4$ and P$_5$ is independently H or a hydroxyl protecting group; and

R$_6$ is H, and P$_6$ is H or a hydroxyl protecting group; or R$_6$ and P$_6$ combine to form a double bond.

In a thirteenth aspect, the invention provides a compound of formula (VA), formula (VB), or formula (VC):

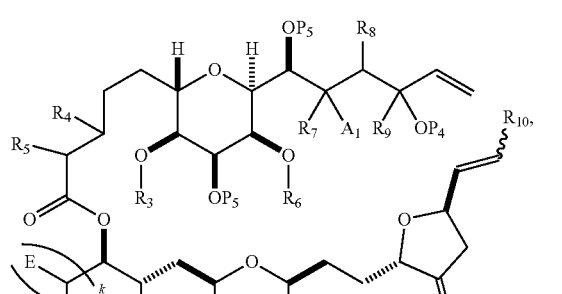
(VA)

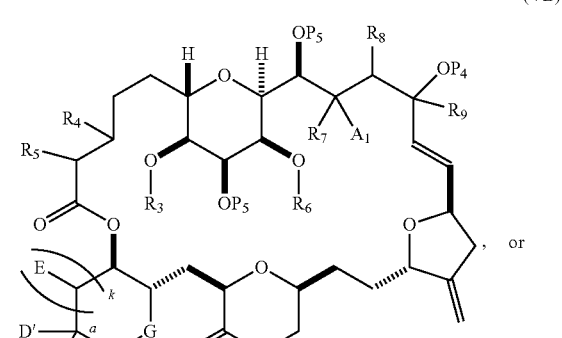
(VB)

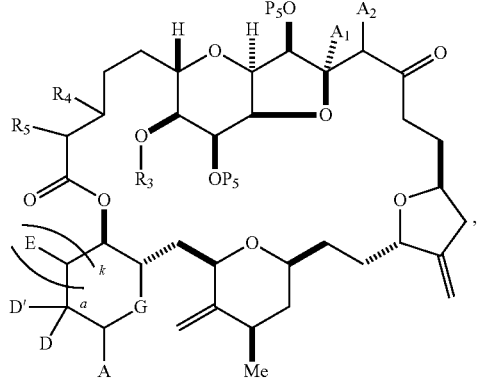
(VC)

or a salt or a tautomer thereof, where each of D and D' is independently H, optionally substituted alkyl, or OP$_1$, provided that only one of D and D' is OP$_1$, where P$_1$ is H, alkyl, or a hydroxyl protecting group; A is a group of formula (1) or a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, the group of formula (1) having the structure:

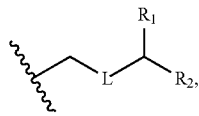
(1)

where

L is —(CH(OP$_2$))—, —(C(OH)(OP$_2$))—, or —C(O)—;

R$_1$ is H, or R$_1$ and P$_1$ combine to form a bond;

R$_2$ is H or —(CH$_2$)$_n$OP$_3$, and each of P$_2$ and P$_3$ is independently H, optionally substituted alkyl, or a hydroxyl protecting group, or P$_2$ and P$_3$, together with the atoms to which each is attached, combine to form a ketal, a cyclic carbonate, a dicarbonyl-dioxo, or silylene-dioxo; or R$_2$ and P$_2$ combine to form an optionally substituted ethylene or a structure selected from the group consisting of:

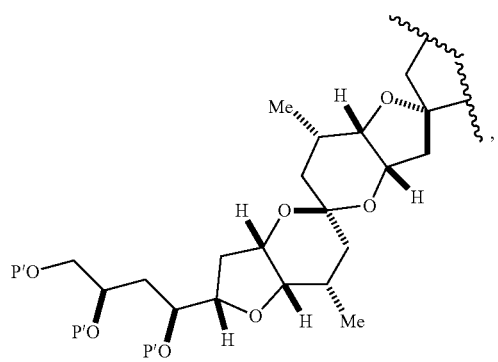

-continued

[chemical structure], and

[chemical structure], where each P' is independently H or a hydroxyl protecting group;

E is optionally substituted alkyl or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2;

(a1) R$_3$ is H or a hydroxyl protecting group, R$_4$ is alkyl ether, and R$_5$ is H;

(a2) R$_3$ is H or a hydroxyl protecting group, and R$_4$ and R$_5$ combine to form a double bond;

or (a3) R$_3$ and R$_4$ combine to form a bond, and R$_5$ is H;

(b1) A$_1$ and R$_7$ combine to form oxo, R$_6$ is H or a hydroxyl protecting group, and R$_8$ is H;

or (b2) A$_1$ is H or OP'', where P'' is H or a hydroxyl protecting group, and:

(i) R$_6$ is H or a hydroxyl protecting group, and R$_7$ and R$_8$ combine to form a double bond;

or (ii) R$_6$ and R$_7$ combine to form a bond, and R$_8$ is H or OP'';

(c1) R$_9$ is H, and P$_4$ is H or a hydroxyl protecting group;

or (c2) R$_9$ and P$_4$ combine to form a double bond;

R$_{10}$ is H or —CH$_2$X$_1$CH$_2$CH=CH$_2$, where X$_1$ is O, —C(R$_{11}$)$_2$—, or NP$_6$, and where each R$_{11}$ is independently H or —COOR$_{12}$, P$_6$ is an N-protecting group, and R$_{12}$ is alkyl;

each P$_5$ is independently H or a hydroxyl protecting group; and

In a fourteenth aspect, the invention provides a compound of formula (VIA):

(VIA)

[chemical structure]

or a salt or a tautomer thereof, where each of D and D' is independently H, optionally substituted alkyl, or OP$_1$, provided that only one of D and D' is OP$_1$, where P$_1$ is H, alkyl, or a hydroxyl protecting group; A is a group of formula (1) or a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, the group of formula (1) having the structure:

(1)

[chemical structure]

where

L is —(CH(OP$_2$))—, —(C(OH)(OP$_2$))—, or —C(O)—;

R$_1$ is H, or R$_1$ and P$_1$ combine to form a bond;

R$_2$ is H or —(CH$_2$)$_n$OP$_3$, and each of P$_2$ and P$_3$ is independently H, optionally substituted alkyl, or a hydroxyl protecting group, or P$_2$ and P$_3$, together with the atoms to which each is attached, combine to form a ketal, a cyclic carbonate, a dicarbonyl-dioxo, or silylene-dioxo; or R$_2$ and P$_2$ combine to form an optionally substituted ethylene or a structure selected from the group consisting of:

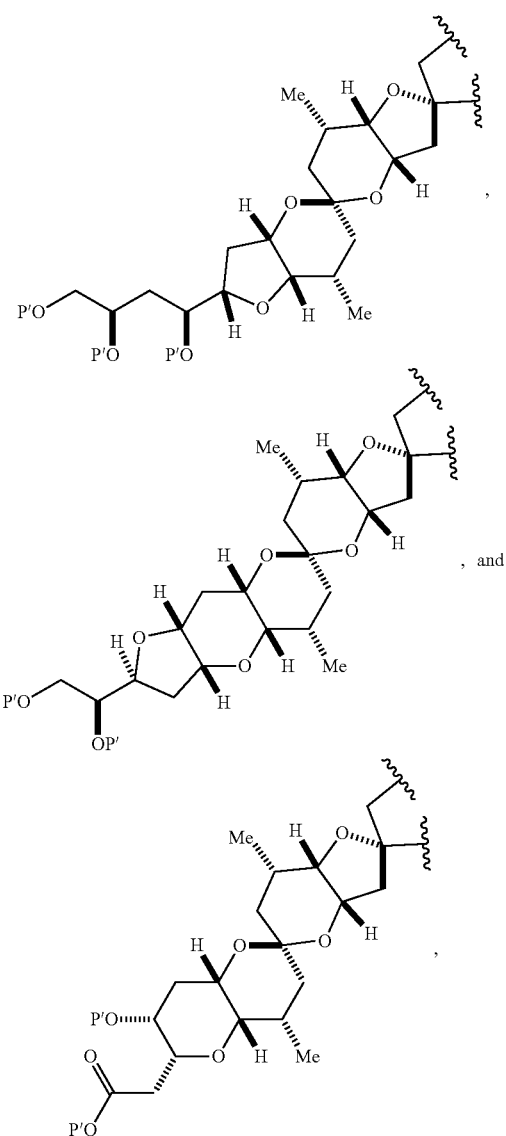

, and where each P' is independently H or a hydroxyl protecting group;

E is optionally substituted alkyl or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2;

Y is iodide, bromide, or trifluoromethanesulfonate;

b designates (R)-stereogenic center, and Z is a sulfonate, chloride, bromide, or iodide; or b designates (S)-stereogenic center, and Z is OR$_6$, where R$_6$ is a hydroxyl protecting group;

A$_1$ and R$_4$ combine to form oxo, R$_3$ is H or a hydroxyl protecting group, and R$_5$ is H;

or

A$_1$ is H or OP''', where P''' is H or a hydroxyl protecting group, and:

(i) R$_3$ is H or a hydroxyl protecting group, and R$_4$ and R$_5$ combine to form a double bond;

or (ii) R$_3$ and R$_4$ combine to form a bond, and R$_5$ is H or OP''';

each P$_4$ is independently H or a hydroxyl protecting group, and X$_1$ is oxo or X$_1$, together with the carbon atom to which it is attached, is —(CH(OP$_Y$))—, wherein P$_Y$ is H or a hydroxyl protecting group; or both P$_4$ groups and X$_1$, together with the atoms to which each is attached, combine to form ketal.

In a fifteenth aspect, the invention provides a compound of formula (VIB):

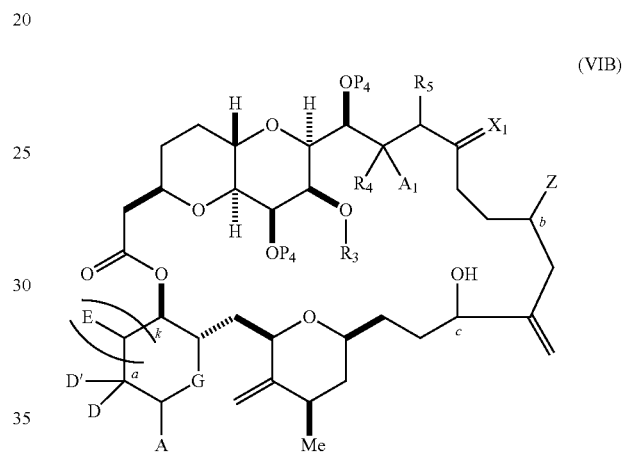

(VIB)

or a salt or a tautomer thereof, where b designates (R)-stereogenic center, c designates (S)-stereogenic center, and Z is a sulfonate, chloride, bromide, or iodide;

or b designates (S)-stereogenic center, c designates (R)-stereogenic center, and Z is OR$_6$, where R$_6$ is a hydroxyl protecting group;

each of D and D' is independently H, optionally substituted alkyl, or OP$_1$, provided that only one of D and D' is OP$_1$, where P$_1$ is H, alkyl, or a hydroxyl protecting group; A is a group of formula (1) or a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, the group of formula (1) having the structure:

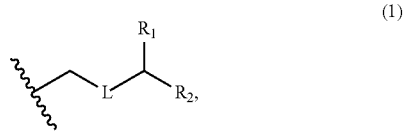

(1)

where

L is —(CH(OP$_2$))—, —(C(OH)(OP$_2$))—, or —C(O)—;

$R_1$ is H, or $R_1$ and $P_1$ combine to form a bond;

$R_2$ is H or —(CH$_2$)$_n$OP$_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

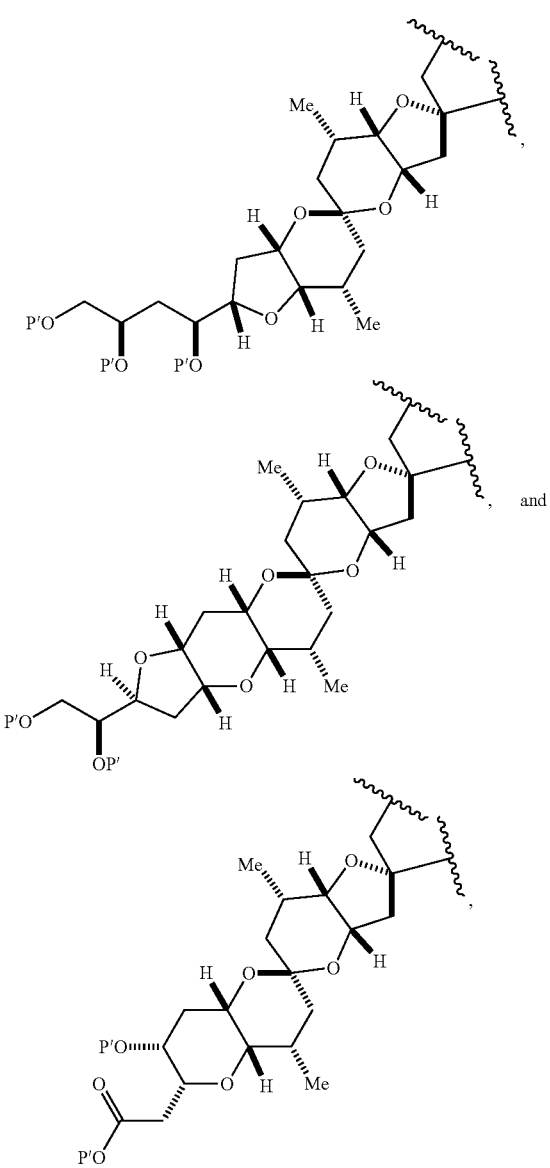

where each P' is independently H or a hydroxyl protecting group;

E is optionally substituted alkyl or optionally substituted alkoxy;

G is O, S, CH$_2$, or NR$_N$, where R$_N$ is H, an N-protecting group, or optionally substituted alkyl;

k is 0 or 1;

n is 0, 1, or 2;

$A_1$ and $R_4$ combine to form oxo, $R_3$ is H or a hydroxyl protecting group, and $R_5$ is H;

or $A_1$ is H or OP''', where P''' is H or a hydroxyl protecting group, and:

(i) $R_3$ is H or a hydroxyl protecting group, and $R_4$ and $R_5$ combine to form a double bond;

or (ii) $R_3$ and $R_4$ combine to form a bond, and $R_5$ is H or OP''';

each $P_4$ is independently H or a hydroxyl protecting group, and $X_1$ is oxo or $X_1$, together with the carbon atom to which it is attached, is —(CH(OP$_Y$))—, wherein $P_Y$ is H or a hydroxyl protecting group; or both $P_4$ groups and $X_1$, together with the atoms to which each is attached, combine to form ketal.

In a sixteenth aspect, the invention provides a compound of formula (VIIA) or formula (VIIB):

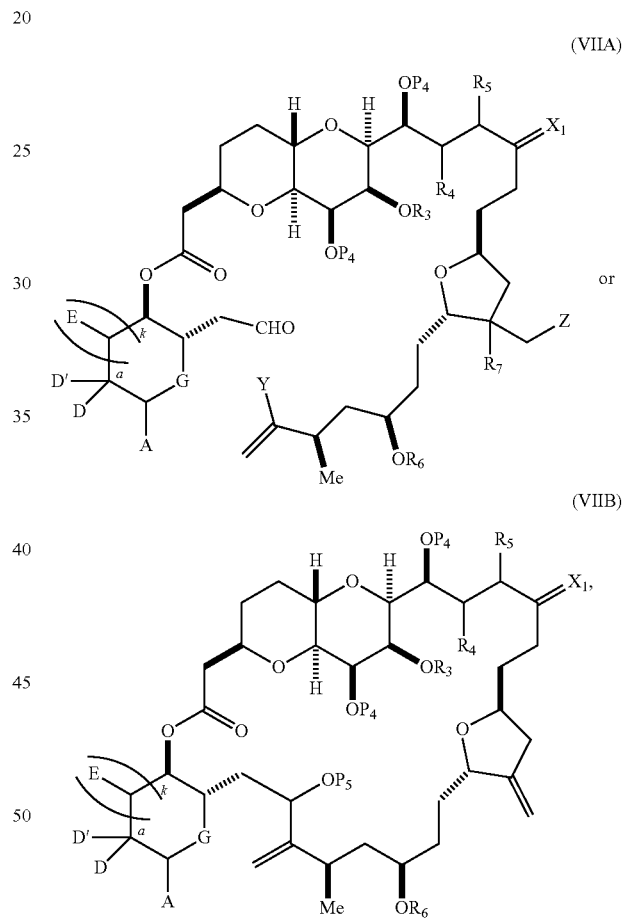

or a salt thereof, where each of D and D' is independently H, optionally substituted alkyl, or OP$_1$, provided that only one of D and D' is OP$_1$, where P$_1$ is H, alkyl, or a hydroxyl protecting group; A is a group of formula (1) or a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, the group of formula (1) having the structure:

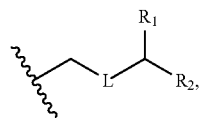
(1)

where
L is —(CH(OP$_2$))—, —(C(OH)(OP$_2$))—, or —C(O)—;
R$_1$ is H, or R$_1$ and P$_1$ combine to form a bond;
R$_2$ is H or —(CH$_2$)$_n$OP$_3$, and each of P$_2$ and P$_3$ is independently H, optionally substituted alkyl, or a hydroxyl protecting group, or P$_2$ and P$_3$, together with the atoms to which each is attached, combine to form a ketal, a cyclic carbonate, a dicarbonyl-dioxo, or silylene-dioxo; or R$_2$ and P$_2$ combine to form an optionally substituted ethylene or a structure selected from the group consisting of:

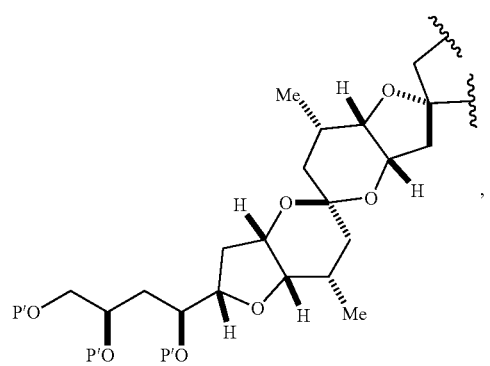

,

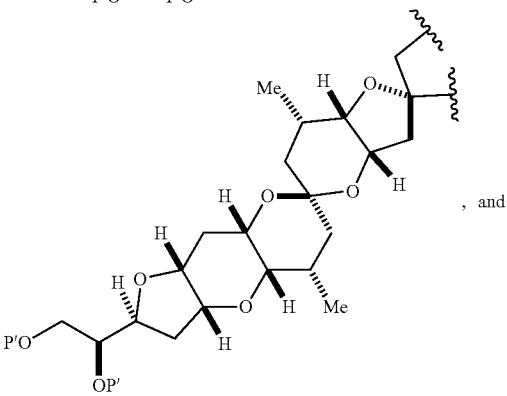

, and

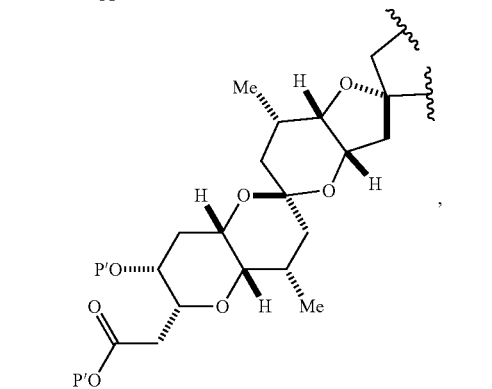

, where each P' is independently H or a hydroxyl protecting group;

E is optionally substituted alkyl or optionally substituted alkoxy;
G is O, S, CH$_2$, or NR$_N$, where R$_N$ is H, an N-protecting group, or optionally substituted alkyl;
each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
k is 0 or 1;
n is 0, 1, or 2;
(a1) R$_3$ is H or a hydroxyl protecting group, R$_4$ and R$_5$ combine to form a double bond, each P$_4$ is independently H or a hydroxyl protecting group, and X$_1$, together with the carbon to which it is attached, forms a carbonyl or —(CH(OR$_8$))—;
or
(a2) R$_3$ and R$_4$ combine to form a bond, R$_5$ is H, and each P$_4$ is independently H or a hydroxyl protecting group, and X$_1$, together with the carbon to which it is attached, forms a carbonyl or —(CH(OR$_8$))—;
or
both P$_4$ groups and X$_1$, together with the atoms to which each is attached, combine to form ketal;
(b1) Z is chloride, bromide, or iodide, and R$_6$ and R$_7$ combine to form a bond;
(b2) Z and R$_7$ combine to form a double bond, and R$_6$ is a hydroxyl protecting group;
or
(b3) when Z and R$_7$ are absent, R$_6$ is H or a hydroxyl protecting group;
P$_5$ is H or a hydroxyl protecting group;
where R$_8$ is H or a hydroxyl protecting group.

In a seventeenth aspect, the invention provides a compound of formula (VIIC):

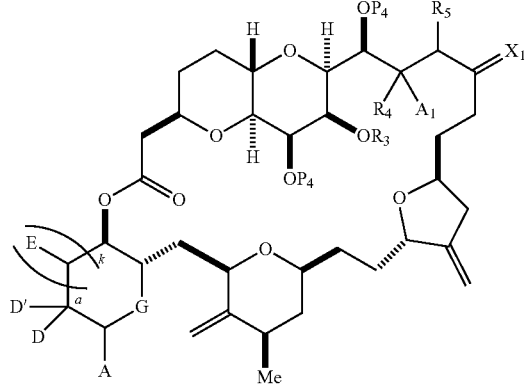

(VIIC)

or a salt or a tautomer thereof,
where
each of D and D' is independently H, optionally substituted alkyl, or OP$_1$, provided that only one of D and D' is OP$_1$, where P$_1$ is H, alkyl, or a hydroxyl protecting group; A is a group of formula (1) or a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

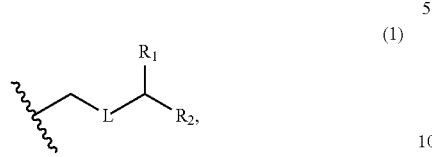
(1)

where

L is —(CH(OP$_2$))—, —(C(OH)(OP$_2$))—, or —C(O)—;

$R_1$ is H, or $R_1$ and $P_1$ combine to form a bond;

$R_2$ is H or —(CH$_2$)$_n$OP$_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

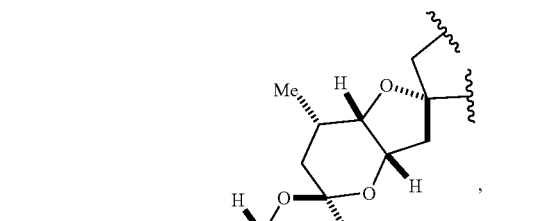

,

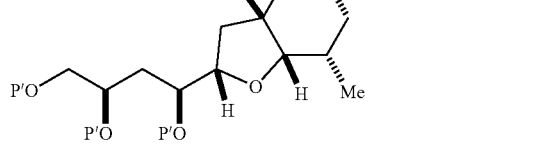

, and

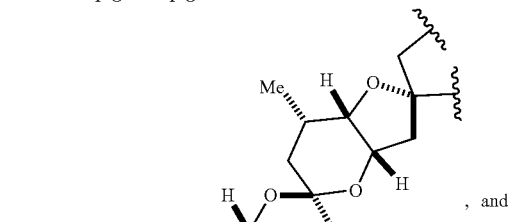

,

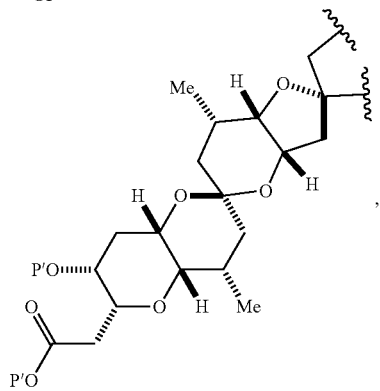

where each P' is independently H or a hydroxyl protecting group;

E is optionally substituted alkyl or optionally substituted alkoxy;

G is O, S, CH$_2$, or NR$_N$, where R$_N$ is H, an N-protecting group, or optionally substituted alkyl;

each $Q_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2;

each $P_4$ is H or a hydroxyl protecting group, and $X_1$ is oxo or $X_1$, together with the carbon atom to which it is attached, is —(CH(OP$_Y$))—, wherein $P_Y$ is H or a hydroxyl protecting group; or both $P_4$ groups and $X_1$, together with the atoms to which each is attached, combine to form a ketal; and $A_1$ and $R_4$ combine to form oxo, $R_3$ is H or a hydroxyl protecting group, and $R_5$ is H;

or $A_1$ is H or OP'', where P'' is H or a hydroxyl protecting group, and:

(i) $R_3$ is H or a hydroxyl protecting group, and $R_4$ and $R_5$ combine to form a double bond;

or (ii) $R_3$ and $R_4$ combine to form a bond, and $R_5$ is H or OP''.

In an eighteenth aspect, the invention provides a compound of formula (VIIIC):

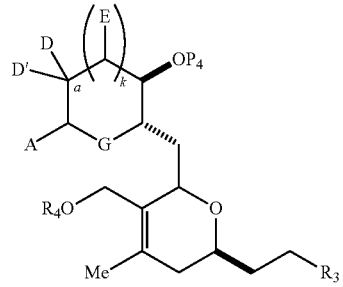
(VIIIC)

or a salt thereof, where each of D and D' is independently H, optionally substituted alkyl, or OP$_1$, provided that only one of D and D' is OP$_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

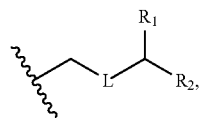
(1)

where

L is —(CH(OP$_2$))—, —(C(OH)(OP$_2$))—, or —C(O)—;

R$_1$ is H, or R$_1$ and P$_1$ combine to form a bond;

R$_2$ is H or —(CH$_2$)$_n$OP$_3$, and each of P$_2$ and P$_3$ is independently H, optionally substituted alkyl, or a hydroxyl protecting group, or P$_2$ and P$_3$, together with the atoms to which each is attached, combine to form a ketal, a cyclic carbonate, a dicarbonyl-dioxo, or silylene-dioxo; or R$_2$ and P$_2$ combine to form an optionally substituted ethylene or a structure selected from the group consisting of:

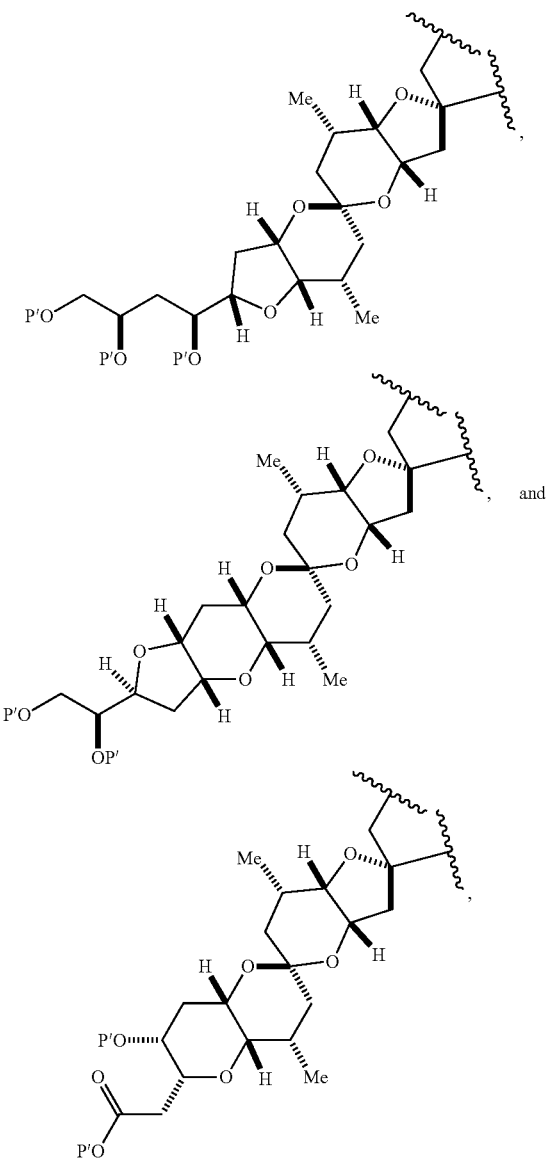

where each P' is independently H or a hydroxyl protecting group;

E is optionally substituted alkyl or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2;

P$_4$ is H or a hydroxyl protecting group; and

R$_3$ is —CH$_2$—OP$_5$, —CH=CH$_2$,

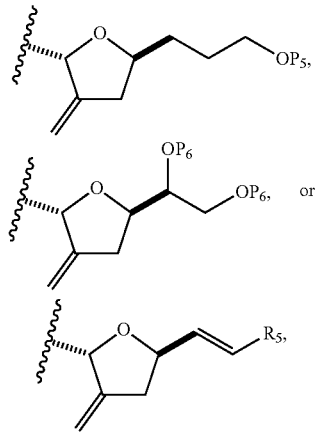

where P$_5$ is H or a hydroxyl protecting group; each P$_6$ is independently a hydroxyl protecting group, or both P$_6$ groups, together with the atoms to which each is attached, combine to form a cyclic protected diol; and R$_5$ is H or —CH$_2$X$_1$CH$_2$CH=CH$_2$, where X$_1$ is O, —CH$_2$—, or NP$_7$, where P$_7$ is a sulfonyl.

The invention also features compounds of formula (IA), (IB), (IC), (IE), (IF), (IIA), (IIB), (IIC), (IICa), (IIIA), (IIIB), (IVA), (IVB), (IVC), (IVD), (IVE), (VA), (VB), (VBa), (VC), (VIA), (VIB), (VIC), (VIIA), (VIIB), (VIIC), (VIID), (VIIE), (VIIF), (VIIG), (VIIIA), (VIIIB), (VIIIC), or (VIIID).

In certain embodiments of formula (IA), (IB), (IC), (IIA), (IIB), (IIIA), (IIIB), (VIA), (VIB), (VIC), (VIIA), (VIIB), and/or (VIIC) of the above aspects, each P$_4$ is independently H or a hydroxyl protecting group, and X$_1$ is oxo; or both P$_4$ groups and X$_1$, together with the atoms to which each is attached, combine to form ketal (e.g., each P$_4$ is independently H or a hydroxyl protecting group, and X$_1$ is oxo).

In particular embodiments of formula (VIIIA) of the above aspects, X is O or X, together with the carbon to which it is attached, forms an acetal (e.g., cyclic acetal).

Definitions

Compounds useful in the invention may be isotopically labeled compounds. Useful isotopes include hydrogen, carbon, nitrogen, and oxygen (e.g., $^2$H, $^3$H, $^{13}$C, $^{14}$C, $^{15}$N, $^{18}$O, and $^{17}O$). Isotopically-labeled compounds can be prepared by synthesizing a compound using a readily available isotopically-labeled reagent in place of a non-isotopically-labeled reagent.

For any of the following chemical definitions, a number following an atomic symbol indicates that total number of atoms of that element that are present in a particular chemical moiety. As will be understood, other atoms, such as hydrogen atoms, or substituent groups, as described herein, may be present, as necessary, to satisfy the valences of the atoms. For example, an unsubstituted $C_2$ alkyl group has the formula —$CH_2CH_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

By "acetal" is meant —O—(CHR)—O—, where R is H, optionally substituted alkyl, optionally substituted alkenyl, optionally substituted aryl, optionally substituted arylalkyl, or a bond to the chain of carbon atoms within an intermediate in the synthesis of the halichondrin macrolide.

By "acyl" is meant —C(O)R, where R is H, alkyl, alkenyl, aryl, or arylalkyl. In exemplary acyl groups, R is H, $C_{1-12}$ alkyl (e.g., $C_{1-8}$, $C_{1-6}$, $C_{1-4}$, $C_{2-7}$, $C_{3-12}$, or $C_{3-6}$ alkyl), $C_{2-12}$ alkenyl (e.g., $C_{2-8}$, $C_{2-6}$, $C_{2-4}$, $C_{3-12}$, or $C_{3-6}$ alkenyl), $C_{6-20}$ aryl (e.g., $C_{6-15}$, $C_{6-10}$, $C_{8-20}$, or $C_{8-15}$ aryl), monocyclic $C_{1-6}$ heteroaryl (e.g., monocyclic $C_{1-4}$ or $C_{2-6}$ heteroaryl), $C_{4-19}$ heteroaryl (e.g., $C_{4-10}$ heteroaryl), ($C_{6-15}$)aryl($C_{1-6}$)alkyl, ($C_{1-6}$)heteroaryl($C_{1-6}$)alkyl, or ($C_{4-19}$)heteroaryl($C_{1-6}$)alkyl. As defined herein, any heteroaryl group present in an acyl group has from 1 to 4 heteroatoms selected independently from O, N, and S. An acyl group can be unsubstituted or substituted (e.g., optionally substituted acyl). In the optionally substituted acyl group, the substituent R is H, optionally substituted alkyl, optionally substituted alkenyl, optionally substituted aryl, or optionally substituted arylalkyl. In some embodiments, acyl is $C_{2-10}$ acyl.

By "acylating agent" is meant a compound that reacts with an amine or a hydroxyl group to produce an amide or an ester, respectively. An acylating agent has a formula R-LG, where R is acyl, and LG is halogen, carbonate, or —OR', where R' is acyl.

By "alkoxide" is meant an anionic compound RO$^-$, where R is alkyl. A counterion for alkoxide can be an alkali metal cation, an alkali earth metal cation, or a tetraalkylammonium cation. Alkoxide can be optionally substituted in the same manner as alkyl.

By "alkoxy" is meant —OR, where R is alkyl. Alkoxy can be optionally substituted in the same manner as alkyl.

By "alkoxyalkyl" is meant —OR, where R is alkyl substituted by alkoxy. Each portion of the alkoxyalkyl can be optionally substituted in the same manner as alkyl.

By "alkoxyaryl" is meant —R'(R")$_n$, where n is 1 or 2, R' is arylene and R" is alkoxy, as defined herein. R' can be further optionally substituted in the same manner as aryl. R" can be optionally substituted in the same manner as alkyl.

By "alkoxyarylalkyl" is meant —R'(R"(R''')$_n$), where n is an integer from 1 to 3, R' is alkylene, R" is arylene, and R''' is alkoxy, as defined herein. R' can be optionally substituted in the same manner as alkyl. R" can be further optionally substituted in the same manner as aryl. R''' can be optionally substituted in the same manner as alkyl.

By "alkyl" is meant a straight or branched chain saturated cyclic (i.e., cycloalkyl) or acyclic hydrocarbon group of from 1 to 12 carbons, unless otherwise specified. In some embodiments, alkyl is $C_{1-6}$ alkyl. Exemplary alkyl groups include $C_{1-8}$, $C_{1-6}$, $C_{1-4}$, $C_{2-7}$, $C_{3-12}$, and $C_{3-6}$ alkyl. Specific examples include methyl, ethyl, 1-propyl, 2-propyl, 2-methyl-1-propyl, 1-butyl, 2-butyl, and the like. Alkyl group can be optionally substituted with 1, 2, 3, or 4 substituents selected from the group consisting of halogen, hydroxy, alkoxy, aryloxy, arylalkyloxy, amino, oxo, alkylthio, alkylenedithio, alkylamino, [alkenyl]alkylamino, [aryl]alkylamino, [arylalkyl]alkylamino, dialkylamino, silyl, sulfonyl, cyano, nitro, carboxyl, and azido.

By "alkylamino" is meant —NHR, where R is alkyl. By "[alkenyl]alkylamino" is meant —NRR', where R is alkyl, and R' is alkenyl. By "[aryl]alkylamino" is meant —NRR', where R is alkyl, and R' is aryl. By "[arylalkyl]alkylamino" is meant —NRR', where R is alkyl, and R' is arylalkyl. By "dialkylamino" is meant —NR$_2$, where each R is alkyl, selected independently.

By "alkylaryl" is meant —R'(R")$_n$, where n is an integer from 1 to 3, R' is arylene, and R" is alkyl. Alkylaryl can be optionally substituted in the same manner as defined for each R' and R" group.

By "alkylene" is meant a multivalent alkyl group. Alkylene groups can be optionally substituted in the same manner as alkyl groups. For example, a $C_1$ alkylene group is —$CH_2$—.

By "alkylenedithio" is meant —S-alkylene-S—. Alkylenedithio can be optionally substituted in the same manner as an alkylene group.

By "alkylhaloaryl" is meant —R'(R")$_n$—R''', where n is an integer from 1 to 5 and R' is arylene, R" is halogen, and R''' is alkylene, as defined herein. R' can be further optionally substituted in the same manner as aryl. R''' can be further optionally substituted in the same manner as alkyl.

By "alkylthio" is meant —SR, where R is alkyl. Alkylthio can be optionally substituted in the same manner as an alkyl group.

By "alkenyl" is meant a straight or branched chain cyclic or acyclic hydrocarbon group of, unless otherwise specified, from 2 to 12 carbons and containing one or more carbon-carbon double bonds. In some embodiments, alkenyl is $C_{2-6}$ alkenyl. Exemplary alkenyl groups include $C_{2-8}$, $C_{2-7}$, $C_{2-6}$, $C_{2-4}$, $C_{3-12}$, and $C_{3-6}$ alkenyl. Specific examples include ethenyl (i.e., vinyl), 1-propenyl, 2-propenyl (i.e., allyl), 2-methyl-1-propenyl, 1-butenyl, 2-butenyl (i.e., crotyl), and the like. Alkenyl group can be optionally substituted in the same manner as alkyl groups. Alkenyl groups, used in any context herein, may also be substituted with an aryl group.

By "amido" is meant —NHR, where R is acyl. Amido can be optionally substituted in the same manner as acyl.

By "aminal" is meant —O—CR$_2$—NR'—, where each R is independently H, optionally substituted alkyl, optionally substituted alkenyl, optionally substituted aryl, or optionally substituted arylalkyl, or both R groups are together optionally substituted alkylene, and R' is H or an N-protecting group. In particular, R' can be an N-protecting group (e.g., Boc).

By "amino" is meant —NR$_2$, where N and R$_2$ combine to form azido, or each R is independently H or an N-protecting group, or both R combine to form an N-protecting group. Amino can be unmasked, when each R is H, or masked, when at least one R is not H. Thus, optionally masked amino can be masked or unmasked amino.

By "aminoalkyl" is meant —R'(R")$_n$, where n is 1 or 2, R' is alkylene, and R" is amino, as defined herein. R' can be optionally substituted in the same manner as an alkyl group.

By "aryl" is meant a monocyclic or multicyclic ring system having one or more aromatic rings, where the ring system is carbocyclic. Exemplary aryl groups include $C_{6-20}$, $C_{6-15}$, $C_{6-10}$, $C_{8-20}$, and $C_{8-15}$ aryl. A preferred aryl group is a $C_{6-10}$ aryl group. Specific examples of carbocyclic aryl groups include phenyl, indanyl, indenyl, naphthyl, phenanthryl, anthracyl, and fluorenyl. Aryl group can be optionally substituted with 1, 2, 3, 4, or 5 substituents selected from the group consisting of alkyl, alkenyl, aryl, arylalkyl, halogen, alkoxy, aryloxy, arylalkyloxy, alkylthio, alkylenedithio, alkylamino, [alkenyl]alkylamino, [aryl]alkylamino, [arylalkyl]alkylamino, dialkylamino, silyl, sulfonyl, cyano, nitro, carboxyl, and azido.

By "arylalkyl" is meant —R'R", where R' is alkylene, and R" is aryl. Arylalkyl can be optionally substituted in the same manner as defined for each R' and R" group.

By "arylalkyloxy" is meant —OR, where R is arylalkyl. Arylalkyloxy can be optionally substituted in the same manner as defined for arylalkyl.

By "arylene" is meant a multivalent aryl group. Arylene groups can be optionally substituted in the same manner as aryl groups. For example, a $C_6$ arylene group is phenylene.

By "aryloxy" is meant —OR, where R is aryl. Aryloxy can be optionally substituted in the same manner as aryl.

By "azido" is meant —$N_3$.

By "boronate" is meant —OBRO—, where R is alkyl, alkenyl, aryl, arylalkyl, alkoxy, or 2,6-diacetamidophenyl. Boronate can be substituted, when R is a substituted alkyl, substituted alkenyl, substituted aryl, substituted arylalkyl, or substituted alkoxy. Alternatively, boronate can be unsubstituted, when R is unsubstituted alkyl, unsubstituted alkenyl, aryl, unsubstituted arylalkyl, unsubstituted alkoxy, or 2,6-diacetamidophenyl.

By "carbamate" is meant a group, when a hydroxyl protecting group, having the formula —OC(O)$NR_2$, or, when an amine protecting group, having the formula —NR'—C(O)OR, where each R and R' is independently H, optionally substituted alkyl, optionally substituted alkenyl, optionally substituted aryl, or optionally substituted arylalkyl.

By "carbonate" is meant —OC(O)OR, where R is optionally substituted alkyl, optionally substituted alkenyl, optionally substituted aryl, or optionally substituted arylalkyl.

By "carbonyl" is meant —C(O)—.

By "carboxyl" is meant —C(O)OH, in free acid, ionized, or salt form.

By "carboxylic acid" is meant R—OH, where R is optionally substituted acyl.

By "carboxylic acid anhydride" is meant R—O—R, where each R is independently optionally substituted acyl.

By "cyclic carbonate" is meant —OC(O)O— that is part of a ring.

By "dicarbonyl" is meant —C(O)—C(O)—. Dicarbonyl-dioxo is —OC(O)—COO—.

By "ester" is meant —OC(O)R, where —C(O)R is an optionally substituted acyl group.

By "ether" is meant —OR, where R is alkyl, alkenyl, arylalkyl, silyl, or 2-tetrahydropyranyl. Ether can be optionally substituted as defined for each R group.

By "halichondrin macrolide" is meant a lactone including the structure of carbons 1-30 as shown in Chart 1, wherein carbons 29 and 30 form part of a five- or six-membered ring.

By "haloalkyl" is meant —R'(R")$_n$, where n is an integer from 1 to 5 and R' is alkylene and R" is halogen, as defined herein. R' can be further optionally substituted in the same manner as alkyl By "haloaryl" is meant —R'(R")$_n$, where n is an integer from 1 to 5 and R' is arylene and R" is halogen, as defined herein. R' can be further optionally substituted in the same manner as aryl.

By "haloarylalkyl" is meant —R'(R"(R'")$_n$), where n is an integer from 1 to 5 and R' is alkylene, R" is arylene, and R'" is halogen, as defined herein. R' can be further optionally substituted in the same manner as alkyl. R" can be further optionally substituted in the same manner as aryl.

By "halogen" is meant fluoro, chloro, bromo, or iodo.

By "heterocyclic radical" is meant a 5-, 6- or 7-membered ring, unless otherwise specified, containing one, two, three, or four heteroatoms independently selected from the group containing nitrogen, oxygen, and sulfur. The 5-membered ring has zero to one double bonds, and the 6- and 7-membered rings have zero to two double bonds. Certain heterocyclyl groups include from 1 to 9 carbon atoms. Other such groups may include up to 12 carbon atoms. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, purinyl, thiadiazolyl (e.g., 1,3,4-thiadiazole), tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl;

1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3,7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Heterocyclic groups also include groups of the formula

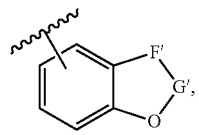

where
F' is selected from the group consisting of —CH$_2$—, —CH$_2$O— and —O—, and G' is selected from the group consisting of —C(O)— and —(C(R')(R''))$_v$—, where each of R' and R'' is, independently, selected from the group consisting of hydrogen or alkyl of one to four carbon atoms, and v is one to three and includes groups, such as 1,3-benzodioxolyl, 1,4-benzodioxanyl, and the like. Any of the heterocyclyl groups mentioned herein may be optionally substituted with one, two, three, four or five substituents independently selected from the group consisting of: (1) alkanoyl (e.g., formyl, acetyl, and the like); (2) alkyl (e.g., alkoxyalkylene, alkylsulfinylalkylene, aminoalkylene, azidoalkylene, acylalkylene, haloalkylene (e.g., perfluoroalkyl), hydroxyalkylene, nitroalkylene, or thioalkoxyalkylene); (3) alkenyl; (4) alkynyl; (5) alkoxy (e.g., perfluoroalkoxy); (6) alkylsulfinyl; (7) aryl; (8) amino; (9) aryl-alkylene; (10) azido; (11) cycloalkyl; (12) cycloalkyl-alkylene; (13) cycloalkenyl; (14) cycloalkenyl-alkylene; (15) halo; (16) heterocyclyl (e.g., heteroaryl); (17) (heterocyclyl)oxy; (18) (heterocyclyl)aza; (19) hydroxy; (20) oxo; (21) nitro; (22) sulfide; (23) thioalkoxy; (24) —(CH$_2$)$_q$CO$_2$R$^A$, where q is an integer from zero to four, and R$^A$ is selected from the group consisting of (a) alkyl, (b) aryl, (c) hydrogen, and (d) aryl-alkylene; (25) —(CH$_2$)$_q$CONR$^B$R$^C$, where q is an integer from zero to four and where R$^B$ and R$^C$ are independently selected from the group consisting of (a) hydrogen, (b) alkyl, (c) aryl, and (d) aryl-alkylene; (26) —(CH$_2$)$_q$SO$_2$R$^D$, where q is an integer from zero to four and where R$^D$ is selected from the group consisting of (a) alkyl, (b) aryl, and (c) aryl-alkylene; (27) —(CH$_2$)$_q$SO$_2$NR$^E$R$^F$, where q is an integer from zero to four and where each of R$^E$ and R$^F$ is, independently, selected from the group consisting of (a) hydrogen, (b) alkyl, (c) aryl, and (d) aryl-alkylene; (28) thiol; (29) aryloxy; (30) cycloalkoxy; (31) arylalkoxy; (31) heterocyclyl-alkylene (e.g., heteroaryl-alkylene); (32) silyl; (33) cyano; and (34) —S(O)R$^H$ where R$^H$ is selected from the group consisting of (a) hydrogen, (b) alkyl, (c) aryl, and (d) aryl-alkylene. In some embodiments, each of these groups can be further substituted as described herein. For example, the alkylene group of an aryl-C$_1$-alkylene or a heterocyclyl-C$_1$-alkylene can be further substituted with an oxo group to afford the respective aryloyl and (heterocyclyl)oyl substituent group. In addition, when a heterocyclyl group is present in a bioreversible group of the invention it may be substituted with an ester, thioester, or disulfide group that is bound to a conjugating moiety, a hydrophilic functional group, or an auxiliary moiety as defined herein.

By "heterocyclic radical alkyl," as used herein, represents an alkyl group substituted with a heterocyclic radical. The heterocyclic radical and alkyl portions may be substituted as the individual groups as described herein.

By "hydroxyalkyl" is meant —R'(R'')$_n$, where n 1 or 2, R' is alkylene and R'' is hydroxyl, as defined herein. R' can be further optionally substituted in the same manner as alkyl.

By "hydroxyaryl" is meant —R'(R'')$_n$, where n is 1 or 2, R' is arylene and R'' is hydroxyl, as defined herein. R' can be further optionally substituted in the same manner as aryl.

By "hydroxyl" is meant —OH.

By "hydroxyl protecting group" is meant any group capable of protecting the oxygen atom to which it is attached from reacting or bonding. Hydroxyl protecting groups are known in the art, e.g., as described in Wuts, Greene's Protective Groups in Organic Synthesis, Wiley-Interscience, 4th Edition, 2006. Exemplary protecting groups (with the oxygen atom to which they are attached) are independently selected from the group consisting of esters, carbonates, carbamates, sulfonates, and ethers. In exemplary ester hydroxyl protecting groups, R of the acyl group is C$_{1-12}$ alkyl (e.g., C$_{1-8}$, C$_{1-6}$, C$_{1-4}$, C$_{2-7}$, C$_{3-12}$, and C$_{3-6}$ alkyl), C$_{2-12}$ alkenyl (e.g., C$_{2-8}$, C$_{2-6}$, C$_{2-4}$, C$_{3-12}$, and C$_{3-6}$ alkenyl), carbocyclic C$_{6-20}$ aryl (e.g., C$_{6-15}$, C$_{6-10}$, C$_{8-20}$, and C$_{8-15}$ aryl), monocyclic C$_{1-6}$ heteroaryl (e.g., C$_{1-4}$ and C$_{2-6}$ heteroaryl), C$_{4-19}$ heteroaryl (e.g., C$_{4-10}$ heteroaryl), (C$_{6-15}$)aryl(C$_{1-6}$)alkyl, (C$_{4-19}$)heteroaryl(C$_{1-6}$)alkyl, or (C$_{1-6}$)heteroaryl(C$_{1-6}$)alkyl. Specific examples of acyl groups for use in esters include formyl, benzoylformyl, acetyl (e.g., unsubstituted or chloroacetyl, trifluoroacetyl, methoxyacetyl, triphenylmethoxyacetyl, and p-chlorophenoxyacetyl), 3-phenylpropionyl, 4-oxopentanoyl, 4,4-(ethylenedithio)pentanoyl, pivaloyl (Piv), vinylpivaloyl, crotonoyl, 4-methoxy-crotonoyl, naphthoyl (e.g., 1- or 2-naphthoyl), and benzoyl (e.g., unsubstituted or substituted, e.g., p-methoxybenzoyl, phthaloyl (including salts, such a triethylamine and potassium), p-bromobenzoyl, and 2,4,6-trimethylbenzoyl). As defined herein, any heteroaryl group present in an ester group has from 1 to 4 heteroatoms selected independently from O, N, and S. In exemplary carbonate hydroxyl protecting groups, R is C$_{1-12}$ alkyl (e.g., C$_{1-8}$, C$_{1-6}$, C$_{1-4}$, C$_{2-7}$, C$_{3-12}$, and C$_{3-6}$ alkyl), C$_{2-12}$ alkenyl (e.g., C$_{2-8}$, C$_{2-6}$, C$_{2-4}$, C$_{3-12}$, and C$_{3-6}$ alkenyl), carbocyclic C$_{6-20}$ aryl (e.g., C$_{6-15}$, C$_{6-10}$, C$_{8-20}$, and C$_{8-15}$ aryl), monocyclic C$_{1-6}$ heteroaryl (e.g., C$_{1-4}$ and C$_{2-6}$ heteroaryl), C$_{4-19}$ heteroaryl (e.g., C$_{4-10}$ heteroaryl), (C$_{6-15}$)aryl(C$_{1-6}$)alkyl, (C$_{4-19}$)heteroaryl(C$_{1-6}$)alkyl, or (C$_{1-6}$)heteroaryl(C$_{1-6}$)alkyl. Specific examples include methyl, 9-fluorenylmethyl, ethyl, 2,2,2-trichloroethyl, 2-(trimethylsilyl)ethyl, 2-(phenylsulfonyl)ethyl, vinyl, allyl, t-butyl, p-nitrobenzyl, and benzyl carbonates. As defined herein, any heteroaryl group present in a carbonate group has from 1 to 4 heteroatoms selected independently from O, N, and S. In exemplary carbamate hydroxyl protecting groups, each R is independently H, C$_{1-12}$ alkyl (e.g., C$_{1-8}$, C$_{1-6}$, C$_{1-4}$, C$_{2-7}$, C$_{3-12}$, and C$_{3-6}$ alkyl), C$_{2-12}$ alkenyl (e.g., C$_{2-8}$, C$_{2-6}$, C$_{2-4}$, C$_{3-12}$, and C$_{3-6}$ alkenyl), carbocyclic C$_{6-20}$ aryl (e.g., C$_{6-15}$, C$_{6-10}$, C$_{8-20}$, and C$_{8-15}$ aryl), monocyclic C$_{1-6}$ heteroaryl (e.g., C$_{1-4}$ and C$_{2-6}$ heteroaryl), C$_{4-19}$ heteroaryl (e.g., C$_{4-10}$ heteroaryl), (C$_{6-15}$)aryl(C$_{1-6}$)alkyl, (C$_{4-19}$)heteroaryl(C$_{1-6}$)alkyl, or (C$_{1-6}$)heteroaryl(C$_{1-6}$)alkyl. Specific examples include N-phenyl and N-methyl-N-(o-nitrophenyl) carbamates. As defined herein, any heteroaryl group present in a carbamate group has from 1 to 4 heteroatoms selected independently from O, N, and S. Exemplary ether hydroxyl protecting groups include $C_{1-12}$ alkyl (e.g., $C_{1-8}$, $C_{1-6}$, $C_{1-4}$, $C_{2-7}$, $C_{3-12}$, and $C_{3-6}$ alkyl), $C_{2-12}$ alkenyl (e.g., $C_{2-8}$, $C_{2-6}$, $C_{2-4}$, $C_{3-12}$, and $C_{3-6}$ alkenyl), $(C_{6-15})$aryl$(C_{1-6})$alkyl, $(C_{4-19})$heteroaryl$(C_{1-6})$alkyl, $(C_{1-6})$heteroaryl$(C_{1-6})$alkyl, $(C_{1-6})$alkoxy$(C_{1-6})$alkyl, $(C_{1-6})$alkylthio$(C_{1-6})$alkyl, $(C_{6-10})$aryl$(C_{1-6})$alkoxy$(C_{1-6})$alkyl, and silyl (e.g., tri$(C_{1-6}$ alkyl)silyl, tri$(C_{6-10}$ aryl or $C_{1-6}$ heteroaryl)silyl, di$(C_{6-10}$ aryl or $C_{1-6}$ heteroaryl)$(C_{1-6}$ alkyl)silyl, and $(C_{6-10}$ aryl or $C_{1-6}$ heteroaryl)di$(C_{1-6}$ alkyl)silyl). Specific examples of alkylethers include methyl and t-butyl, and an example of an alkenyl ether is allyl. Ether hydroxyl protecting groups can be used to protect a carboxyl group (e.g., with a $C_{1-12}$ alkyl (e.g., $C_{1-8}$, $C_{1-6}$, $C_{1-4}$, $C_{2-7}$, $C_{3-12}$, and $C_{3-6}$ alkyl), $(C_{6-15})$aryl$(C_{1-6})$alkyl, $(C_{1-6})$alkoxy$(C_{1-6})$alkyl, $(C_{1-6})$alkylthio$(C_{1-6})$alkyl, or $(C_{6-10})$aryl$(C_{1-6})$alkoxy$(C_{1-6})$alkyl). Examples of alkoxyalkyls and alkylthioalkyls that can be used as ether hydroxyl protecting groups include methoxymethyl, methylthiomethyl, (2-methoxyethoxy)methyl, and β-(trimethylsilyl)ethoxymethyl. Examples of arylalkyl groups that can be used as ether hydroxyl protecting groups include benzyl, p-methoxybenzyl (MPM), 3,4-dimethoxybenzyl, triphenylmethyl (trityl), o-nitrobenzyl, p-nitrobenzyl, p-halobenzyl, 2,6-dichlorobenzyl, p-cyanobenzyl, naphthylmethyl, and 2- and 4-picolyl ethers. Specific examples of silylethers include trimethylsilyl (TMS), triethylsilyl (TES), t-butyldimethylsilyl (TBS), t-butyldiphenylsilyl (TBDPS), triisopropylsilyl (TIPS), and triphenylsilyl (TPS) ethers. An example of an arylalkyloxyalkylether is benzyloxymethyl ether. As defined herein, any heteroaryl group present in an ether group has from 1 to 4 heteroatoms selected independently from O, N, and S. Vicinal or 1,3-diols may be protected with a diol protecting group (e.g., to produce a "cyclic protected diol"), such as acetal (e.g., containing $C_{1-6}$ alkylene), ketal (e.g., containing $C_{3-6}$ alkylene or $C_{3-6}$ cycloalkyl), cyclic silylene, cyclic carbonate, and cyclic boronate. Examples of acetal and ketal groups include methylene-dioxo, ethylidene-dioxo, benzylidene-dioxo, isopropylidene-dioxo, cyclohexylidene-dioxo, and cyclopentylidene-dioxo. An example of a cyclic silylene is di-t-butylsilylene. Another diol protecting group is 1,1,3,3-tetraisopropylsiloxanediyl. Examples of cyclic boronates include methyl, ethyl, phenyl, and 2,6-diacetamidophenyl boronates. Protecting groups may be substituted as is known in the art; for example, aryl and arylalkyl groups, such as phenyl, benzyl, naphthyl, or pyridinyl, can be substituted with $C_{1-6}$ alkyl, $C_{1-6}$ alkoxy, nitro, cyano, carboxyl, or halogen. Alkyl groups, such as methyl, ethyl, isopropyl, n-propyl, t-butyl, n-butyl, and sec-butyl, and alkenyl groups, such as vinyl and allyl, can also be substituted with oxo, arylsulfonyl, halogen, and trialkylsilyl groups. Preferred protecting groups are TBS and Piv. Protecting groups that are orthogonal are removed under different conditions, as in known in the art.

By "imido" is meant —$NR_2$, where each R is independently optionally substituted acyl.

By "ketal" is meant —O—$CR_2$—O—, where each R is independently optionally substituted alkyl, optionally substituted alkenyl, optionally substituted aryl, optionally substituted arylalkyl, or a bond to the chain of carbon atoms within an intermediate in the synthesis of the halichondrin macrolide; or both R groups are together optionally substituted alkylene.

By "macrocyclization" is meant a reaction converting a non-macrocyclic compound into a compound containing at least one n-membered ring, where n is equal to or greater than 16.

By "MNBA" is meant 2-methyl-6-nitrobenzoic anhydride.

By "non-enolizable" is meant a group that, either alone or in combination with a group to which it is attached, cannot form an enol through a deprotonation/reprotonation sequence. For example, a "non-enolizable alkyl" can be bonded to a sulfone group or to a carbonyl group through a quaternary carbon atom (i.e., the carbon atom that is not bonded to a hydrogen atom).

By "non-macrocyclic" is meant a compound not containing rings or containing one or more m-membered rings, where m is less than or equal to 15.

By "N-protecting group" is meant a group protecting a nitrogen atom in a molecule from participating in one or more undesirable reactions during chemical synthesis (e.g., oxidation reactions, or certain nucleophilic and electrophilic substitutions). Commonly used N-protecting groups are disclosed in Wuts, Greene's Protective Groups in Organic Synthesis, Wiley-Interscience, 4th Edition, 2006. Exemplary N-protecting groups include acyl (e.g., formyl, acetyl, trifluoroacetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, and 4-bromobenzoyl); sulfonyl-containing groups (e.g., benzenesulfonyl, p-toluenesulfonyl, o-nitrobenzenesulfonyl, and p-nitrobenzenesulfonyl); carbamate forming groups (e.g., benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl), arylalkyl (e.g., triphenylmethyl); silyl groups (e.g., trimethylsilyl); and imine-forming groups (e.g., diphenylmethylene). Preferred N-protecting groups are acetyl, benzoyl, phenylsulfonyl, p-toluenesulfonyl, p-nitrobenzenesulfonyl, o-nitrobenzenesulfonyl, t-butyloxycarbonyl (Boc), and benzyloxycarbonyl (Cbz).

By "oxo" or (O) is meant =O.

By "pharmaceutically acceptable salt" is meant a salt within the scope of sound medical judgment, suitable for use in contact with the tissues of humans and animals without undue toxicity, irritation, allergic response and the like and commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. A preferred salt is the mesylate salt.

By "silyl" is meant —$SiR_3$, where each R is independently alkyl, alkenyl, aryl, or arylalkyl. Examples of silyl groups include tri($C_{1-6}$ alkyl)silyl, tri($C_{6-10}$ aryl or $C_{1-6}$ heteroaryl)silyl, di($C_{6-10}$ aryl or $C_{1-6}$ heteroaryl)($C_{1-6}$ alkyl) silyl, and ($C_{6-10}$ aryl or $C_{1-6}$ heteroaryl)di($C_{1-6}$ alkyl)silyl. It will be understood that, when a silyl group includes two or more alkyl, alkenyl, aryl, heteroaryl, or arylalkyl groups, these groups are independently selected. As defined herein, any heteroaryl group present in a silyl group has from 1 to 4 heteroatoms selected independently from O, N, and S. Silyl can be optionally substituted in the same manner as defined for each R group.

By "silylene" is meant —$SiR_2$—, where each R is independently alkyl, alkenyl, aryl, arylalkyl, or alkoxy. By "dialkylsilylene" is meant a silylene, where each R is alkyl. Silylene can be optionally substituted in the same manner as defined for each R group. Silylene-dioxo is a group having the formula —O—$SiR_2$—O—.

By "strong base" is meant a Brønsted base, the conjugate acid of which has pKa that is greater than or equal to 13. Non-limiting examples of strong bases include alkyl alkali metals (e.g., butyl lithium or Schlosser's base), Grignard reagents (e.g., alkyl magnesium halide), alkoxides (e.g., tertiary alkoxides, such as t-butoxide), amides (e.g., diisopropylamide, tetramethylpiperidide, or bis(trimethylsilyl) amide), and phosphazene bases (e.g., Schwesinger base).

By "sulfonamide" is meant —NR, where R is sulfonyl.

By "sulfonate" is meant —$OS(O)_2R$, where R is optionally substituted alkyl, optionally substituted alkenyl, optionally substituted aryl, or optionally substituted arylalkyl. In exemplary sulfonates, R is $C_{1-12}$ alkyl (e.g., $C_{1-8}$, $C_{1-6}$, $C_{1-4}$, $C_{2-7}$, $C_{3-12}$, or $C_{3-6}$ alkyl), $C_{2-12}$ alkenyl (e.g., $C_{2-8}$, $C_{2-6}$, $C_{2-4}$, $C_{3-12}$, or $C_{3-6}$ alkenyl), carbocyclic $C_{6-20}$ aryl (e.g., $C_{6-15}$, $C_{6-10}$, $C_{8-20}$, or $C_{8-15}$ aryl), monocyclic $C_{1-6}$ heteroaryl (e.g., $C_{1-4}$ and $C_{2-6}$ heteroaryl), $C_{4-19}$ heteroaryl (e.g., $C_{4-10}$ heteroaryl), ($C_{6-15}$)aryl($C_{1-6}$)alkyl, ($C_{4-19}$)heteroaryl($C_{1-6}$)alkyl, or ($C_1$-6)heteroaryl($C_{1-6}$)alkyl. As defined herein, any heteroaryl group present in a sulfonate group has from 1 to 4 heteroatoms selected independently from O, N, and S.

By "sulfonyl" is meant —$S(O)_2R$, where R is optionally substituted alkyl, optionally substituted alkenyl, optionally substituted aryl, optionally substituted arylalkyl, or silyl. Preferred R groups for sulfonyl are the same as those described above for sulfonates.

By "thioacetal" is meant —S—(CHR)—S—, where R is H, optionally substituted alkyl, optionally substituted alkenyl, optionally substituted aryl, or optionally substituted arylalkyl.

By "thioketal" is meant —S—($CR_2$)—S—, where each R is independently optionally substituted alkyl, optionally substituted alkenyl, optionally substituted aryl, or optionally substituted arylalkyl.

By "triflate" is meant trifluoromethanesulfonate.

The pKa values recited herein refer to the pKa values of a conjugate Brønsted acid in water at room temperature, unless stated otherwise.

BRIEF DESCRIPTION OF THE DRAWINGS

FIG. 1 is a scheme showing preparation of a halichondrin macrolide involving a C.2-C.3 bond-forming macrocyclization through Horner-Wadsworth-Emmons olefination.

FIG. 2 is a scheme showing preparation of a halichondrin macrolide involving a C.2-C.3 bond-forming macrocyclization through ring-closing olefin metathesis.

FIG. 3 is a scheme showing preparation of a halichondrin macrolide involving a C.3-C.4 bond-forming macrocyclization through ring-closing olefin metathesis.

DETAILED DESCRIPTION

Figure 4:
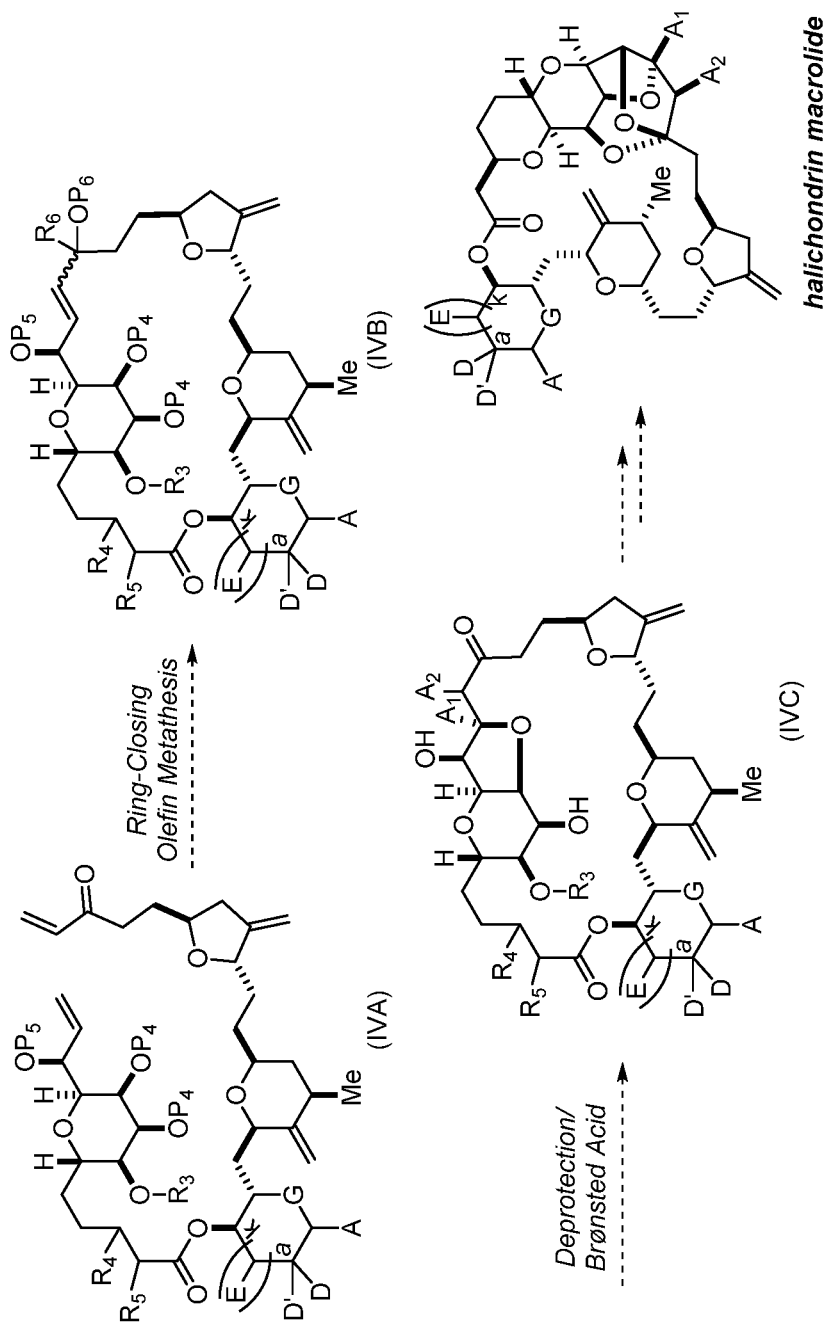
FIG. 4 is a scheme showing preparation of a halichondrin macrolide involving a C.12-C.13 bond-forming macrocyclization through ring-closing olefin metathesis.

The present invention provides methods for the synthesis of a halichondrin macrolide (see Chart 1) through a macrocyclization. Preferably, the halichondrin macrolide is a halichondrin B macrolide. The macrocyclizations of the present invention involve subjecting a non-macrocyclic intermediate to a carbon-carbon bond-forming reaction (e.g., an olefination reaction (e.g., Horner-Wadsworth-Emmons olefination), catalytic Ring-Closing Olefin Metathesis, or Nozaki-Hiyama-Kishi reaction) to afford a macrocyclic intermediate (e.g., a compound of formula (IB), (IIIB), (IVB), (VB), (VIB), or (VIIB)). The carbon-carbon bond forming reaction provides C.2-C.3, C.3-C.4, C.12-C.13, C.15-C.16, C.19-C.20, or C.26-C.27 bond in the structure of a halichondrin macrolide. The carbon-atom numbering scheme for a halichondrin macrolide is shown in Chart 1.

Chart 1

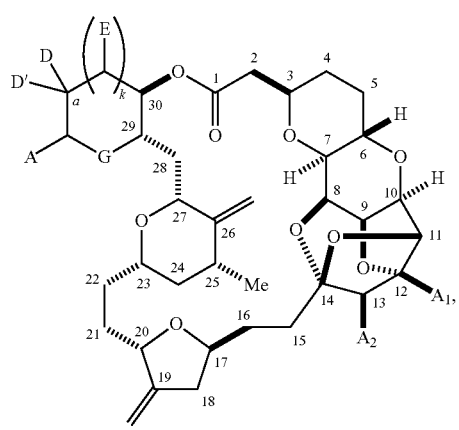

in which each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

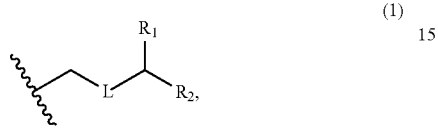

(1)

where

L is —(CH(OP$_2$))—, —(C(OH)(OP$_2$))—, or —C(O)—;

$R_1$ is H, or $R_1$ and $P_1$ combine to form a bond;

$R_2$ is H or —(CH$_2$)$_n$OP$_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

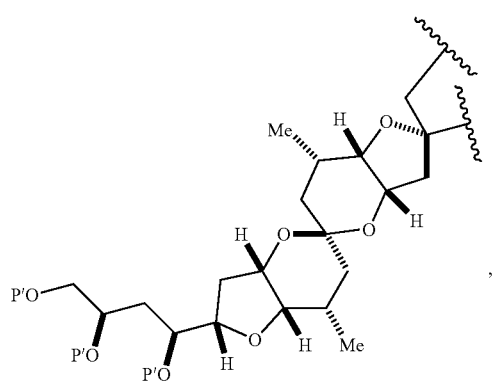

, and

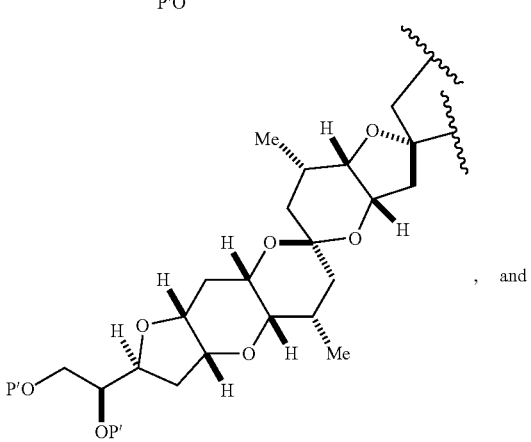

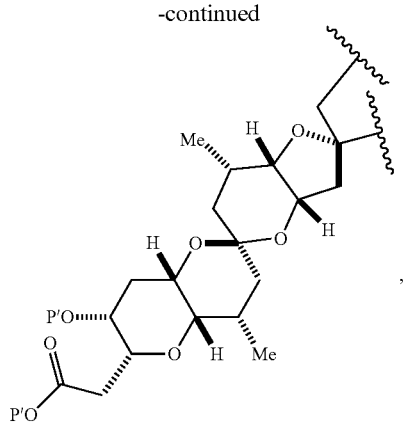

, where each P' is independently H or a hydroxyl protecting group;

each of $A_1$ and $A_2$ is independently H or OP'", where each P'" is independently H or a hydroxyl protecting group;

E is optionally substituted alkyl or optionally substituted alkoxy;

G is O, S, CH$_2$, or NR$_N$, where R$_N$ is H, an N-protecting group, or optionally substituted alkyl;

each $Q_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2.

In some embodiments of the halichondrin macrolide, C and D' are not the same, and a designates (S)-stereogenic center. In certain embodiments of the halichondrin macrolide, one of D and D' is optionally substituted alkyl or $OP_1$, the other of D and D' is H, and G is O. In particular embodiments of the halichondrin macrolide, one and only one of D and D' is $OP_1$, where $P_1$ is H, alkyl, or a hydroxyl protecting group. In one embodiment of the halichondrin macrolide, k is 1, E is optionally substituted alkyl (e.g., Me); and D is a group of formula (1); in further embodiments, L is —(CH(OP$_2$))—, $R_1$ and $P_1$ combine to form a bond, $R_2$ is —(CH$_2$)$_n$OP$_3$, each of $P_2$ and $P_3$ is H, and n is 1 or 2 (e.g., n is 2).

The invention also provides intermediates in the synthesis of halichondrin and analogs of the macrolide in the structure of halichondrin and methods of preparing the same, as described herein.

C.2-C.3 Bond-Forming Macrocyclization

The macrocyclization reaction of the invention can be a carbon-carbon bond-forming reaction (e.g., Horner-Wadsworth-Emmons olefination) that provides a C.2-C.3 bond in a halichondrin macrolide. The general synthetic sequence including Horner-Wadsworth-Emmons olefination that can be used to prepare a halichondrin macrolide is shown in FIG. 1. As shown in FIG. 1, the non-macrocyclic intermediate in the synthesis of the halichondrin macrolide can be a compound of formula (IA):

(IA)

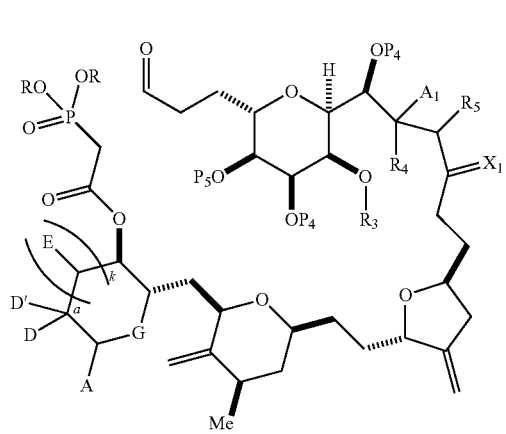

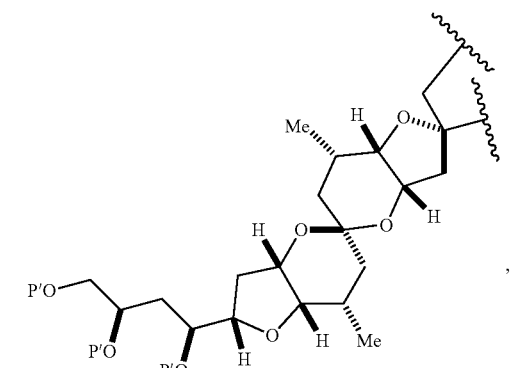

, and or a salt or a tautomer thereof,
in which
each R is independently optionally substituted alkyl or optionally substituted aryl;
each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

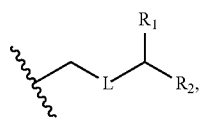
(1)

where
L is $-(CH(OP_2))-$, $-(C(OH)(OP_2))-$, or $-C(O)-$;
$R_1$ is H, or $R_1$ is H, or $R_1$ and $P_1$ combine to form a bond;
$R_2$ is H or $-(CH_2)_nOP_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

where each P' is independently H or a hydroxyl protecting group;
E is optionally substituted alkyl or optionally substituted alkoxy;
G is O, S, $CH_2$, or $NR_N$, where $R_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
k is 0 or 1;
n is 0, 1, or 2;
$A_1$ and $R_4$ combine to form oxo, $R_3$ is H or a hydroxyl protecting group, and $R_5$ is H;

or

A$_1$ is H or OP''', where P''' is H or a hydroxyl protecting group, and:
  (i) R$_3$ is H or a hydroxyl protecting group, and R$_4$ and R$_5$ combine to form a double bond;
  or
  (ii) R$_3$ and R$_4$ combine to form a bond, and R$_5$ is H or OP''';
each P$_4$ is independently H or a hydroxyl protecting group, and X$_1$ is oxo or X$_1$, together with the carbon atom to which it is attached, is —(CH(OP$_Y$))—, where P$_Y$ is H or a hydroxyl protecting group; or both P$_4$ groups and X$_1$, together with the atoms to which each is attached, combine to form ketal; and P$_5$ is H or a hydroxyl protecting group.

In certain embodiments of the compound of formula (IA), R$_3$ is H or a hydroxyl protecting group, R$_4$ and R$_5$ combine to form a double bond, P$_4$ is independently H or a hydroxyl protecting group, and X$_1$ is oxo. In other embodiments of the compound of formula (IA), R$_3$ and R$_4$ combine to form a bond, and R$_5$ is H.

A macrocyclic intermediate in the synthesis of a halichondrin macrolide can be a compound of formula (IB), which can be produced by reacting the compound of formula (IA) with an organic base and a Lewis acid. The compound of formula (IB) has the following structure:

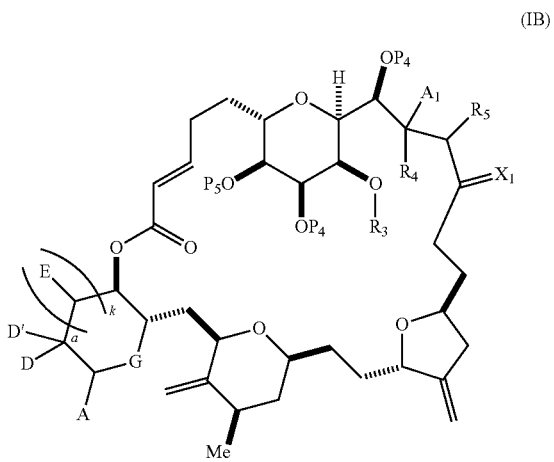

(IB)

or a salt or a tautomer thereof,
where all variables are as defined for compound of formula (IA).

The reaction conditions that can be used to convert the compound of formula (IA) into the compound of formula (IB) include those known in the art for Horner-Wadsworth-Emmons reaction, e.g., Masamune-Roush conditions or Helquist protocol. In particular, the compound of formula (IA) can be reacted with an organic base (e.g., an organic base, the conjugate acid of which has a pKa of from 11±2) and a Lewis acid (e.g., a salt of Li, Mg, or Zn). Non-limiting examples of an organic base that can be used in the Horner-Wadsworth-Emmons reaction include trialkylamines (e.g., triethylamine or Hünig's base), DBU, and DBN. Non-limiting examples of Lewis acids that can be used in the Horner-Wadsworth-Emmons reaction include LiCl, Zn(OTf)$_2$, and MgCl$_2$.

The compound of formula (IB), in which, e.g., P$_5$ is a hydroxyl protecting group, can be converted into a halichondrin macrolide by reacting the compound of formula (IB) with a hydroxyl protecting group removing agent (e.g., a fluoride source, if the hydroxyl protecting group is a silyl group).

If, in the compound of formula (IB), each P$_4$ is H, and X$_1$ is oxo, the synthesis may further involve a reaction with a Brønsted acid (e.g., a Brønsted acid having a pKa of 5±3) after the reaction of the compound of formula (IB) with a hydroxyl protecting group removing agent (e.g., to convert P$_4$ from a hydroxyl protecting group into H).

If, in the compound of formula (IB), X$_1$ is oxo, R$_3$ is a hydroxyl protecting group, and R$_4$ and R$_5$ combine to form a double bond, treatment with a hydroxyl protecting group removing agent can provide the compound of formula (IB), in which R$_3$ and R$_4$ combine to form a bond, and R$_5$ is H.

The compound of formula (IA) or formula (IB), in which X$_1$, together with the carbon atom to which it is attached, is —(CH(OP$_Y$))—, where P$_Y$ is H, may be treated with an oxidizing agent capable of oxidizing hydroxyl to a carbonyl group (e.g., Dess-Martin periodinane or a dimethylsulfonium compound) to give the compound of formula (IA) or formula (IB), in which X$_1$ is oxo.

Preparation of certain compounds of formula (IB) may further involve conversion of the compound of formula (IB), in which A$_1$ is H, and R$_4$ and R$_5$ combine to form a double bond, into the compound of formula (IB) in which R$_4$ and A$_1$ combine to form oxo. In a non-limiting example, the enone in the compound of formula (IB), in which R$_4$ and R$_5$ combine to form a double bond can be converted into a C.12-C.13 epoxide using a nucleophilic peroxide agent, e.g., t-butyl hydroperoxide, which can then be converted into the compound of formula (IB), in which A$_1$ and R$_4$ combine to form oxo, using methods known in the art, e.g., by reacting with a bidentate phosphine ligand and a source of Pd(0) (see, e.g., Muzart, J., *Eur. J. Org. Chem.*, 4717-4741, 2011). Thus, the compound of formula (IB), in which A$_1$ is OP''', can be prepared. Other transformations may involve α-oxygenation to produce the compound of formula (VIB), in which R$_5$ is OP'''.

As described herein, one of skill in the art can identify the sequence of reactions involving hydroxyl protecting group removing agents and Brønsted acids to convert the compound of formula (IB) into a halichondrin macrolide.

C.2-C.3 Bond-Forming Macrocyclization

The macrocyclization reaction of the invention can be a carbon-carbon bond-forming reaction (e.g., catalytic Ring-Closing olefin Metathesis (RCM)) that provides a C.2-C.3 bond in a halichondrin macrolide. The general synthetic sequence including RCM that can be used to prepare the halichondrin macrolide is shown in FIG. 2. As shown in FIG. 2, the non-macrocyclic intermediate in the synthesis of the halichondrin macrolide can be a compound of formula (IIA):

(IIA)

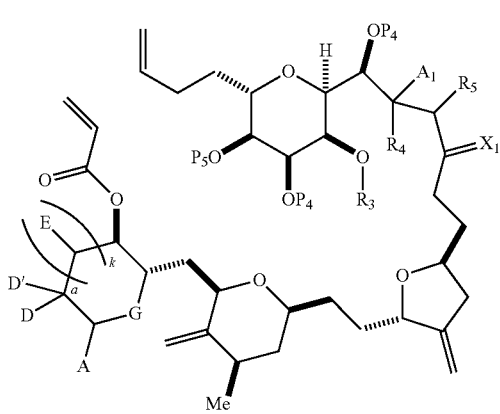

or a salt or a tautomer thereof,
in which
each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

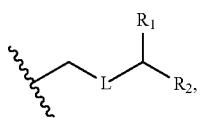  (1)

where
L is —(CH($OP_2$))—, —(C(OH)($OP_2$))—, or —C(O)—;
$R_1$ is H, or $R_1$ and $P_1$ combine to form a bond;
$R_2$ is H or —($CH_2$)$_n$$OP_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

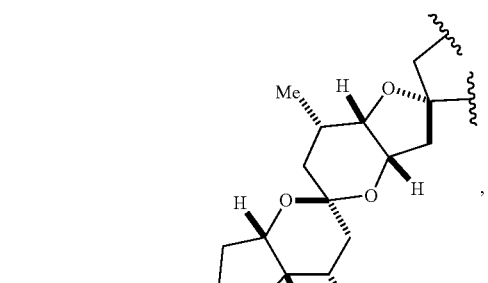

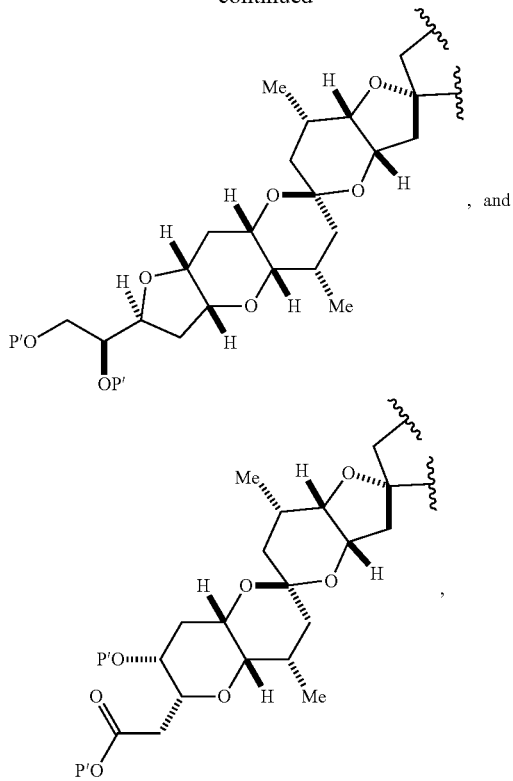

where each P' is independently H or a hydroxyl protecting group;
E is optionally substituted alkyl or optionally substituted alkoxy;
G is O, S, $CH_2$, or $NR_N$, where $R_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, (CO)$OR_A$, O(CO)$R_A$, (CO)$NR_BR_A$, or O(CO)$NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
k is 0 or 1;
n is 0, 1, or 2;
$A_1$ and $R_4$ combine to form oxo, $R_3$ is H or a hydroxyl protecting group, and $R_5$ is H;
or
$A_1$ is H or OP''', where P''' is H or a hydroxyl protecting group, and:
(i) $R_3$ is H or a hydroxyl protecting group, and $R_4$ and $R_5$ combine to form a double bond;
or
(ii) $R_3$ and $R_4$ combine to form a bond, and $R_5$ is H or OP''';
each $P_4$ is independently H or a hydroxyl protecting group, and $X_1$ is oxo or $X_1$, together with the carbon atom to which it is attached, is —(CH($OP_Y$))—, where $P_Y$ is H or a hydroxyl protecting group; or both $P_4$ groups and $X_1$, together with the atoms to which each is attached, combine to form ketal; and
$P_5$ is H or a hydroxyl protecting group.

In certain embodiments of the compound of formula (IIA), $R_3$ is H or a hydroxyl protecting group, $R_4$ and $R_5$ combine to form a double bond, $P_4$ is independently H or a hydroxyl protecting group, and $X_1$ is oxo. In particular embodiments of formula (IIA), $X_1$, together with the carbon atom to which it is attached, is —(CH(OP$_Y$))—, where P$_Y$ is H. In some embodiments of formula (IIA), $X_1$ is oxo. In other embodiments of the compound of formula (IIA), $R_3$ and $R_4$ combine to form a bond, and $R_5$ is H.

A macrocyclic intermediate in the synthesis of a halichondrin macrolide can be a compound of formula (IB), which can be produced by reacting the compound of formula (IIA) with an olefin metathesis catalyst. The compound of formula (IB) has the following structure:

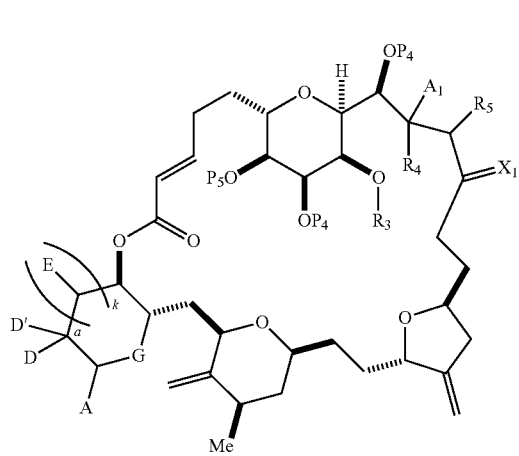

(IB)

or a salt or a tautomer thereof,
where all variables are as defined for compound of formula (IIA).

The catalysts that can be used to convert the compound of formula (IIA) to the compound of formula (IB) can be those known in the art. Olefin metathesis catalysts include Ru-carbene complexes (e.g., Grubbs and Hoveyda-Grubbs catalysts). Olefin metathesis-competent catalysts that may be used in this reaction are known in the art (e.g., second generation Hoveyda-Grubbs-type catalysts, e.g., those in which the Ru-benzylidene moiety is modified to include electron-withdrawing and/or electron-donating groups).

The compound of formula (IIA) or formula (IB), in which $X_1$, together with the carbon atom to which it is attached, is —(CH(OP$_Y$))—, where P$_Y$ is H, may be treated with an oxidizing agent capable of oxidizing hydroxyl to a carbonyl group (e.g., Dess-Martin periodinane or a dimethylsulfonium compound) to give the compound of formula (IIA) or formula (IB), in which $X_1$ is oxo.

The halichondrin macrolide can be prepared from the compound of formula (IB) as described herein.

C.3-C.4 Bond-Forming Macrocyclization

The macrocyclization reaction of the invention can be a carbon-carbon bond-forming reaction (e.g., catalytic Ring-Closing olefin Metathesis (RCM)) that provides a C.3-C.4 bond in a halichondrin macrolide. The general synthetic sequence including RCM that can be used to prepare the halichondrin macrolide is shown in FIG. 3. As shown in FIG. 3, the non-macrocyclic intermediate in the synthesis of the halichondrin macrolide can be a compound of formula (IIIA):

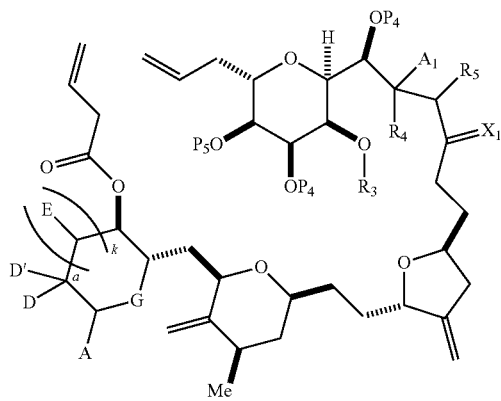

(IIIA)

or a salt or a tautomer thereof,
where
each of D and D' is independently H, optionally substituted alkyl, or OP$_1$, provided that only one of D and D' is OP$_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

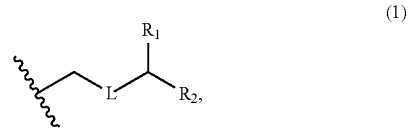

(1)

where
L is —(CH(OP$_2$))—, —(C(OH)(OP$_2$))—, or —C(O)—;
$R_1$ is H, or $R_1$ and $P_1$ combine to form a bond;
$R_2$ is H or —(CH$_2$)$_n$OP$_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

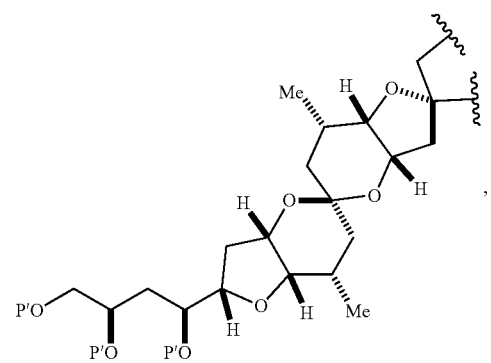

-continued

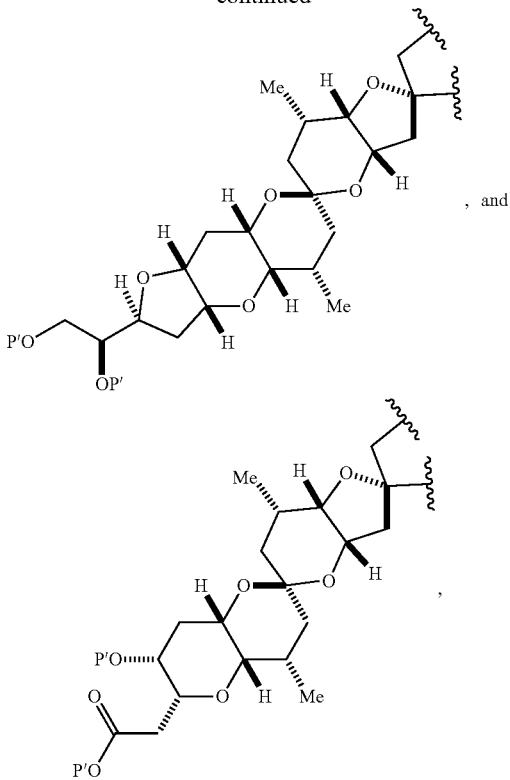

, and where each P' is independently H or a hydroxyl protecting group;
E is optionally substituted alkyl or optionally substituted alkoxy;
G is O, S, $CH_2$, or $NR_N$, where $R_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
k is 0 or 1;
n is 0, 1, or 2;
$A_1$ and $R_4$ combine to form oxo, $R_3$ is H or a hydroxyl protecting group, and $R_5$ is H;
or
$A_1$ is H or OP''', where P''' is H or a hydroxyl protecting group, and:
  (i) $R_3$ is H or a hydroxyl protecting group, and $R_4$ and $R_5$ combine to form a double bond;
  or
  (ii) $R_3$ and $R_4$ combine to form a bond, and $R_5$ is H or OP''';
each $P_4$ is independently H or a hydroxyl protecting group, and $X_1$ is oxo or $X_1$, together with the carbon atom to which it is attached, is —(CH(OP$_Y$))—, wherein P$_Y$ is H or a hydroxyl protecting group; or both $P_4$ groups and $X_1$, together with the atoms to which each is attached, combine to form ketal; and
$P_5$ is H or a hydroxyl protecting group.

In certain embodiments of the compound of formula (IIIA), $R_3$ is H or a hydroxyl protecting group, $R_4$ and $R_5$ combine to form a double bond, $P_4$ is independently H or a hydroxyl protecting group, and $X_1$ is oxo. In other embodiments of the compound of formula (IIIA), $R_3$ and $R_4$ combine to form a bond, and $R_5$ is H. In particular embodiments of formula (IIIA), $X_1$, together with the carbon atom to which it is attached, is —(CH(OP$_Y$))—, where P$_Y$ is H. In some embodiments of formula (IIIA), $X_1$ is oxo.

A macrocyclic intermediate in the synthesis of a halichondrin macrolide can be a compound of formula (IIIB), which can be produced by reacting the compound of formula (IIIA) with an olefin metathesis catalyst. The compound of formula (IIIB) has the following structure:

(IIIB)

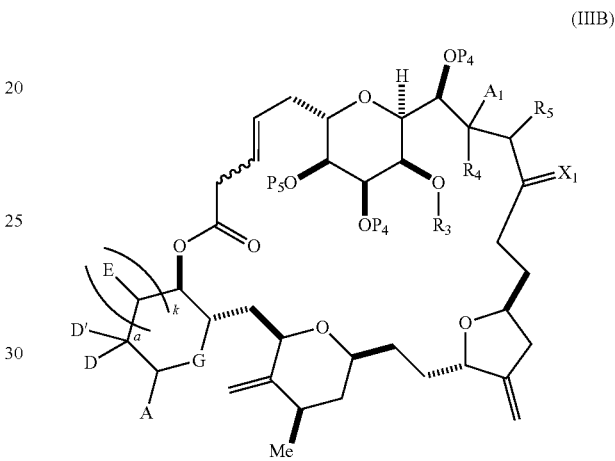

or a salt or a tautomer thereof,
where all variables are as defined for the compound of formula (IIIA).

The catalysts that can be used to convert the compound of formula (IIIA) to the compound of formula (IIIB) can be those known in the art. Olefin metathesis catalysts include Ru-carbene complexes (e.g., Grubbs and Hoveyda-Grubbs catalysts). Olefin metathesis-competent catalysts that may be used in this reaction are known in the art (e.g., second generation Hoveyda-Grubbs-type catalysts, e.g., those in which the Ru-benzylidene moiety is modified to include electron-withdrawing and/or electron-donating groups).

The halichondrin macrolide can be prepared from the compound of formula (IIIB), as described for the synthesis involving the compound of formula (IB), as the C.3-C.4 double bond can undergo isomerization to give the compound of formula (IB) described herein upon exposure to basic (e.g., isomerization mediated by a hydroxyl protecting group removing agent, such as a fluoride source) or acidic (e.g., isomerization mediated by a Brønsted acid) conditions.

The compound of formula (IIIA) or formula (IIIB), in which $X_1$, together with the carbon atom to which it is attached, is —(CH(OP$_Y$))—, where P$_Y$ is H, may be treated with an oxidizing agent capable of oxidizing hydroxyl to a carbonyl group to give the compound of formula (IIIA) or formula (IIIB), in which $X_1$ is oxo.

Preparation of the halichondrin macrolide may further involve conversion of the compound of formula (IIIB), in which $A_1$ is H, and $R_4$ and $R_5$ combine to form a double bond, into the compound of formula (VIB) in which $R_4$ and $A_1$ combine to form oxo. In a non-limiting example, the enone in the compound of formula (IIIB), in which $R_4$ and $R_5$ combine to form a double bond can be converted into a C.12-C.13 epoxide using a nucleophilic peroxide agent, e.g., t-butyl hydroperoxide, which can then be converted into the compound of formula (IIIB), in which $A_1$ and $R_4$ combine to form oxo, using methods known in the art, e.g., by reacting with a bidentate phosphine ligand and a source of Pd(0) (see, e.g., Muzart, J., *Eur. J. Org. Chem.*, 4717-4741, 2011). Thus, the halichondrin macrolide, in which $A_1$ is OP''', can be prepared. Other transformations may involve α-oxygenation to produce the halichondrin macrolide, in which $R_5$ is OP'''.

C.12-C.13 Bond-Forming Macrocyclization

The macrocyclization reaction of the invention can be a carbon-carbon bond-forming reaction (e.g., catalytic Ring-Closing olefin Metathesis (RCM)) that provides a C.12-C.13 bond in a halichondrin macrolide. The general synthetic sequence including RCM that can be used to prepare the halichondrin macrolide is shown in FIG. 4. As shown in FIG. 4, the non-macrocyclic intermediate in the synthesis of the halichondrin macrolide can be a compound of formula (IVA):

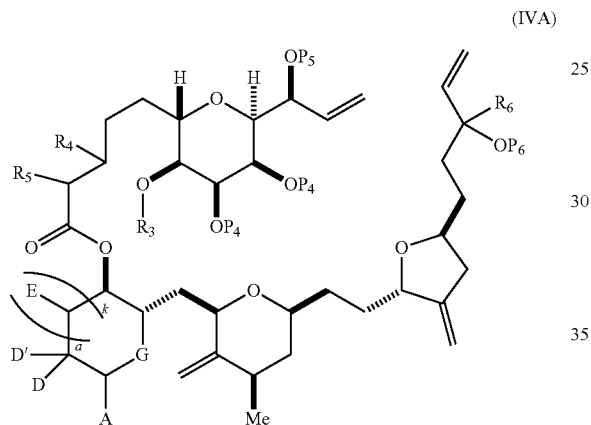

(IVA)

or a salt thereof,
where
each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

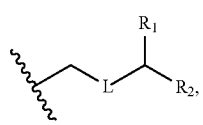

(1)

where
L is —(CH(OP$_2$))—, —(C(OH)(OP$_2$))—, or —C(O)—;
$R_1$ is H, or $R_1$ and $P_1$ combine to form a bond;
$R_2$ is H or —(CH$_2$)$_n$OP$_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

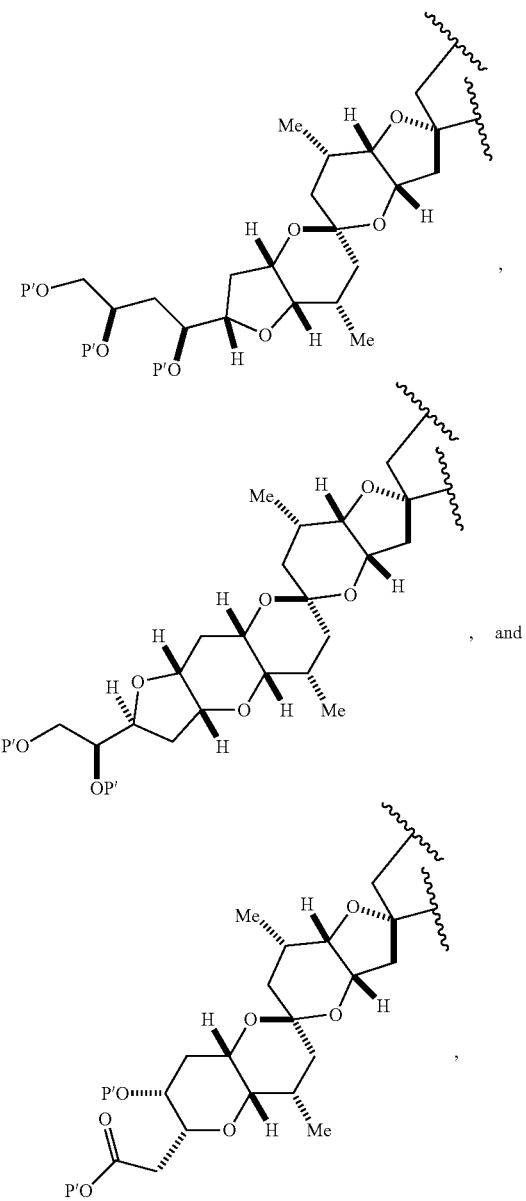

, and

, where each P' is independently H or a hydroxyl protecting group;
E is optionally substituted alkyl or optionally substituted alkoxy;
G is O, S, CH$_2$, or NR$_N$, where $R_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;
n is 0, 1, or 2;
(i) $R_3$ is H or a hydroxyl protecting group, $R_4$ is alkyl ether, and $R_5$ is H;
(ii) $R_3$ is H or a hydroxyl protecting group, and $R_4$ and $R_5$ combine to form a double bond;
or
(iii) $R_3$ and $R_4$ combine to form a bond, and $R_5$ is H;
each $P_4$ and $P_5$ is independently H or a hydroxyl protecting group; and
$R_6$ is H, and $P_6$ is H or a hydroxyl protecting group; or $R_6$ and $P_6$ combine to form a double bond.

In certain embodiments of the compound of formula (IVA), $P_5$ is H. In particular embodiments of the compound of formula (IVA), $R_3$ and $R_4$ combine to form a bond, and $R_5$ is H. In some embodiments, $R_6$ is H, and $P_6$ is H or a hydroxyl protecting group. In other embodiments, $R_6$ and $P_6$ combine to form a double bond.

A macrocyclic intermediate in the synthesis of a halichondrin macrolide can be a compound of formula (IVB), which can be produced by reacting the compound of formula (IVA) with an olefin metathesis catalyst. The compound of formula (IVB) has the following structure:

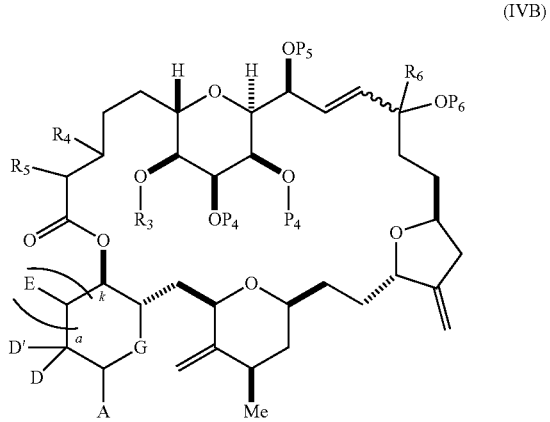

(IVB)

or a salt thereof,
where all variables are as defined for the compound of formula (IVA).

The catalysts that can be used to convert the compound of formula (IVA) to the compound of formula (IVB) can be those known in the art. Olefin metathesis catalysts include Ru-carbene complexes (e.g., Grubbs and Hoveyda-Grubbs catalysts). Olefin metathesis-competent catalysts that may be used in this reaction are known in the art (e.g., second generation Hoveyda-Grubbs-type catalysts, e.g., those in which the Ru-benzylidene moiety is modified to include electron-withdrawing and/or electron-donating groups).

The compound of formula (IVB) (e.g., the compound of formula (IVB), in which $R_6$ and $P_6$ combine to form a double bond) can be converted to the halichondrin macrolide by a reaction with a Brønsted acid (if each of $P_4$ and $P_5$ is independently H or a hydroxyl protecting group capable of being deprotected by the Brønsted acid). Alternatively, if at least one $P_4$ or $P_5$ is a hydroxyl protecting group that is not capable of being deprotected by the Brønsted acid, the compound of formula (IVB) can be reacted with a hydroxyl protecting group removing agent to effect the removal of at least one hydroxyl protecting group, provided that the product of the reaction is the compound of formula (IVC):

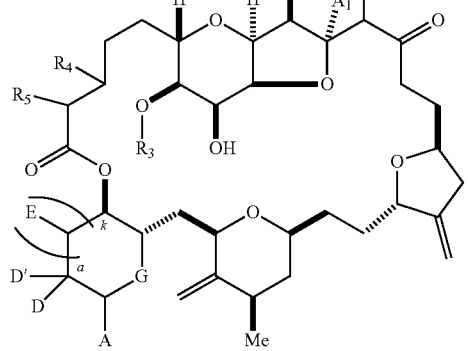

(IVC)

or a salt thereof,
where each of $A_1$ and $A_2$ is H or OP‴, where P‴ is H or a hydroxyl protecting group;
and the remaining variables are as defined for the compound of formula (IVA).

In a non-limiting example of the transformation of the compound of formula (IVB) to provide the compound of formula (IVC), at least one of $P_4$ and $P_5$ is a silyl, and the hydroxyl protecting group removing agent is a fluoride source.

The compound of formula (IVC) can then be converted to the halichondrin macrolide by a reaction with a Brønsted acid.

If, in the compound of formula (IVB) or (IVC), $R_3$ is a hydroxyl protecting group, and $R_4$ and $R_5$ combine to form a double bond, treatment with a hydroxyl protecting group removing agent can provide the compound of formula (IVB) or (IVC), in which $R_3$ and $R_4$ combine to form a bond, and $R_5$ is H.

Preparation of the compound of formula (IVC) from the compound of formula (IVB) may further involve reaction with a hydroxyl protecting group removing agent to convert $P_6$ in the compound of formula (IVB) to H and subsequent reaction with an oxidizing agent capable of converting a hydroxyl group into a carbonyl (e.g., capable of oxidizing allylic alcohol into an enone). In a non-limiting example, the enone in the compound of formula (IVB) formed through the oxidation can then be converted into a C.12-C.13 epoxide using a nucleophilic peroxide agent, e.g., t-butyl hydroperoxide, which can then be converted into the compound of formula (IVB), in which $A_1$ and $R_4$ combine to form oxo, using methods known in the art, e.g., by reacting with a bidentate phosphine ligand and a source of Pd(0) (see, e.g., Muzart, J., Eur. J. Org. Chem., 4717-4741, 2011). Thus, the compound of formula (IVC), in which $A_1$ is OP‴, can be prepared. Other transformations may involve α-oxygenation to produce the compound of formula (IVC), in which $A_2$ is OP‴.

As described herein, one of skill in the art can identify the sequence of reactions involving the reactions described above to convert the compound of formula (IVB) into a halichondrin macrolide with or without the isolation of the compound of formula (IVC).

C.15-C.16 Bond-Forming Macrocyclization

Figure 5:
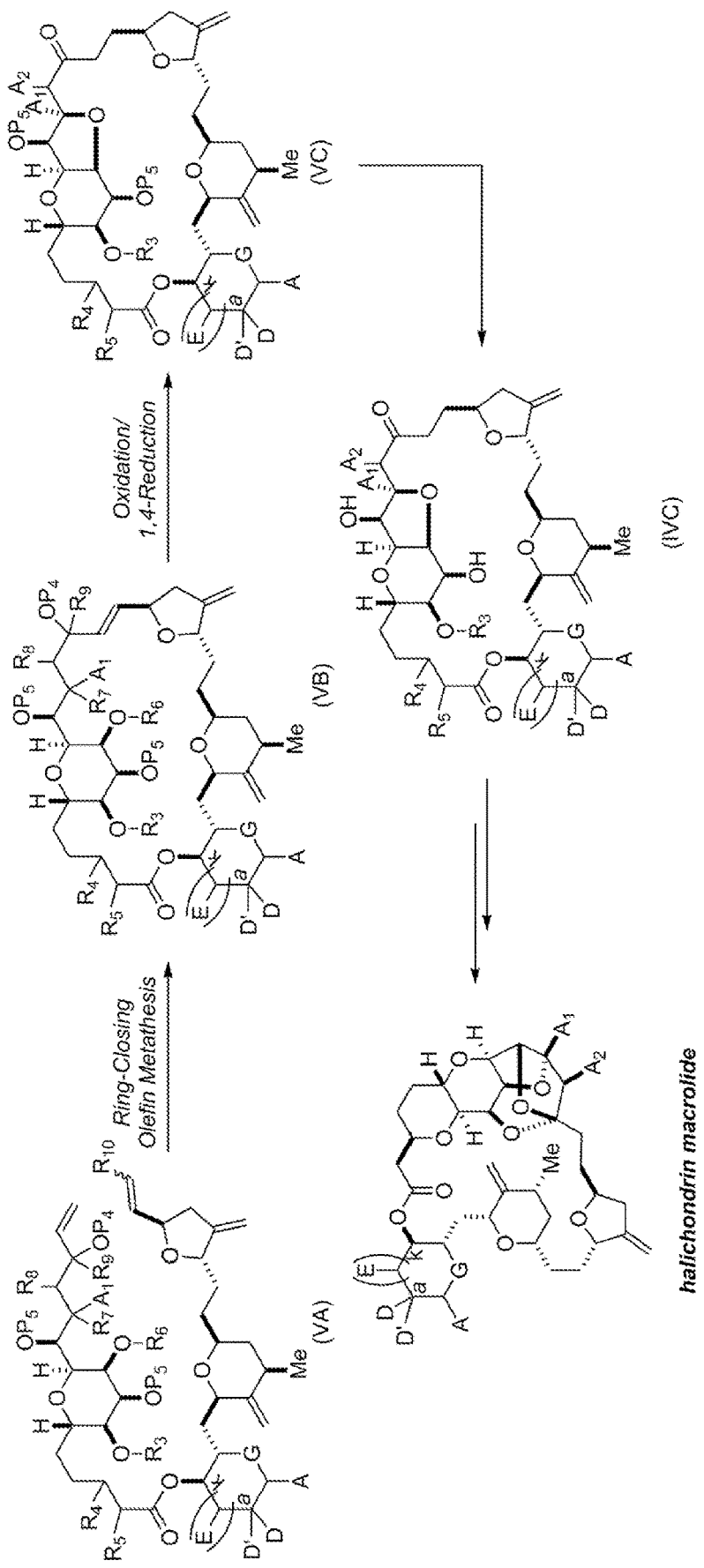
FIG. 5 is a scheme showing preparation of a halichondrin macrolide involving a C.15-C.16 bond-forming macrocyclization through ring-closing olefin metathesis.

The macrocyclization reaction of the invention can be a carbon-carbon bond-forming reaction (e.g., catalytic Ring-Closing olefin Metathesis (RCM)) that provides a C.15-C.16 bond in a halichondrin macrolide. The general synthetic sequence including RCM that can be used to prepare the halichondrin macrolide is shown in FIG. 5. As shown in FIG. 5, the non-macrocyclic intermediate in the synthesis of the halichondrin macrolide can be a compound of formula (VA):

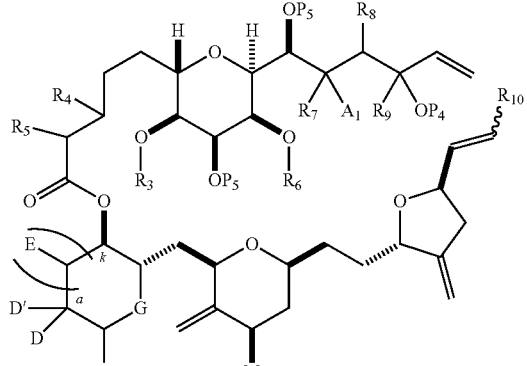

(VA)

or a salt or a tautomer thereof, where each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

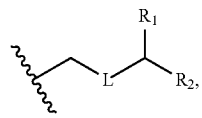

(1)

where

L is $-(CH(OP_2))-$, $-(C(OH)(OP_2))-$, or $-C(O)-$;

$R_1$ is H, or $R_1$ and $P_1$ combine to form a bond;

$R_2$ is H or $-(CH_2)_nOP_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

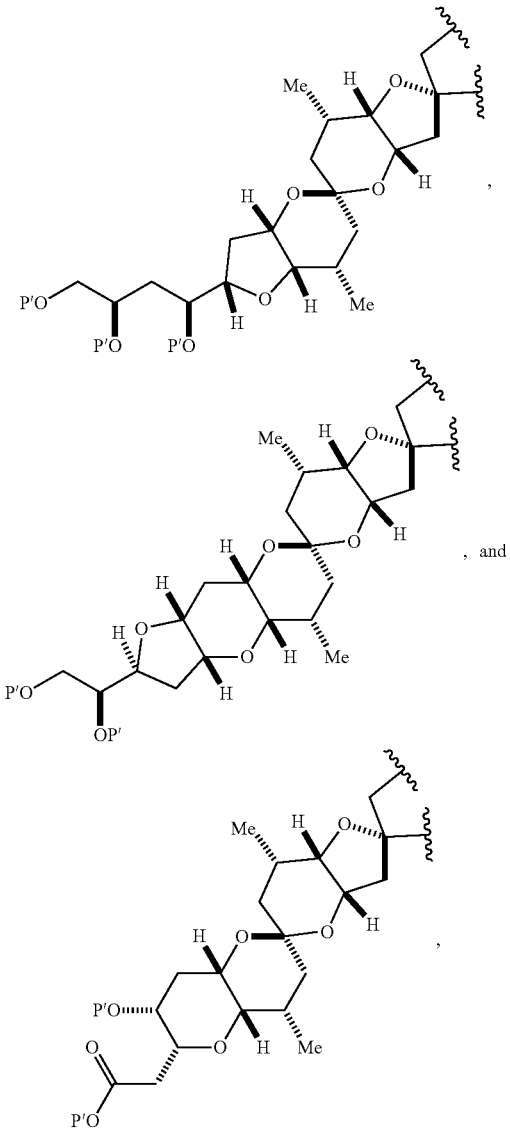

, and

, where each P' is independently H or a hydroxyl protecting group;

E is optionally substituted alkyl or optionally substituted alkoxy;

G is O, S, $CH_2$, or $NR_N$, where $R_N$ is H, an N-protecting group, or optionally substituted alkyl;

each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2;

(a1) $R_3$ is H or a hydroxyl protecting group, $R_4$ is alkyl ether, and $R_5$ is H;

(a2) $R_3$ is H or a hydroxyl protecting group, and $R_4$ and $R_5$ combine to form a double bond;

or (a3) $R_3$ and $R_4$ combine to form a bond, and $R_5$ is H;

(b1) $A_1$ and $R_7$ combine to form oxo, $R_6$ is H or a hydroxyl protecting group, and $R_8$ is H;

or (b2) $A_1$ is H or OP''', where P''' is H or a hydroxyl protecting group, and:

(i) $R_6$ is H or a hydroxyl protecting group, and $R_7$ and $R_8$ combine to form a double bond;

or (ii) $R_6$ and $R_7$ combine to form a bond, and $R_8$ is H or OP''';

(c1) $R_9$ is H, and $P_4$ is H or a hydroxyl protecting group;

or (c2) $R_9$ and $P_4$ combine to form a double bond;

$R_{10}$ is H or $-CH_2X_1CH_2CH=CH_2$, where $X_1$ is O, $-C(R_{11})_2-$, or $NP_6$, and where each $R_{11}$ is independently H or $-COOR_{12}$, $P_6$ is an N-protecting group, and $R_{12}$ is alkyl; and each $P_5$ is independently H or a hydroxyl protecting group.

In certain embodiments of the compound of formula (VA), $R_6$ and $R_7$ combine to form a bond, and $R_8$ is H. In particular embodiments of the compound of formula (VA), $R_3$ and $R_4$ combine to form a bond, and $R_5$ is H. In some embodiments of the compound of formula (VA), each $P_5$ is independently a hydroxyl protecting group. In further embodiments of the compound of formula (VA), $R_9$ is H, and $P_4$ is a hydroxyl protecting group. In other embodiments, $A_1$ is H.

A macrocyclic intermediate in the synthesis of a halichondrin macrolide can be a compound of formula (VB), which can be produced by reacting the compound of formula (VA) with an olefin metathesis catalyst. The compound of formula (VB) has the following structure:

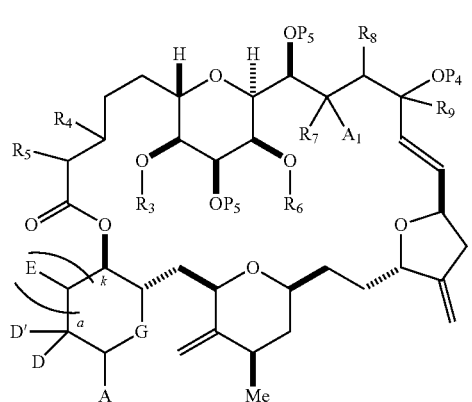

(VB)

or a salt or a tautomer thereof, where all variables are as defined for the compound of formula (VA).

The catalysts that can be used to convert the compound of formula (VA) to the compound of formula (VB) can be those known in the art. Olefin metathesis catalysts include Ru-carbene complexes (e.g., Grubbs and Hoveyda-Grubbs catalysts). Olefin metathesis-competent catalysts that may be used in this reaction are known in the art (e.g., second generation Hoveyda-Grubbs-type catalysts, e.g., those in which the Ru-benzylidene moiety is modified to include electron-withdrawing and/or electron-donating groups).

The compound of formula (VB) can be reacted with a hydroxyl protecting group removing agent and, optionally, an oxidizing agent (e.g., when $R_9$ is H in the compound of formula (VB)) capable of converting an alcohol to a carbonyl group (e.g., capable of converting an allylic alcohol to an enone) to afford the compound of formula (VBa):

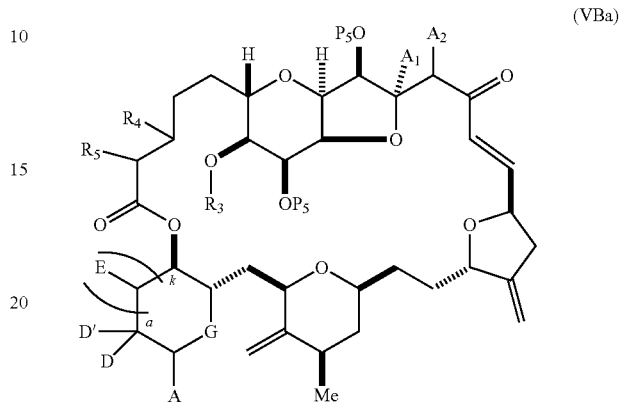

(VBa)

or a salt thereof, where $A_2$ is H or OP''', and the remaining variables are as defined for the compound of formula (VA).

The compound of formula (VBa) can be reacted with a 1,4-reducing agent to furnish the compound of formula (VC):

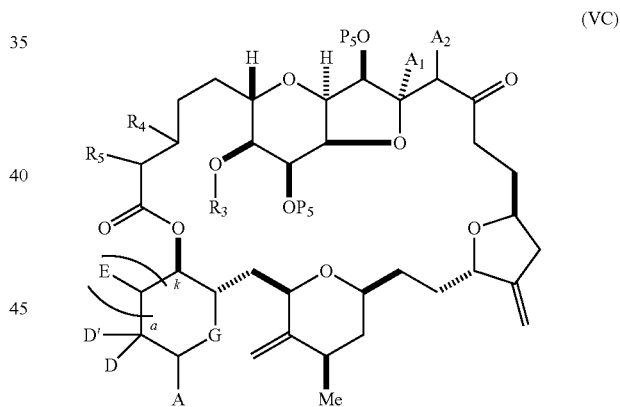

(VC)

or a salt thereof, where all variables are as defined for the compound of formula (VBa).

The 1,4-reducing agents include copper (I) hydrides, which can be isolated (e.g., Stryker's reagent) or prepared in situ (e.g., from a copper (I) or copper (II) salt and a hydride source). Catalytic quantities of a copper salt (either copper (I) or copper (I) salt) in combination with stoichiometric or superstoichiometric quantities of a hydride source (e.g., a borohydride salt, borane, PMHS, or a hydrosilane (e.g., $Ph_2SiH_2$)). A non-limiting example of the reaction conditions that can be used in the reaction sequence from the compound of formula (VB) to the compound of formula (VC) are described, e.g., in Baker et al., *Org. Lett.*, 10:289-292, 2008, the disclosure of which is incorporated herein by reference. Other metals can be used to catalyze 1,4-reduction, e.g., Ru, Pd, and Ir compounds.

Alternatively, if $R_9$ and $P_4$ combine to form a double bond in the compound of formula (VB), the reaction of the compound of formula (VB) with a hydroxyl protecting group removing agent can furnish the compound of formula (VC) directly.

If the compound of formula (VC) includes hydroxyl protecting groups as $P_5$, these hydroxyl protecting groups can be removed with a hydroxyl protecting group removing agent to give the compound of formula (IVC):

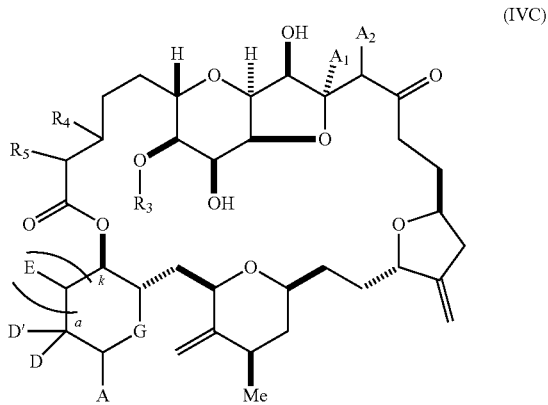

(IVC)

or a salt thereof,
where all variables are as defined for the compound of formula (VBa).

The halichondrin macrolide can be prepared from the compound of formula (IVC) as described herein.

C.19-C.20 Bond-Forming Macrocyclization

Figure 6:
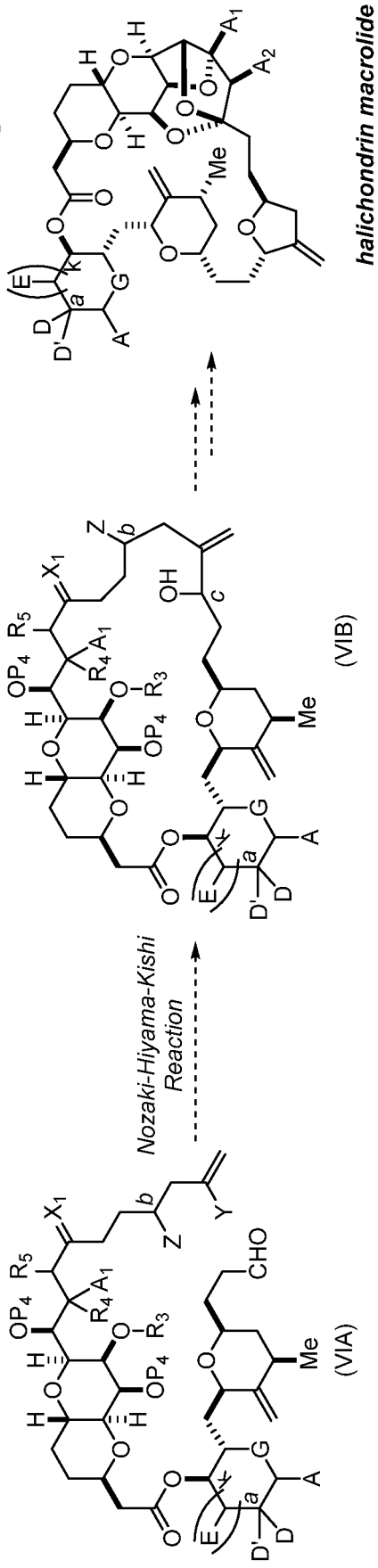
FIG. 6 is a scheme showing preparation of a halichondrin macrolide involving a C.19-C.20 bond-forming macrocyclization through Nozaki-Hiyama-Kishi reaction.

The macrocyclization reaction of the invention can be a carbon-carbon bond-forming reaction (e.g., Nozaki-Hiyama-Kishi reaction (NHK)) that provides a C.19-C.20 bond in a halichondrin macrolide. The general synthesis sequence including NHK that can be used to prepare the halichondrin macrolide is shown in FIG. 6. As shown in FIG. 6, the non-macrocyclic intermediate in the synthesis of the halichondrin macrolide can be a compound of formula (VIA):

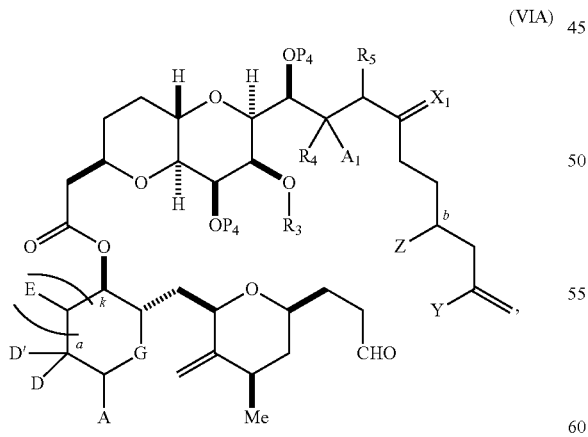

(VIA)

or a salt or a tautomer thereof,
where
b designates (R)-stereogenic center, and Z is a sulfonate, chloride, bromide, or iodide; or b designates (S)-stereogenic center, and Z is $OR_6$, where $R_6$ is a hydroxyl protecting group;

each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

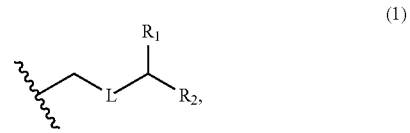

(1)

where
L is —(CH(OP_2))—, —(C(OH)(OP_2))—, or —C(O)—;

$R_1$ is H, or $R_1$ and $P_1$ combine to form a bond;

$R_2$ is H or —(CH_2)_nOP_3, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

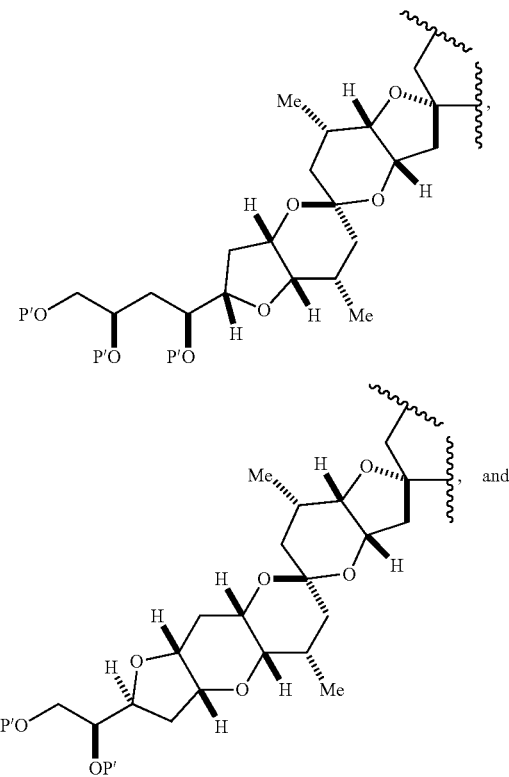

-continued

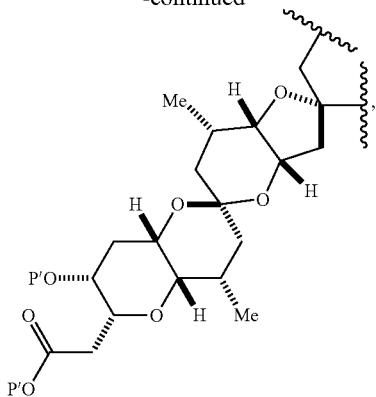

where each P' is independently H or a hydroxyl protecting group;

E is optionally substituted alkyl or optionally substituted alkoxy;

G is O, S, $CH_2$, or $NR_N$, where $R_N$ is H, an N-protecting group, or optionally substituted alkyl;

each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2;

Y is iodide, bromide, or trifluoromethanesulfonate;

$A_1$ and $R_4$ combine to form oxo, $R_3$ is H or a hydroxyl protecting group, and $R_5$ is H;

or $A_1$ is H or OP''', where P''' is H or a hydroxyl protecting group, and:

(i) $R_3$ is H or a hydroxyl protecting group, and $R_4$ and $R_5$ combine to form a double bond;

or (ii) $R_3$ and $R_4$ combine to form a bond, and $R_5$ is H or OP''';

and each $P_4$ is independently H or a hydroxyl protecting group, and $X_1$ is oxo; or both $P_4$ groups and $X_1$, together with the atoms to which each is attached, combine to form ketal.

In particular embodiments of the compound of formula (VIA), $R_3$ and $R_4$ combine to form a bond, and $R_5$ is H. In some embodiments of the compound of formula (VIA), both $P_4$ groups and $X_1$, together with the atoms to which each is attached, combine to form ketal.

An intermediate in the synthesis of the halichondrin macrolide can be a compound of formula (VIB), which can be produced by subjecting the compound of formula (VIA) to Nozaki-Hiyama-Kishi reaction conditions (e.g., by reacting with a Cr(II) salt and a Ni(II) salt). The compound of formula (VIB) has the following structure:

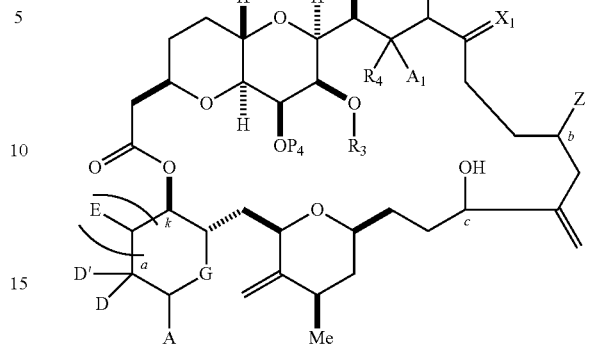

or a salt or a tautomer thereof, where b designates (R)-stereogenic center, c designates (S)-stereogenic center, and Z is a sulfonate, chloride, bromide, or iodide;

or b designates (S)-stereogenic center, c designates (R)-stereogenic center, and Z is $OR_6$, where $R_6$ is a hydroxyl protecting group;

and the remaining variables are as defined for the compound of formula (VIA).

Nozaki-Hiyama-Kishi reaction conditions that may be used to prepare the compound of formula (VIB) from the compound of formula (VIA) can be those known in the art. Nozaki-Hiyama-Kishi reaction on the compound of formula (VIA) can include reacting the compound of formula (VIA) with a Cr(II) salt and a Ni(II) salt. Ancillary ligands can be used in combination with the metal salts. In a non-limiting example, a substituted 1,10-phenanthroline can be used in combination with a Ni(II) salt. Chiral ancillary ligands can be used to render the reaction stereoselective. In a non-limiting example, chiral N-(dihydrooxazolyl-phenyl)-sulfonamides can be used with a Cr(II) salt to control the stereochemistry of the carbonyl carbon, to which a vinyl nucleophile is added in the course of Nozaki-Hiyama-Kishi reaction.

The compound of formula (VIB) can be converted to the halichondrin macrolide using the step of nucleophilic ring-closing of the compound of formula (VIB).

In particular, the compound of formula (VIB) (in which Z is a sulfonate, chloride, bromide, or iodide; b designates (R)-stereogenic center; and c designates (S)-stereogenic center) can be converted to the halichondrin macrolide directly, e.g., upon isolation from the Nozaki-Hiyama-Kishi reaction mixture (e.g., by treatment with a base) or by contacting a mixture containing the product of the Nozaki-Hiyama-Kishi reaction with silica gel. Additionally, the compound of formula (VIB) can be reacted with a hydroxyl protecting group removing agent (before or after the step of nucleophilic ring-closing) if, e.g., each of $P_4$ is a hydroxyl protecting group, optionally, with a subsequent reaction with a Brønsted acid to form a compound, in which both $P_4$ groups and $X_1$, together with the atoms to which each is attached, combine to form ketal.

Alternatively, if, in the compound of formula (VIB), b designates (S)-stereogenic center, c designates (R)-stereogenic center, and Z is $OR_6$, where $R_6$ is a hydroxyl protecting group, the step of nucleophilic ring-closing of the compound of formula (VIB) can be effected after the hydroxyl group attached to the carbon atom designated with c is converted into a leaving group (e.g., a sulfonate by a reaction with a sulfonyl electrophile, such as a sulfonyl chloride or a sulfonyl anhydride). In these embodiments, the step of nucleophilic ring-closing can be carried out by, e.g., first, reacting the compound of formula (VIB), after the conversion of the hydroxyl into the leaving group, with a hydroxyl protecting group removing agent to convert $R_6$ into H and then reacting the product with a base.

Preparation of certain compounds of formula (VIB) may further involve conversion of the compound of formula (VIB), in which $A_1$ is H, and $R_4$ and $R_5$ combine to form a double bond, into the compound of formula (VIB) in which $R_4$ and $A_1$ combine to form oxo. In a non-limiting example, the enone in the compound of formula (VIB), in which $R_4$ and $R_5$ combine to form a double bond can be converted into a C.12-C.13 epoxide using a nucleophilic peroxide agent, e.g., t-butyl hydroperoxide, which can then be converted into the compound of formula (VIB), in which $A_1$ and $R_4$ combine to form oxo, using methods known in the art, e.g., by reacting with a bidentate phosphine ligand and a source of Pd(0) (see, e.g., Muzart, *J., Eur. J. Org. Chem.*, 4717-4741, 2011). Thus, the compound of formula (VIB), in which $A_1$ is OP''', can be prepared. Other transformations may involve α-oxygenation to produce the compound of formula (VIB), in which $R_5$ is OP'''.

One of skill in the art will recognize that any unprotected hydroxyl groups can be protected with a hydroxyl protecting group, if the unprotected hydroxyl groups are not intended for reacting in the step of nucleophilic ring-closing.

C.26-C.27 Bond-Forming Macrocyclization

Figure 7:
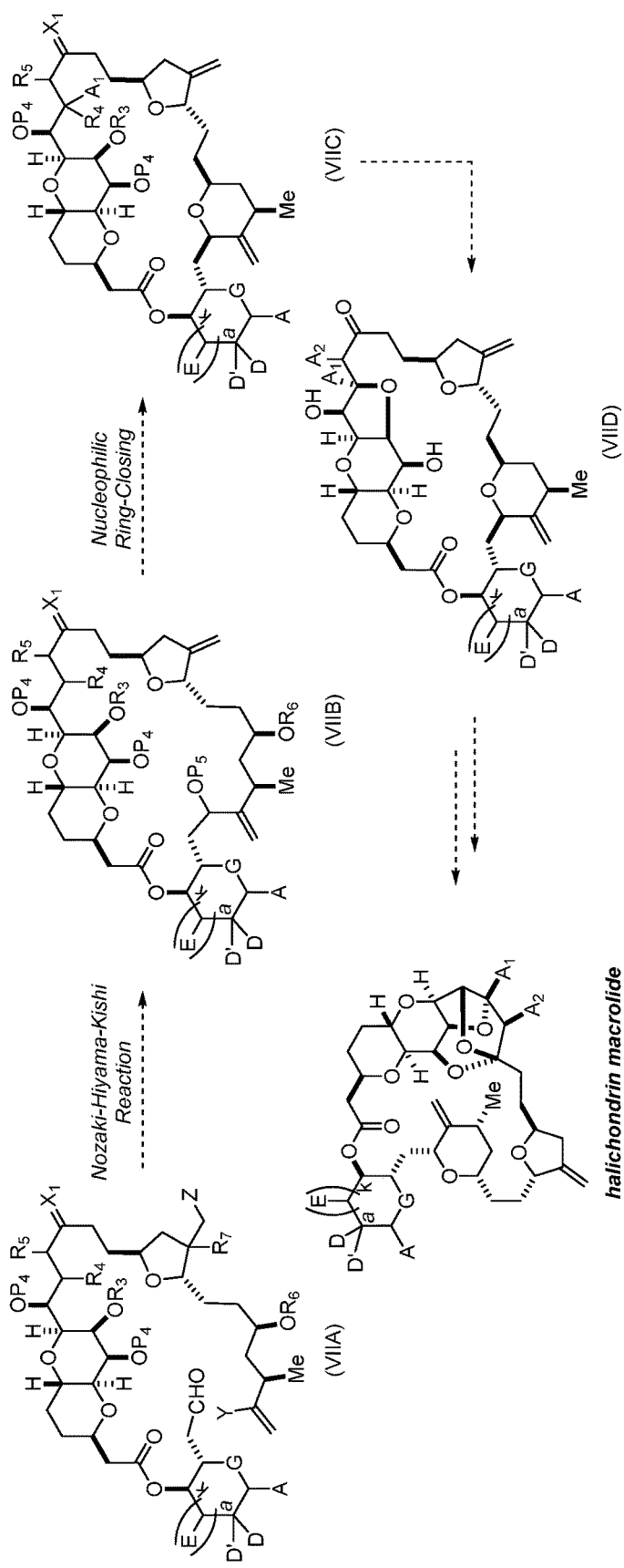
FIG. 7 is a scheme showing preparation of a halichondrin macrolide involving a C.26-C.27 bond-forming macrocyclization through Nozaki-Hiyama-Kishi reaction.

The macrocyclization reaction of the invention can be a carbon-carbon bond-forming reaction (e.g., Nozaki-Hiyama-Kishi reaction (NHK)) that provides a C.26-C.27 bond in a halichondrin macrolide. The general synthesis sequence including NHK that can be used to prepare the halichondrin macrolide is shown in FIG. 7. As shown in FIG. 7, the non-macrocyclic intermediate in the synthesis of the halichondrin macrolide can be a compound of formula (VIIA):

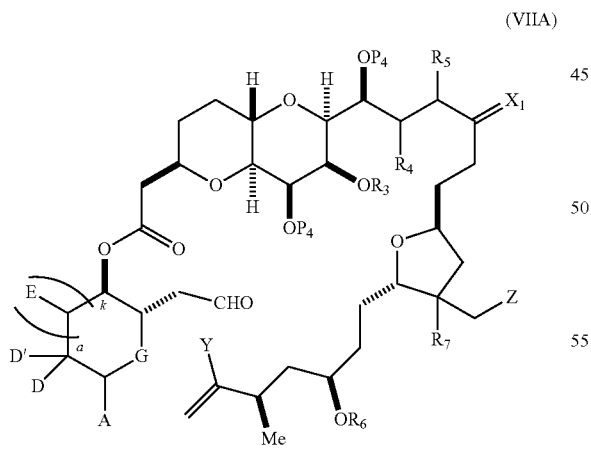

where
each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

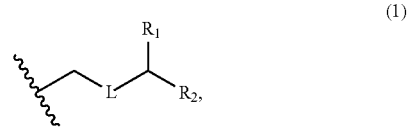

where

L is —(CH(OP$_2$))—, —(C(OH)(OP$_2$))—, or —C(O)—;

$R_1$ is H, or $R_1$ and $P_1$ combine to form a bond;

$R_2$ is H or —(CH$_2$)$_n$OP$_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

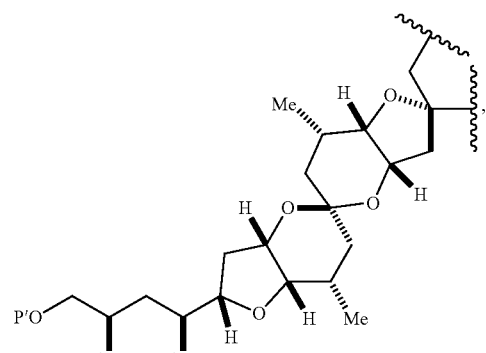

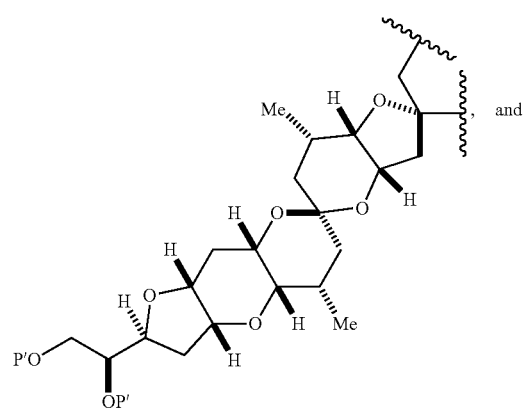

-continued

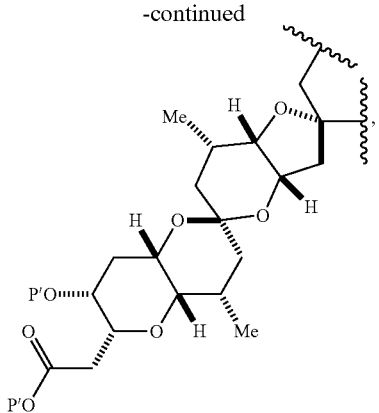

where each P' is independently H or a hydroxyl protecting group;
  E is optionally substituted alkyl or optionally substituted alkoxy;
  G is O, S, $CH_2$, or $NR_N$, where $R_N$ is H, an N-protecting group, or optionally substituted alkyl;
  each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
  k is 0 or 1;
  n is 0, 1, or 2;
  Y is iodide, bromide, or trifluoromethanesulfonate; and
  (a1) $R_3$ is H or a hydroxyl protecting group, $R_4$ and $R_5$ combine to form a double bond, each $P_4$ is independently H or a hydroxyl protecting group, and $X_1$, together with the carbon to which it is attached, forms a carbonyl or —$(CH(OR_8))$—, where $R_8$ is H or a hydroxyl protecting group;
  or
  (a2) $R_3$ and $R_4$ combine to form a bond, $R_5$ is H, and each $P_4$ is independently H or a hydroxyl protecting group, and $X_1$, together with the carbon to which it is attached, forms a carbonyl or —$(CH(OR_8))$—;
  or
  both $P_4$ groups and $X_1$, together with the atoms to which each is attached, combine to form ketal;
  (b1) Z is chloride, bromide, or iodide, and $R_6$ and $R_7$ combine to form a bond;
  or
  (b2) Z and $R_7$ combine to form a double bond, and $R_6$ is H or a hydroxyl protecting group.

In particular embodiments of the compound of formula (VIIA), Z and $R_7$ combine to form a double bond, and $R_6$ is a hydroxyl protecting group. In some embodiments of the compound of formula (VIIA), each $P_4$ is independently H or a hydroxyl protecting group, and $X_1$, together with the carbon to which it is attached, forms a carbonyl or —(CH($OR_8$))—. In certain embodiments of the compound of formula (VIIA), $R_3$ is H or a hydroxyl protecting group, $R_4$ and $R_5$ combine to form a double bond.

An intermediate in the synthesis of the halichondrin macrolide can be a compound of formula (VIIB), which can be produced by subjecting the compound of formula (VIIA) to Nozaki-Hiyama-Kishi reaction conditions (e.g., by reacting with a Cr(II) salt and a Ni(II) salt). The compound of formula (VIIB) has the following structure:

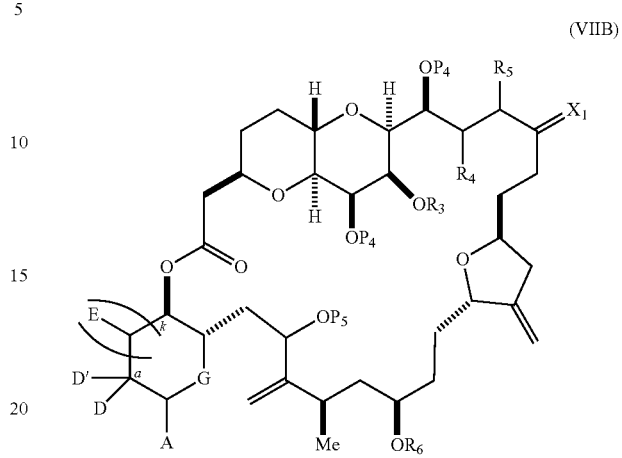

(VIIB)

or a salt thereof,
  where each of $P_5$ and $R_6$ is independently H or a hydroxyl protecting group, and the remaining variables are as defined for the compound of formula (VIIA).

Nozaki-Hiyama-Kishi reaction conditions that may be used to prepare the compound of formula (VIIB) from the compound of formula (VIIA) can be those known in the art. Nozaki-Hiyama-Kishi reaction on the compound of formula (VIIA) can include reacting the compound of formula (VIIA) with a Cr(II) salt and a Ni(II) salt. Ancillary ligands can be used in combination with the metal salts. In a non-limiting example, a substituted 1,10-phenanthroline can be used in combination with a Ni(II) salt. Chiral ancillary ligands can be used to render the reaction stereoselective. In a non-limiting example, chiral N-(dihydrooxazolyl-phenyl)-sulfonamides can be used with a Cr(II) salt to control the stereochemistry of the carbonyl carbon, to which a vinyl nucleophile is added in the course of Nozaki-Hiyama-Kishi reaction.

The compound of formula (VIIB) can be converted to a compound of formula (VIIC) through the step of nucleophilic ring-closing of the compound of formula (VIIB), where the compound of formula (VIIC) has the following structure:

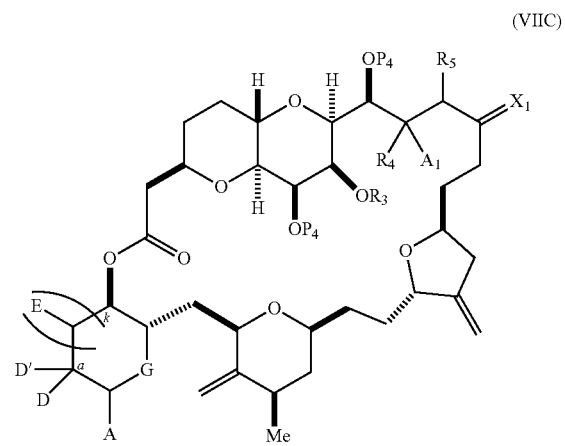

(VIIC)

or a salt or a tautomer thereof, where each $P_4$ is H or a hydroxyl protecting group, and $X_1$ is oxo; or both $P_4$ groups and $X_1$, together with the atoms to which each is attached, combine to form a ketal;

$A_1$ and $R_4$ combine to form oxo, $R_3$ is H or a hydroxyl protecting group, and $R_5$ is H;

or $A_1$ is H or OP'", where P'" is H or a hydroxyl protecting group, and:
  (i) $R_3$ is H or a hydroxyl protecting group, and $R_4$ and $R_5$ combine to form a double bond;
  or
  (ii) $R_3$ and $R_4$ combine to form a bond, and $R_5$ is H or OP'";

and the remaining variables are as defined for the compound of formula (VIIA).

The step of nucleophilic ring-closing of the compound of formula (VIIB) can be effected after the hydroxyl group produced by the NHK reaction is converted into a leaving group (e.g., a sulfonate by a reaction with a sulfonyl electrophile, such as a sulfonyl chloride or a sulfonyl anhydride). In these embodiments, the step of nucleophilic ring-closing can be carried out by reacting the compound of formula (VIB), in which $R_6$ is H, after the conversion of the hydroxyl into the leaving group, with a strong base (e.g., alkoxide).

Preparation of the compound of formula (VIIC) can involve Vasella fragmentation prior to the step of nucleophilic ring-closing, if Z and $R_7$ combine to form a double bond, and $R_6$ is a hydroxyl protecting group in the compound of formula (VIIB).

The compound of formula (VIIC) can be reacted with a hydroxyl protecting group removing agent to give a compound of formula (VIID):

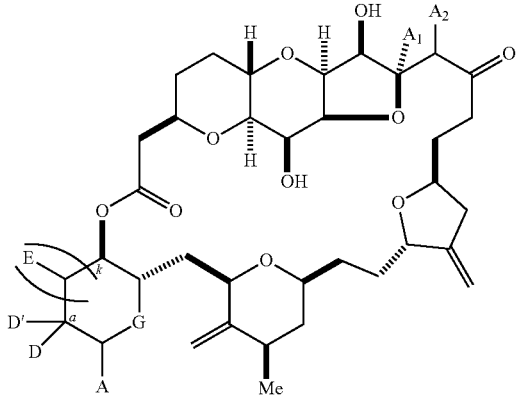

(VIID)

or a salt thereof, where each of $A_1$ and $A_2$ is independently H or OP'", and the remaining variables are as defined for the compound of formula (VIIC).

The compound of formula (VIID) can be converted to the halichondrin macrolide by reacting with a Brønsted acid (e.g., a pyridinium salt, such as pyridinium p-toluene sulfonate).

In some embodiments, the preparation of the halichondrin macrolide from the compound of formula (VIIA) can further involve an oxidation reaction (e.g., contacting the compound of formula (VIIA), (VIIB), or (VIIC), in which $X_1$ is —(CH(OR$_8$))— and $R_8$ is H, with an oxidizing agent capable of oxidizing an alcohol to a carbonyl group).

Preparation of the compound of formula (VIID) from the compound of formula (VIIB) may further involve conversion of the compound of formula (VIIB), in which $R_4$ and $R_5$ combine to form a double bond into the compound of formula (VIIC) in which $R_4$ and $A_1$ combine to form oxo. In a non-limiting example, the enone in the compound of formula (VIIB), in which $R_4$ and $R_5$ combine to form a double bond can be converted into a C.12-C.13 epoxide using a nucleophilic peroxide agent, e.g., t-butyl hydroperoxide, which can then be converted into the compound of formula (VIIC), in which $A_1$ and $R_4$ combine to form oxo, using methods known in the art, e.g., by reacting with a bidentate phosphine ligand and a source of Pd(0) (see, e.g., Muzart, J., Eur. J. Org. Chem., 4717-4741, 2011). Thus, the compound of formula (VIID), in which $A_1$ is OP'", can be prepared. Other transformations may involve α-oxygenation to produce the compound of formula (VIID), in which $A_2$ is OP'".

One of skill in the art will recognize that any unprotected hydroxyl groups can be protected with a hydroxyl protecting group, if the unprotected hydroxyl groups are not intended for reacting in the step of nucleophilic ring-closing.

Synthesis of Non-Macrocyclic Intermediates

The compounds of formula (IA), (IIA), (IIIA), (IVA), (VA), (VIA), and (VIIA) can be prepared using methods and intermediates disclosed, e.g., in U.S. Pat. Nos. 5,338,865 and 5,436,238; in International Patent application No. PCT/US2014/063960; and in Towle et al., Annual Meeting of the American Association for Cancer Research, Apr. 6-10, 2002, 5721; Wang et al., Bioorg. Med. Chem. Lett., 10:1029-1032, 2000; Aicher et al., J. Am. Chem. Soc., 114:3162-3164, 1992; Ueda et al., J. Am. Chem. Soc., 136:5171-5176; and Yamamoto et al., J. Am. Chem. Soc., 134:893-896, 2012; each of which is incorporated herein by reference in its entirety.

Compound (IA)

The compound of formula (IA) can be prepared using methods described in the references incorporated by reference above. In particular, the compound of formula (IA) can be prepared from compound (IC), in which $P_X$ is H, and compound (ID), e.g., using esterification reaction conditions (e.g., Shiina esterification reaction conditions (e.g., using MNBA) or Yamaguchi esterification reaction conditions, e.g., the reaction conditions described in Aicher et al., J. Am. Chem. Soc., 114:3162-3164, 1992).

The compound of formula (IC) has the following structure

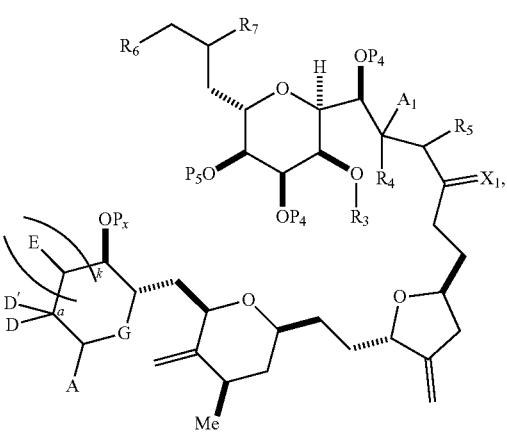

(IC)

where
each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

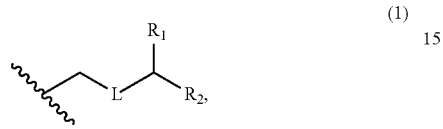

(1)

where

L is —(CH($OP_2$))—, or —C(O)—;

$R_1$ is H, or $R_1$ and $P_1$ combine to form a bond;

$R_2$ is H or —(CH$_2$)$_n$OP$_3$, and each of $P_2$ and $P_3$ is independently optionally substituted alkyl or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

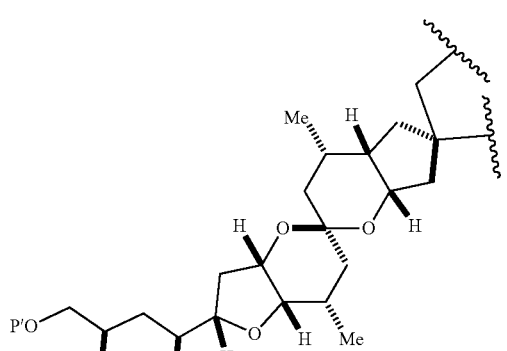

,

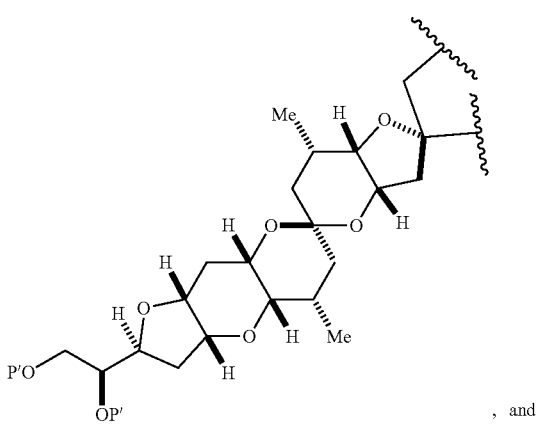

, and

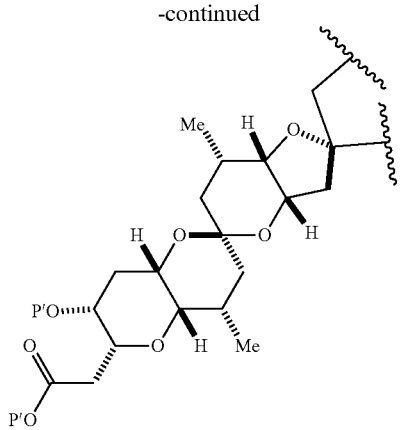

, where each P' is independently a hydroxyl protecting group;

E is optionally substituted alkyl or optionally substituted alkoxy;

G is O, S, $CH_2$, or $NR_N$, where $R_N$ is H, an N-protecting group, or optionally substituted alkyl;

each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

$P_X$ is H or a hydroxyl protecting group;

k is 0 or 1;

n is 0, 1, or 2;

$A_1$ and $R_4$ combine to form oxo, $R_3$ is H or a hydroxyl protecting group, and $R_5$ is H;

or $A_1$ is H or OP''', and:

(i) $R_3$ is H or a hydroxyl protecting group, and $R_4$ and $R_5$ combine to form a double bond;

or (ii) $R_3$ and $R_4$ combine to form a bond, and $R_5$ is H or OP''';

$R_6$ is OP''' and $R_7$ is H, or $R_6$ and $R_7$ combine to form a double bond;

each $P_4$ is independently a hydroxyl protecting group, and $X_1$ is oxo or $X_1$, together with the carbon atom to which it is attached, is —(CH(OP$_Y$))—, wherein $P_Y$ is H or a hydroxyl protecting group; or both $P_4$ groups and $X_1$, together with the atoms to which each is attached, combine to form ketal; and $P_5$ is a hydroxyl protecting group; and where each P''' is independently H or a hydroxyl protecting group.

The compound of formula (IC), in which $X_1$ is oxo, can be prepared by reacting an oxidizing agent capable of oxidizing hydroxyl to a carbonyl group (e.g., Dess-Martin periodinane) with the compound of formula (IC), in which $X_1$, together with the carbon atom to which it is attached, is —(CH(OP$_Y$))—, where $P_Y$ is H.

The compound of formula (ID) has the following structure: $(RO)_2P(O)CH_2COOH$, where each R is independently optionally substituted alkyl or optionally substituted aryl.

The preparation of the compound of formula (IA) from the compound of formula (IC) and the compound of formula (ID) may involve a hydroboration/oxidation reaction to furnish the aldehyde group in the compound of formula (IA) after the esterification reaction, if $R_6$ and $R_7$ combine to form a double bond in the compound of formula (IC). Alternatively, the preparation of the compound of formula (IA) from the compound of formula (IC) and the compound of formula (ID) may involve reacting the esterification product with a hydroxyl protecting group removing agent and then reacting the product with an oxidizing agent capable of converting a hydroxyl group into a carbonyl to furnish the aldehyde group in the compound of formula (IA), if, in the compound of formula (IC) $R_6$ is OP and $R_7$ is H.

The compound of formula (IC) can be prepared from a compound of formula (IE) and the compound of formula (IF), e.g., using Nozaki-Hiyama-Kishi reaction conditions, as described herein. The hydroxyl group used in the subsequent esterification reaction can be deprotected using a hydroxyl protecting group removing agent. Specifically, the preparation of the compound of formula (IC), in which $P_X$ is H, may further involve treating the compound of formula (IC), in which $P_X$ is a hydroxyl protecting group, with a hydroxyl protecting group removing agent.

The compound of formula (IE) has the following structure:

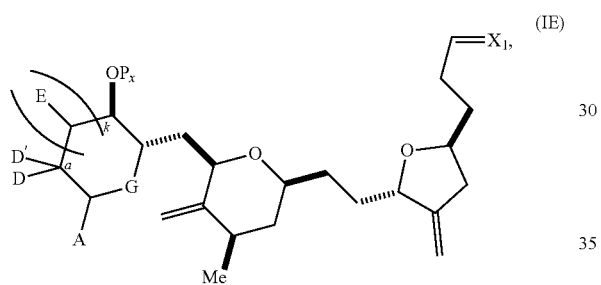

(IE)

where each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

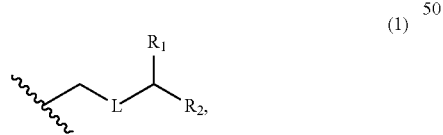

(1)

where

L is —(CH(OP$_2$))—, or —C(O)—;

$R_1$ is H, or $R_1$ and $P_1$ combine to form a bond;

$R_2$ is H or —(CH$_2$)$_n$OP$_3$, and each of $P_2$ and $P_3$ is independently optionally substituted alkyl or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

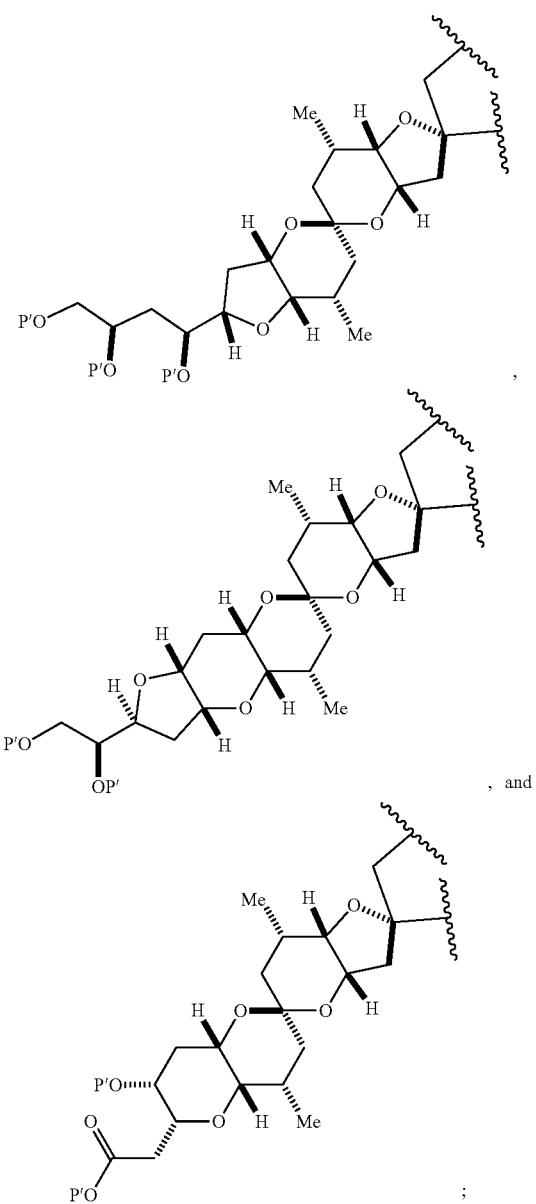

, and

;

each P' is independently a hydroxyl protecting group;

E is optionally substituted alkyl or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

$P_X$ is a hydroxyl protecting group;

k is 0 or 1;

n is 0, 1, or 2; and $X_1$ is oxo.

The compound of formula (IF) has the following structure:

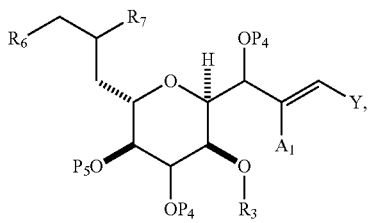

(IF)

where each $R_3$, $P_4$, and $P_5$ is independently a hydroxyl protecting group;

$A_1$ is H or OP''', where P''' is a hydroxyl protecting group;

$R_6$ is $OP_5$, and $R_7$ is H, or $R_6$ and $R_7$ combine to form a double bond;

and

Y is chloro, bromo, iodo, trifluoromethanesulfonate, or trialkylsilane.

The compound of formula (IE), in which $X_1$ is oxo, can be reacted with the compound of formula (IF) under the Nozaki-Hiyama-Kishi reaction conditions, as described herein.

The compound of formula (IE) can be accessed, e.g., from the compound of formula (VIIID).

The compound of formula (IF) can be prepared using methods known in the art, e.g., those described in WO 2015/066729.

The preparation of compound (IA) may further involve reactions deprotecting protected hydroxyl groups or protecting unprotected hydroxyl groups using methods described herein.

Compound (IIA)

The compound of formula (IIA) can be prepared using methods described in the references incorporated by reference above. In particular, the compound of formula (IIIA) can be prepared from acrylic acid a compound of formula (IIB), e.g., using esterification reaction conditions (e.g., Shiina esterification reaction conditions (e.g., using MNBA) or Yamaguchi esterification reaction conditions, e.g., the reaction conditions described in Aicher et al., *J. Am. Chem. Soc.*, 114:3162-3164, 1992).

The compound of formula (IIB) has the following structure:

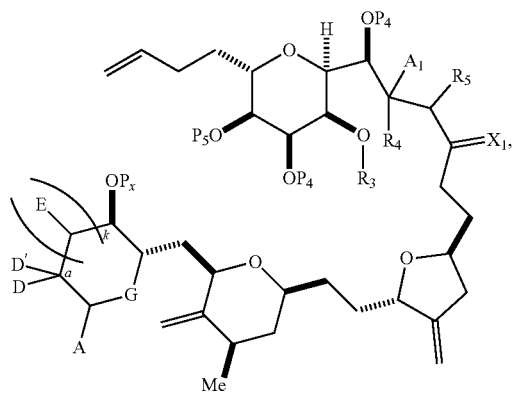

(IIB)

where each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

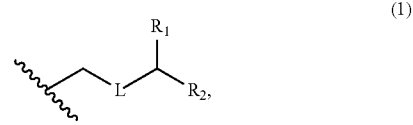

(1)

where

L is $-(CH(OP_2))-$, or $-C(O)-$;

$R_1$ is H, or $R_1$ and $P_1$ combine to form a bond;

$R_2$ is H or $-(CH_2)_n OP_3$, and each of $P_2$ and $P_3$ is independently optionally substituted alkyl or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

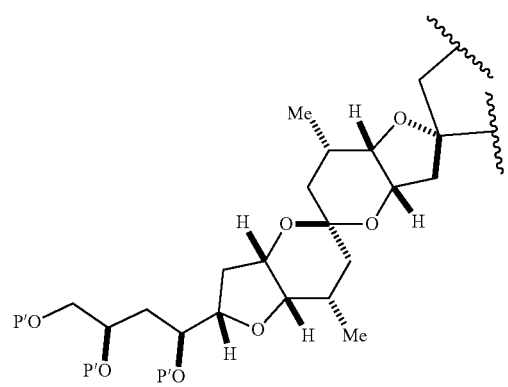

,

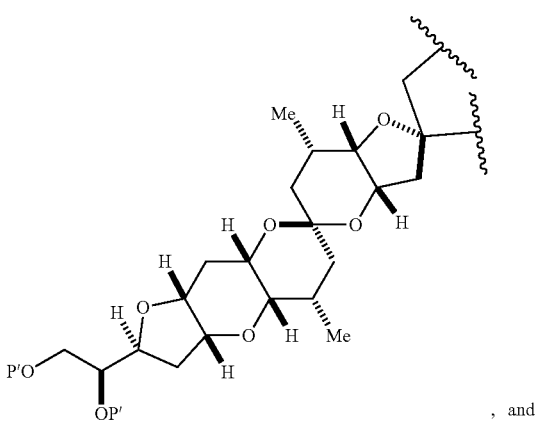

, and

-continued

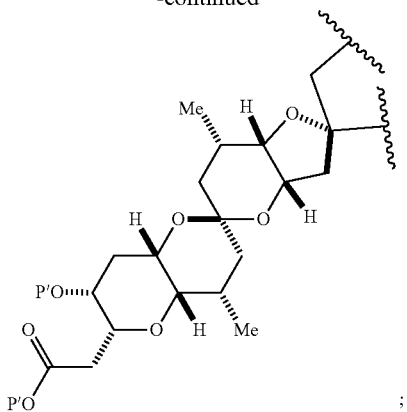

where each P' is independently a hydroxyl protecting group;
E is optionally substituted alkyl or optionally substituted alkoxy;
G is O, S, $CH_2$, or $NR_N$, where $R_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
$P_X$ is H or a hydroxyl protecting group;
k is 0 or 1;
n is 0, 1, or 2;
  $A_1$ and $R_4$ combine to form oxo, $R_3$ is H or a hydroxyl protecting group, and $R_5$ is H;
  or
  $A_1$ is H or OP''', where P''' is H or a hydroxyl protecting group, and:
    (i) $R_3$ is H or a hydroxyl protecting group, and $R_4$ and $R_5$ combine to form a double bond;
    or
    (ii) $R_3$ and $R_4$ combine to form a bond, and $R_5$ is H or OP''';
each $P_4$ is independently a hydroxyl protecting group, and $X_1$ is oxo or $X_1$, together with the carbon atom to which it is attached, is —(CH(OP$_Y$))—, wherein $P_Y$ is H or a hydroxyl protecting group; or both $P_4$ groups and $X_1$, together with the atoms to which each is attached, combine to form ketal; and
$P_5$ is a hydroxyl protecting group.

The compound of formula (IIB), in which $X_1$ is oxo, can be prepared by reacting an oxidizing agent capable of oxidizing hydroxyl to a carbonyl group (e.g., Dess-Martin periodinane or a dimethylsulfonium compound) with the compound of formula (IIB), in which $X_1$, together with the carbon atom to which it is attached, is —(CH(OP$_Y$))—, where $P_Y$ is H.

The compound of formula (IIB), in which $P_X$ is H, can be prepared by reacting a hydroxyl protecting group removing agent with the compound of formula (IIB), in which $P_X$ is a hydroxyl protecting group.

In non-limiting examples, the compound of formula (IIB) can be prepared from a compound of formula (IE) and a compound of formula (IIC) (e.g., via the compound of formula (IICa).

The preparation of the compound of formula (IIB) may further involve hydroboration/oxidation reaction with subsequent olefination (e.g., Wittig reaction (e.g., with $Ph_3PCH_2$) to provide a terminal alkene). For example, compound of formula (IIC) may be subjected to hydroboration/oxidation sequence to produce an aldehyde, which upon treatment with $Ph_3PCH_2$, produces the compound of formula (IICa).

The compound of formula (IIC) has the following structure:

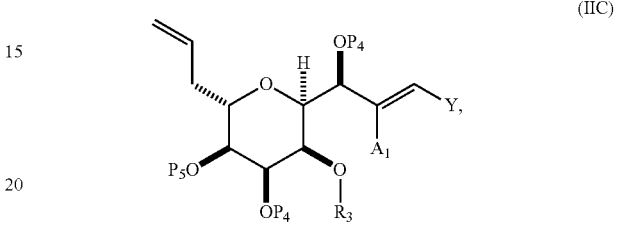

(IIC)

where
$A_1$ is H or OP''', where P''' is H or a hydroxyl protecting group;
each $R_3$, $P_4$, and $P_5$ is independently a hydroxyl protecting group; and
Y is chloro, bromo, iodo, or trifluoromethanesulfonate.

The compound of formula (IICa) has the following structure:

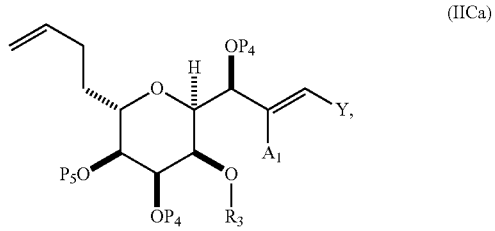

(IICa)

where all variables are as defined for formula (IIC).

The compound of formula (IE), in which $X_1$ is oxo, can be reacted with the compound of formula (IIC) under the Nozaki-Hiyama-Kishi reaction conditions, as described herein.

The compound of formula (IIC) can be prepared using methods known in the art, e.g., those described in WO 2015/066729.

The preparation of compound (IIA) may also involve reactions deprotecting protected hydroxyl groups or protecting unprotected hydroxyl groups using methods described herein.

Compound (IIIA)

The compound of formula (IIIA) can be prepared using methods described in the references incorporated by reference above. In particular, the compound of formula (IIIA) can be prepared from but-3-enoic acid a compound of formula (IC), in which $R_6$ and $R_7$ combine to form a double bond, e.g., using esterification reaction conditions (e.g., Shiina esterification reaction conditions (e.g., using MNBA) or Yamaguchi esterification reaction conditions, e.g., the reaction conditions described in Aicher et al., *J. Am. Chem. Soc.*, 114:3162-3164, 1992). The preparation of compound (IIIA) may also involve reactions deprotecting protected hydroxyl groups or protecting unprotected hydroxyl groups using methods described herein.

Compound (IVA)

The compound of formula (IVA) can be prepared using methods described in the references incorporated by reference above. In particular, the compound of formula (IVA) can be prepared from a compound of formula (IVD) and a compound of formula (IVE), e.g., using esterification reaction conditions (e.g., Shiina esterification reaction conditions (e.g., using MNBA) or Yamaguchi esterification reaction conditions, e.g., the reaction conditions described in Aicher et al., *J. Am. Chem. Soc.*, 114:3162-3164, 1992).

The compound of formula (IVD) has the following structure:

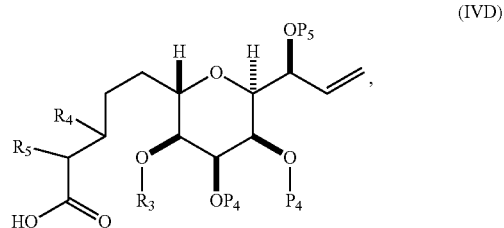
(IVD)

where (i) $R_3$ is a hydroxyl protecting group, $R_4$ is alkyl ether, and $R_5$ is H;

(ii) $R_3$ is a hydroxyl protecting group, and $R_4$ and $R_5$ combine to form a double bond;

or (iii) $R_3$ and $R_4$ combine to form a bond, and $R_5$ is H;

each $P_4$ and $P_5$ is independently a hydroxyl protecting group.

The compound of formula (IVE) has the following structure:

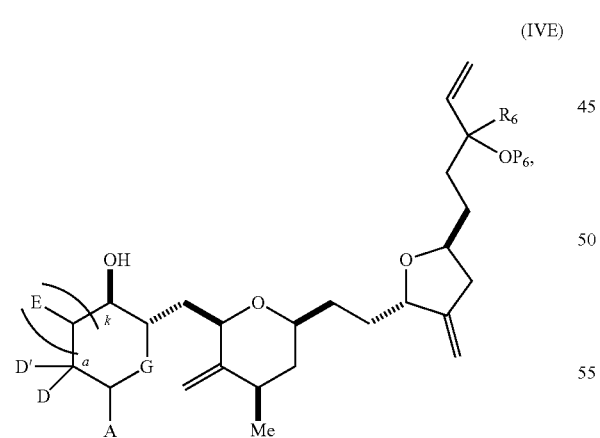
(IVE)

where each of D and D' is independently H, optionally substituted alkyl, or $OP_1$; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

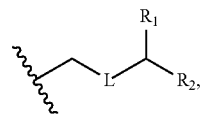
(1)

where

L is —(CH(OP$_2$))— or —C(O)—;

$R_1$ and $P_1$ combine to form a bond; or $R_1$ is H, and $P_1$ is alkyl;

$R_2$ is H or —(CH$_2$)$_n$OP$_3$, and each of $P_2$ and $P_3$ is independently optionally substituted alkyl or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

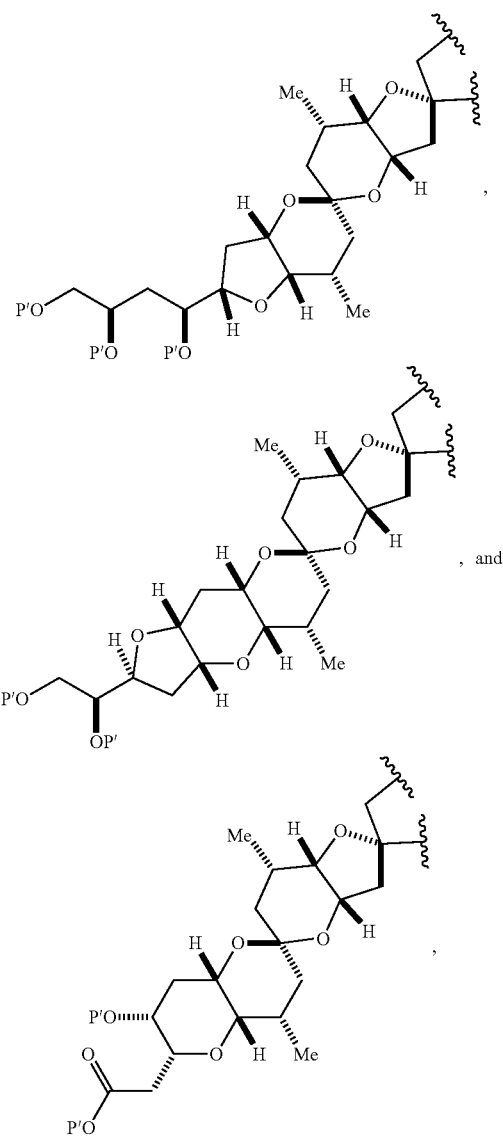

where each P' is independently a hydroxyl protecting group;

E is optionally substituted alkyl or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2; and

R$_6$ is H, and P$_6$ is H or a hydroxyl protecting group; or R$_6$ and P$_6$ combine to form a double bond.

The compound (IVE) can be prepared using methods known in the art or using the allene-Prins method described herein. In particular, after the allene-Prins reaction and allylic reduction, the substrate, in which R$_3$ is

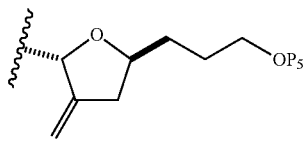

can be subjected to a reaction sequence involving reactions with oxidizing agents capable of oxidizing an alcohol to a carbonyl and vinyl addition to carbonyl.

The preparation of compound (IVA) may also involve reactions deprotecting protected hydroxyl groups or protecting unprotected hydroxyl groups using methods described herein.

Compound (VA)

The compound of formula (VA) can be prepared using methods described in the references incorporated by reference above. In particular, the compound of formula (VA) can be prepared from a compound of formula (VE) and a compound of formula (VD), in which P$_X$ is H, e.g., using esterification reaction conditions (e.g., Shiina esterification reaction conditions (e.g., using MNBA) or Yamaguchi esterification reaction conditions, e.g., the reaction conditions described in Aicher et al., *J. Am. Chem. Soc.*, 114: 3162-3164, 1992).

The compound of formula (VE) has the following structure:

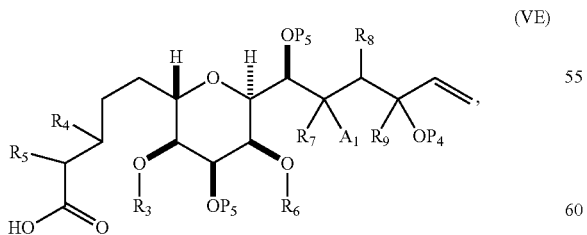

(VE)

where (a1) R$_3$ is H or a hydroxyl protecting group, R$_4$ is alkyl ether, and R$_5$ is H;

(a2) R$_3$ is H or a hydroxyl protecting group, and R$_4$ and R$_5$ combine to form a double bond;

or (a3) R$_3$ and R$_4$ combine to form a bond, and R$_5$ is H;

(b1) R$_6$ is a hydroxyl protecting group, and R$_7$ and R$_8$ combine to form a double bond;

or (b2) R$_6$ and R$_7$ combine to form a bond, and R$_8$ is H;

(c1) R$_9$ is H, and P$_4$ is a hydroxyl protecting group;

or (c2) R$_9$ and P$_4$ combine to form a double bond;

each P$_5$ is independently a hydroxyl protecting group; and

A$_1$ is H or OP''', where P''' is a hydroxyl protecting group.

The compound of formula (VD) has the following structure:

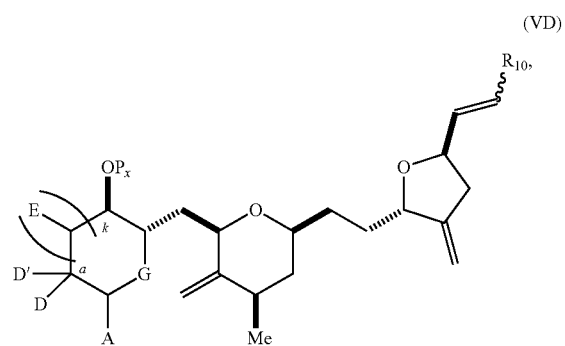

(VD)

where each of D and D' is independently H, optionally substituted alkyl, or OP$_1$; A is a group of formula (1) or a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, the group of formula (1) having the structure:

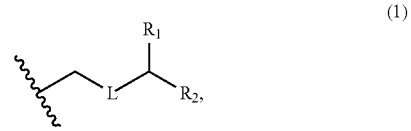

(1)

where

L is —(CH(OP$_2$))—, —(C(OH)(OP$_2$))—, or —C(O)—;

R$_1$ and P$_1$ combine to form a bond; or R$_1$ is H, and P$_1$ is a hydroxyl protecting group or alkyl;

R$_2$ is H or —(CH$_2$)$_n$OP$_3$, and each of P$_2$ and P$_3$ is independently optionally substituted alkyl or a hydroxyl protecting group, or P$_2$ and P$_3$, together with the atoms to which each is attached, combine to form a ketal, a cyclic carbonate, a dicarbonyl-dioxo, or silylene-dioxo; or R$_2$ and P$_2$ combine to form an optionally substituted ethylene or a structure selected from the group consisting of:

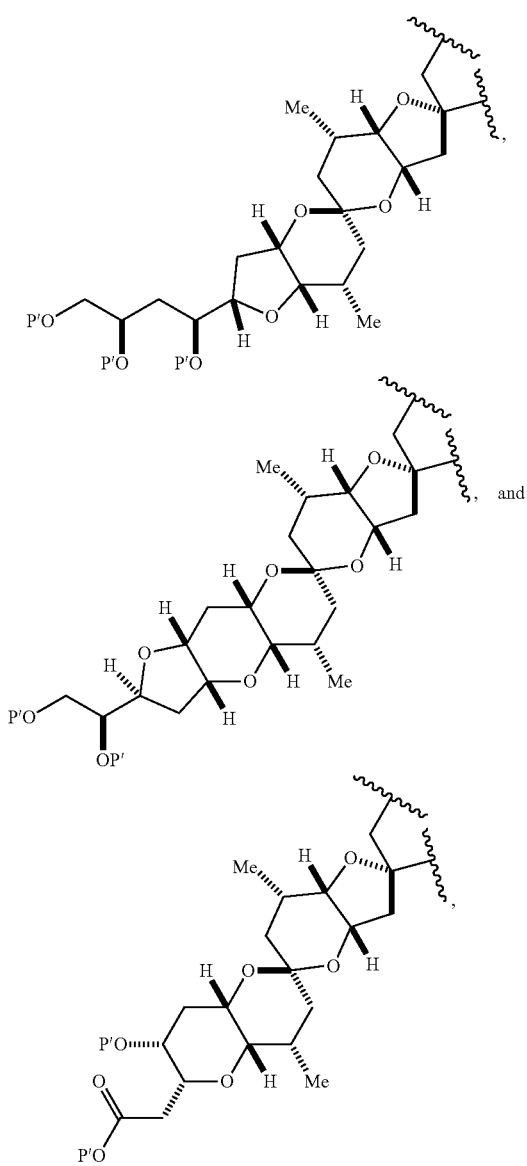

where each P' is independently a hydroxyl protecting group;
E is optionally substituted alkyl or optionally substituted alkoxy;
G is O, S, $CH_2$, or $NR_N$, where $R_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
$P_X$ is H or a hydroxyl protecting group;
k is 0 or 1;
n is 0, 1, or 2; and
$R_{10}$ is H or $-CH_2X_1CH_2CH=CH_2$, where $X_1$ is O, $-C(R_{11})_2-$, or $NP_6$, and where each $R_{11}$ is independently H or $-COOR_{12}$, $P_6$ is an N-protecting group, and $R_{12}$ is alkyl.

The compound of formula (VD), in which $P_X$ is H, can be prepared by reacting a hydroxyl protecting group removing agent with the compound of formula (VD), in which $P_X$ is a hydroxyl protecting group.

The compound of formula (VD) can be prepared using methods known in the art or using the allene-Prins method described herein. For example, the compound of formula (VD), in which $R_{10}$ is $-CH_2X_1CH_2CH=CH_2$, can be prepared from the compound of formula (VF):

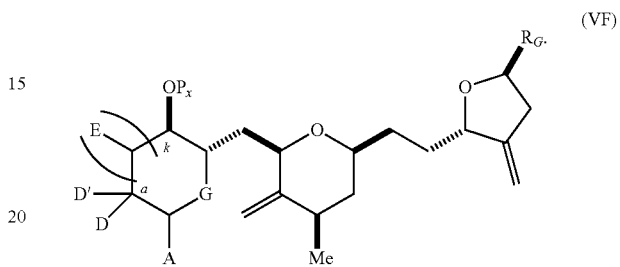

where $R_G$ is $-CHO$, $-CH=CH-COOR_H$, where $R_H$ is H or a hydroxyl protecting group, and all remaining variables are as defined for formula (VD).

Thus, in a non-limiting example, the compound of formula (VF), in which $R_G$ is $-CHO$, may be subjected to Horner-Wadsworth-Emmons reaction conditions (e.g., with $(EtO)_2P(O)-CH_2-COOR_H$) to produce the compound of formula (VF), in which $R_G$ is $-CH=CH-COOR_H$. The latter compound may be treated with a 1,2-reducing agent (e.g., DIBAL) followed by a quench with allyl halide (e.g., allyl bromide) to give the compound of formula (VD).

The compound of formula (VF) may be prepared from the compound of formula (VIIID). In a non-limiting example, the compound of formula (VIIID), in which $R_3$ is $-CH_2-OP_5$, and $P_5$ is a hydroxyl protecting group, may be treated with a hydroxyl protecting group removing agent (e.g., if $P_5$ is Piv, the hydroxyl protecting group removing agent may be DIBAL), followed by an oxidizing agent capable of oxidizing hydroxyl to a carbonyl group (e.g., Dess-Martin periodinane), to give the compound of formula (VF), in which $R_G$ is $-CHO$.

The preparation of compound (VA) may also involve reactions deprotecting protected hydroxyl groups or protecting unprotected hydroxyl groups using methods described herein.

Compound (VIA)

The compound of formula (VIA) can be prepared using methods described in the references incorporated by reference above. In particular, the compound of formula (VIA) can be prepared from a compound of formula (VIC) and a compound of formula (VID), e.g., using esterification reaction conditions (e.g., Shiina esterification reaction conditions (e.g., using MNBA) or Yamaguchi esterification reaction conditions, e.g., the reaction conditions described in Aicher et al., *J. Am. Chem. Soc.*, 114:3162-3164, 1992).

The compound of formula (VIC) has the following structure:

(VIC)

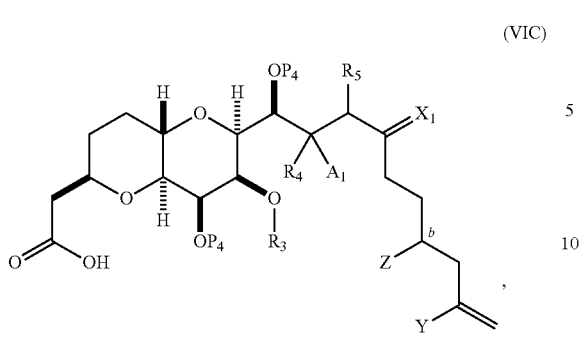

or a tautomer thereof
where
b designates (R)-stereogenic center, and Z is a sulfonate, chloride, bromide, or iodide; or b designates (S)-stereogenic center, and Z is $OR_6$, where $R_6$ is a hydroxyl protecting group;
Y is iodide, bromide, or trifluoromethanesulfonate;
(i) $R_3$ is H or a hydroxyl protecting group, and $R_4$ and $R_5$ combine to form a double bond;
or
(ii) $R_3$ and $R_4$ combine to form a bond, and $R_5$ is H;
each $P_4$ is independently a hydroxyl protecting group, and $X_1$ is oxo or $X_1$, together with the carbon atom to which it is attached, is —(CH($OP_Y$))—, wherein $P_Y$ is H or a hydroxyl protecting group; or both $P_4$ groups and $X_1$, together with the atoms to which each is attached, combine to form ketal.

The compound of formula (VID) has the following structure:

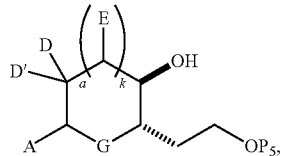

(VID)

where
each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

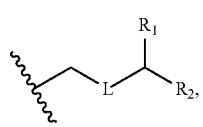

(1)

where
L is —(CH($OP_2$))—, —(C(OH)($OP_2$))—, or —C(O)—;
$R_1$ and $P_1$ combine to form a bond; or $R_1$ is absent or H, and $P_1$ is absent, a hydroxyl protecting group, or alkyl;

$R_2$ is H or —$(CH_2)_n OP_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

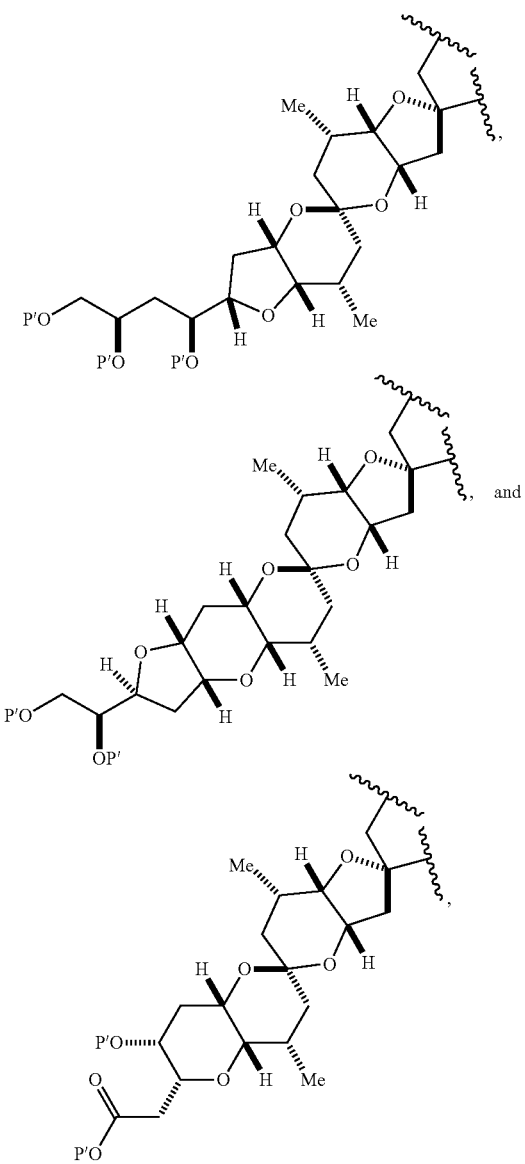

where each P' is independently a hydroxyl protecting group;
E is optionally substituted alkyl or optionally substituted alkoxy;
G is O, S, $CH_2$, or $NR_N$, where $R_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2; and $P_5$ is a hydroxyl protecting group

The compound of formula (VIC) can be prepared using methods described in WO 2015/066729.

The preparation of compound (VIA) may also involve reactions deprotecting protected hydroxyl groups or protecting unprotected hydroxyl groups using methods described herein.

Compound (VIIA)

The compound of formula (VIIA) can be prepared using methods described in the references incorporated by reference above. In particular, the compound of formula (VIIA) can be prepared from a compound of formula (VIIE):

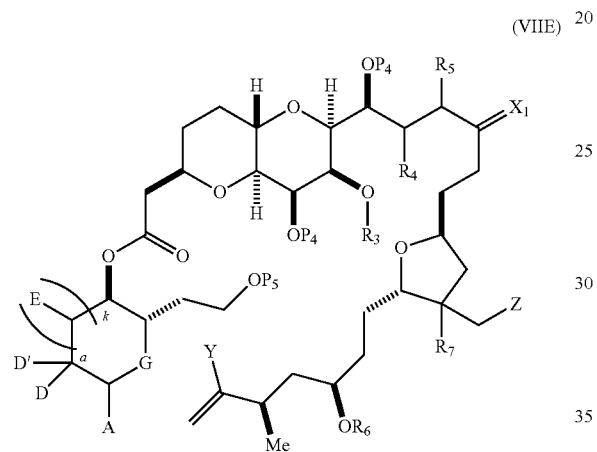

(VIIE)

or a salt or a tautomer thereof, where each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

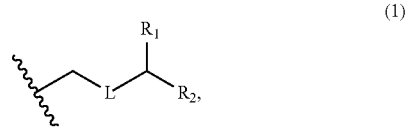

(1)

where

L is —(CH(OP$_2$))—, —(C(OH)(OP$_2$))—, or —C(O)—;

$R_1$ is H, or $R_1$ and $P_1$ combine to form a bond;

$R_2$ is H or —(CH$_2$)$_n$OP$_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

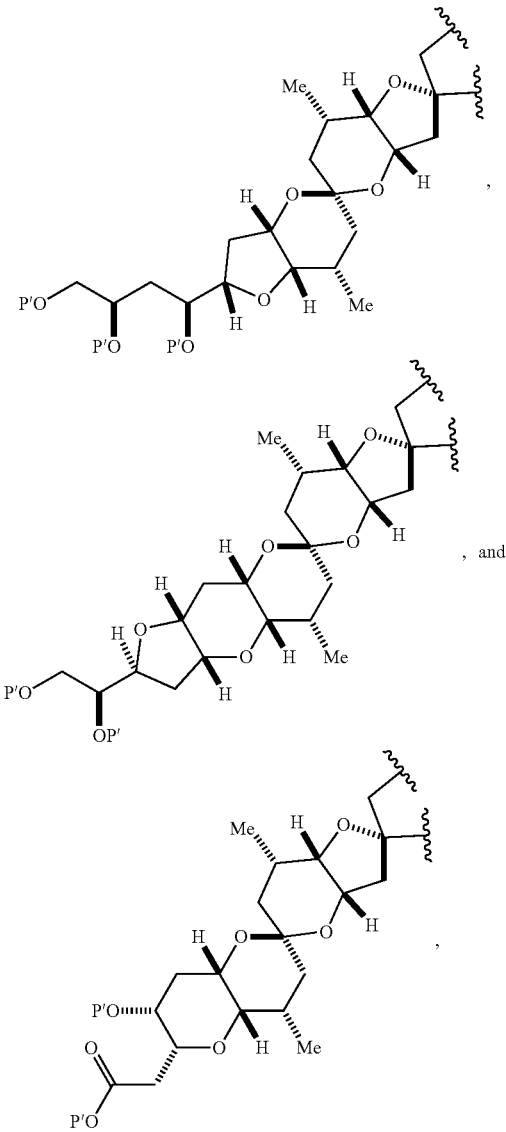

where each P' is independently H or a hydroxyl protecting group;

E is optionally substituted alkyl or optionally substituted alkoxy;

G is O, S, CH$_2$, or NR$_N$, where R$_N$ is H, an N-protecting group, or optionally substituted alkyl;

each $Q_1$ is independently $OR_4$, $SR_4$, $SO_2R_4$, $OSO_2R_4$, $NR_BR_4$, $NR_B(CO)R_4$, $NR_B(CO)(CO)R_4$, $NR_4(CO)NR_BR_4$, $NR_B(CO)OR_4$, $(CO)OR_4$, $O(CO)R_4$, $(CO)NR_BR_4$, or $O(CO)NR_BR_4$, where each of $R_4$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2;

Y is iodide, bromide, or trifluoromethanesulfonate;

$P_5$ is H or a hydroxyl protecting group; and (a1) $R_3$ is H or a hydroxyl protecting group, $R_4$ and $R_5$ combine to form a double bond, each $P_4$ is independently H or a hydroxyl protecting group, and $X_1$, together with the carbon to which it is attached, forms a carbonyl or —(CH(OR$_8$))—, where $R_8$ is H or a hydroxyl protecting group;

or (a2) $R_3$ and $R_4$ combine to form a bond, $R_5$ is H, and each $P_4$ is independently H or a hydroxyl protecting group, and $X_1$, together with the carbon to which it is attached, forms a carbonyl or —(CH(OR$_8$))—;

or both $P_4$ groups and $X_1$, together with the atoms to which each is attached, combine to form ketal;

(b1) Z is chloride, bromide, or iodide, and $R_6$ and $R_7$ combine to form a bond;

or (b2) Z and $R_7$ combine to form a double bond, and $R_6$ is H or a hydroxyl protecting group.

The preparation of the compound of formula (VIIA) can involve oxidizing the compound of formula (VIIE) (e.g., the compound of formula (VIIE), in which $P_5$ is H or a hydroxyl protecting group), e.g., by reacting with an oxidizing agent capable of oxidizing hydroxyl to a carbonyl group. The mixture containing the oxidizing agent can also act as a hydroxyl protecting group removing agent.

The compound of formula (VIIE) can be formed by reacting a compound of formula (VIIF) with the compound of formula (VIIG). The compound of formula (VIIF) has the following structure:

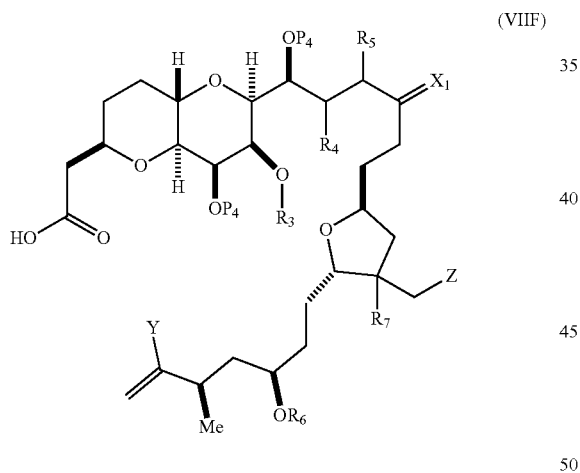

(VIIF)

or a salt or a tautomer thereof, where

Y is iodide, bromide, or trifluoromethanesulfonate; and (a1) $R_3$ is H or a hydroxyl protecting group, $R_4$ and $R_5$ combine to form a double bond, each $P_4$ is independently H or a hydroxyl protecting group, and $X_1$, together with the carbon to which it is attached, forms a carbonyl or —(CH(OR$_8$))—, where $R_8$ is H or a hydroxyl protecting group;

or (a2) $R_3$ and $R_4$ combine to form a bond, $R_5$ is H, and each $P_4$ is independently H or a hydroxyl protecting group, and $X_1$, together with the carbon to which it is attached, forms a carbonyl or —(CH(OR$_8$))—;

or both $P_4$ groups and $X_1$, together with the atoms to which each is attached, combine to form ketal;

(b1) Z is chloride, bromide, or iodide, and $R_6$ and $R_7$ combine to form a bond;

or (b2) Z and $R_7$ combine to form a double bond, and $R_6$ is H or a hydroxyl protecting group.

The compound of formula (VIIG) has the following structure:

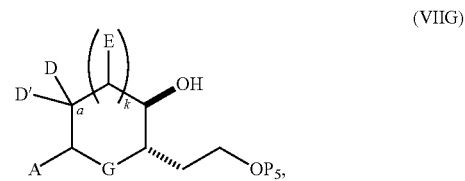

(VIIG)

or a salt thereof, each of D and D' is independently H, optionally substituted alkyl, or OP$_1$, provided that only one of D and D' is OP$_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

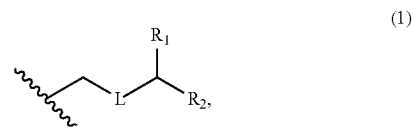

(1)

where

L is —(CH(OP$_2$))—, —(C(OH)(OP$_2$))—, or —C(O)—;

$R_1$ is H, or $R_1$ and $P_1$ combine to form a bond;

$R_2$ is H or —(CH$_2$)$_n$OP$_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

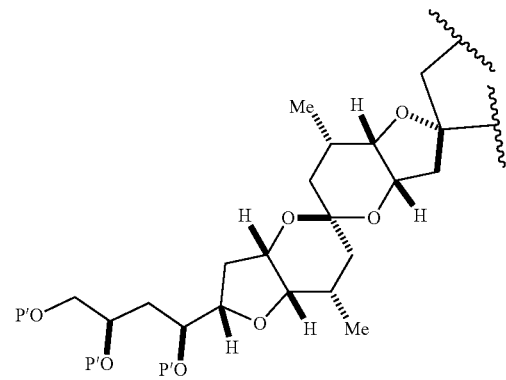

-continued

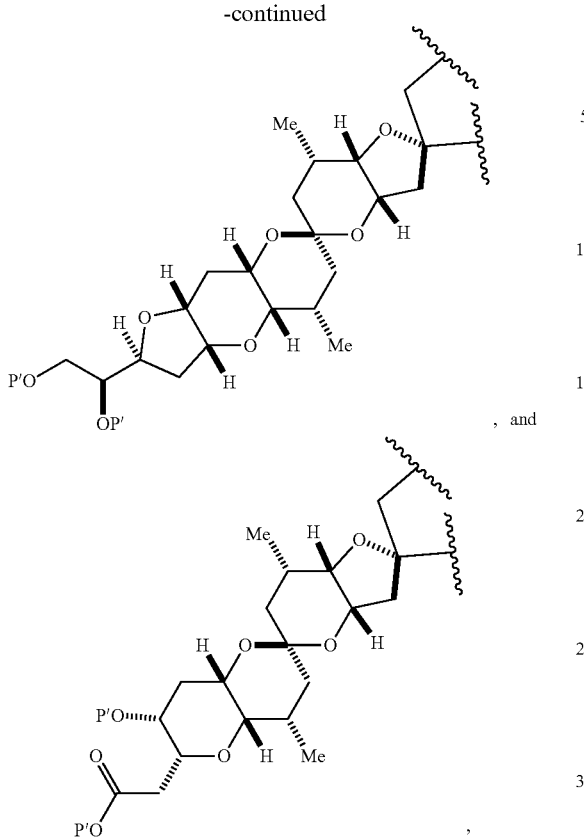

, and where each P' is independently H or a hydroxyl protecting group;
E is optionally substituted alkyl or optionally substituted alkoxy;
G is O, S, $CH_2$, or $NR_N$, where $R_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
k is 0 or 1;
n is 0, 1, or 2; and
$P_5$ is H or a hydroxyl protecting group.

Allene-Prins Reaction in the Preparation of Fragments (e.g., C.14-C.38 Fragment) of Halichondrin The invention further features a method of preparing a fragment of halichondrin macrolide (e.g., C.20-C.35, C.20-C.38, C.16-C.35, C.16-C.38, C.14-C35, and C.14-C.38 fragments), which can be an intermediate in the synthesis of halichondrin macrolide or a salt thereof. The advantages of the process relative to the current synthesis of C.14-C.35, C.14-C.38, C.16-C.35, C.16-C.38, C.20-C.35, and C.20-C.38 fragments of halichondrin include non-metal mediated assembly that does not employ a C.23 leaving group. Additionally, the method obviates the need for a chiral ligand. The method involves performing an allene-Prins reaction on a compound of formula (VIIIA), a compound of formula (VIIIB), and $R_4OH$ to afford the intermediate in the synthesis of halichondrin macrolide, where $R_4$ is an optionally substituted acyl;
where the compound of formula (VIIIA) has the following structure:

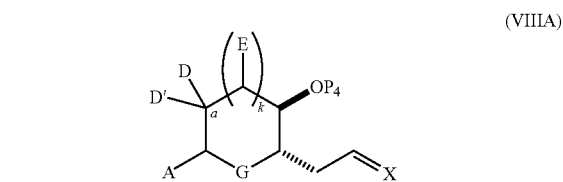

(VIIIA)

or a salt thereof,
where
each of D and D' is independently H, optionally substituted alkyl, or $OP_1$, provided that only one of D and D' is $OP_1$, where $P_1$ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (1) having the structure:

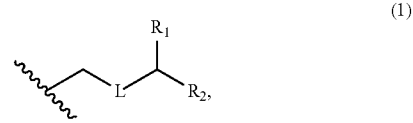

(1)

where
L is —(CH($OP_2$))—, —(C(OH)($OP_2$))—, or —C(O)—;
$R_1$ is H, or $R_1$ and $P_1$ combine to form a bond;
$R_2$ is H or —($CH_2$)$_n OP_3$, and each of $P_2$ and $P_3$ is independently H, optionally substituted alkyl, or a hydroxyl protecting group, or $P_2$ and $P_3$, together with the atoms to which each is attached, combine to form a ketal, a cyclic carbonate, a dicarbonyl-dioxo, or silylene-dioxo; or $R_2$ and $P_2$ combine to form an optionally substituted ethylene or a structure selected from the group consisting of:

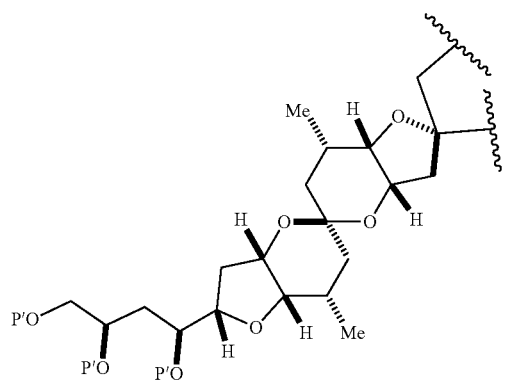

-continued

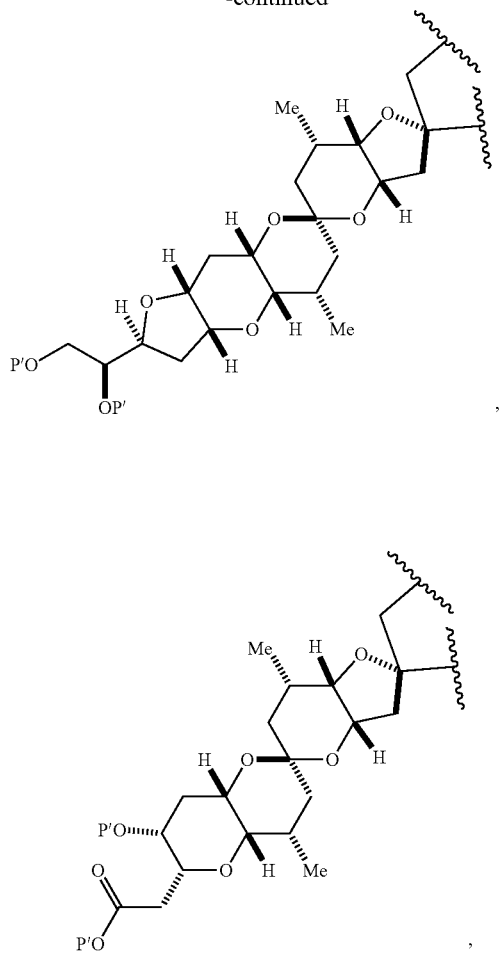
, and

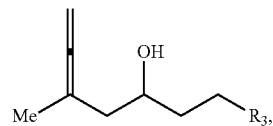 (VIIIB)

where
R₃ is —CH₂—OP₅, —CH=CH₂,

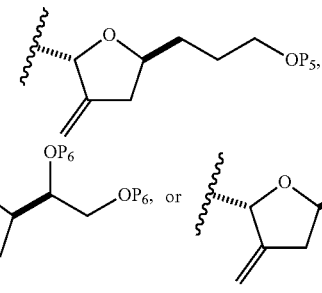

where P₅ is H or a hydroxyl protecting group; each P₆ is independently a hydroxyl protecting group, or both P₆ groups, together with the atoms to which each is attached, combine to form a cyclic protected diol; and R₅ is H or —CH₂X₁CH₂CH=CH₂, where X₁ is O, —CH₂—, or NP₇, where P₇ is a sulfonyl;
and where the intermediate is a compound of formula (VIIIC):

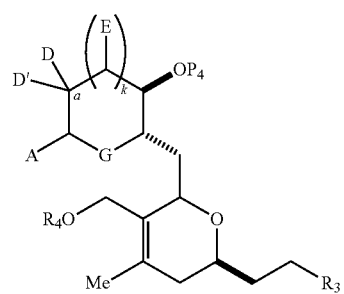 (VIIIC)

or a salt thereof,
where a designates (R)-stereogenic center or (S)-stereogenic center.

where each P' is independently H or a hydroxyl protecting group;
- E is optionally substituted alkyl or optionally substituted alkoxy;
- G is O, S, CH₂, or NR_N, where R_N is H, an N-protecting group, or optionally substituted alkyl;
- each Q₁ is independently OR_A, SR_A, SO₂R_A, OSO₂R_A, NR_BR_A, NR_B(CO)R_A, NR_B(CO)(CO)R_A, NR_A(CO)NR_BR_A, NR_B(CO)OR_A, (CO)OR_A, O(CO)R_A, (CO)NR_BR_A, or O(CO)NR_BR_A, where each of R_A and R_B is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
- k is 0 or 1;
- n is 0, 1, or 2;
- X is O, or X, together with the carbon atom to which it is attached, forms —(C(OP_Z)₂)—, wherein each P_Z is independently optionally substituted alkyl or optionally substituted aryl, or both P_Z combine to form optionally substituted alkylene or optionally substituted arylene; and
- P₄ is H or a hydroxyl protecting group;
where the compound of formula (VIIIB) has the following structure:

In some embodiments, a designates (S)-stereogenic center. In certain embodiments, one and only one of D and D' is optionally substituted alkyl or OP₁. In other embodiments, one and only one of D and D' is OP₁, where P₁ is H, alkyl, or a hydroxyl protecting group. In yet other embodiments, A is a group of formula (1). In still other embodiments, L is —(CH(OP₂))—. In particular embodiments, R₁ and P₁ combine to form a bond. In certain embodiments, G is O. In further embodiments, E is optionally substituted alkyl (e.g., methyl). In some embodiments, k is 1. In particular embodiments, R₂ is —(CH₂)_nOP₃ (e.g., n is 1 or 2). In further embodiments, at least one of P₂ and P₃ is a hydroxyl protecting group.

The reaction conditions that can be used to prepare the compound of formula (VIIIC) using allene-Prins reaction are those known in the art for Prins reaction and can include reacting the compound of formula (VIIIA), the compound of formula (VIIIB), and R₄OH with a Lewis acid (e.g., boron trifluoride or a solvate thereof).

The compound of formula (VIIIC) can be subjected to allylic reducing conditions to afford a compound of formula (VIIID):

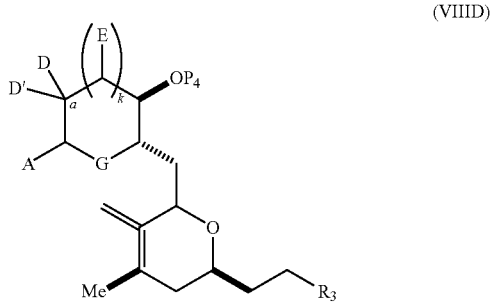

(VIIID)

or a salt thereof,
where
each of D and D' is independently H, optionally substituted alkyl, or OP₁, provided that only one of D and D' is OP₁, where P₁ is H, alkyl, or a hydroxyl protecting group; A is a group of formula (1) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and Q₁, the group of formula (1) having the structure:

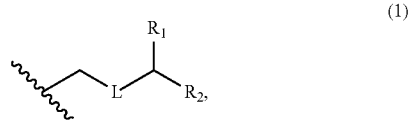

(1)

where
L is —(CH(OP₂))—, —(C(OH)(OP₂))—, or —C(O)—;
R₁ is H, or R₁ and P₁ combine to form a bond;
R₂ is H or —(CH₂)ₙOP₃, and each of P₂ and P₃ is independently H, optionally substituted alkyl, or a hydroxyl protecting group, or P₂ and P₃, together with the atoms to which each is attached, combine to form a ketal, a cyclic carbonate, a dicarbonyl-dioxo, or silylene-dioxo; or R₂ and P₂ combine to form an optionally substituted ethylene or a structure selected from the group consisting of:

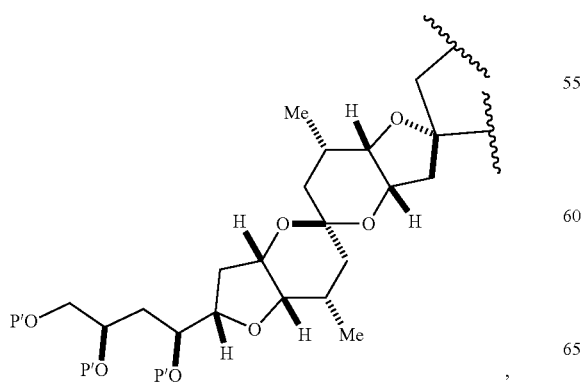

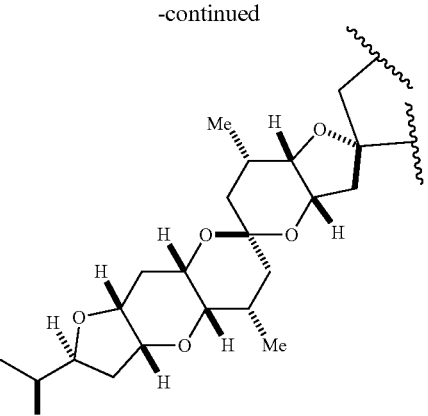

, and

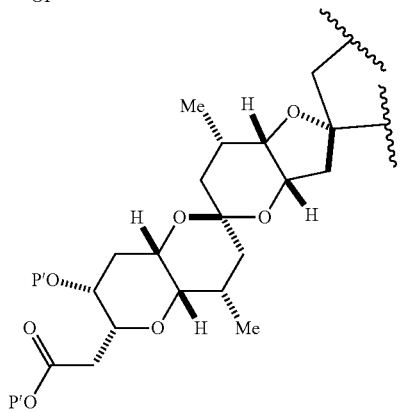

, where each P' is independently H or a hydroxyl protecting group;
E is optionally substituted alkyl or optionally substituted alkoxy;
G is O, S, CH₂, or NR_N, where R_N is H, an N-protecting group, or optionally substituted alkyl;
each Q₁ is independently OR_A, SR_A, SO₂R_A, OSO₂R_A, NR_BR_A, NR_B(CO)R_A, NR_B(CO)(CO)R_A, NR_A(CO)NR_BR_A, NR_B(CO)OR_A, (CO)OR_A, O(CO)R_A, (CO)NR_BR_A, or O(CO)NR_BR_A, where each of R_A and R_B is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
k is 0 or 1;
n is 0, 1, or 2;
and
P₄ is H or a hydroxyl protecting group; and
R₃ is —CH₂—OP₅, —CH=CH₂,

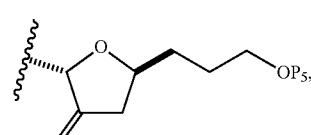

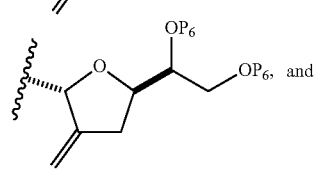

, and

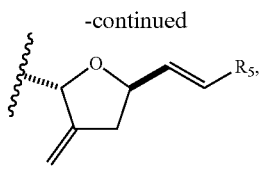

where P$_5$ is H or a hydroxyl protecting group; each P$_6$ is independently a hydroxyl protecting group, or both P$_6$ groups, together with the atoms to which each is attached, combine to form a cyclic protected diol; and R$_5$ is H or —CH$_2$X$_1$CH$_2$CH=CH$_2$, where X$_1$ is O, —CH$_2$—, or NP$_7$, where P$_7$ is a sulfonyl.

Preparation of a compound of formula (VIIIB) is described in detail in International Patent Application No. PCT/US2014/063960, and the disclosure of the preparation is incorporated herein by reference in its entirety.

Compounds

The present invention also provides compounds that can be used in the synthesis of a halichondrin macrolide, e.g., the compounds of formula (IA), (IB), (IC), (IE), (IF), (IIA), (IIB), (IIC), (IICa), (IIIA), (IIIB), (IVA), (IVB), (IVC), (IVD), (IVE), (VA), (VB), (VBa), (VC), (VIA), (VIB), (VIC), (VIIA), (VIIB), (VIIC), (VIID), (VIIE), (VIIF), (VIIG), (VIIIA), (VIIIB), (VIIIC), or (VIIID).

Oxidizing Agents Capable of Converting an Alcohol to a Carbonyl Group

Oxidizing agents capable of converting an alcohol to a carbonyl group are known in the art. Non-limiting examples of these oxidizing agents include Dess-Martin periodinane, TEMPO (in the presence of bleach or BAIB), a dimethylsulfonium compound (e.g., dimethylchlorosulfonium chloride), aluminum trialkoxide with an excess of a ketone (e.g., acetone), and catalytic tetrapropylammonium perruthenate (TPAP) (in the presence of N-methylmorpholine oxide). The dimethylsulfonium compound can be prepared in situ under the conditions known for Parikh-Doering oxidation, Swern oxidation, Corey-Kim oxidation, or Pfitzner-Moffatt oxidation. An oxidation reaction of an alcohol to a carbonyl group (e.g., a ketone) can be performed using aluminum trialkoxide and an excess of a ketone (e.g., acetone) under the conditions known in the art for Oppenauer oxidation. Allylic and benzylic alcohols can also be oxidized with MnO$_2$.

Reducing Agents

Reducing agents that can be used in the methods of the invention are those known in the art. A reducing agent can be an electron-transfer reducing agent, a metal hydride, or a metalloid hydride. Non-limiting examples of electron-transfer reducing agent include alkali metals in oxidation state (0), alkali earth metals in oxidation state (0), alkali arenides, lanthanide (II) salts (e.g., SmI$_2$), Zn(0), Fe(0), and Mn(0).

Non-limiting examples of metal hydrides and metalloid hydrides include boron hydride compounds (e.g., NaBH$_4$, LiBH$_4$, LiB(Et)$_3$H, selectrides (e.g., L-selectride), and boranes (e.g., 9-BBN and alpine borane)), aluminum hydride compounds (e.g., LiAlH$_4$, Red-Al®, and alanes (e.g., DIBAL)), hydrosilanes (e.g., PMHS and Ph$_2$SiH$_2$), hydrostannanes (e.g., Bu$_3$SnH), copper hydride complexes (e.g., Stryker's reagent), palladium hydride complexes, platinum hydride complexes, iridium hydride complexes, rhodium hydride complexes, and ruthenium hydride complexes. Reducing agents can be formed in situ, e.g., a copper hydride complex can be formed by a reaction of a copper salt with, e.g., a boron hydride compound or a hydrosilane. Thus, some reducing reagents (e.g., boron hydride compounds, hydrosilanes, and hydrostannanes) can be used in combination with a catalytic quantity of a metal salt (e.g., Cu, Pd, Pt, Ir, Rh, or Ru salt). Alternatively, catalytic reducing agents can be metal salts (e.g., aluminum isopropoxide or a ruthenium complex) in combination with an alcohol, which undergo transfer hydrogenation of carbonyl-containing compounds without intermediacy of a metal hydride. Non-limiting examples of transfer hydrogenation reactions include Meerwein-Ponndorf-Verley reduction (e.g., using aluminum isopropoxide/isopropanol) and Ru-catalyzed transfer hydrogenation (e.g., Hashiguchi et al., J. Am. Chem. Soc., 117:7562-7563, 1995).

When a substrate is an α,β-unsaturated carbonyl compound (e.g., an α,β-enone), a reducing agent can be a 1,2-reducing agent or a 1,4-reducing agent. For example, a reaction between an α,β-unsaturated carbonyl compound and a 1,2-reducing agent can afford, e.g., an allylic alcohol (or an allylic amine, if the starting compound is an enamide), whereas a reaction between an α,β-unsaturated carbonyl compound and a 1,4-reducing agent can afford an α,β-saturated compound and can leave the carbonyl group intact after work up of the reaction mixture. Non-limiting examples of 1,2-reducing agents include metal hydrides and metalloid hydrides, e.g., aluminum hydride compounds, boron hydride compounds (e.g., CeCl$_3$ with NaBH$_4$), and ruthenium hydride complexes. Non-limiting examples of 1,4-reducing agents include boron hydride compounds, hydrostannanes, copper hydride complexes (e.g., Stryker's reagent), palladium hydride complexes, platinum hydride complexes, iridium hydride complexes, rhodium hydride complexes, and ruthenium hydride complexes.

A compound having an allylic leaving group (e.g., a carboxylate, a halide, or a sulfonate) can be treated with an allylic reducing agent to replace the leaving group with a hydrogen atom. A non-limiting example of allylic reducing agent is a palladium salt in combination with a formic acid salt (e.g., trialkylammonium formate).

Hydroxyl Protecting Groups and Hydroxyl Protecting Group Removing Agents

Hydroxyl protecting groups can be as defined herein. In particular, a hydroxyl protecting group can be an acyl, a sulfonyl, an arylalkyl (e.g., benzyl or p-methoxybenzyl), an aryl (e.g., p-methoxyphenyl), or an optionally substituted silyl (e.g., TMS, TES, TBS, TIPS, TBDPS, DMPS, or TPS). Hydroxyl protecting groups, hydroxyl protecting agents, and hydroxyl protecting reaction conditions can be selected to protect selectively certain hydroxyl groups in a compound, while leaving other hydroxyl groups unprotected. The choice of hydroxyl protecting groups for a compound can facilitate subsequent deprotection strategies, as some hydroxyl protecting groups can be removed in the presence of others using appropriate hydroxyl protecting group removing agents. Some of these strategies involving the choice of silyl hydroxyl protecting groups are discussed in, e.g., *Silicon-Based Blocking Agents*, Gelest, Inc., 2011.

Hydroxyl protecting group removing agents are those agents that can react with a compound having a protected hydroxyl group to afford the compound with a deprotected hydroxyl group. Hydroxyl protecting group removing agents and deprotection reaction conditions can be those known in the art. In a non-limiting example, hydroxyl masked as silyl ether can be unmasked by a reaction with a fluoride source (e.g., a fluoride salt, such as KF or TBAF). Alternatively, hydroxyl protected as TMS or TES ether can be deprotected by a reaction with a Brønsted acid (e.g., a carboxylic acid). In another non-limiting example, hydroxyl protected as an ester can be deprotected by a reaction with a C$_{1-6}$ alkoxide (e.g., alkali C$_{1-6}$ alkoxide or alkali earth C$_{1-6}$ alkoxide). In yet another non-limiting example, hydroxyl protected as an arylalkyl ether (e.g., 1-arylalk-1-yl ether) can be deprotected using a reduction reaction, e.g., with Pd/C and H$_2$ or with Na/NH$_3$. Alternatively, hydroxyl protected as an alkoxyarylalkyl ether (e.g., MPM ether) can be deprotected by a reaction with 2,3-dichloro-5,6-dicyano-1,4-benzoquinone (DDQ). In still another non-limiting example, hydroxyl protected as alkoxyalkyl ether (e.g., 1-alkoxyalk-1-yl) or THP ether can be deprotected by a reaction with a Brønsted acid. Cyclic protected diols, such as acetals or ketals (e.g., as 2-alkyl-1,3-dioxolane, 2,2-dialkyl-1,3-dioxolane, 2-alkyl-1,3-dioxane, or 2,2-dialkyl-1,3-dioxane), can be deprotected by a reaction with a Brønsted acid (e.g., a carboxylic acid).

Dihydroxylation and Oxidative Carbon-Carbon Bond Cleavage

Dihydroxylation reaction produces diols from olefins. The reaction conditions can be those known in the art. Dihydroxylation reaction may be direct (e.g., Sharpless dihydroxylation, Upjohn dihydroxylation, or Milas dihydroxylation) or indirect (e.g., through epoxidation/hydrolysis, diborylation/oxidation, or carboxylation/hydrolysis (e.g., Woodward reaction or Prévost reaction)). A direct dihydroxylation reaction can be performed using an osmium complex (e.g., OsO$_4$ or osmate salt). A catalytic quantity of the osmium complex can be used in the dihydroxylation reactions in combination with an additional oxidizing agent (e.g., N-methylmorpholine N-oxide or hydrogen peroxide). The dihydroxylation reaction can be rendered stereoselective by including a chiral ligand (e.g., in AD-mix, which is a mixture of osmate and a chiral ligand).

When a dihydroxylation reaction is performed with an osmium complex and a periodate salt as oxidizing agent, the carbon-carbon double bond of an olefin can be cleaved to afford two carbonyl groups. The transformation of an olefin to two carbonyl groups is referred to herein as a cleavage reaction. Cleavage reaction conditions can be those known in the art. Non-limiting examples of cleavage reaction conditions can be ozonolysis reaction conditions or a reaction with an osmium complex (e.g., OsO$_4$ or osmate salt) and a periodate salt. A vicinal diol can be cleaved by sodium periodate or potassium permanganate.

Epimerizations

Epimerization reactions can be used to invert a stereogenic center having an undesired stereochemical identity. For example, through epimerization, R stereogenic center can be converted to S stereogenic center and vice versa. Epimerization of a stereogenic sp$^3$-carbon bonded to one hydrogen atom and to one hydroxyl group can be achieved through a reaction sequence involving oxidation of the hydroxyl group to a carbonyl group followed by a 1,2-reduction reaction. The 1,2-reduction reaction can provide the desired stereochemical identity diastereoselectively, or the reaction can be carried out using a chiral catalyst, chiral auxiliary, or a chiral reducing agent. Non-limiting examples of chiral reducing agents include alpine borane and prapine borane. Non-limiting examples of 1,2-reduction reactions involving chiral catalysts are Corey-Bakshi-Shibata reduction, Noyori hydrogenation, and Noyori transfer hydrogenation. The oxidation/reduction reaction sequence can be carried out in situ using dynamic kinetic resolution. A dynamic kinetic resolution can further involve a reaction with a hydroxyl protecting agent, which removes the desired stereoisomer from the reduction/oxidation equilibrium. In a non-limiting example, a dynamic kinetic resolution of chiral secondary alcohols can involve reduction/oxidation equilibration using $\eta^5$-Ph$_5$CpRu(CO)$_2$H in combination with enantioselective esterification using isopropenyl acetate catalyzed by a lipase enzyme (e.g., lipase B from *Candida Antarctica*, see, e.g., Martin-Matute et al., *J. Am. Chem. Soc.*, 127:8817-8825, 2005).

Epimerization can also be carried out on a compound containing a tetrahydropyran-2-yl-acetaldehyde moiety, in which carbon 2 of the pyran ring exhibits an undesired stereochemical identity. Contacting this compound with L-proline can provide equilibrium between two stereoisomers. If other, non-equilibrating stereogenic centers are present in the compound, the most stable stereoisomer will be present in a larger quantity relative to other stereoisomer(s) in equilibrium with the most stable stereoisomer.

The following examples are meant to illustrate the invention. They are not meant to limit the invention in any way.

EXAMPLES

Example 1—C.2-C.3 Macrocyclization Through Horner-Wadsworth-Emmons Olefination

A halichondrin macrolide 3 can be prepared according to the below sequence.

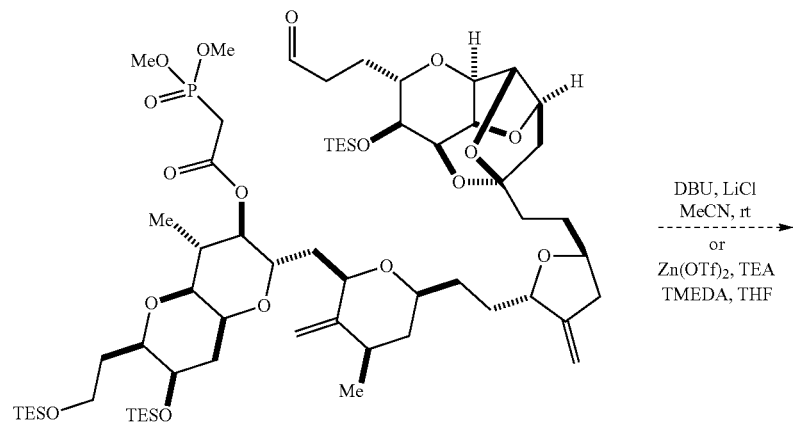

1

-continued

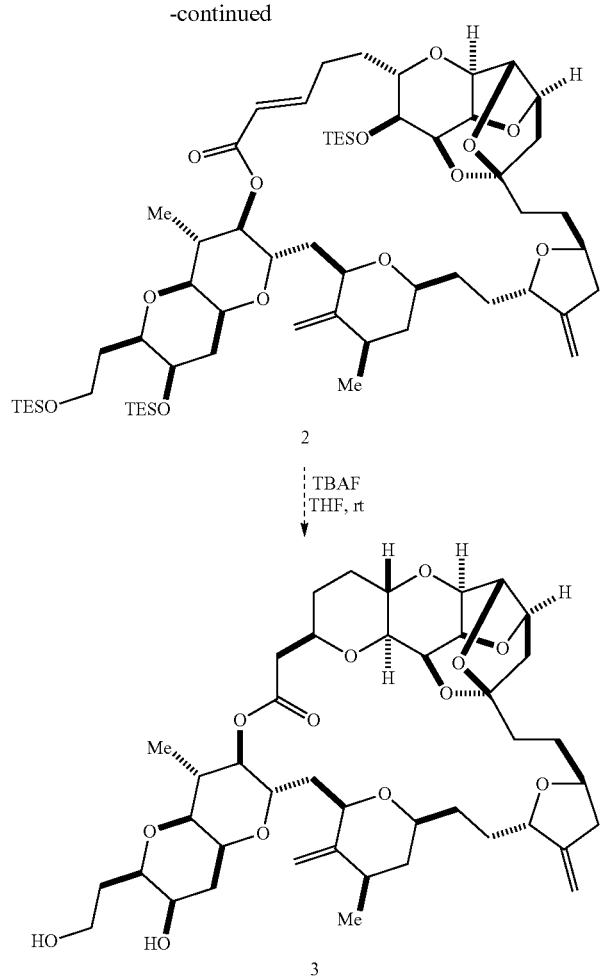

2

↓ TBAF
  THF, rt

3

Compound 1 can be converted to compound 2 through the Horner-Wadsworth-Emmons olefination (e.g., under Masamune conditions or according to Helquist protocol). Compound 2 can be converted to compound 3 after global deprotection (e.g., removal of silyl groups with a fluoride source, such as TBAF).

Example 2—C.2-C.3 Macrocyclization Through Ring-Closing Olefin Metathesis

A halichondrin macrolide 3 was prepared according to the below sequence.

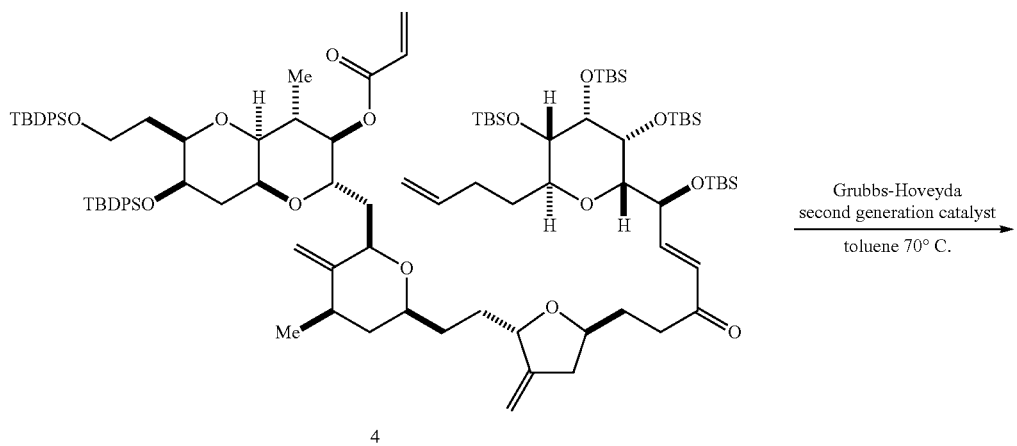

4

-continued
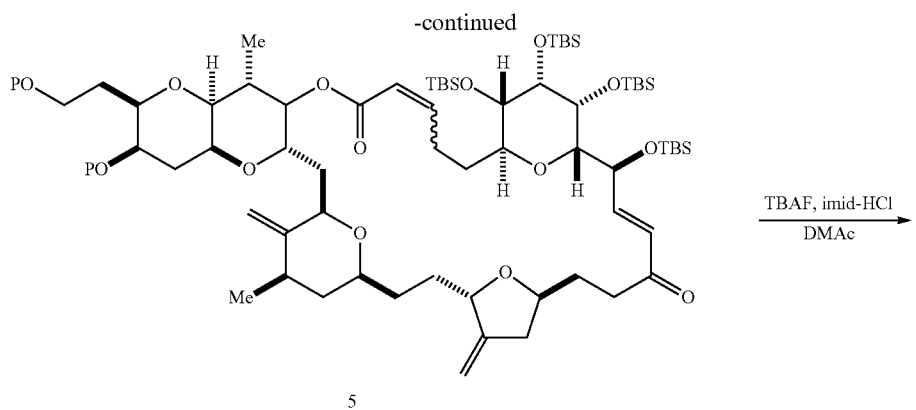
5
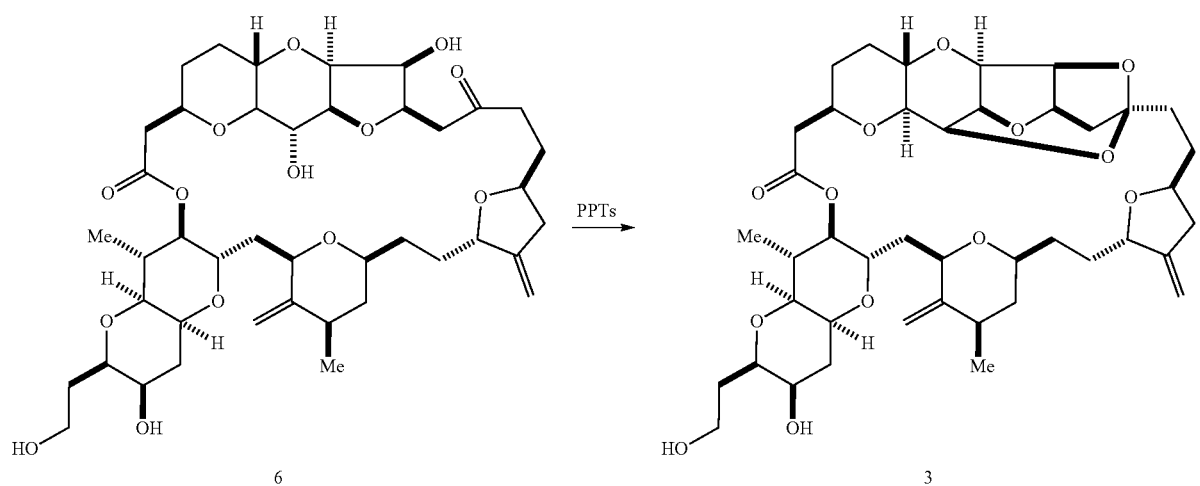
Ring-Closing Olefin Metathesis
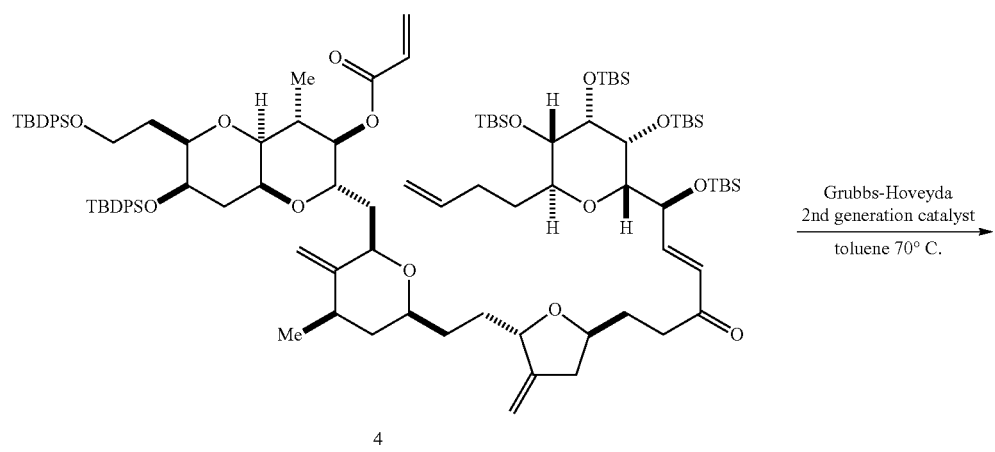

-continued

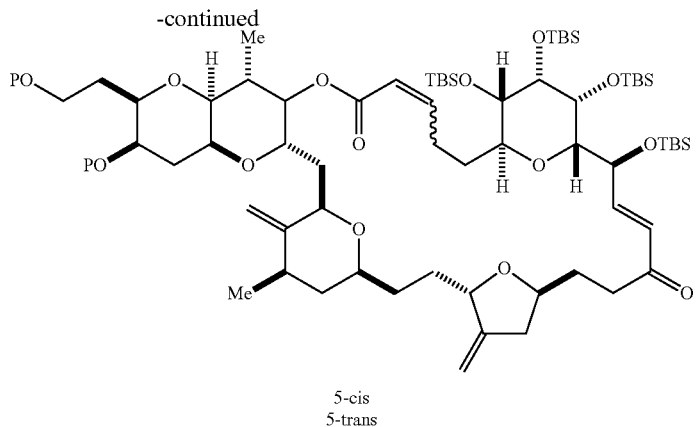

5-cis
5-trans

Compound 4 (0.047 g, 0.027 mmol) was dissolved in toluene (57.0 mL) and 1,4-benzoquinone (1 mg, 10 μmol), and Hoveyda-Grubbs 2nd generation catalyst (3 mg, 5.3 μmol) was added. The reaction mixture was warmed to 70° C. Upon completion (2 h), DMSO (9.51 μL, 0.134 mmol) was added, and the solution was allowed to stir at room temperature for 16 h. After concentration, the resulting green residue was purified by column chromatography (Biotage Ultra cartridge, 10 g, heptane/EtOAc) to provide two RCM adducts, 5-cis and 5-trans with cis impurity (19 mg total, 0.011 mmol, 41%, 3:1 ratio cis/trans). 5-cis: $^1$H NMR (400 MHz, BENZENE-$d_6$) δ=7.97-7.88 (m, 2H), 7.80 (dd, J=2.9, 6.4 Hz, 2H), 7.76-7.66 (m, 4H), 7.28-7.17 (m, 12H), 6.66-6.55 (m, 1H), 6.04 (d, J=15.6 Hz, 1H), 5.30 (dd, J=3.7, 6.8 Hz, 1H), 5.02 (s, 1H), 4.92 (t, J=1.0 Hz, 1H), 4.89 (br. s., 1H), 4.87 (s, 1H), 4.77-4.73 (m, 1H), 4.77-4.73 (m, 1H), 4.75 (s, 1H), 4.65 (br. s., 1H), 4.47 (br. s., 1H), 4.20 (dd, J=3.7, 6.8 Hz, 1H), 4.16-4.09 (m, 2H), 4.03-3.89 (m, 3H), 3.80-3.66 (m, 3H), 3.43 (d, J=9.4 Hz, 4H), 3.33 (d, J=3.5 Hz, 1H), 3.22 (d, J=9.4 Hz, 1H), 2.96-2.90 (m, 1H), 2.85-2.75 (m, 1H), 2.63-2.44 (m, 1H), 2.31 (d, J=5.5 Hz, 1H), 2.25-1.97 (m, 2H), 1.96-1.57 (m, 1H), 1.52-1.23 (m, 1H), 1.21 (s, 1H), 1.15-1.13 (m, 1H), 1.08 (s, 1H), 1.15 (s, 1H), 0.99-0.97 (m, 1H), 0.93 (s, 1H), 0.85-0.85 (m, 1H), 0.85 (s, 1H), 0.92 (s, 1H), 0.81 (br. s., 1H), 0.39 (s, 1H), 0.32-0.30 (m, 1H), 0.30 (s, 1H), 0.30-0.29 (m, 1H), 0.30 (s, 1H), 1.21 (s, 9H), 1.14 (s, 9H), 1.13-1.12 (m, 3H), 1.08 (s, 9H), 0.98 (s, 9H), 0.97-0.95 (m, J=2.0 Hz, 3H), 0.93 (s, 9H), 0.85 (s, 9H), 0.30 (s, 3H), 0.30 (s, 3H), 0.18 (s, 3H), 0.14 (s, 3H), 0.13 (s, 3H), 0.11 (s, 3H), 0.01 (s, 3H), −0.11 (s, 3H)

Compound 3

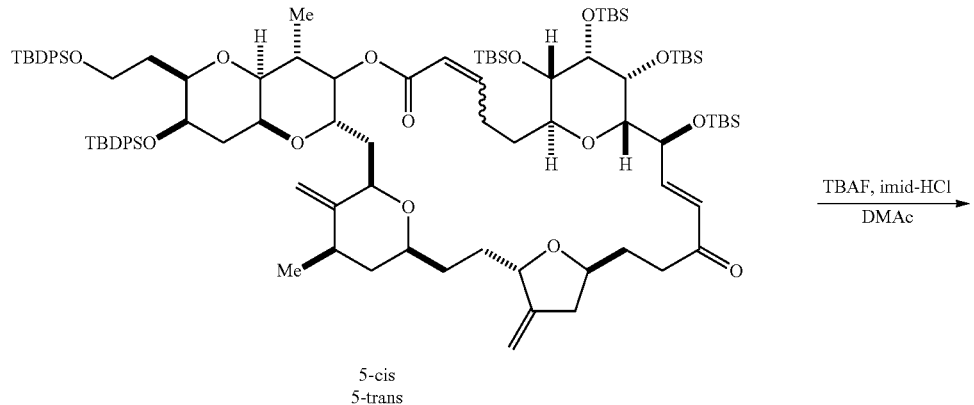

5-cis
5-trans

→ TBAF, imid-HCl / DMAc

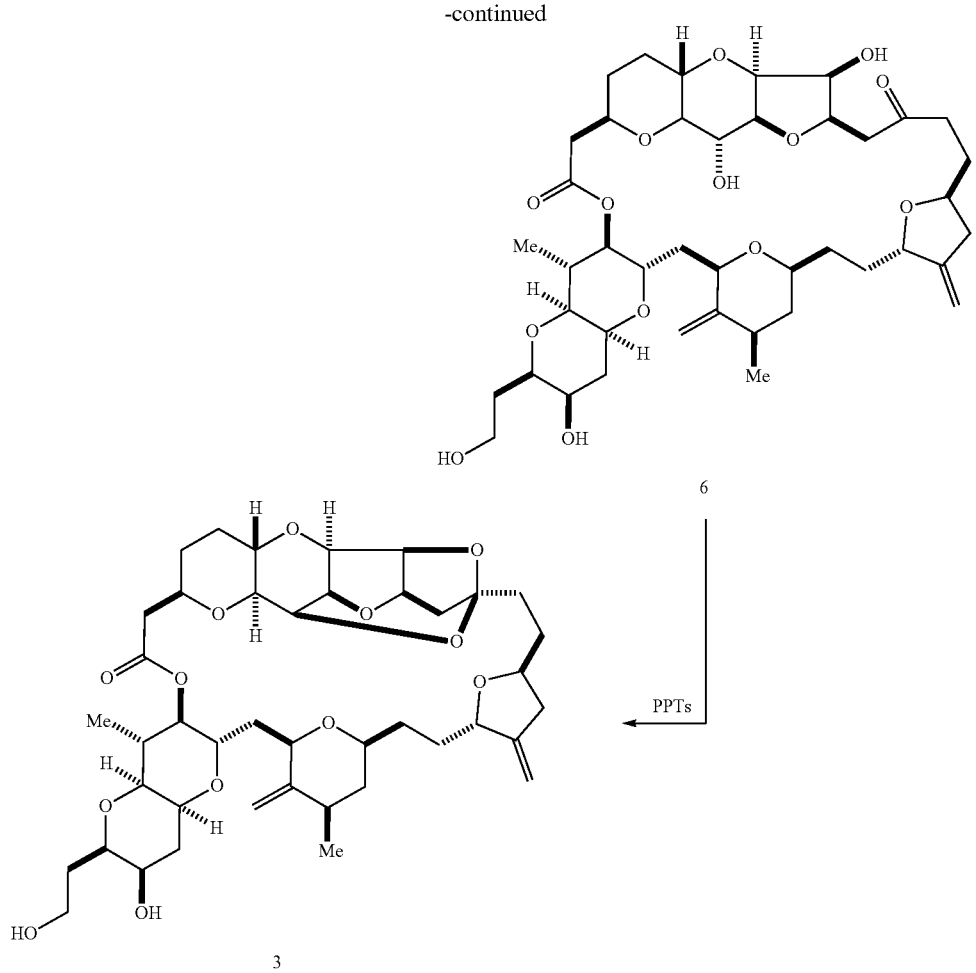

The mixture of compounds 5-cis and 5-trans (0.019 g, 0.011 mmol) was dissolved in N,N-dimethylacetamide (0.304 mL, 3.27 mmol). Imidazole hydrochloride (5.76 mg, 0.055 mmol) and TBAF (0.110 mL, 0.11 mmol) were added, and the reaction monitored by LCMS. Upon completion, water (5 mL) was added. Extraction with heptane removed lypophilic impurities. The aqueous layer was then extracted with toluene (5 mL) followed by toluene/THF (3:1 v/v, 4×8 mL). Brine was added to the aqueous layer to assist the recovery after the third extraction. The organic layers were combined and washed with saturated NaCl (2×6 mL). The organic layers were then dried over $MgSO_4$, filtered, and concentrated. The colorless residue was azeotroped with acetonitrile/water (3:1, v/v) at 30° C. to provide compound 6 (27 mg, 310% mass recovery) as a pale tan solid that was used directly in the next step. LCMS (Cl): calcd. 790, found, Na ion 813 (M+1+22(Na)). Crude 6 was dissolved in DCM (0.087 mL, 1.352 mmol), and PPTS (0.028 g, 0.11 mmol) was added. The reaction was monitored by LCMS. At 2 h, product forms as determined by M+1 of 773.

The residue (8.70 mg, 11.00 μmol) was dissolved in dichloromethane (0.5 mL) at ambient temperature and PPTS (18 mg, 72 μmol) was added. The reaction mixture was filtered through a $SiO_2$ plug (0.75 cm×2 cm) using EtOAc/MeOH to provide 5.5 mg of residue after concentration. The structure was confirmed by LCMS comparison with an authentic standard.

| UPLC column: | Waters Acquity UPLC HSS T3 1.8 μm, 2.1*50 mm, Part no. 186003538, Serial no. 01753602015820 | | |
| --- | --- | --- | --- |
| Temperature: | 50° C. | | |
| Flow rate: | 0.8 mL/min | | |
| Gradient: | Time, min | %-Solvent A | %-Solvent B |
| | Initial | 97 | 3 |
| | 0.1 | 97 | 3 |
| | 2.0 | 1 | 99 |
| | 2.5 | 1 | 99 |
| | 2.51 | 97 | 3 |
| | 3.0 | 97 | 3 |
| Injection volume: | 1 μL | | |
| UV Detection: | PDA 210-400 nm | | |
| Mass Detection(SQD): | ES(+), mass scan 100.00 to 2000.00 | | |
| Run time: | 3 min | | |

Compound 3 standard, RT 1.90 min, ES + (M + 1) 773

Found, RT 1.90 min, ES + (M + 1) 773

Compound 4 was prepared according to the below sequence:

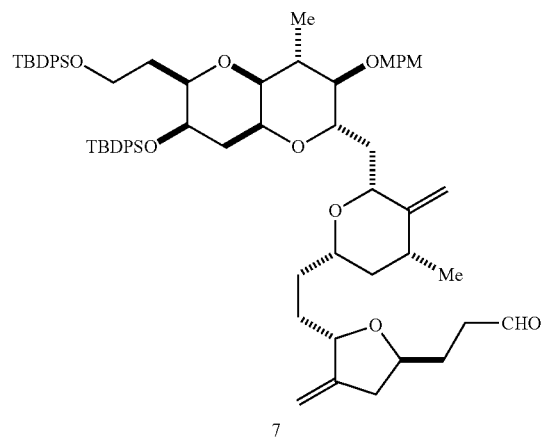
7
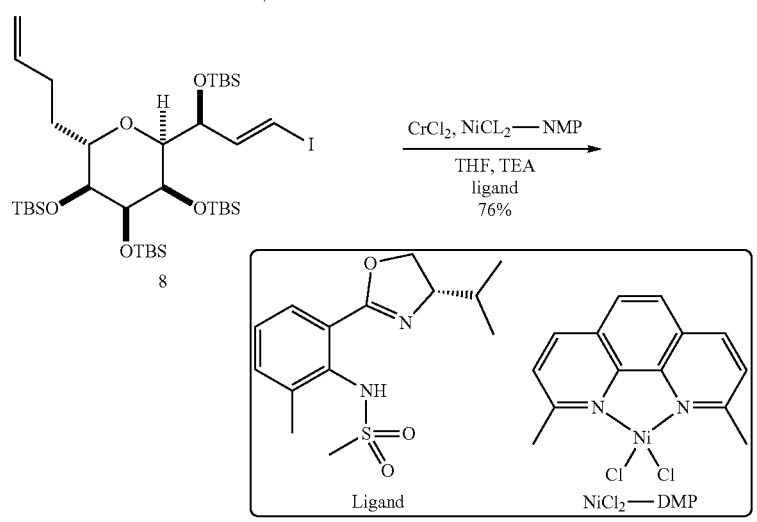
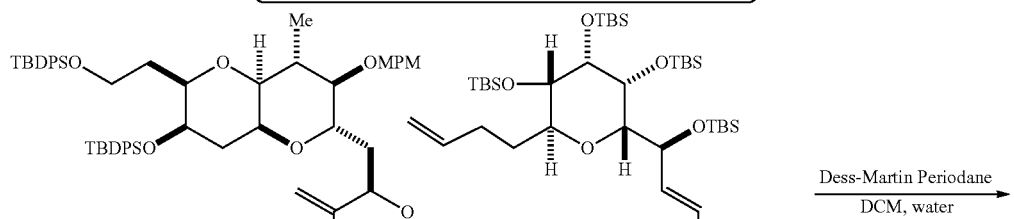
9
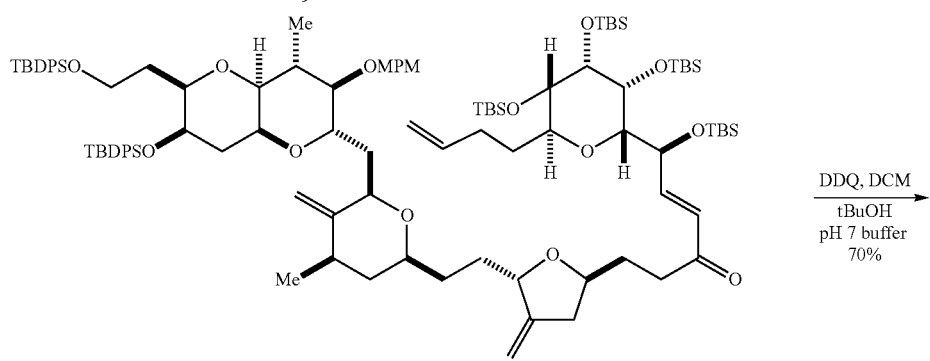
10

-continued

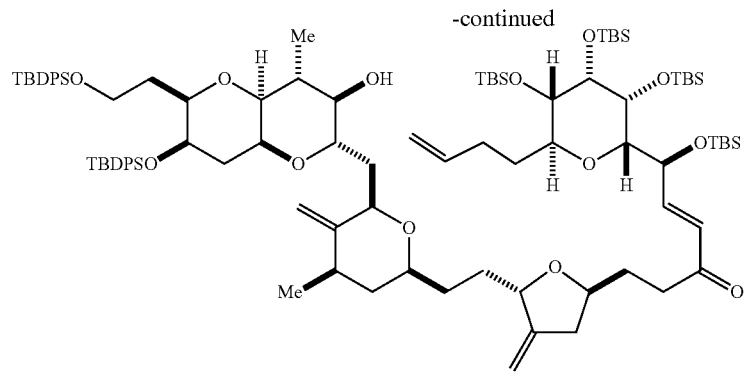

11 acryloyl chloride, TEA, DCM →

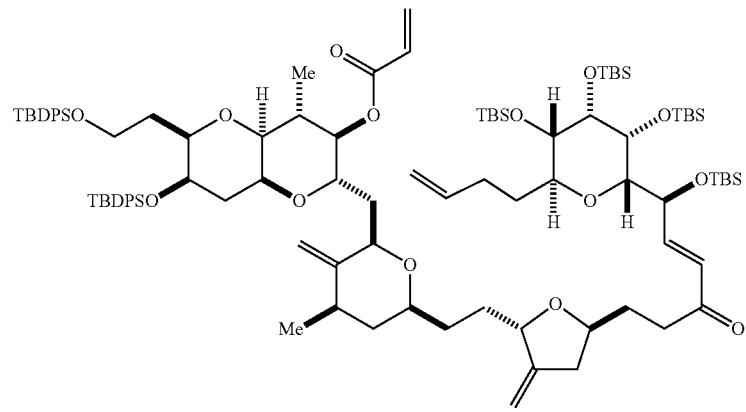

4

35

(6S,E)-6-((2S,3R,4S,5S,6S)-6-(but-3-en-1-yl)-3,4,5-tris((tert-butyldimethylsilyl)oxy)tetrahydro-2H-pyran-2-yl)-6-((tert-butyldimethylsilyl)oxy)-1-((2S,5S)-5-(2-((2S,4R,6R)-6-(((2S,3R,4R,4aS,6R,7R,8aS)-7-((tert-butyldiphenyisilyl)oxy)-6-(2-((tert-butyldiphenyisilyl)oxy)ethyl)-3-((4-methoxybenzyl)oxy)-4-methyloctahydropyrano[3,2-b]pyran-2-yl)methyl)-4-methyl-5-methylenetetrahydro-2H-pyran-2-yl)ethyl)-4-methylenetetrahydrofuran-2-yl)hex-4-en-3-ol

40

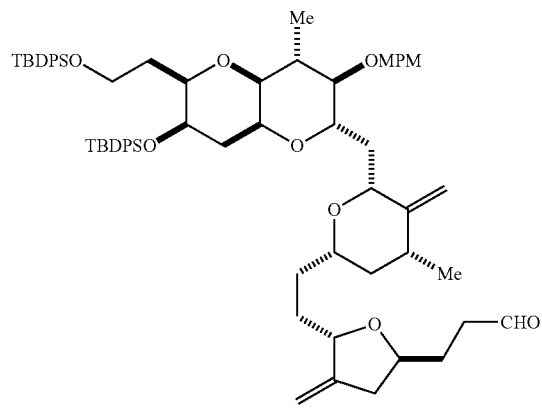

7

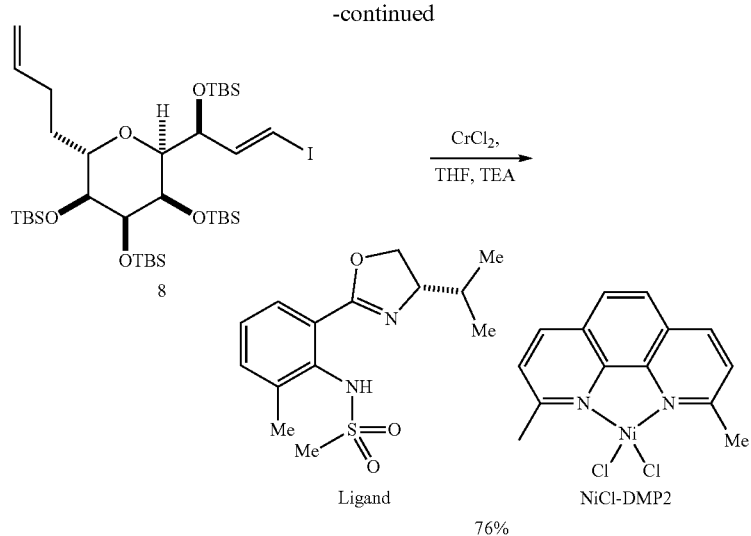

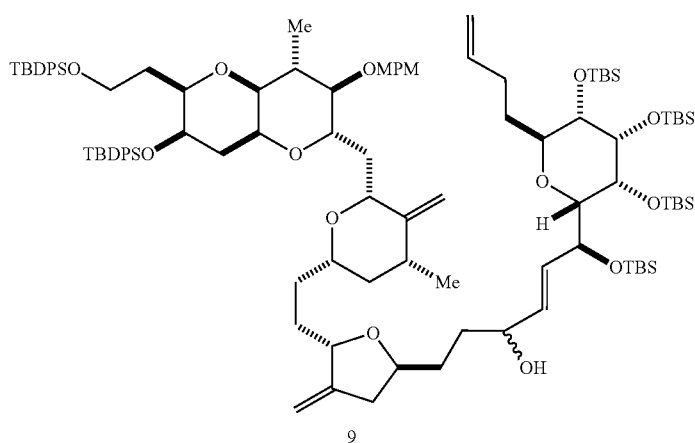

Compound 8 (0.200 g, 0.242 mmol) and compound 7 (0.175 g, 0.156 mmol) were dissolved in $N_2$ sparged THF (0.5 mL). In a separate flask, the ligand (0.255 g, 0.86 mmol) and chromium(II) chloride (0.106 g, 0.862 mmol) were suspended in $N_2$ Sparged THF (1.5 mL) at 30° C. Triethylamine (0.12 mL, 0.861 mmol) was added, and the green solution was stirred for 30 minutes before cooling to 0° C., at which time, Ni-DMP complex (8.00 mg, 0.024 mmol) was added. The solution of compounds 7 and 8 was added, and the reaction warmed to room temperature. Upon completion, the reaction was cooled to 0° C., and ethylenediamine (0.158 ml, 2.345 mmol) was added and the stirred for 1 h. Water (2 mL) was added followed by heptane (10 mL) after 10 min. The phases were separated, and the aqueous phase was extracted with MTBE twice. The combined extracts were sequentially washed with HCl (1 N), water, and brine. After drying with $MgSO_4$, the filtrates were concentrated to provide a pale green solid. Heptane trituration provided a solution that was loaded directly on a Redisep cartridge (4 g, heptane/EtOAc) and provided the compound 9 (217 mg, 0.119 mmol, 76%, (est. 3:1 ratio of diastereomers)). The product was used without further purification in the next step.

(S,E)-6-((2S,3R,4S,5S,6S)-6-(but-3-en-1-yl)-3,4,5-tris((tert-butyldimethylsilyl)oxy)tetrahydro-2H-pyran-2-yl)-6-((tert-butyldimethylsilyl)oxy)-1-((2S,5S)-5-(2-((2S,4R,6R)-6-(((2S,3R,4R,4aS,6R,7R,8aS)-7-((tert-butyldiphenylsilyl)oxy)-6-(2-((tert-butyldiphenylsilyl)oxy)ethyl)-3-((4-methoxybenzyl)oxy)-4-methyloctahydropyrano[3,2-b]pyran-2-yl)methyl)-4-methyl-5-methylenetetrahydro-2H-pyran-2-yl)ethyl)-4-methylenetetrahydrofuran-2-yl)hex-4-en-3-one

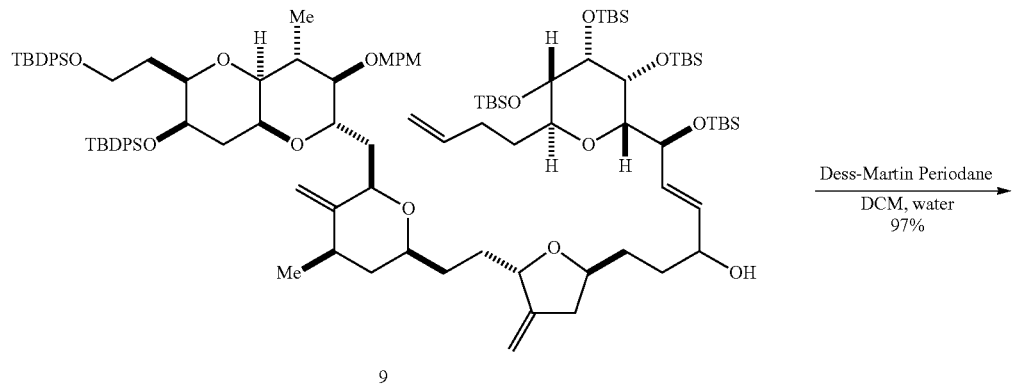

9

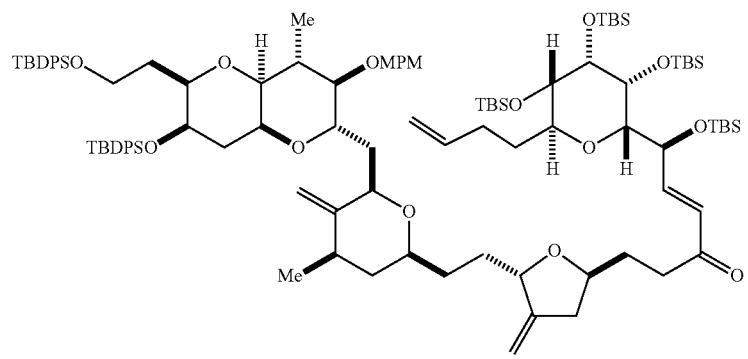

10

Compound 9 (0.217 g, 0.119 mmol) was dissolved in DCM (2.170 mL), and water (0.107 µL) was added followed by Dess-Martin periodinane (0.061 g, 0.143 mmol). Upon completion, aqueous sodium bicarbonate (2 mL) was added, and the mixture was stirred for 15 minutes before extracting with DCM (3×2 mL). The combined extracts were washed with water and dried ($Na_2SO_4$) to provide 246 mg of crude product as a white foam. The material was purified using a Redisep cartridge (4 g, conditioned with 9:1:heptane/EtOAc, loaded with 1:1 heptane/DCM, and eluted as a single 30 mL fraction of heptane/EtOAc (9:1, (v/v)). After concentration, 15 (211 mg, 0.116 mmol, 97%) was provided as a white crunchy foam. $^1$H NMR (400 MHz, $CDCl_3$) δ=d=7.92-7.84 (m, 2H), 7.79 (dd, J=2.9, 6.4 Hz, 2H), 7.77-7.70 (m, 4H), 7.34-7.16 (m, 14H), 6.78 (d, J=1.0 Hz, 2H), 6.62 (d, J=1.0 Hz, 1H), 5.96-5.81 (m, 1H), 5.88 (d, J=5.9 Hz, 1H), 5.39-5.30 (m, 1H), 5.35 (dd, J=4.1, 6.8 Hz, 1H), 5.11-5.03 (m, 1H), 5.12-5.02 (m, 1H), 4.96 (d, J=10.9 Hz, 1H), 5.00-4.92 (m, 1H), 4.85 (s, 1H), 4.82-4.79 (m, 1H), 4.79-4.76 (m, 1H), 4.79 (d, J=8.2 Hz, 1H), 4.50 (t, J=5.5 Hz, 1H), 4.40 (d, J=7.8 Hz, 1H), 4.25-4.19 (m, 1H), 4.18-4.11 (m, 1H), 4.11-4.00 (m, 1H), 3.96 (dd, J=5.1, 9.4 Hz, 1H), 3.85-3.67 (m, 1H), 3.61-3.41 (m, 2H), 3.34-3.25 (m, 3H), 3.20-3.10 (m, 2H), 2.85-2.57 (m, 1H), 2.55-2.30 (m, 2H), 2.28-1.89 (m, 7H), 1.89-1.76 (m, 4H), 1.76-1.28 (m, 3H), 1.18 (s, 7H), 1.24-1.16 (m, 6H), 1.15 (s, 1 OH), 1.09 (s, 9H), 0.97 (s, 11H), 0.96 (br. s., 4H), 0.93 (s, 9H), 0.91 (s, 9H), 0.85 (t, J=6.8 Hz, 4H), 0.33 (br. s., 3H), 0.32 (br. s., 3H), 0.19-0.17 (m, 3H), 0.14 (br. s., 3H), 0.14-0.13 (m, 3H), 0.12 (s, 6H), 0.07-0.05 (m, 3H), 0.07-0.05 (m, 3H), 0.01--0.03 (m, 1H), −0.01 (s, 3H).

(S,E)-6-((2R,3R,4S,5S,6S)-6-(but-3-en-1-yl)-3,4,5-tris((tert-butyldimethylsilyl)oxy)tetrahydro-2H-pyran-2-yl)-6-((tert-butyldimethylsilyl)oxy)-1-((2S,5S)-5-(2-((2S,4R,6R)-6-(((2S,3R,4R,4aS,6R,7R,8aS)-7-((tert-butyldiphenylsilyl)oxy)-6-(2-((tert-butyldiphenylsilyl)oxy)ethyl)-3-hydroxy-4-methyloctahydropyrano[3,2-b]pyran-2-yl)methyl)-4-methyl-5-methylenetetrahydro-2H-pyran-2-yl)ethyl)-4-methylenetetrahydrofuran-2-yl)hex-4-en-3-one

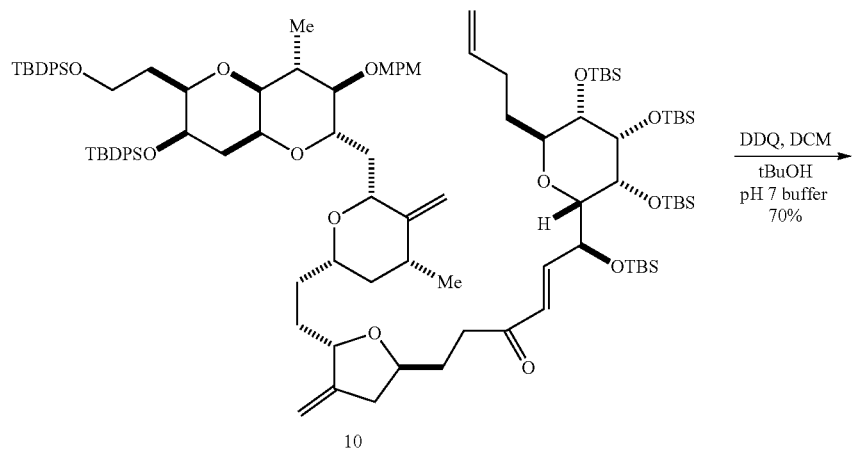

10

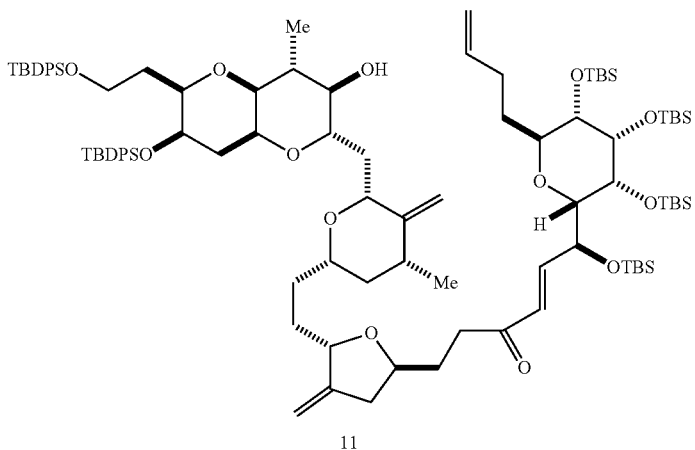

11

Compound 10 (0.211 g, 0.116 mmol) was dissolved in DCM (4.22 mL), t-BuOH (0.042 mL) and pH 7 phosphate buffer were added (0.422 mL). DDQ (53 mg, 0.23 mmol) was added. Upon completion, aqueous sodium bicarbonate (10 mL) was added, and the solution stirred for 10 minutes before it was extracted with heptane (3×5 mL). The combined extracts were washed with aqueous sodium bicarbonate and water before drying with $Na_2SO_4$. The filtrate was concentrated, and residue was purified by column chromatography (Biotage Ultra cartridge, 10 g, heptane/EtOAc) to provide 16 (139 mg, 0.083 mmol, 70%). $^1$H NMR (400 MHz, BENZENE-d6) δ=7.93-7.84 (m, 2H), 7.84-7.67 (m, 7H), 7.34-7.14 (m, 11H), 6.62 (d, J=1.0 Hz, 1H), 5.96-5.82 (m, 1H), 5.35 (dd, J=4.3, 7.4 Hz, 1H), 5.08 (d, J=15.6 Hz, 1H), 4.97 (d, J=10.2 Hz, 2H), 4.92 (s, 2H), 4.89 (s, 3H), 4.86 (s, 3H), 4.75 (s, 3H), 4.48-4.34 (m, 2H), 4.25-4.18 (m, 1H), 4.16 (s, 1H), 4.13-4.07 (m, 1H), 4.07-3.95 (m, 2H), 3.95-3.85 (m, 1H), 3.85-3.75 (m, 1H), 3.75-3.60 (m, 3H), 3.52-3.42 (m, 4H), 3.33-3.26 (m, 1H), 3.12-3.08 (m, 1H), 2.86-2.72 (m, 2H), 2.72-2.58 (m, 3H), 2.54-2.00 (m, 11H), 1.98-1.20 (m, 11H), 1.12 (s, 9H), 1.28-1.11 (m, 60H), 1.10 (s, 9H), 0.98 (s, 9H), 0.93-0.91 (m, 3H), 0.87 (s, 9H), 0.85 (s, 9H), 0.83 (s, 9H), 0.33 (br. s., 3H), 0.32 (br. s., 3H), 0.18 (s, 3H), 0.15 (s, 3H), 0.14 (br. s., 3H), 0.12 (s, 3H), 0.06 (s, 3H), −0.01 (s, 3H)

(2S,3R,4S,4aS,6R,7R,8aS)-2-(((2R,4R,6S)-6-(2-((2S,5S)-5-((S,E)-6-((2R,3R,4S,5S,6S)-6-(but-3-en-1-yl)-3,4,5-tris((tert-butyldimethylsilyl)oxy)tetrahydro-2H-pyran-2-yl)-6-((tert-butyldimethylsilyl)oxy)-3-oxohex-4-en-1-yl)-3-methylenetetrahydrofuran-2-yl)ethyl)-4-methyl-3-methylenetetrahydro-2H-pyran-2-yl)methyl)-7-((tert-butyldiphenylsilyl)oxy)-6-(2-((tert-butyldiphenylsilyl)oxy)ethyl)-4-methyloctahydropyrano[3,2-b]pyran-3-yl acrylate

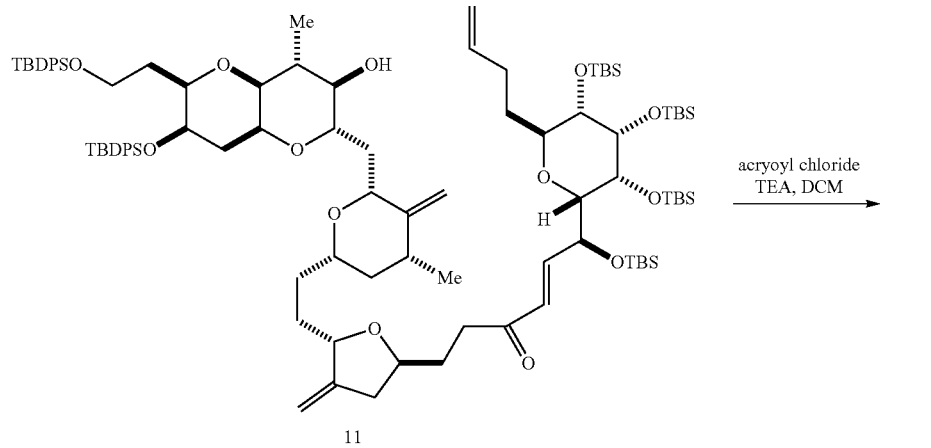

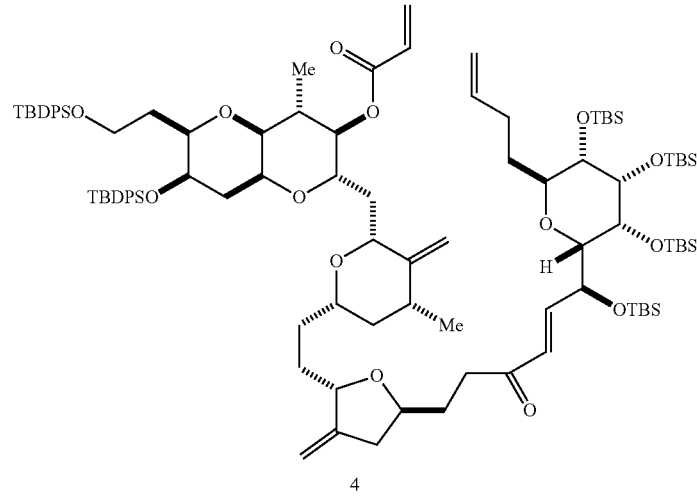

Compound 11 (0.082 g, 0.048 mmol) was dissolved in DCM (820 μL), and the resulting solution was cooled to 0° C. Triethylamine (0.05 mL, 0.359 mmol) was added, followed by acryoyl chloride (4 μL, 0.049 mmol). Additional 0.05 mL TEA and 6 μL acryoyl chloride were added. Upon completion of the reaction, saturated sodium bicarbonate (5 mL) was added, and the reaction mixture was extracted with heptane (3×3 mL). The combined extracts were washed with water and dried ($Na_2SO_4$). After concentration, the residue was purified by column chromatography (Biotage Ultra cartridge, 10 g, heptane/EtOAc) to provide compound 4 (48 mg, 0.027 mmol, 57%) and a mixture of compounds 16 and 17 (35 mg). $^1H$ NMR (400 MHz, BENZENE-$d_6$) δ=7.95-7.86 (m, 3H), 7.79 (dd, J=3.1, 6.6 Hz, 3H), 7.73-7.66 (m, 7H), 7.34-7.27 (m, 1H), 7.26-7.15 (m, 7H), 6.66-6.57 (m, 1H), 6.34 (dd, J=1.6, 17.6 Hz, 1H), 5.99 (dd, J=10.2, 17.2 Hz, 1H), 5.94-5.80 (m, 1H), 5.35 (dd, J=4.1, 7.2 Hz, 1H), 5.31-5.25 (m, 1H), 5.15-4.92 (m, 1H), 4.91-4.83 (m, 3H), 4.77 (s, 1H), 4.51-4.41 (m, 1H), 4.34 (t, J=1.0 Hz, 1H), 4.25-4.19 (m, 1H), 4.16 (s, 1H), 4.09-3.95 (m, 4H), 3.89 (dt, J=4.7, 9.4 Hz, 1H), 3.80 (t, J=8.8 Hz, 1H), 3.75-3.68 (m, 1H), 3.66 (br. s., 2H), 3.60-3.49 (m, 1H), 3.42-3.35 (m, 2H), 3.29 (d, J=1.0 Hz, 1H), 2.95 (t, J=1.6 Hz, 1H), 2.86-2.61 (m, 2H), 2.56-2.33 (m, 3H), 2.31-1.34 (m, 15H), 2.30-2.00 (m, 2H), 1.12 (s, 9H), 1.09 (s, 9H), 1.06 (d, J=1.0 Hz, 3H), 0.97 (s, 9H), 0.95 (d, J=1.0 Hz, 3H), 0.93 (s, 97H), 0.91 (s, 9H), 0.85 (s, 9H), 0.32 (br. s., 3H), 0.18 (s, 3H), 0.14 (s, 3H), 0.13 (br. s., 3H), 0.12 (s, 3H), 0.07-0.05 (m, 3H), 0.06 (s, 3H), −0.01 (s, 3H)

Compound 8 was prepared as shown in the following sequence:

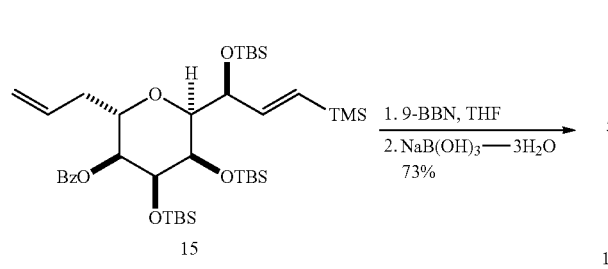

15

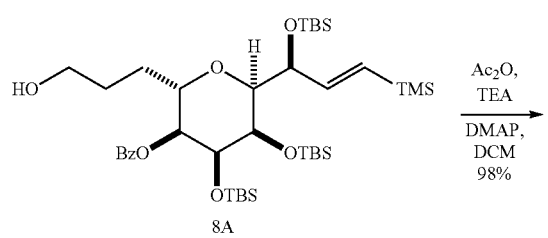

8A

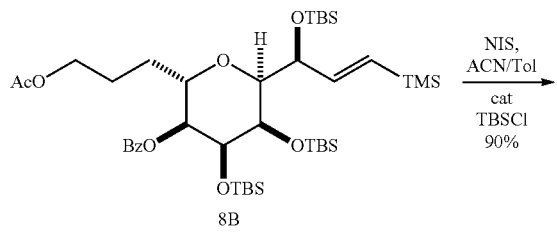

8B

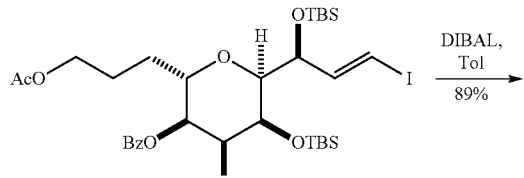

8C

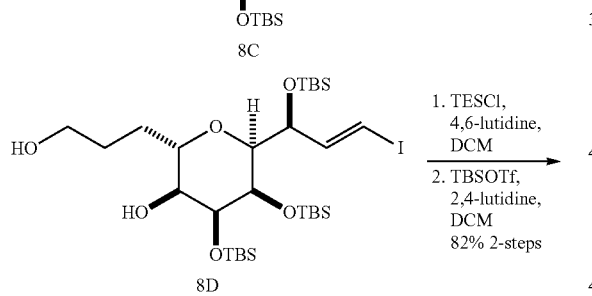

8D

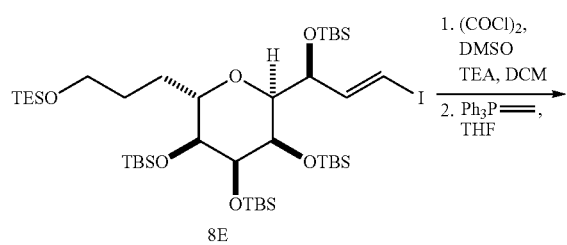

8E

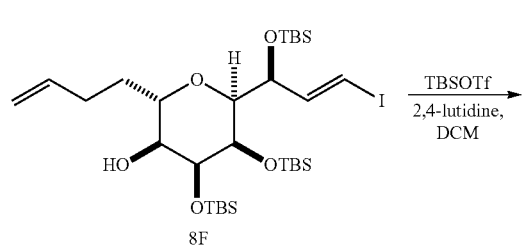

8F

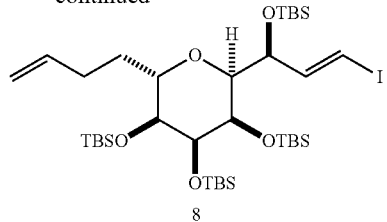

8

(2S,3S,4S,5R,6S)-4,5-bis((tert-butyldimethylsilyl)oxy)-6-((S,E)-1-((tert-butyldimethylsilyl)oxy)-3-(trimethylsilyl)allyl)-2-(3-hydroxypropyl)tetrahydro-2H-pyran-3-yl benzoate

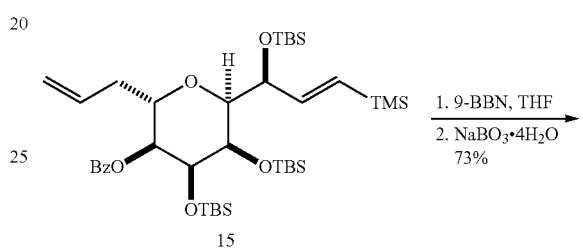

15

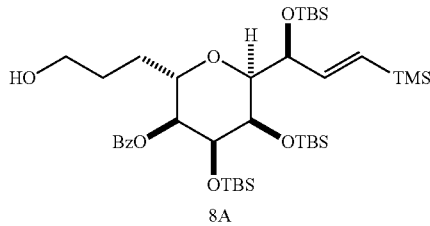

8A

Compound 15 (1.160 g, 1.548 mmol) was dissolved in THF (10 mL), and 9-borabicyclo[3.3.1]nonane (5.0 mL, 2.50 mmol) was added. Upon completion, the solution was cooled to 0° C., and water (10 mL) was added followed by sodium perborate tetrahydrate (1.429 g, 9.288 mmol). The mixture was stirred for 12 h. Aqueous sodium bicarbonate was added, and the mixture was extracted twice with heptane/MTBE (1:1 (v/v)). The combined organic layers were washed with aqueous sodium bicarbonate followed by water and then dried over sodium sulfate. The resulting solution was concentrated, and the resulting residue was purified by column chromatography to provide 0.820 g (1.13 mmol, 73%) of compound 8A. $^1$H NMR (400 MHz, CDCl$_3$) δ=8.09 (br. s., 1H), 7.44-7.36 (m, 1H), 7.27-7.22 (m, 2H), 7.18-7.13 (m, 2H), 5.96 (br. s., 1H), 5.21 (br. s., 1H), 4.47 (br. s., 1H), 4.11 (br. s., 2H), 4.01-3.91 (m, 3H), 3.65 (br. s., 3H), 3.30 (br. s., 1H), 0.96 (s, 9H), 0.89 (s, 9H), 0.87 (s, 9H), 0.16-0.08 (m, 27H).

(2S,3S,4S,5R,6S)-2-(3-acetoxypropyl)-4,5-bis((tert-butyldimethylsilyl)oxy)-6-((S,E)-1-((tert-butyldimethylsilyl)oxy)-3-(trimethylsilyl)allyl)tetrahydro-2H-pyran-3-yl benzoate

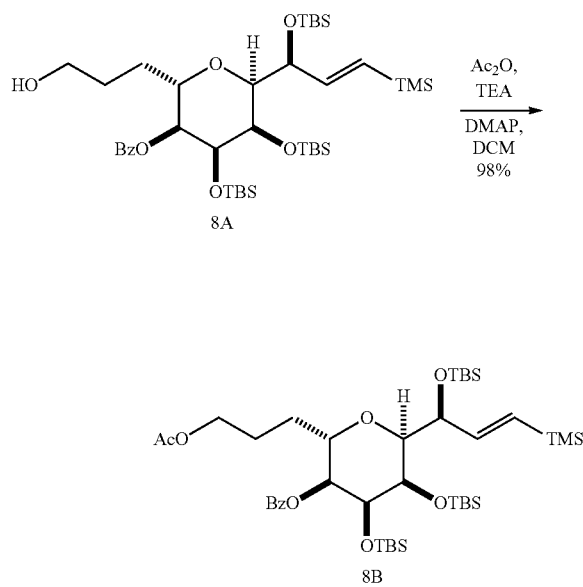

Compound 8A (0.870 g, 1.134 mmol) was dissolved in DCM (8.70 ml) and cooled to 0° C. Triethylamine (1 mL, 7.175 mmol) and DMAP (0.014 g, 0.113 mmol) were added followed by Ac₂O (0.214 mL, 2.268 mmol). Upon completion, saturated aqueous sodium bicarbonate (30 mL) was added. The mixture was extracted with MTBE (3×20 mL). The combined extracts were washed with saturated aqueous sodium bicarbonate, then water, and then brine. After drying over Na₂SO₄, the solution was concentrated to provide compound 8B (0.895 g, 1.106 mmol, 98%) as a colorless oil. ¹H NMR (400 MHz, CDCl₃) δ=8.12-8.04 (m, 1H), 7.55-7.48 (m, 1H), 7.43-7.34 (m, 2H), 6.49-6.44 (m, 1H), 5.97-5.89 (m, 1H), 5.18-5.09 (m, 1H), 4.46-4.33 (m, 1H), 4.14-4.01 (m, 3H), 3.96-3.89 (m, 2H), 3.20 (s, 3H), 3.00-2.97 (m, 1H), 2.35-2.33 (m, 1H), 2.06-1.99 (m, 2H), 1.81-1.74 (m, 1H), 1.64-1.54 (m, 2H), 0.96 (s, 9H), 0.88 (s, 9H), 0.86 (s, 9H), 0.18-0.08 (m, 9H), 0.07 (s, 6H), 0.04 (s, 6H), −0.05--0.11 (m, 23)

(2S,3S,4S,5R,6S)-2-(3-acetoxypropyl)-4,5-bis((tert-butyldimethylsilyl)oxy)-6-((S,E)-1-((tert-butyldimethylsilyl)oxy)-3-iodoallyl)tetrahydro-2H-pyran-3-yl benzoate

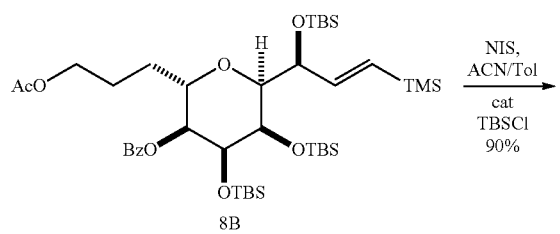

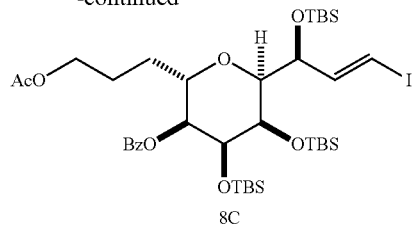

Compound 8B (0.895 g, 1.106 mmol) was dissolved in toluene (5.37 ml) and acetonitrile (10.74 mL, 205.633 mmol). t-Butyldimethylchlorosilane (0.017 g, 0.111 mmol) was added, and the solution was warmed to 30° C. NIS (1.990 g, 8.846 mmol) was added. Upon completion, the reaction mixture was poured into a solution of sodium thiosulfate (2 g) in saturated aqueous sodium bicarbonate (40 mL). MTBE (20 mL) was added, and the mixture stirred for 45 minutes. The MTBE layer was removed in vacuo, and the aqueous layer was extracted with MTBE (2×20 mL). The combined MTBE extracts were washed with 10% (w/v) aqueous sodium thiosulfate, followed by water and then by brine. The solution was dried over MgSO₄ and concentrated to provide crude 8C (857 g, 0.993 mmol, 90%) as pale yellow oil. ¹H NMR (400 MHz, CDCl₃) δ=8.06 (br. s., 2H), 7.53 (br. s., 1H), 7.40 (br. s., 2H), 6.73 (br. s., 1H), 6.38 (d, J=14.8 Hz, 1H), 5.20 (br. s., 1H), 5.01 (br. s., 1H), 4.67-4.56 (m, 1H), 4.54-4.46 (m, 1H), 4.44-4.36 (m, 1H), 4.17-3.98 (m, 3H), 3.98-3.82 (m, 2H), 3.34-3.19 (m, 1H), 2.72 (s, 1H), 2.33 (s, 1H), 2.14-1.88 (m, 3H), 1.88-1.50 (m, 4H), 1.37-1.17 (m, 2H), 0.94 (s, 9H), 0.88 (s, 9H), 0.87 (s, 10H), 0.05 (s, 18H)

(2S,3S,4S,5R,6S)-4,5-bis((tert-butyldimethylsilyl)oxy)-6-((S,E)-1-((tert-butyldimethylsilyl)oxy)-3-iodoallyl)-2-(3-hydroxypropyl)tetrahydro-2H-pyran-3-ol

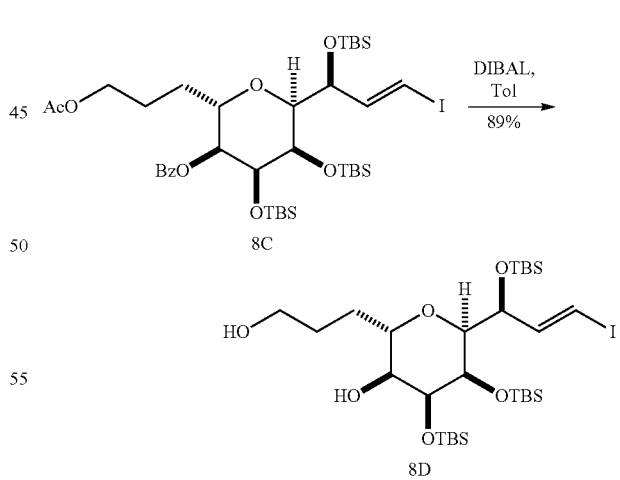

Compound 8C (0.814 g, 0.943 mmol) was dissolved in toluene (8.14 mL) and cooled to −10° C. DIBAL (4.72 ml, 4.716 mmol) was added. After 15 minutes, methanol (0.191 mL, 4.716 mmol) was added followed by aqueous HCl (0.1 N, 20 mL). The mixture was stirred for 15 minutes and the extracted with MTBE three times. The combined extracts were washed with water and brine before drying over $Na_2SO_4$. The resulting solution was concentrated in vacuo, and the residue was purified by column chromatography (Biotage Ultra cartridge, 25 g; heptane/EtOAc) to provide compound 8D (601 g, 0.838 mmol, 89%).

(2S,3S,4S,5R,6S)-4,5-bis((tert-butyldimethylsilyl)oxy)-6-((S,E)-1-((tert-butyldimethylsilyl)oxy)-3-iodoallyl)-2-(3-((triethylsilyl)oxy)propyl)tetrahydro-2H-pyran-3-ol

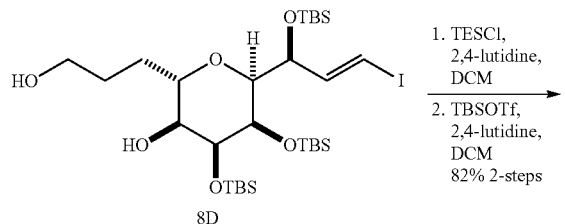

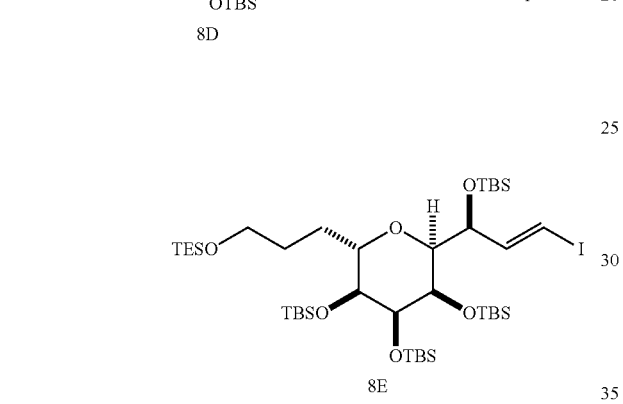

Step 1. Compound 8D (0.601 g, 0.838 mmol) in DCM (6.01 mL) was cooled to 0° C. 2,4-Lutidine (0.291-220, mL, 2.515 mmol) was added followed by chlorotriethylsilane (0.148 mL, 0.88 mmol). Upon completion, saturated aqueous sodium bicarbonate (20 mL) was added, and the mixture was extracted with DCM (3×20 mL). The combined extracts were washed with water. After drying over $Na_2SO_4$, the organic layers were concentrated to provide crude TES-ether (0.697 g).

Step 2. The TES-ether (0.697 g) was dissolved in DCM (6.97 mL) and cooled to 0° C. 2,4-Dimethylpyridine (0.388 mL, 3.354 mmol) was added followed by t-butyldimethylsilyl trifluoromethanesulfonate (0.231 mL, 1.006 mmol). Upon completion, saturated aqueous sodium bicarbonate (20 mL) was added, and the mixture was extracted with MTBE (3×20 mL). The combined extracts were washed with water, HCl (0.1 N), water, and then aqueous sodium bicarbonate. After drying, the filtrate was concentrated to a colorless oil and purified by column chromatography (Biotage Snap 25 cartridge, heptane/EtOAc) to provided compound 8E (0.650 g, 0.687 mmol, 82%). $^1$H NMR (400 MHz, $CDCl_3$) b=6.80-6.57 (m, 1H), 6.26 (dd, J=0.8, 14.5 Hz, 1H), 4.58-4.25 (m, 1H), 3.92-3.66 (m, 3H), 3.64-3.55 (m, 3H), 3.05 (d, J=8.6 Hz, 1H), 1.68-1.55 (m, 1H), 1.51-1.38 (m, 1H), 1.49-1.33 (m, 2H), 1.00-0.83 (m, 36H), 0.60 (q, J=8.2 Hz, 6H), 0.13--0.03 (m, 33H)

(((2S,3R,4S,5S,6S)-2-((S,E)-1-((tert-butyldimethylsilyl)oxy)-3-iodoallyl)-6-(3-((triethylsilyl)oxy)propyl)tetrahydro-2H-pyran-3,4,5-triyl)tris(oxy))tris(tert-butyldimethylsilane)

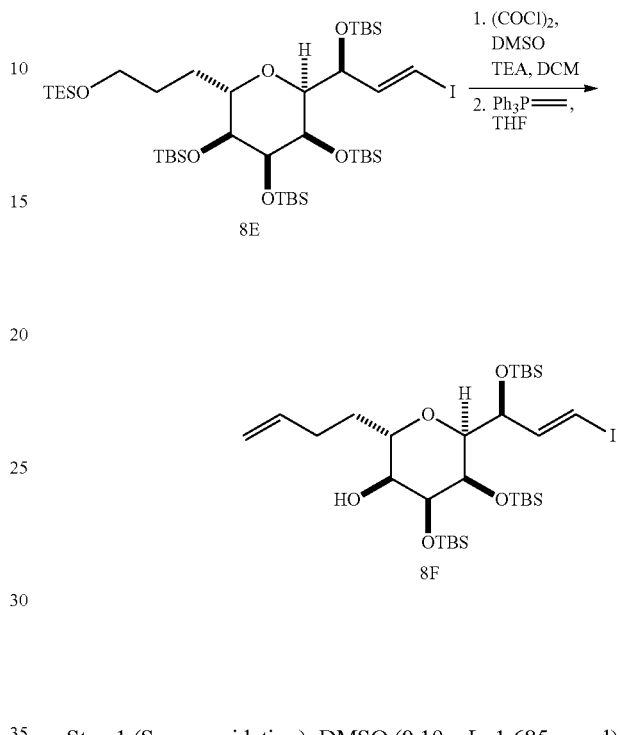

Step 1 (Swern oxidation): DMSO (0.19 mL, 1.685 mmol) in DCM (0.4 mL) was added to oxalyl chloride (2 M in DCM, 0.357 mL, 0.715 mmol) in DCM (1 mL) at −78° C. After 10 minutes, a solution of compound 8E (0.169 g, 0.179 mmol) in DCM (1 mL with a 1 mL rinse) was added dropwise at −78° C. The solution was warmed to −40° C. and stirred for 30 min. The solution was cooled to −78° C. and triethylamine (0.299 mL, 2.145 mmol) was added. The reaction mixture was warmed to 0° C. and HCl (0.1 N) was added. The mixture was extracted with DCM three times. The organic layers were combined, washed with water and then dried with $Na_2SO_4$. Concentration provided the aldehyde (171 mg, 134% mass recovery) as a pale yellow oil that was used directly in step 2.

Step 2. (Wittig reaction): Methyltriphenylphosphonium bromide (0.255 g, 0.715 mmol) was suspended in THF (1.6 mL) and cooled to 0° C. Butyllithium (2M in cyclohexane, 0.349 ml, 0.697 mmol) was added, and the resulting solution was stirred for 30 min. The aldehyde was dissolve THF (1.6 mL) and added to the ylide mixture. Upon completion, HCl (0.1 N) was added and the mixture extracted with heptane (3×20 mL). The combined organics were washed with water followed by aqueous sodium bicarbonate. After drying with $Na_2SO_4$, the filtrate was concentrated to provide crude compound 8F (0.155 g, 0.217 mmol, 122% mass recovery, contaminated with $PPh_3$). $^1$H NMR (400 MHz, $CDCl_3$) δ=6.70 (q, J=6.3 Hz, 1H), 6.38-6.22 (m, 1H), 5.88-5.71 (m, 1H), 5.13-4.96 (m, 2H), 4.39-4.28 (m, 1H), 3.78 (s, 3H), 3.69-3.62 (m, 2H), 3.06-3.01 (m, 1H), 2.21-2.01 (m, 1H), 2.20-2.00 (m, 1H), 1.82-1.63 (m, 1H), 1.45-1.20 (m, 1H), 0.92 (s, 9H), 0.90 (s, 9H), 0.88 (s, 9H), 0.11 (s, 3H), 0.10 (s, 3H), 0.09 (s, 3H), 0.07 (s, 3H), 0.05 (s, 3H), 0.04 (s, 3H)

(((2S,3S,4S,5R,6S)-2-(but-3-en-1-yl)-6-((S,E)-1-((tert-butyldimethylsilyl)oxy)-3-iodoallyl)tetrahydro-2H-pyran-3,4,5-triyl)tris(oxy))tris(tert-butyldimethylsilane)

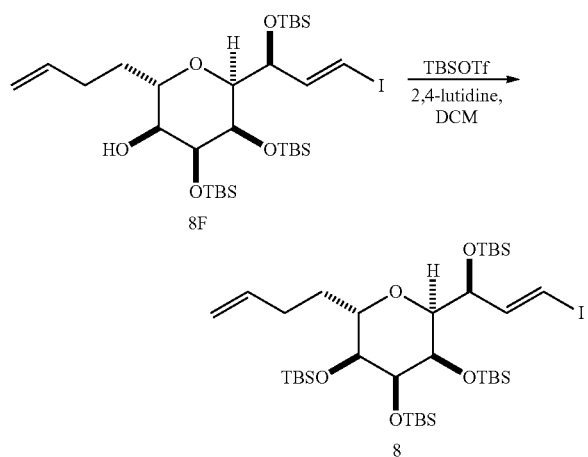

Compound 8F (0.127 g, 0.178 mmol) was dissolved in dichloromethane (1.270 mL) and cooled to 0° C. 2,4-Dimethylpyridine (0.057 g, 0.534 mmol) was added followed by t-butyldimethylsilyl trifluoromethanesulfonate (0.049 ml, 0.214 mmol). After 3 h, additional 2,4-dimethylpyridine (0.4 mL) and t-butyldimethylsilyl trifluoromethanesulfonate (0.1 mL) were added. Upon completion, aqueous sodium bicarbonate was added, and the reaction was stirred for 15 min. The product was extracted with heptane (3×10 mL). The combined extracts were washed with water, HCl (1 N, 2×10 mL), and water. After drying with $Na_2SO_4$/$MgSO_4$, the filtrate was concentrated to provide a pale yellow oil that was purified by column chromatography (Biotage Ultra cartridge, 10 g, H/EtOAc) to provide compound 8 (141 mg, 0.17 mmol, 95% over 3-steps (Swern, Wittig, TBS-protection)).

Example 3—C.3-C.4 Macrocyclization Through Ring-Closing Olefin Metathesis

A halichondrin macrolide 3 can be prepared according to the below sequence.

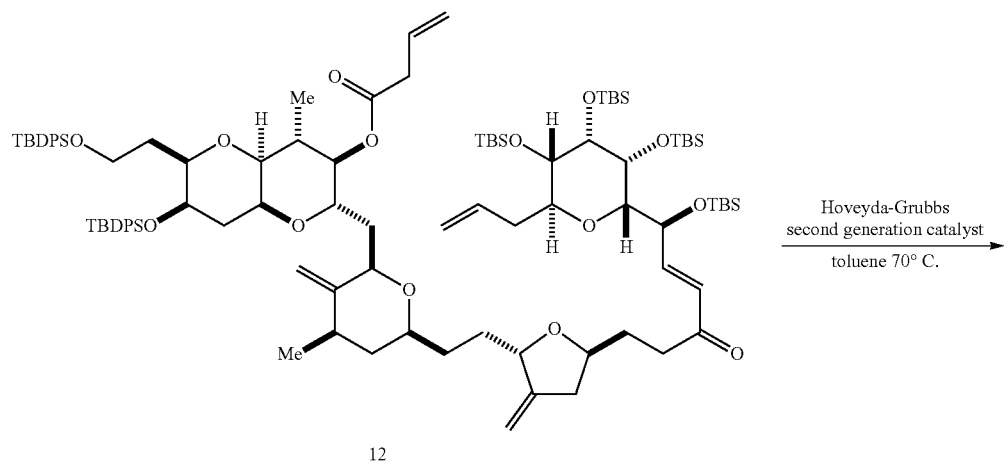

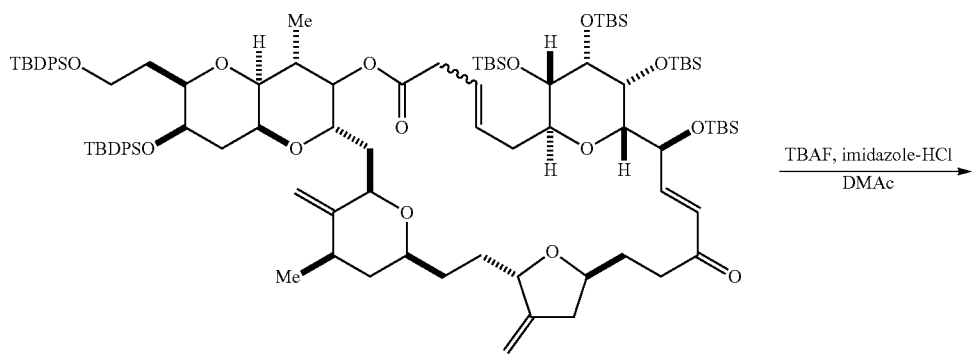

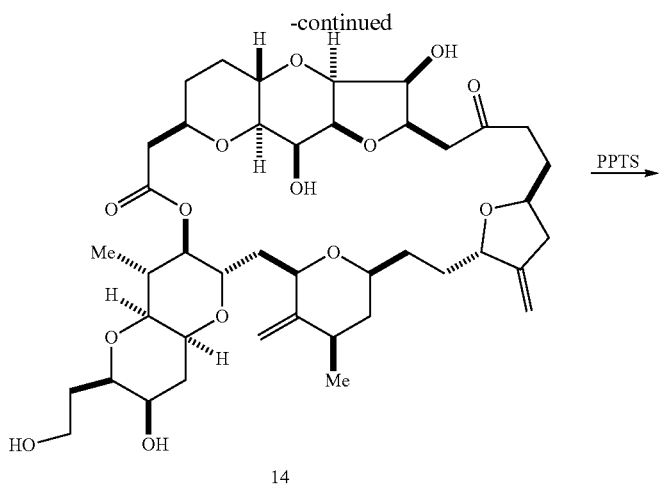
14
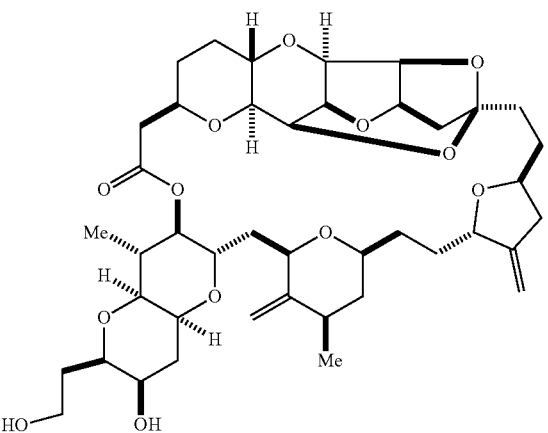
3
Compound 12 can be prepared according to the following sequence:
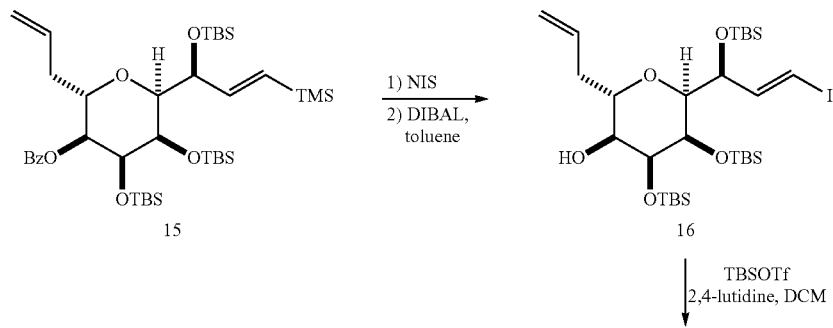

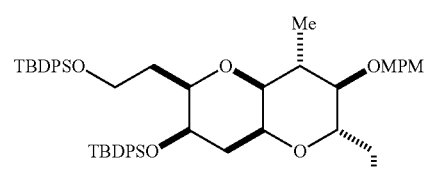
7
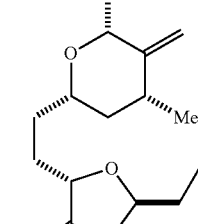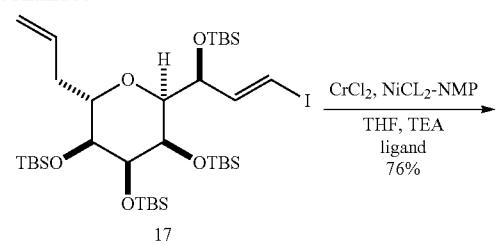
17
CrCl₂, NiCL₂-NMP
THF, TEA
ligand
76%
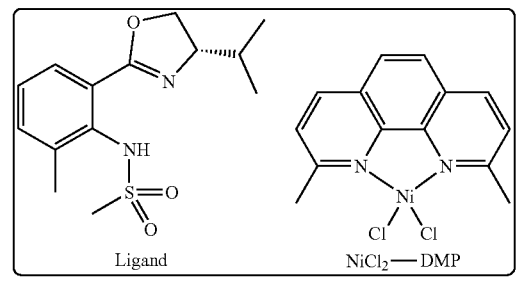
Ligand    NiCl₂—DMP
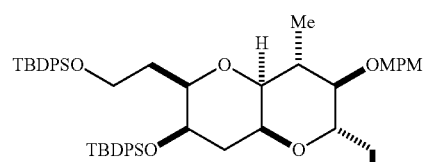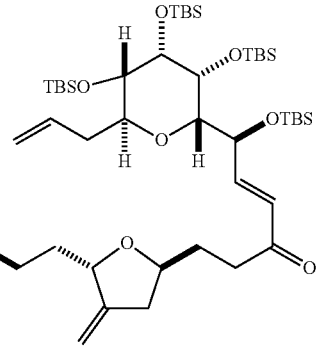
18
Dess-Martin Periodane
DCM, water
97%
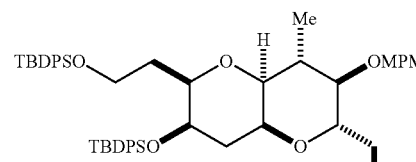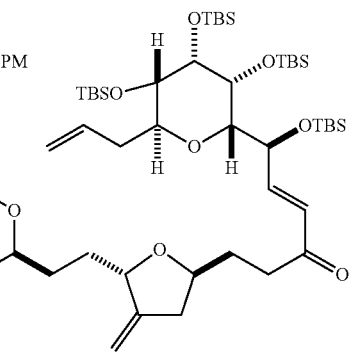
19
DDQ, DCM
tBuOH
pH 7 buffer
70%
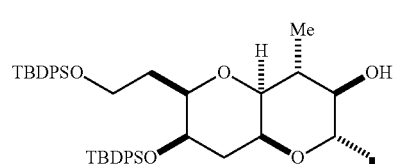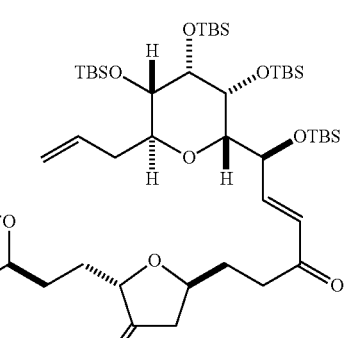
20
3-butenoic acid,
MNBA
TEA, DMAP,
DCM

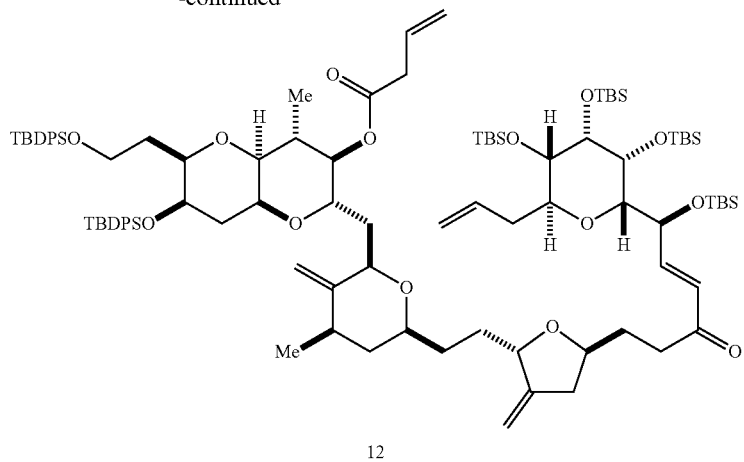
12
Example 4—C. 12-C. 13 Macrocyclization Through Ring-Closing Olefin Metathesis
A halichondrin macrolide 3 can be prepared according to the below sequence.
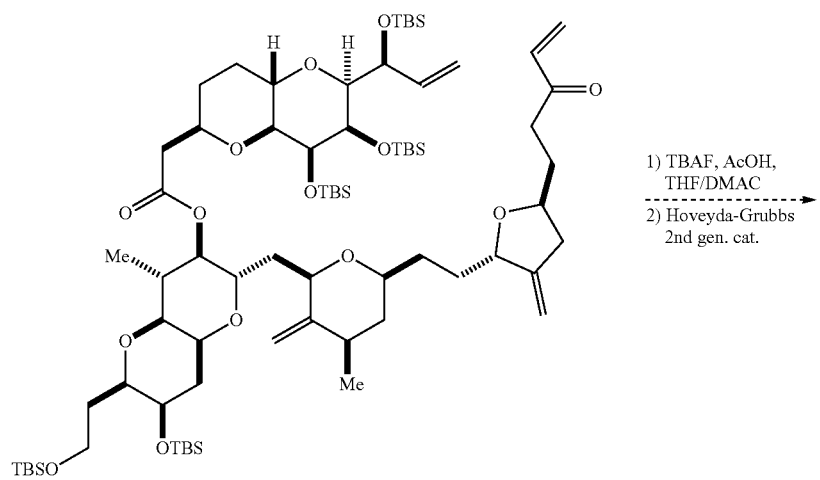
21
1) TBAF, AcOH, THF/DMAC
2) Hoveyda-Grubbs 2nd gen. cat.
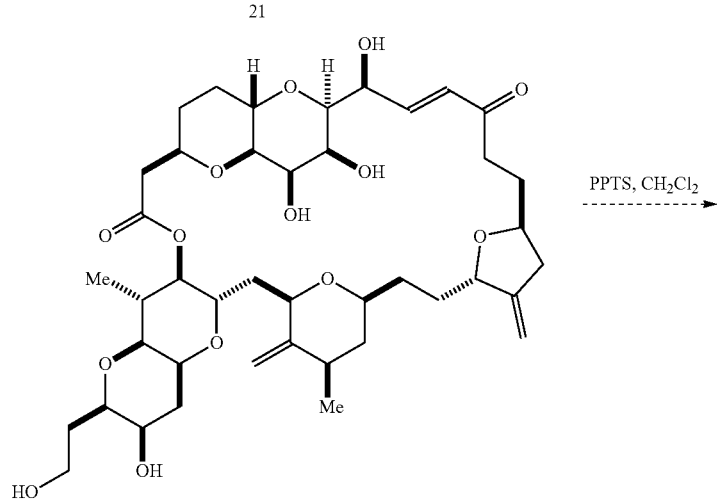
22
PPTS, CH$_2$Cl$_2$

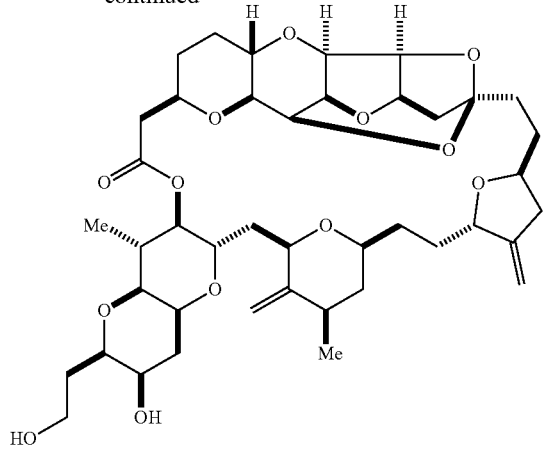

3

Compound 21 can be converted to compound 22 through the catalytic ring-closing olefin metathesis (e.g., with catalytic quantities of Hoveyda-Grubbs $2^{nd}$ generation catalyst). Compound 22 can be converted to compound 3 after global deprotection (e.g., removal of silyl groups with a fluoride source, such as TBAF).

Example 5—C. 15-C. 16 Macrocyclization Through Ring-Closing Olefin Metathesis

A halichondrin macrolide 3 can be prepared according to the below sequence.

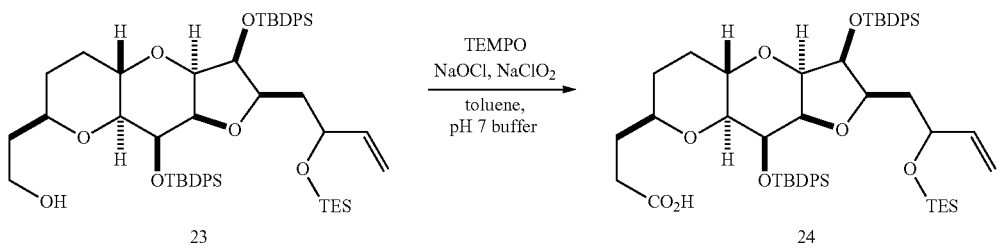

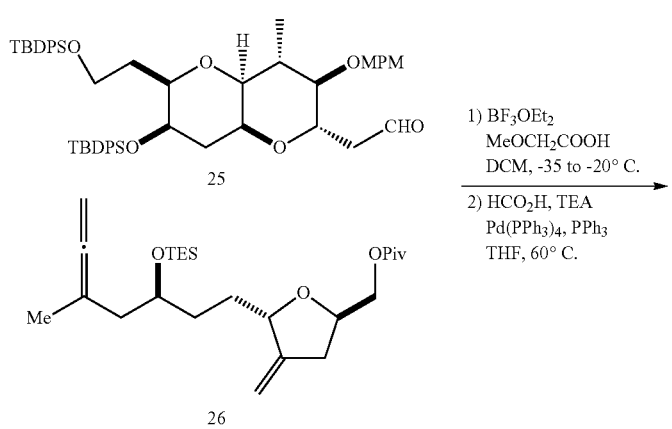

-continued
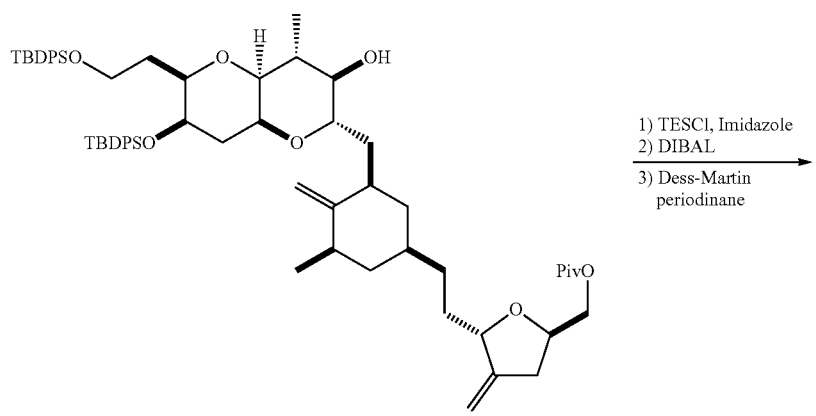
27
1) TESCl, Imidazole
2) DIBAL
3) Dess-Martin periodinane
→
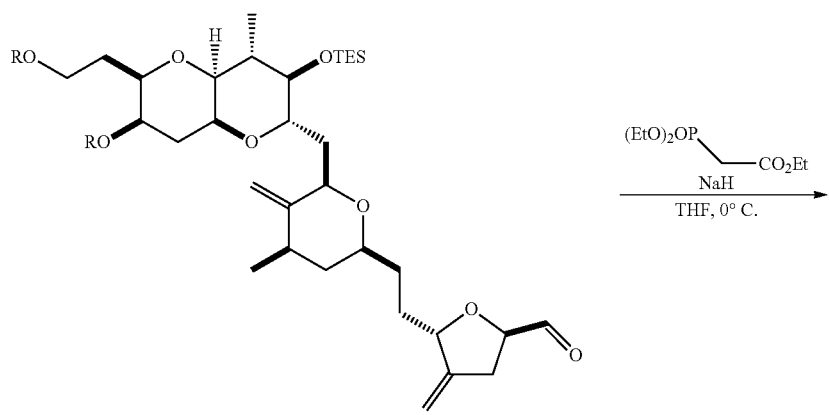
R = TBDPS
28
$(EtO)_2OP\diagdown\diagup CO_2Et$
NaH
―――――
THF, 0° C.
→
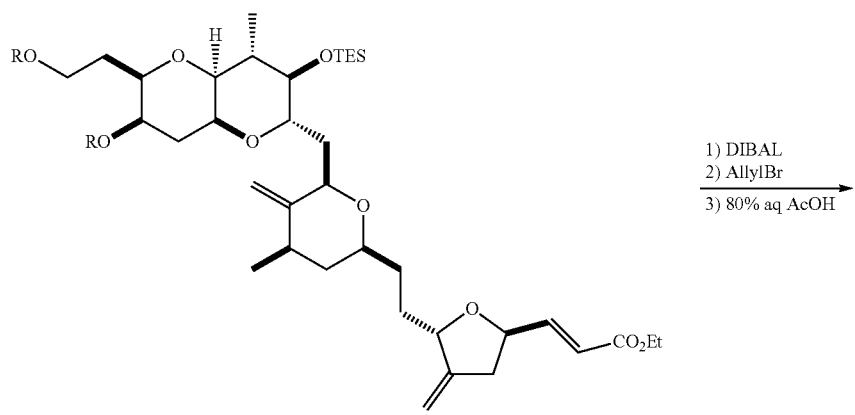
29
1) DIBAL
2) AllylBr
3) 80% aq AcOH
→

-continued

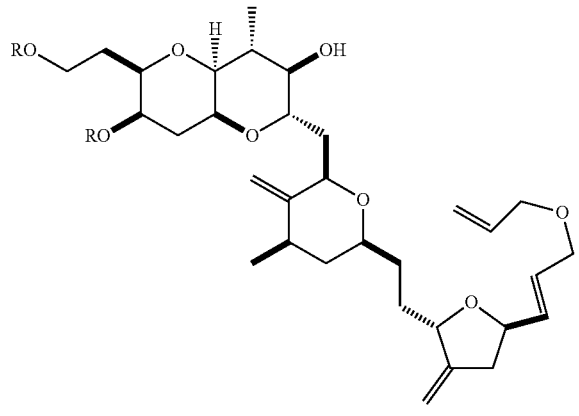

30

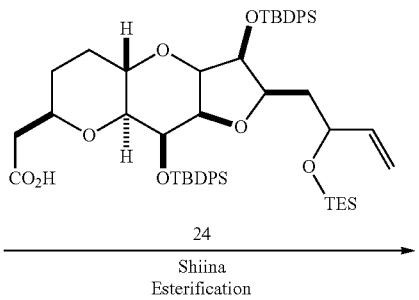

24

Shiina Esterification
→

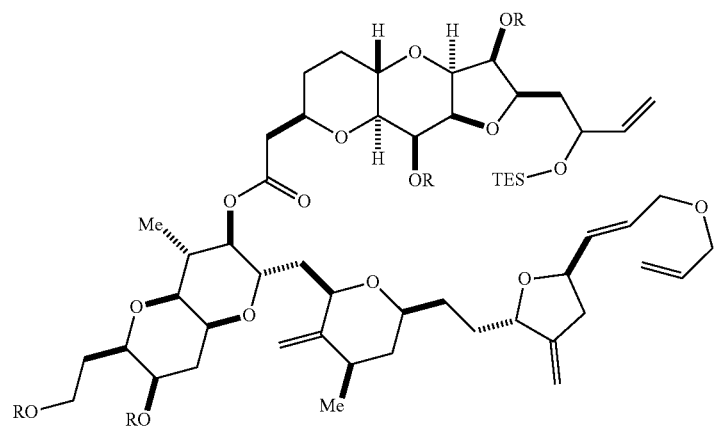

R = TBDPS
31

2-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)acetic acid

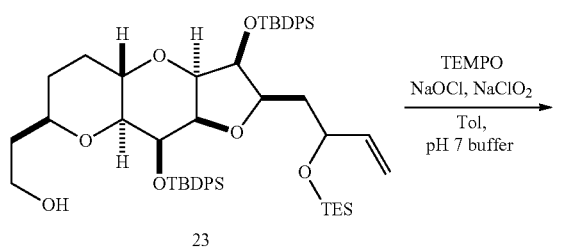

23

TEMPO
NaOCl, NaClO$_2$
Tol, pH 7 buffer
→

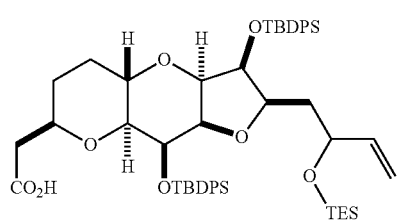

24

2-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)ethanol (compound 23. 70 mg, 0.076 mmol) and TEMPO (1.187 mg, 7.597 µmol) were dissolved in toluene (2 mL) at ambient temperature. To the resulting solution were added pH 7 phosphate buffer (1 mL), a solution of sodium chlorite (42.9 mg, 0.38 mmol) in water (1 mL), and 4% bleach (a solution of sodium hypochlorite in water) (0.012 mL, 7.597 µmol) slowly. After being stirred overnight, the reaction mixture was treated with sodium bisulfite (63.2 mg, 0.608 mmol) and water (5 mL). The resulting mixture was extracted twice with MTBE (10 mL each time). The combined organic layers were washed with 30% aqueous NaCl (2.0 mL) and dried over MgSO$_4$.

Filtration, concentration in vacuo, and purification by silica gel column chromatography using a 25-66% gradient of ethyl acetate in n-heptane as eluent provided 54 mg of the target product as a white foam solid. $^1$H NMR (1:1 diastereomeric mixture, 400 MHz, CDCl$_3$) δ ppm 0.50-0.66 (m, 6H) 0.86-1.01 (m, 9H) 1.05-1.17 (m, 18H) 1.30-1.45 (m, 3H) 1.55-1.65 (m, 1.5H) 1.68-1.79 (m, 1.5H) 1.87-1.99 (m, 1H) 2.09-2.25 (m, 1.5H) 2.38 (d, J=5.5 Hz, 1H) 2.94 (dd, J=9.4, 4.3 Hz, 0.5H) 3.11 (dd, J=9.6, 6.4 Hz, 0.5H) 3.34 (t, J=4.9 Hz, 0.5H) 3.46-3.54 (m, 1H) 3.58 (t, J=4.7 Hz, 0.5H) 3.62-3.78 (m, 2H) 3.88 (t, J=6.3 Hz, 0.5H) 3.95-4.09 (m, 1H) 4.16-4.25 (m, 2H) 4.26-4.42 (m, 1.5H) 4.95-5.18 (m, 2H) 5.71 (m, J=6.3 Hz, 1H) 7.27-7.45 (m, 12H) 7.64-7.77 (m, 8H)

((2R,5S)-5-(2-((2S,4R,6R)-6-(((2S,3R,4R,4aS,6R, 7R,8aS)-7-((tert-butyldiphenylsilyl)oxy)-6-(2-((tert-butyldiphenylsilyl)oxy)ethyl)-3-hydroxy-4-methyl-octahydropyrano[3,2-b]pyran-2-yl)methyl)-4-methyl-5-methylenetetrahydro-2H-pyran-2-yl)ethyl)-4-methylenetetrahydrofuran-2-yl)methyl pivalate

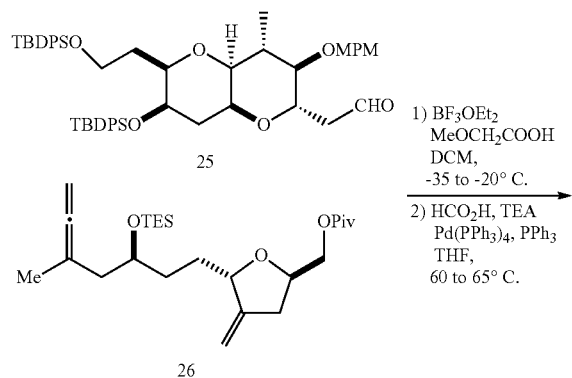

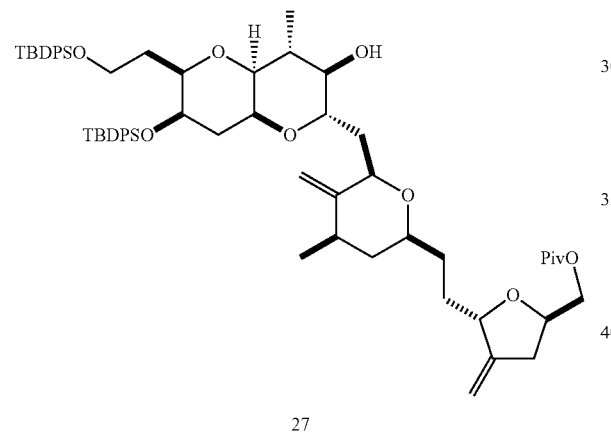

A solution of 2-((2S,3R,4R,4aS,6R,7R,8aS)-7-((tert-butyldiphenylsilyl)oxy)-6-(2-((tert-butyldiphenylsilyl)oxy)ethyl)-3-((4-methoxybenzyl)oxy)-4-methyloctahydropyrano[3,2-b]pyran-2-yl)acetaldehyde (compound 25; 340 mg, 0.347 mmol) and ((2R,5S)-5-((S)-5-methyl-3-((triethylsilyl)oxy)hepta-5,6-dien-1-yl)-4-methylenetetrahydrofuran-2-yl)methyl pivalate (compound 26; 197 mg, 0.452 mmol) in dichloromethane (10 mL) was cooled to −37° C. Methoxyacetic acid (0.533 mL, 6.946 mmol) and BF₃.OEt₂ (0.132 mL, 1.042 mmol) were added, and the resulting solution was stirred for 3 h between −20 to −35° C. The reaction mixture was then treated with sat. NaHCO₃ (15 mL) and extracted twice with MTBE (30.3 mL each). The organic layers were combined, washed with 30% aqueous NaCl (15 mL), and dried over MgSO₄. Filtration, concentration in vacuo, and purification by silica gel column chromatography using a 20-50% gradient of ethyl acetate in n-heptane as eluent provided 0.367 g of a mixture of the target product and byproducts, identified as compound 25 that underwent MPM deprotection and compound 26 that underwent TES deprotection. Without further purification, the mixture was dissolved in THF (7.5 mL). In another reactor, Pd(PPh₃)₄ (0.037 g, 0.032 mmol) and triphenylphosphine (0.034 g, 0.128 mmol) were dissolved in THF (2 mL) and treated with formic acid (0.123 mL, 3.204 mmol) and triethylamine (0.447 mL, 3.204 mmol). The resulting solution was added to the substrate solution prepared above. After being stirred for 20 h at 60 to 65° C., the reaction mixture was diluted with MTBE (20 mL) and washed with sat. aq. NaHCO₃ (5 mL) and 30% aqueous NaCl (5 mL). The organic layer was dried over MgSO₄, filtered, and concentrated in vacuo. The residue was purified by silica gel column chromatography using a 20-100% gradient of ethyl acetate in n-heptane as eluent to give 98 mg of the target product. ¹H NMR (400 MHz, CDCl₃) δ ppm 1.01 (s, 9H) 1.05 (s, 9H) 1.10 (d, J=6.3 Hz, 3H) 1.13 (d, J=7.8 Hz, 3H) 1.20 (s, 9H) 1.28-1.37 (m, 1H) 1.45-1.73 (m, 8H) 1.77-1.85 (m, 1H) 1.91-2.15 (m, 5H) 2.24-2.33 (m, 1H) 2.37-2.47 (m, 1H) 2.63-2.74 (m, 1H) 3.22 (t, J=2.5 Hz, 1H) 3.29-3.38 (m, 1H) 3.49 (d, J=8.2 Hz, 1H) 3.55-3.64 (m, 2H) 3.68 (d, J=2.0 Hz, 1H) 3.72-3.82 (m, 3H) 3.91 (t, J=5.9 Hz, 1H) 4.01 (dd, J=11.7, 4.7 Hz, 1H) 4.05-4.10 (m, 1H) 4.13 (dd, J=11.7, 4.7 Hz, 1H) 4.22-4.34 (m, 1H) 4.41-4.52 (m, 1H) 4.77-4.84 (m, 2H) 4.90 (d, J=2.0 Hz, 1H) 4.99 (d, J=2.3 Hz, 1H) 7.28-7.44 (m, 12H) 7.60 (dq, J=8.1, 1.5 Hz, 4H) 7.66-7.69 (m, 2H) 7.75-7.78 (m, 2H)

((2R,5S)-5-(2-((2S,4R,6R)-6-(((2S,3R,4S,4aS,6R, 7R,8aS)-7-((tert-butyldiphenylsilyl)oxy)-6-(2-((tert-butyldiphenylsilyl)oxy)ethyl)-4-methyl-3-((triethylsilyl)oxy)octahydropyrano[3,2-b]pyran-2-yl) methyl)-4-methyl-5-methylenetetrahydro-2H-pyran-2-yl)ethyl)-4-methylenetetrahydrofuran-2-yl)methyl pivalate

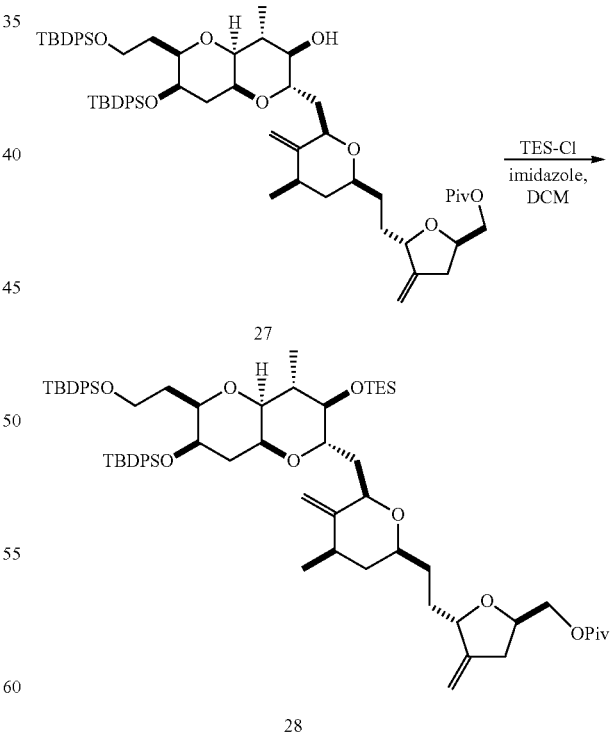

((2R,5S)-5-(2-((2S,4R,6R)-6-(((2S,3R,4R,4aS,6R,7R, 8aS)-7-((tert-butyldiphenylsilyl)oxy)-6-(2-((tert- butyldiphenylsilyl)oxy)ethyl)-3-hydroxy-4-methyloctahydropyrano[3,2-b]pyran-2-yl)methyl)-4-methyl-5- methylenetetrahydro-2H-pyran-2-yl)ethyl)-4-methylenetetrahydrofuran-2-yl)methyl pivalate (compound 27; 98 mg, 0.093 mmol) was dissolved in dichloromethane (5 mL) and treated with imidazole (31.5 mg, 0.463 mmol) and chlorotriethylsilane (0.047 mL, 0.278 mmol) at ambient temperature. After 15 h, the reaction was quenched with saturated aqueous NH$_4$Cl (27% (w/v)) (10 mL). The resulting mixture was extracted twice with MTBE (20 mL). The combined organic layers were washed with 30% aqueous NaCl (5.0 mL) and dried over MgSO$_4$. Filtration, concentration in vacuo, and purification by silica gel column chromatography using a 10-50% gradient of ethyl acetate in n-heptane as eluent provided 94 mg of the target product. $^1$H NMR (400 MHz, CDCl$_3$) δ ppm 0.65 (q, J=7.8 Hz, 6H) 0.97 (t, J=7.8 Hz, 9H) 1.02 (s, 9H) 1.04 (s, 9H) 1.06-1.10 (m, 6H) 1.20 (s, 9H) 1.44-1.52 (m, 2H) 1.58-1.68 (m, 4H) 1.71-1.84 (m, 3H) 1.85-2.01 (m, 2H) 2.07-2.23 (m, 2H) 2.35-2.45 (m, 1H) 2.63-2.75 (m, 1H) 3.18-3.28 (m, 2H) 3.43-3.51 (m, 2H) 3.57-3.61 (m, 2H) 3.64-3.72 (m, 1H) 3.74-3.85 (m, 3H) 4.01 (dd, J=11.7, 4.7 Hz, 1H) 4.12 (dd, J=11.3, 5.1 Hz, 1H) 4.23-4.31 (m, 1H) 4.39-4.47 (m, 1H) 4.78 (s, 1H) 4.84 (br. s., 1H) 4.86 (br. s., 1H) 4.97 (s, 1H) 7.29-7.44 (m, 12H) 7.61-7.71 (m, 8H)

((2R,5S)-5-(2-((2S,4R,6R)-6-(((2S,3R,4S,4aS,6R,7R,8aS)-7-((tert-butyidiphenylsilyl)oxy)-6-(2-((tert-butyldiphenylsilyl)oxy)ethyl)-4-methyl-3-((triethylsilyl)oxy)octahydropyrano[3,2-b]pyran-2-yl)methyl)-4-methyl-5-methylenetetrahydro-2H-pyran-2-yl)ethyl)-4-methylenetetrahydrofuran-2-yl)methanol

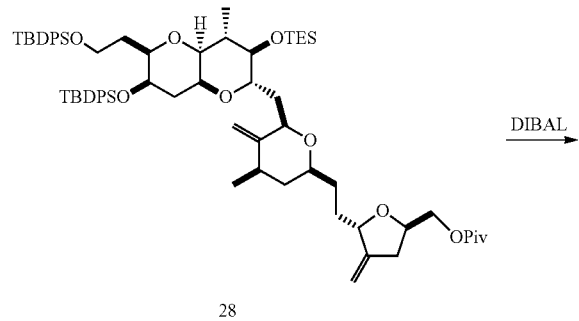

28

((2R,5S)-5-(2-((2S,4R,6R)-6-(((2S,3R,4S,4aS,6R,7R,8aS)-7-((tert-butyldiphenylsilyl)oxy)-6-(2-((tert-butyldiphenylsilyl)oxy)ethyl)-4-methyl-3-((triethylsilyl)oxy)octahydropyrano[3,2-b]pyran-2-yl)methyl)-4-methyl-5-methylenetetrahydro-2H-pyran-2-yl)ethyl)-4-methylenetetrahydrofuran-2-yl)methyl pivalate (compound 28; 94 mg, 0.08 mmol) was dissolved in dichloromethane (3.0 mL) and cooled to −78° C. DIBAL in toluene (1.0 M, 0.24 mL) was charged at this temperature. After being stirred for 1 h between −65 to −78° C., the reaction mixture was treated with MeOH (0.5 mL) and a Rochelle's salt solution (5.0 mL). The resulting mixture was warmed to ambient temperature and extracted with MTBE (15 mL). The organic layers were washed 30% aqueous NaCl (5.0 mL) and dried over MgSO$_4$. Filtration and concentration in vacuo provided the target product (86 mg), which was used in next step without further purification. $^1$H NMR (400 MHz, CDCl$_3$) δ ppm 0.65 (q, J=8.1 Hz, 6H) 0.97 (t, J=7.8 Hz, 9H) 1.02 (s, 9H) 1.04 (s, 9H) 1.06-1.10 (m, 6H) 1.45-1.52 (m, 2H) 1.58-1.69 (m, 4H) 1.72-1.83 (m, 3H) 1.83-1.98 (m, 3H) 2.09-2.25 (m, 2H) 2.37-2.46 (m, 1H) 2.56-2.65 (m, 1H) 3.18-3.27 (m, 2H) 3.43-3.53 (m, 3H) 3.55-3.64 (m, 3H) 3.65-3.72 (m, 1H) 3.74-3.85 (m, 1H) 4.10-4.21 (m, 1H) 4.37-4.44 (m, 1H) 4.78 (s, 1H) 4.84 (d, J=2.0 Hz, 1H) 4.86 (s, 1H) 4.97 (d, J=2.3 Hz, 1H) 7.30-7.42 (m, 12H) 7.61-7.71 (m, 8H)

(E)-ethyl 3-((2R,5S)-5-(2-((2S,4R,6R)-6-(((2S,3R,4S,4aS,6R,7R,8aS)-7-((tert-butyldiphenylsilyl)oxy)-6-(2-((tert-butyldiphenylsilyl)oxy)ethyl)-4-methyl-3-((triethylsilyl)oxy)octahydropyrano[3,2-b]pyran-2-yl)methyl)-4-methyl-5-methylenetetrahydro-2H-pyran-2-yl)ethyl)-4-methylenetetrahydrofuran-2-yl)acrylate

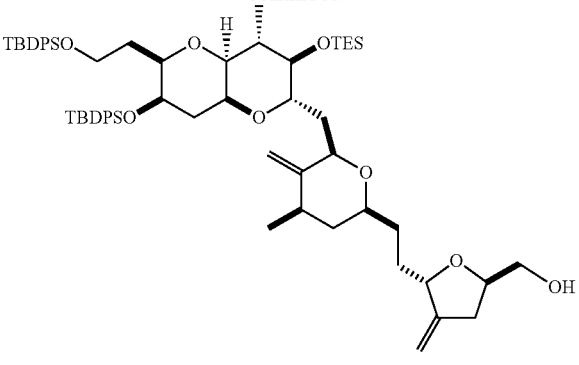

35

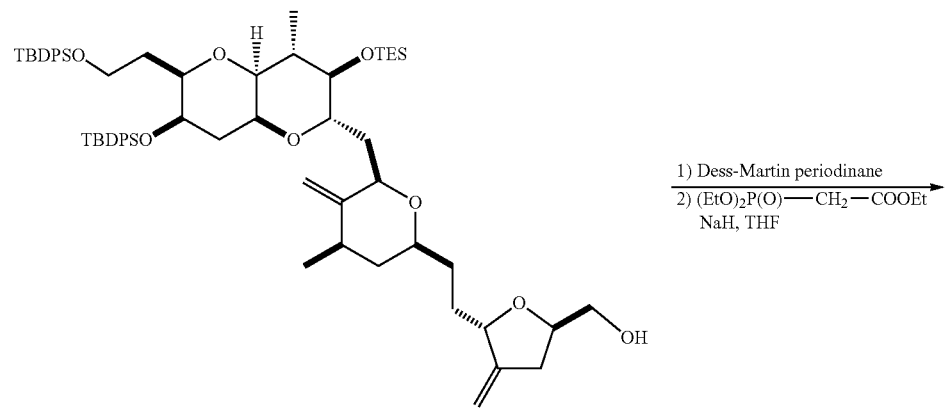

35

-continued

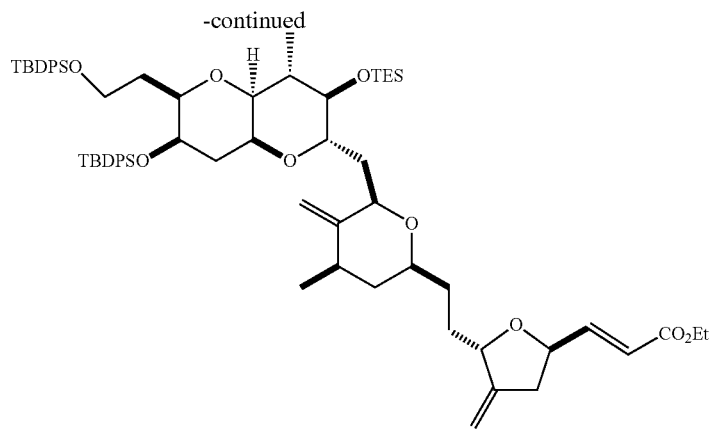

29

To a solution of ((2R,5S)-5-(2-((2S,4R,6R)-6-(((2S,3R,4S,4aS,6R,7R,8aS)-7-((tert-butyldiphenylsilyl)oxy)-6-(2-((tert-butyldiphenylsilyl)oxy)ethyl)-4-methyl-3-((triethylsilyl)oxy)octahydropyrano[3,2-b]pyran-2-yl)methyl)-4-methyl-5-methylenetetrahydro-2H-pyran-2-yl)ethyl)-4-methylenetetrahydrofuran-2-yl)methanol (compound 35; 86 mg, 0.079 mmol) in dichloromethane (3.0 mL) at ambient temperature was added sodium bicarbonate (26.6 mg, 0.316 mmol) and Dess-Martin periodinane (50.3 mg, 0.119 mmol). After being stirred for 2 h, the reaction mixture was diluted with MTBE (20 ml) and treated with a saturated aqueous $Na_2S_2O_3$ solution (10 mL) and water (5.0 mL). The resulting mixture was stirred for 0.5 h at ambient temperature, and the layers were separated. The organic layer was washed with a saturated aqueous $NaHCO_3$ solution (10 mL) twice and 30% aqueous NaCl (5.0 mL) and dried over $MgSO_4$. Filtration followed by concentration in vacuo gave the target product ((2R,5S)-5-(2-((2S,4R,6R)-6-(((2S,3R,4S,4aS,6R,7R,8aS)-7-((tert-butyldiphenylsilyl)oxy)-6-(2-((tert-butyldiphenylsilyl)oxy)ethyl)-4-methyl-3-((triethylsilyl)oxy)octahydropyrano[3,2-b]pyran-2-yl)methyl)-4-methyl-5-methylenetetrahydro-2H-pyran-2-yl)ethyl)-4-methylenetetrahydrofuran-2-carbaldehyde, 80 mg) as an oil. Without further purification, the crude product was dissolved in THF (4.0 mL) and cooled to 0° C. In an another reaction flask, ethyl 2-(diethoxyphosphoryl)acetate (73.7 μL, 0.368 mmol) was dissolved in THF (2.7 mL), cooled to 0° C., and treated with 60% sodium hydride (13.26 mg, 0.332 mmol). After 20 min at 0° C., the resulting solution was added to the starting material reactor. After 30 min, saturated aqueous $NH_4Cl$ (27% (w/v)) (8.0 mL), water (2.8 mL), and MTBE (20 mL) were added, and the resulting mixture was warmed to ambient temperature. The layers were separated, and the aqueous layer was extracted with MTBE (12 mL). The combined organic layers were washed with 30% aqueous NaCl (10 mL) and dried over $MgSO_4$. Filtration, concentration in vacuo, and purification by silica gel column chromatography using a 20-50% gradient of ethyl acetate in n-heptane as eluent provided 71 mg of the target product (compound 29). $^1$H NMR (400 MHz, $CDCl_3$) δ ppm 0.65 (q, J=8.1 Hz, 6H) 0.97 (t, J=8.2 Hz, 9H) 1.02 (s, 9H) 1.04 (s, 9H) 1.06-1.10 (m, 6H) 1.45-1.52 (m, 2H) 1.57-1.70 (m, 5H) 1.72-1.83 (m, 3H) 1.83-1.98 (m, 2H) 2.08-2.23 (m, 2H) 2.38-2.47 (m, 1H) 2.76-2.86 (m, 1H) 3.18-3.28 (m, 2H) 3.43-3.51 (m, 2H) 3.56-3.62 (m, 2H) 3.64-3.71 (m, 1H) 3.73-3.85 (m, 3H) 4.19 (q, J=7.3 Hz, 2H) 4.40-4.47 (m, 1H) 4.60-4.69 (m, 1H) 4.78 (s, 1H) 4.86 (s, 2H) 4.98 (d, J=2.0 Hz, 1H) 6.00 (dd, J=15.6, 1.6 Hz, 1H) 6.87 (dd, J=15.6, 5.1 Hz, 1H) 7.30-7.42 (m, 12H) 7.61-7.71 (m, 8H)

(E)-3-((2R,5S)-5-(2-((2S,4R,6R)-6-(((2S,3R,4S,4aS,6R,7R,8aS)-7-((tert-butyldiphenylsilyl)oxy)-6-(2-((tert-butyldiphenylsilyl)oxy)ethyl)-4-methyl-3-((triethylsilyl)oxy)octahydropyrano[3,2-b]pyran-2-yl)methyl)-4-methyl-5-methylenetetrahydro-2H-pyran-2-yl)ethyl)-4-methylenetetrahydrofuran-2-yl)prop-2-en-1-ol

29

-continued

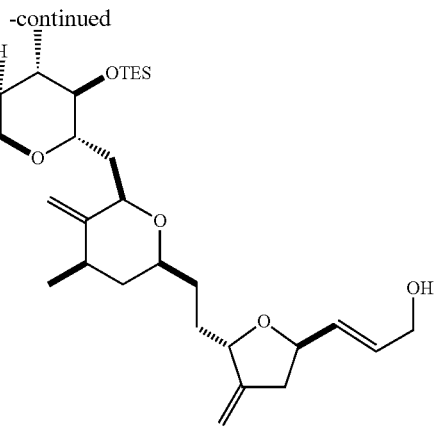

R = TBDPS
36

To a solution of (E)-ethyl 3-((2R,5S)-5-(2-((2S,4R,6R)-6-(((2S,3R,4S,4aS,6R,7R,8aS)-7-((tert-butyldiphenylsilyl)oxy)-6-(2-((tert-butyldiphenylsilyl)oxy)ethyl)-4-methyl-3-((triethylsilyl)oxy)octahydropyrano[3,2-b]pyran-2-yl)methyl)-4-methyl-5-methylenetetrahydro-2H-pyran-2-yl)ethyl)-4-methylenetetrahydrofuran-2-yl)acrylate (compound 29; 71 mg, 0.061 mmol) in dichloromethane (4 mL), at −78° C., was added a solution of DIBAL-H in toluene (1.0 M, 0.246 mL, 0.246 mmol). After being stirred for 1 h between −65 to −78° C., the reaction mixture was treated with MeOH (0.5 mL) and a Rochelle's salt solution (5.0 mL). The resulting mixture was warmed to ambient temperature and extracted twice with MTBE (15 mL). The combined organic layers were washed 30% aqueous NaCl (5.0 mL) and dried over MgSO$_4$. Filtration and concentration in vacuo provided the target product (compound 36, 68 mg), which was used in the next step without further purification. $^1$H NMR (400 MHz, CDCl$_3$) δ ppm 0.65 (q, J=8.1 Hz, 6H) 0.97 (t, J=8.2 Hz, 9H) 1.02 (s, 9H) 1.04 (s, 9H) 1.06-1.10 (m, 6H) 1.45-1.52 (m, 2H) 1.57-1.70 (m, 4H) 1.72-1.83 (m, 3H) 1.84-1.98 (m, 2H) 2.08-2.22 (m, 2H) 2.34-2.42 (m, 1H) 2.68-2.76 (m, 1H) 3.20-3.28 (m, 2H) 3.43-3.50 (m, 2H) 3.56-3.62 (m, 2H) 3.64-3.71 (m, 1H) 3.73-3.85 (m, 3H) 4.14 (br s, 2H) 4.40-4.43 (m, 1H) 4.49 (q, J=6.6 Hz, 1H) 4.78 (s, 1H) 4.83 (d, J=1.9 Hz, 1H) 4.86 (s, 1H) 4.97 (d, J=1.9 Hz, 1H) 5.70-5.76 (m, 1H) 5.83-5.89 (m, 1H) 7.30-7.43 (m, 12H) 7.61-7.72 (m, 8H)

(((2R,3R,4aS,6S,7R,8S,8aS)-6-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-2-(2-((tert-butyldiphenylsilyl)oxy)ethyl)-8-methyl-7-((triethylsilyl)oxy)octahydropyrano[3,2-b]pyran-3-yl)oxy)(tert-butyl)diphenylsilane

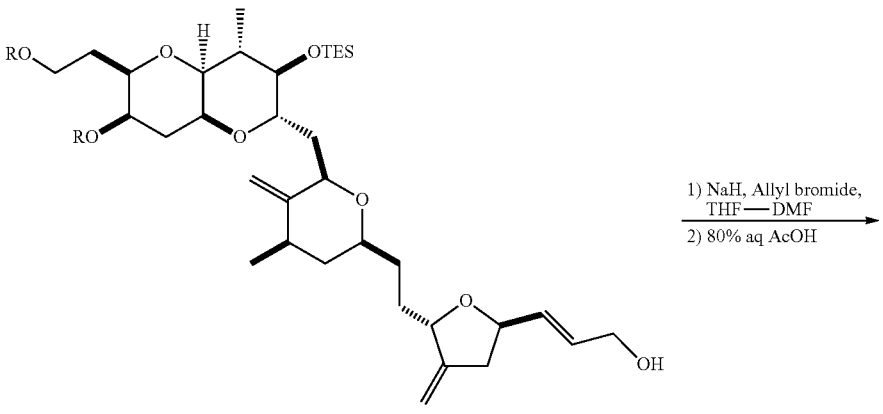

R = TBDPS
36

1) NaH, Allyl bromide, THF—DMF
2) 80% aq AcOH

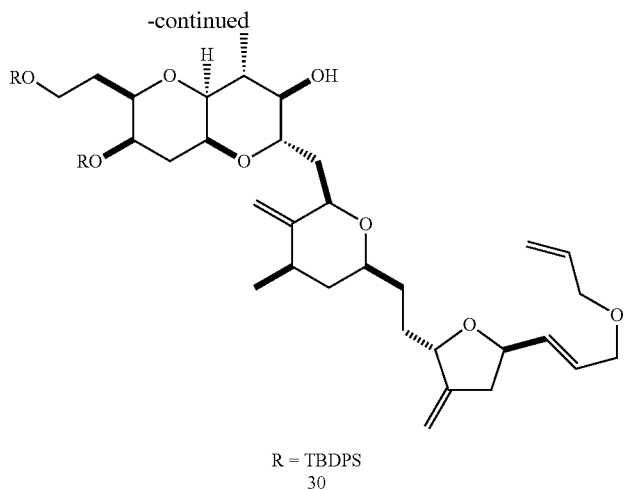

R = TBDPS
30

To a solution of (E)-3-((2R,5S)-5-(2-((2S,3R,4S,4aS,6R,7R,8aS)-7-((tert-butyldiphenylsilyl)oxy)-6-(2-((tert-butyldiphenylsilyl)oxy)ethyl)-4-methyl-3-((triethylsilyl)oxy)octahydropyrano[3,2-b]pyran-2-yl)methyl)-4-methyl-5-methylenetetrahydro-2H-pyran-2-yl)ethyl)-4-methylenetetrahydrofuran-2-yl)prop-2-en-1-ol (compound 36, 68 mg, 0.061 mmol) in THF (2.0 mL) at 0° C. was added sodium hydride (60% in oil, 6.1 mg, 0.15 mmol). The resulting slurry was stirred at ambient temperature for 20 min. Allyl bromide (0.032 mL, 0.37 mmol) and DMF (0.5 mL, 6.5 mmol) were then added. The resulting mixture was stirred for 16 h at ambient temperature. Saturated aqueous NH₄Cl (27% (w/v)) (5.0 mL), water (1.0 mL), and MTBE (10 mL) were added. The layers were separated, and the aqueous layer was extracted with MTBE (10 mL). The combined organic layers were washed with 30% aqueous NaCl (3.0 mL) and dried over MgSO₄. Filtration and concentration in vacuo provided 71 mg of the target product. Without further purification, the crude product ((((2R,3R,4aS,6S,7R,8S,8aS)-6-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-2-(2-((tert-butyldiphenylsilyl)oxy)ethyl)-8-methyl-7-((triethylsilyl)oxy)octahydropyrano[3,2-b]pyran-3-yl)oxy)(tert-butyl)diphenylsilane) (72 mg) was dissolved in acetic acid (4.0 mL) and treated with water (1.0 mL) at ambient temperature. After 5 h, the reaction mixture was concentrated in vacuo. The resulting residue was purified by silica gel column chromatography using a 20-33% gradient of ethyl acetate in n-heptane as eluent to give 54 mg of the target product (compound 30). ¹H NMR (400 MHz, CDCl₃) δ ppm 1.00 (s, 9H) 1.04-1.06 (m, 9H) 1.08-1.15 (m, 6H) 1.45-1.76 (m, 11H) 1.80 (br. s., 1H) 1.91-2.15 (m, 5H) 2.24-2.34 (m, 1H) 2.36-2.45 (m, 1H) 2.67-2.76 (m, 1H) 3.22 (br. s., 1H) 3.33 (br. s., 1H) 3.49 (d, J=7.8 Hz, 1H) 3.55-3.65 (m, 2H) 3.68 (br. s., 1H) 3.72-3.83 (m, 3H) 3.91 (t, J=5.9 Hz, 1H) 3.95-3.99 (m, 4H) 4.07 (q, J=5.6 Hz, 1H) 4.41-4.53 (m, 2H) 4.81 (br. s., 1H) 4.81-4.84 (m, 1H) 4.88 (d, J=2.0 Hz, 1H) 4.98 (d, J=2.0 Hz, 1H) 5.18 (d, J=10.2 Hz, 1H) 5.27 (dd, J=17.2, 1.6 Hz, 1H) 5.73 (dd, J=16.0, 5.1 Hz, 1H) 5.79 (dd, J=15.2, 5.1 Hz, 1H) 5.85-5.97 (m, 1H) 7.30-7.43 (m, 12H) 7.57-7.79 (m, 8H)

(2S,3R,4S,4aS,6R,7R,8aS)-2-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-7-((tert-butyldiphenylsilyl)oxy)-6-(2-((tert-butyldiphenylsilyl)oxy)ethyl)-4-methyloctahydropyrano[3,2-b]pyran-3-yl 2-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)acetate

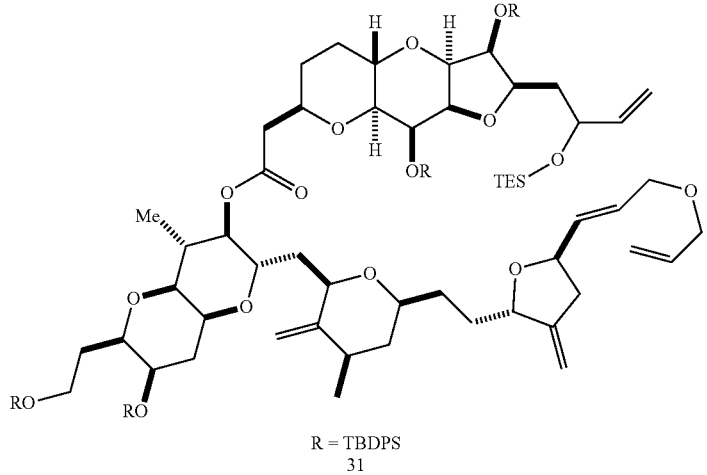

R = TBDPS
31

To a solution of 2-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)acetic acid (compound 24, 66 mg, 0.071 mmol) in dichloromethane (2 mL) at ambient temperature were added TEA (0.022 mL, 0.156 mmol), 2-methyl-6-nitrobenzoic anhydride (26.8 mg, 0.078 mmol) and 4-dimethylaminopyridine (3.17 mg, 0.026 mmol). After 10 min, the resulting solution was added to a solution of (2S,3R,4R,4aS,6R,7R,8aS)-2-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-7-((tert-butyldiphenylsilyl)oxy)-6-(2-((tert-butyldiphenylsilyl)oxy)ethyl)-4-methyloctahydropyrano[3,2-b]pyran-3-ol (compound 30, 54 mg, 0.052 mmol) in dichloromethane (1.0 ml). After being stirred overnight, the reaction mixture was treated with a saturated aqueous NH$_4$Cl solution (5.0 mL). The resulting mixture was stirred for 30 min and extracted twice with MTBE (10 mL each).

The combined organic layers were washed with 30% aqueous NaCl (5.0 mL) and dried over MgSO$_4$. Filtration, concentration in vacuo, and purification by silica gel column chromatography using a 10-33% gradient of ethyl acetate in n-heptane as eluent provided 87 mg of the target product (compound 31). $^1$H NMR (1:1 diastereomeric mixture, 400 MHz, CDCl$_3$) δ ppm 0.46-0.62 (m, 6H) 0.83-0.98 (m, 12H) 1.00 (s, 9H) 1.06 (s, 9H) 1.07-1.15 (m, 6H) 1.25-2.04 (m, 19H) 2.08-2.24 (m., 2.5H) 2.32-2.44 (m, 1.5H) 2.66-2.76 (m, 1H) 2.86-2.96 (m, 1H) 3.22-3.28 (m, 1H) 3.37-3.42 (m, 0.5H) 3.46-3.71 (m, 6.5H) 3.73-3.86 (m, 4H) 3.93-4.00 (m, 4H) 4.05-4.23 (m., 3H) 4.27-4.34 (m, 1H) 4.40-4.46 (m, 1H) 4.49 (q, J=6.4 Hz, 1H) 4.58-4.68 (m, 1H) 4.70 (s, 1H) 4.76 (s, 1H) 4.84 (br. s., 1H) 4.90-5.14 (m, 2H) 4.95-4.97 (m, 1H) 5.17 (d, J=10.6 Hz, 1H) 5.27 (dd, J=17.4, 1.8 Hz, 1H) 5.59-5.70 (m, 1H) 5.73 (dd, J=15.6, 5.1 Hz, 1H) 5.80 (dd, J=15.6, 5.1 Hz, 1H) 5.84-5.97 (m, 1H) 7.27-7.43 (m, 24H) 7.55-7.79 (m, 16H)

Compound 31 can be transformed into compound 3 according to the following sequence:

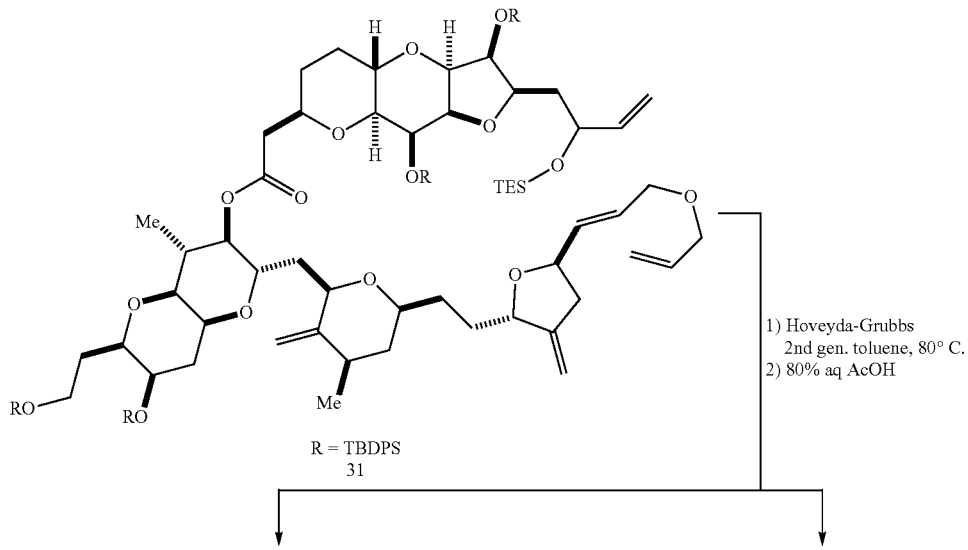

R = TBDPS
31

1) Hoveyda-Grubbs 2nd gen. toluene, 80° C.
2) 80% aq AcOH

-continued
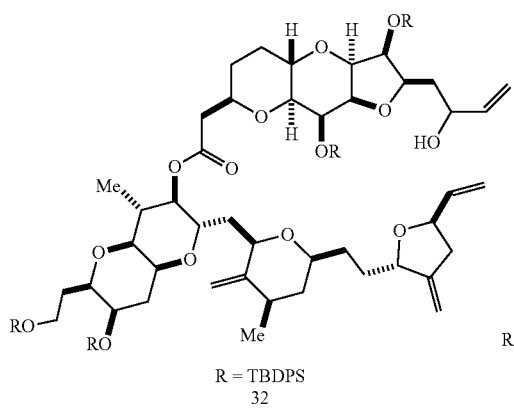
191
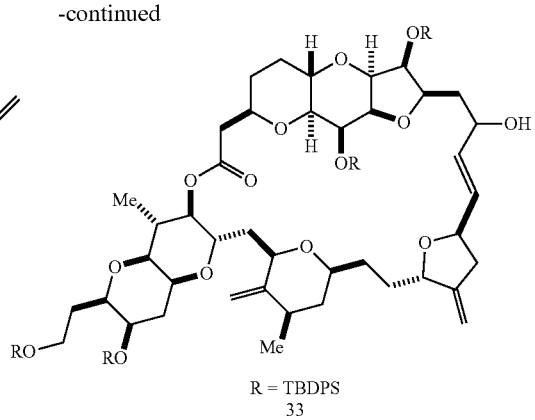
192
1) Dess-Martin [O]
2) Stryker's Reagent
Hoveyda-Grubbs 2nd gen.
Tol. 80° C.
20% overall
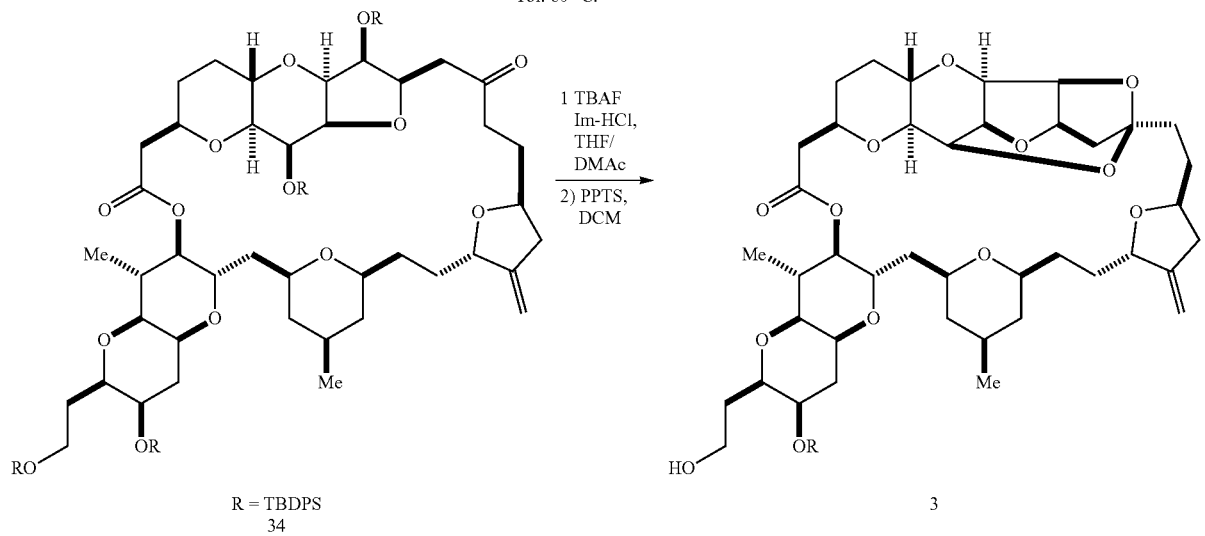
1) TBAF Im-HCl, THF/DMAc
2) PPTS, DCM
Ring-Closing Olefin Metathesis
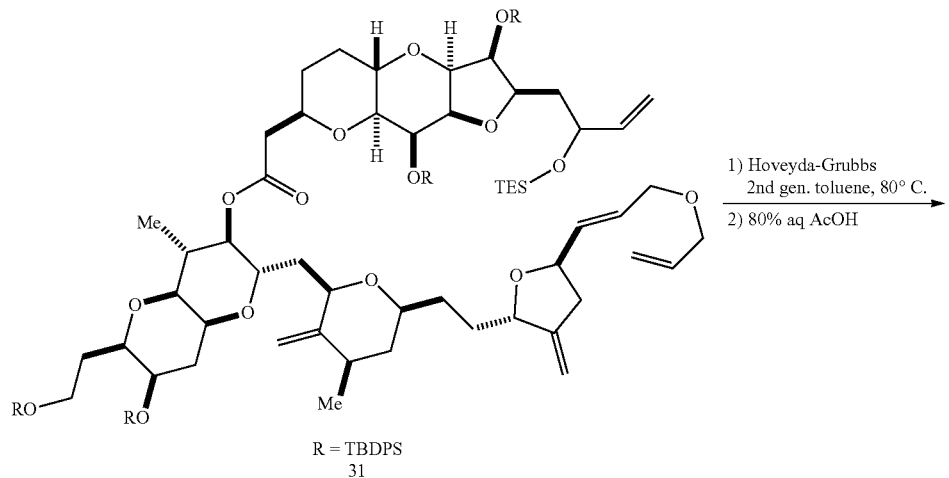
1) Hoveyda-Grubbs 2nd gen. toluene, 80° C.
2) 80% aq AcOH

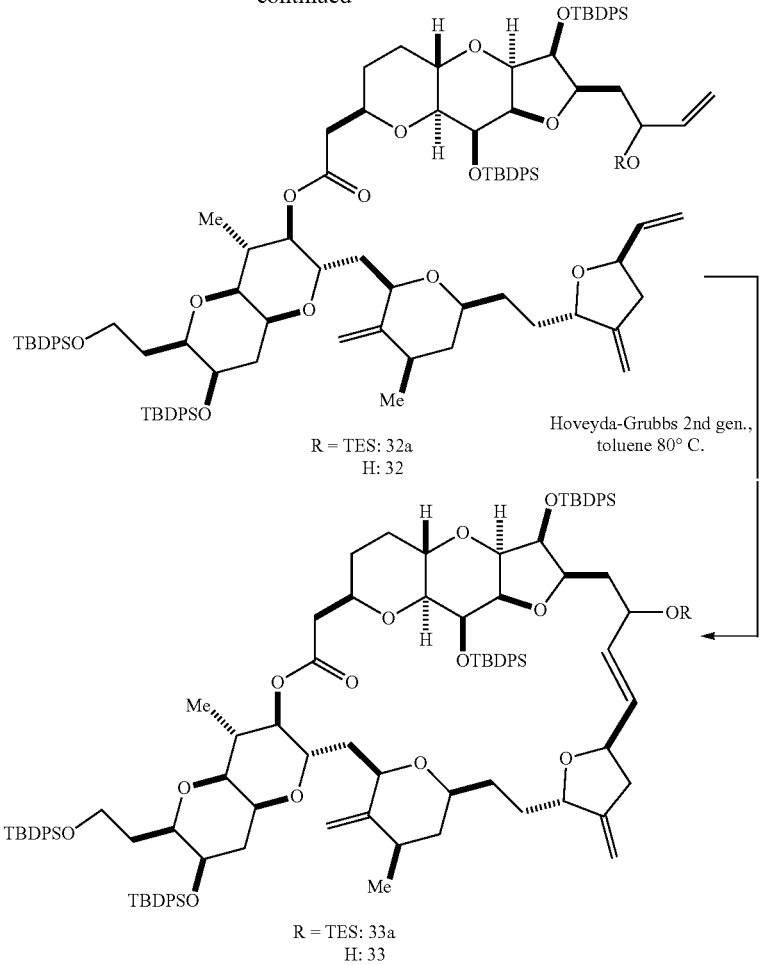

R = TES: 32a
H: 32

Hoveyda-Grubbs 2nd gen.,
toluene 80° C.

R = TES: 33a
H: 33

To a solution of (2S,3R,4S,4aS,6R,7R,8aS)-2-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-7-((tert-butyldiphenylsilyl)oxy)-6-(2-((tert-butyldiphenylsilyl)oxy)ethyl)-4-methyloctahydropyrano[3,2-b]pyran-3-yl 2-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)acetate (compound 31, 87 mg, 0.044 mmol) in toluene (61 mL) at 80° C. was added quinone (4.8 mg, 0.044 mmol) and a solution of Hoveyda-Grubbs 2nd generation catalyst (5.59 mg, 8.891 μmol) in toluene (10 mL). After being stirred at 80° C. for 8 h, the reaction mixture was cooled to ambient temperature and treated with DMSO (0.063 mL, 0.889 mmol). The resulting solution was stirred overnight and concentrated in vacuo. Silica gel column chromatography of the residue using a 20-33% gradient of ethyl acetate in n-heptane as eluent afforded 71 mg of a mixture of the target product (compound 33a) and compound 32a: MS m/z 1908.0 and 1936.0 [M+Na]⁺. The mixture was dissolved in THF (2.0 mL) at ambient temperature. To the solution was added acetic acid (3.2 mL) and water (0.8 mL). After being stirred for 3 h at ambient temperature, the resulting mixture was concentrated in vacuo. The residue was purified by silica gel column chromatography using a 10-33% gradient of ethyl acetate in n-heptane as eluent to give 46 mg of a mixture of compound 33 and compound 32. The mixture was dissolved in dichloromethane (45 mL) and treated with Hoveyda-Grubbs 2nd generation catalyst (2.91 mg, 4.63 μmol) at reflux (45° C. oil bath) over 15 h. The reaction mixture was cooled to ambient temperature and concentrated in vacuo. Purification by silica gel column chromatography of the residue using a 15-33% gradient of ethyl acetate in n-heptane as eluent afforded 15 mg of the target product (compound 33). $^1$H NMR (major isomer, 400 MHz, CDCl$_3$) δ ppm 0.99-1.10 (m, 42H) 1.25-2.27 (m, 19H) 2.32-2.42 (m, J=7.4 Hz, 3H) 2.45-2.51 (m, 1H) 2.55 (dd, J=14.9, 3.1 Hz, 1H) 2.69-2.79 (m, 1H) 2.85 (t, J=9.0 Hz, 1H) 3.17-3.27 (m, 1H) 3.33-3.55 (m, 4H) 3.59-3.81 (m, 11H) 3.87-3.95 (m, 1H) 4.15 (dd, J=8.6, 3.9 Hz, 1H) 4.29-4.39 (m, 2H) 4.41-4.48 (m, 1H) 4.49-4.55 (m, 1H) 4.58-4.67 (m, 2H) 4.76 (s, 1H) 4.83 (s, 1H) 4.92 (br. s., 2H) 5.77 (ddd, J=15.6, 7.6, 1.4 Hz, 1H) 6.31 (dd, J=15.4, 4.5 Hz, 1H) 7.30-7.43 (m, 24H) 7.58-7.77 (m, 16H)

(2S,3R,4S,4aS,6R,7R,8aS)-7-((tert-butyldiphenyisilyl)oxy)-6-(2-((tert-butyldiphenyisilyl)oxy)ethyl)-4-methyl-2-(((2R,4R,6S)-4-methyl-3-methylene-6-(2-((2S,5R)-3-methylene-5-vinyltetrahydrofuran-2-yl)ethyl)tetrahydro-2H-pyran-2-yl)methyl)octahydropyrano[3,2-b]pyran-3-yl 2-((2R,3S,3aR,4aS,7R,8aS,9S,9aR)-3,9-bis((tert-butyldiphenylsilyl)oxy)-2-(2-hydroxybut-3-en-1-yl)decahydrofuro[3,2-b]pyrano[2,3-e]pyran-7-yl)acetate ¹H NMR (compound 32, 400 MHz, CDCl₃) δ ppm 1.00-1.11 (m, 42H) 1.25-2.03 (m, 19H) 2.12-2.22 (m, 2H) 2.33-2.42 (m, 2H) 2.72 (ddd, J=15.3, 6.7, 1.8 Hz, 1H) 2.95 (dd, J=9.8, 4.3 Hz, 1H) 3.24 (dd, J=5.7, 3.7 Hz, 1H) 3.47-3.56 (m, 3H) 3.59-3.69 (m, 5H) 3.72-3.80 (m, 3H) 3.81-3.88 (m, 1H) 3.99-4.08 (m, 1H) 4.10-4.20 (m, 2H) 4.25 (dd, J=6.3, 4.3 Hz, 1H) 4.41-4.50 (m, 2H) 4.67 (t, J=8.0 Hz, 1H) 4.72 (s, 1H) 4.78 (s, 1H) 4.85 (d, J=2.0 Hz, 1H) 4.96 (d, J=2.0 Hz, 1H) 5.04 (d, J=10.2 Hz, 1H) 5.10 (d, J=10.2 Hz, 1H) 5.16 (d, J=16.8 Hz, 1H) 5.23 (d, J=17.2 Hz, 1H) 5.72 (ddd, J=16.9, 10.6, 6.1 Hz, 1H) 5.84 (ddd, J=17.0, 10.4, 6.3 Hz, 1H) 7.27-7.45 (m, 24H) 7.56-7.78 (m, 16H)
Compound 37

Compound 33 (25.5 mg, 0.015 mmol) was dissolved in dichloromethane (1.0 ml) at ambient temperature. Sodium bicarbonate (12.3 mg, 0.146 mmol) and Dess-Martin periodinane (18.6 mg, 0.044 mmol) were added, and the resulting mixture was stirred at ambient temperature overnight. MTBE (10.0 ml), water (2.0 mL) and a saturated aqueous sodium thiosulfate solution (5 mL) were added. The resulting mixture was stirred at ambient temperature over 30 min. The organic layer was separated out, washed with 30% aqueous NaCl (3.0 mL), and dried over MgSO₄. Filtration, concentration in vacuo, and purification by silica gel column chromatography using a 10-33% gradient of ethyl acetate in n-heptane as eluent provided 17 mg of the target product (compound 37). ¹H NMR (400 MHz, CDCl₃) δ ppm 0.97-1.17 (m, 42H) 1.28-2.25 (m, 20H) 2.49 (dd, J=16.0, 7.0 Hz, 1H) 2.56 (dd, J=15.0, 10.0 Hz, 1H) 2.72 (dd, J=15.2, 3.5 Hz, 1H) 2.75-2.82 (m, 1H) 2.98 (t, J=8.8 Hz, 1H) 3.19-3.25 (m, 1H) 3.36 (d, J=12.5 Hz, 1H) 3.42 (t, J=4.3 Hz, 1H) 3.48-3.57 (m, 4H) 3.60-3.70 (m, 5H) 3.71-3.82 (m, 3H) 3.90 (td, J=10.4, 3.9 Hz, 1H) 4.01 (ddd, J=10.6, 7.4, 3.1 Hz, 1H) 4.08 (dd, J=8.0, 4.5 Hz, 1H) 4.24-4.35 (m, 2H) 4.55-4.59 (m, 1H) 4.62 (t, J=7.4 Hz, 1H) 4.66-4.73 (m, 1H) 4.76 (s, 1H) 4.85

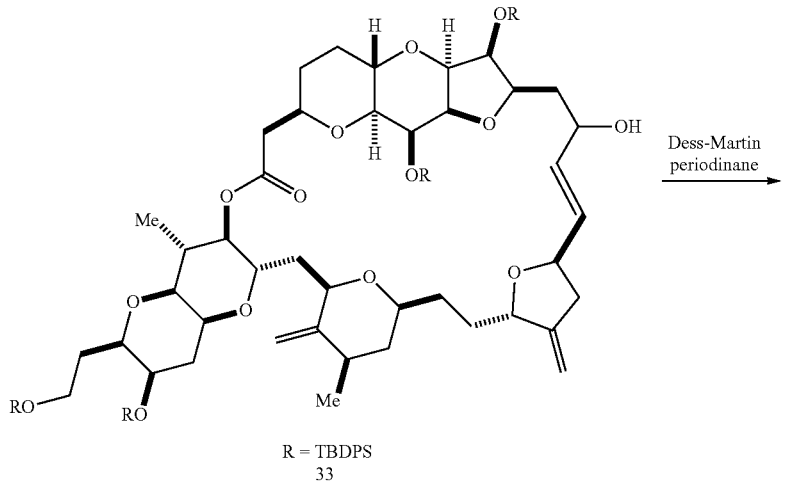

R = TBDPS
33

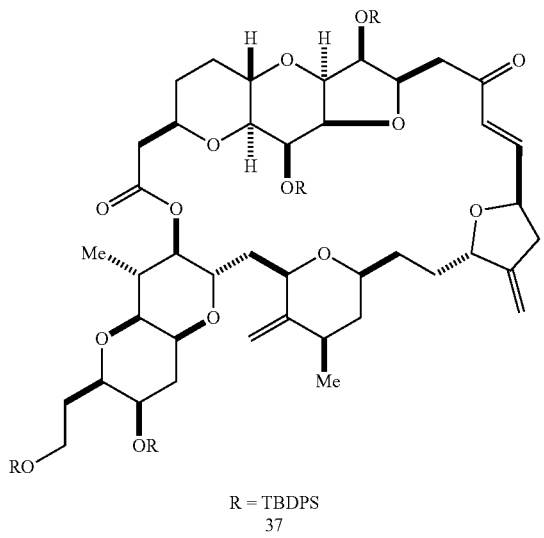

R = TBDPS
37

(s, 1H) 4.91 (s, 1H) 5.00 (d, J=1.6 Hz, 1H) 6.41 (d, J=16.0 Hz, 1H) 6.86 (dd, J=16.2, 5.7 Hz, 1H) 7.28-7.43 (m, 24H) 7.57-7.77 (m, 16H)

Compound 34

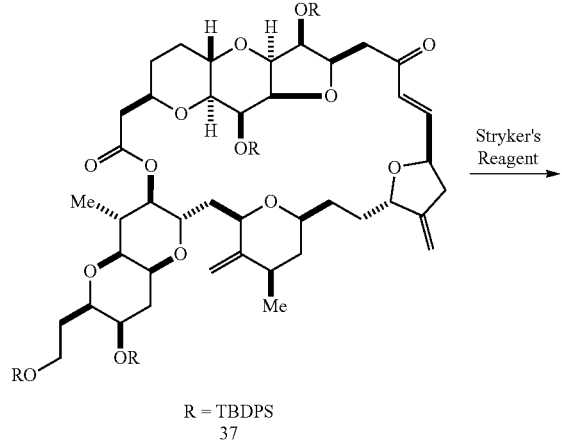

R = TBDPS
37

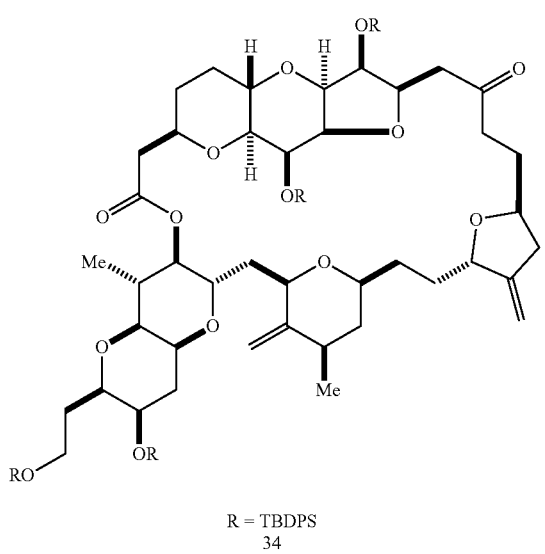

R = TBDPS
34

Compound 37 (4.0 mg, 2.3 μmol) was dissolved in deoxygenated toluene (0.6 mL) at ambient temperature. Deoxygenated (purged with nitrogen for 40 min) water (2.4 μL, 0.13 mmol) was added followed by hydrido(triphenylphosphine)copper(I) hexamer (9.0 mg, 4.6 μmol). After being stirred for 1 h, the reaction mixture was treated with air. Copper-containing decomposition products precipitated. Concentration in vacuo followed by purification by column chromatography using a 10-33% gradient of ethyl acetate in n-heptane as eluent afforded 3.0 mg of the target product (compound 34). $^1$H NMR (400 MHz, CDCl$_3$) δ ppm 0.98-1.14 (m, 42H) 1.28-2.40 (m, 22H) 2.55-2.77 (m, 4H) 2.81-2.90 (m, 1H) 2.91 (t, J=9.2 Hz, 1H) 3.06 (t, J=11.7 Hz, 1H) 3.20 (dd, J=6.3, 3.9 Hz, 1H) 3.39-3.47 (m, 2H) 3.50-3.57 (m, 2H) 3.62-3.69 (m, 3H) 3.72 (dd, J=6.1, 4.5 Hz, 1H) 3.75-3.85 (m, 3H) 3.94-4.02 (m, 1H) 4.09 (dd, J=8.4, 3.7 Hz, 2H) 4.26-4.32 (m, 1H) 4.33-4.39 (m, 1H) 4.43-4.48 (m, 1H) 4.64 (t, J=7.0 Hz, 1H) 4.77 (s, 1H) 4.84 (s, 1H) 4.86 (s, 1H) 4.93 (s, 1H) 7.28-7.44 (m, 24H) 7.57-7.77 (m, 16H)

Compound 3

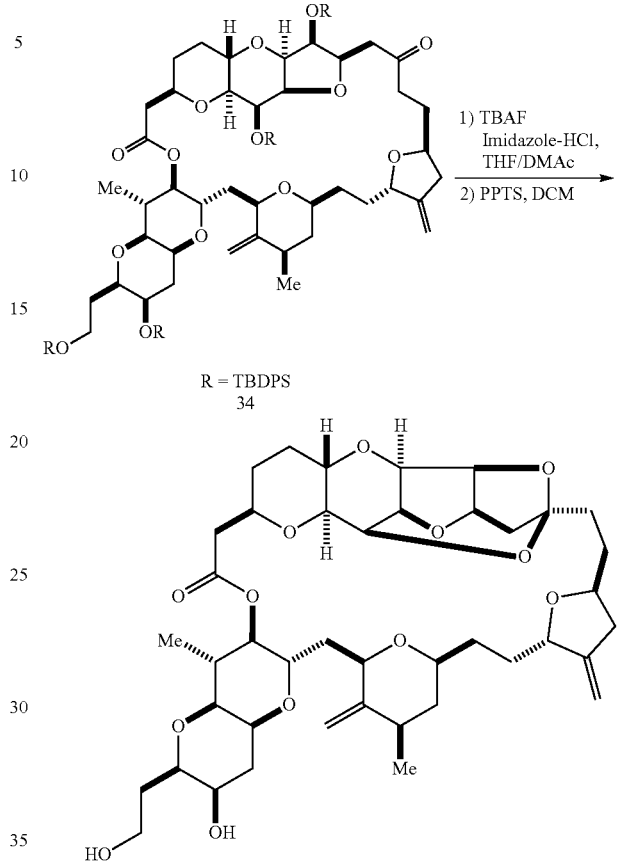

To compound 34 (3.0 mg, 1.72 μmol) in a vial was added THF (0.6 mL) and N,N-dimethylacetamide (0.21 mL) at ambient temperature. A mixture of TBAF (1.0 M in THF, 52 μL, 0.052 mmol) and imidazole hydrochloride (2.7 mg, 0.026 mmol) was added, and the resulting mixture was stirred over 3 days at ambient temperature. 30% aqueous NaCl (2.0 mL) was added, and the resulting mixture was extracted twice with a mixture of THF (5.0 mL) and toluene (5.0 mL). The combined organic layers were concentrated with a stream of nitrogen. The residue was dissolved in dichloromethane (1.0 mL) at ambient temperature, and PPTS (18 mg, 72 μmol) was added. Once all starting material was consumed (2 h), the reaction mixture was purified by silica gel column chromatography using a 0-10% gradient of methanol in ethyl acetate as eluent to give 0.9 mg of the target product (compound 3). The structure was confirmed by $^1$H NMR comparison with the reported spectrum. $^1$H NMR (400 MHz, CDCl$_3$) δ ppm 1.10 (d, J=6.3 Hz, 3H) 1.18 (d, J=7.8 Hz, 3H) 1.27-2.40 (m, 25H) 2.41 (dd, J=16.8, 2.7 Hz, 1H) 2.53 (dd, J=17.2, 10.2 Hz, 1H) 2.76-2.86 (m, 1H) 2.90 (dd, J=9.8, 2.3 Hz, 1H) 3.29 (s, 1H) 3.52-3.57 (m, 2H) 3.64 (d, J=10.9 Hz, 1H) 3.69-3.89 (m, 5H) 4.04 (dd, J=6.3, 4.3 Hz, 1H) 4.10-4.15 (m, 1H) 4.18 (dd, J=6.4, 4.5 Hz, 1H) 4.21-4.28 (m, 1H) 4.36 (d, J=11.7 Hz, 1H) 4.38-4.44 (m, 2H) 4.50 (t, J=2.3 Hz, 1H) 4.58-4.62 (m, 1H) 4.68 (t, J=4.5 Hz, 1H) 4.80 (br. s., 2H) 4.98 (br. s., 1H) 5.08 (s, 1H)

Example 6—C.19-C.20 Macrocyclization Through Nozaki-Hiyama-Kishi Reaction
A halichondrin macrolide 3 can be prepared according to the below sequence.
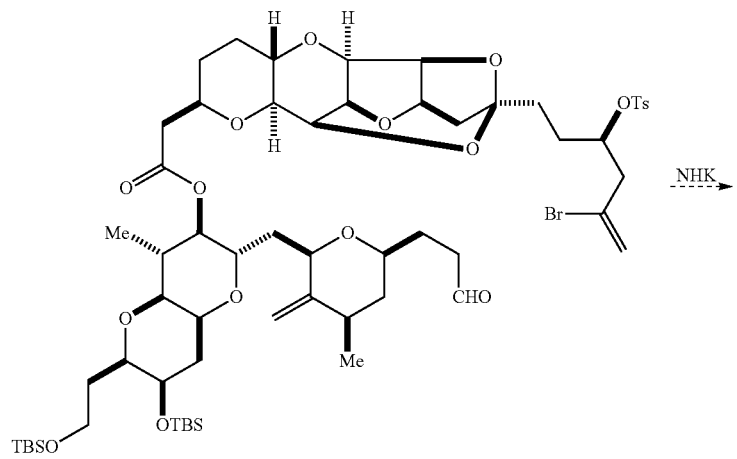
38
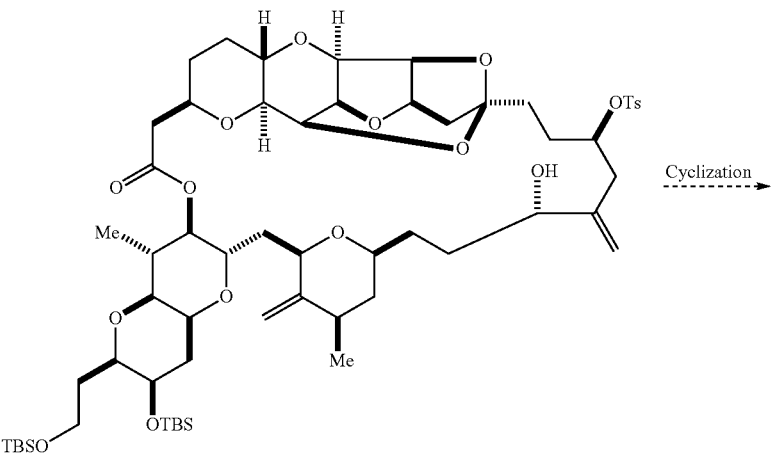
39
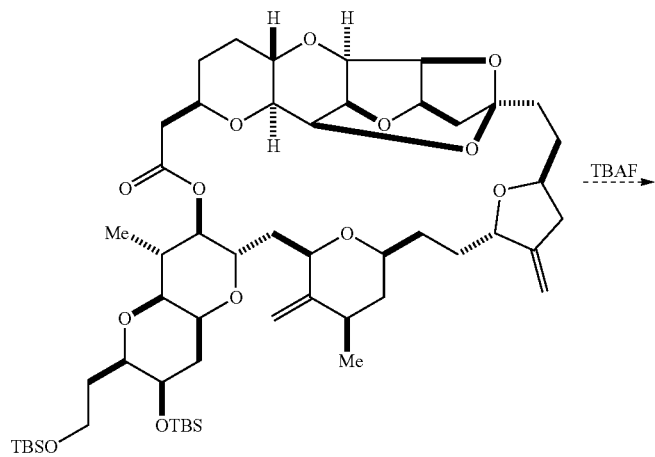
40
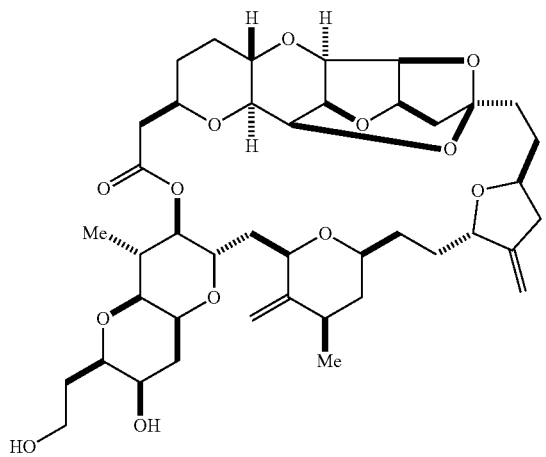
3

Compound 38 can be converted to compound 39 through the Nozaki-Hiyama-Kishi reaction (e.g., with Cr(II) and Ni(II) salts). Compound 39 can give compound 40 through nucleophilic ring-closing substitution reaction. Compound 40 can be converted to compound 3 after global deprotection (e.g., removal of silyl groups with a fluoride source, such as TBAF).

Example 7—C.26-C.27 Macrocyclization Through Nozaki-Hiyama-Kishi Reaction

A halichondrin macrolide 3 can be prepared according to the below sequence.

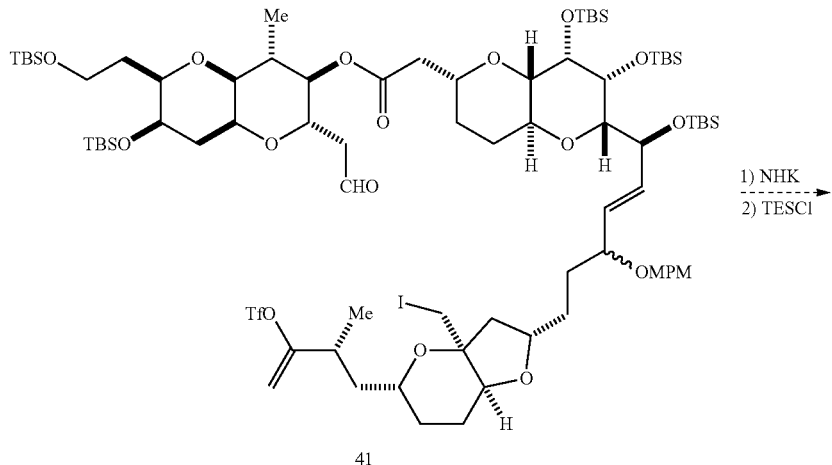

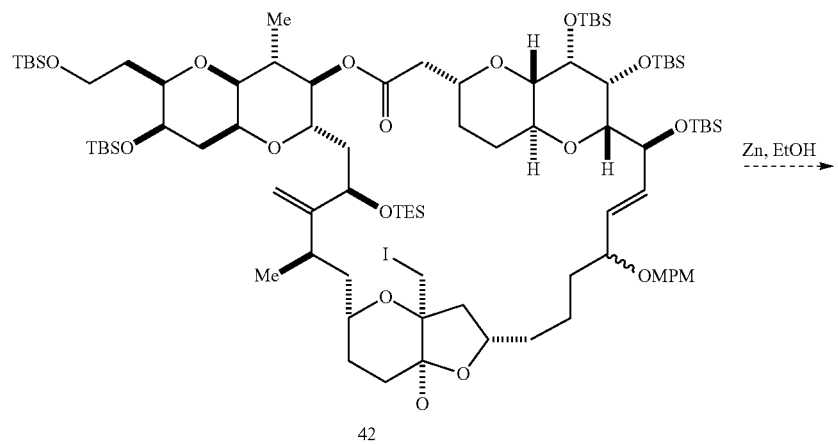

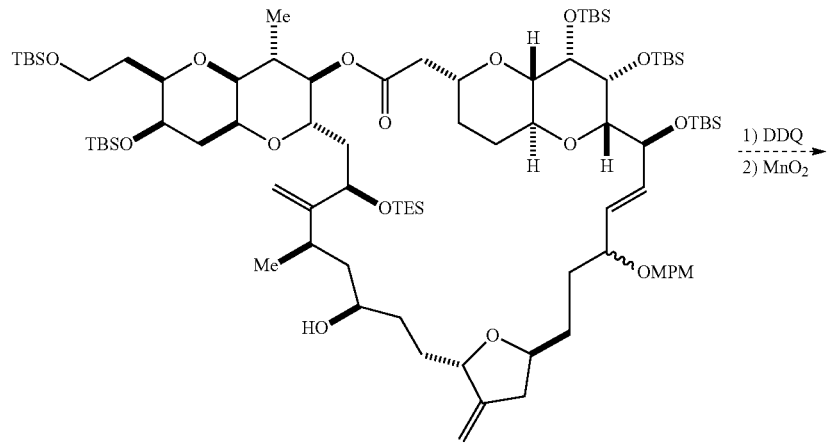

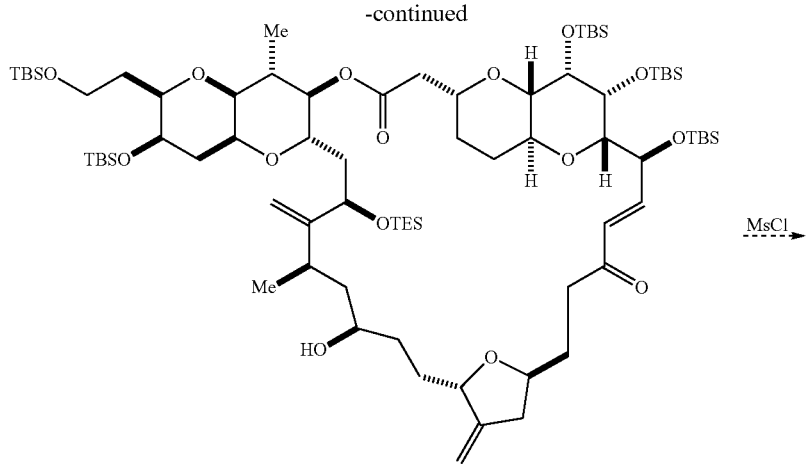

44

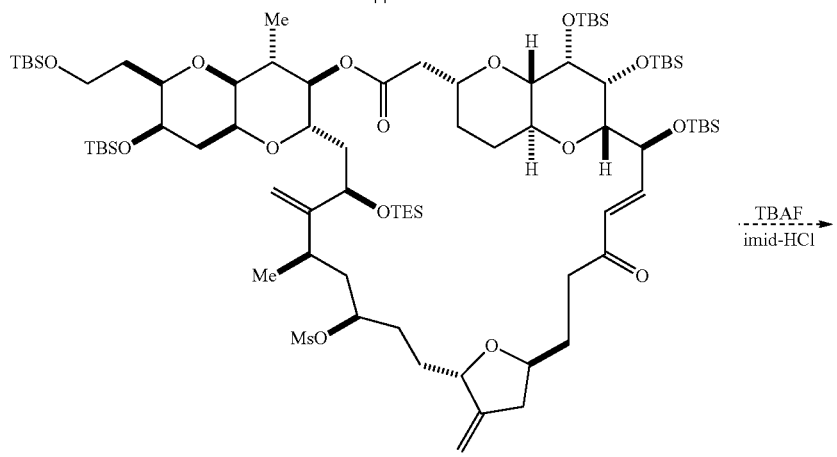

45

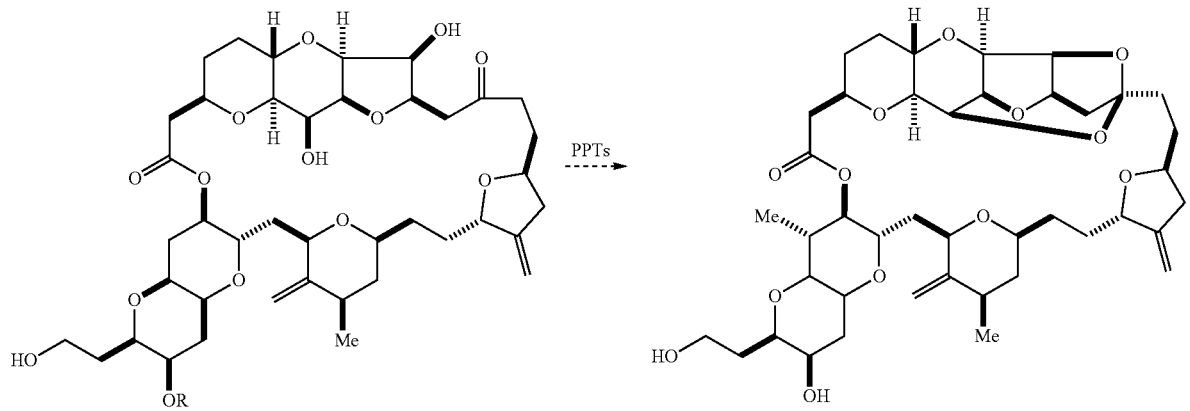

46            3

Compound 41 can be converted to compound 42 through the Nozaki-Hiyama-Kishi reaction (e.g., with Cr(II) and Ni(II) salts) with subsequent silylation of the formed hydroxyl by chlorotriethylsilane. Compound 42 can be subjected to Vasella fragmentation conditions to provide 43. DDQ deprotection of the MPM-group and selective oxidation of the resulting allylic alcohol by manganese (II) oxide can provide 44. The remaining hydroxyl group can be reacted with methanesulfonyl chloride to give compound 45. Global desilylation of 45 with tetrabutylammonium fluoride (TBAF) can form the compound 46 by nucleophilic displacement of the mesylate and conjugate addition of a deprotected alcohol to an enone. Compound 46 can be reacted with a Brønsted acid (e.g., PPTs) to afford compound 3.

Example 8—C. 14-C.38 Halichondrin Intermediate Through Allene-Prins Reaction

A halichondrin C.14-C.38 intermediate 53 can be prepared according to the below sequence.

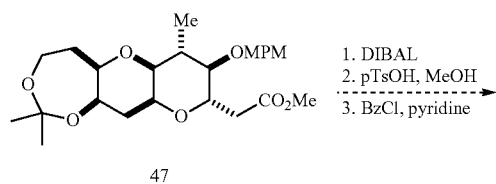 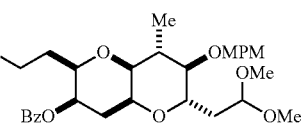 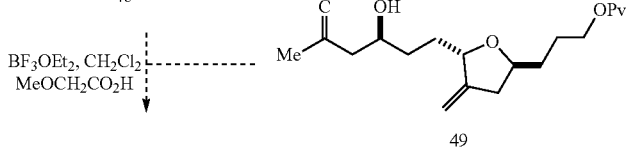

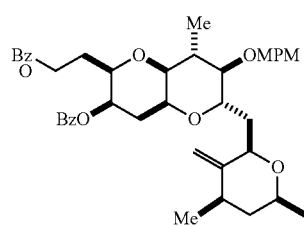 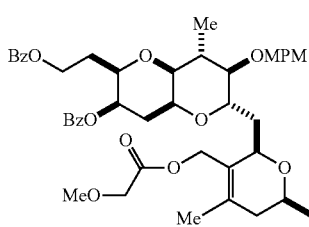

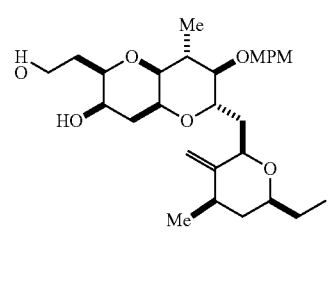 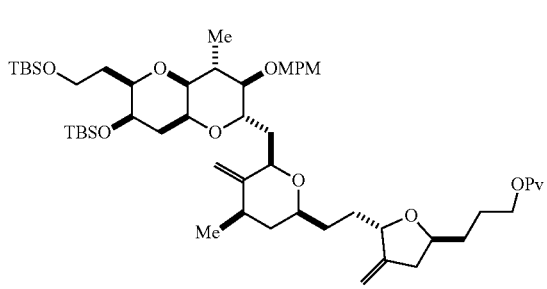

Compound 47 (Aicher et al. Tetrahedron Letters, 33:1549-1552, 1992) can be converted to 48 in a three step process [(1) diisobutylaluminum hydride reduction to the aldehyde, (2) Acid catalyzed acetonide deprotection and dimethylacetal formation and (3) benzoylation]. The allene-Prins reaction between 48 and 49 can be achieved by treatment with boron trifluoride diethyl etherate and methoxyacetic acid to provide 50. Allylic reduction of the methoxyacetate can be accomplished using tetrakis(triphenylphosphine)palladium(0) with formic acid and triethylamine resulting in 51. Deprotection of the benzoate groups can be achieved by treatment with magnesium methoxide to provide 52. Finally, treatment of 52 with tert-butyldimethylsilyl chloride can provide the known C.14-C.38 halichondrin intermediate 53 (Aicher et al. J. Am. Chem. Soc., 114:3162-3164, 1992).

OTHER EMBODIMENTS

Various modifications and variations of the described compositions and methods of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

The invention claimed is:

1. A compound of formula (IC), formula (IIB), or formula (VIIE):

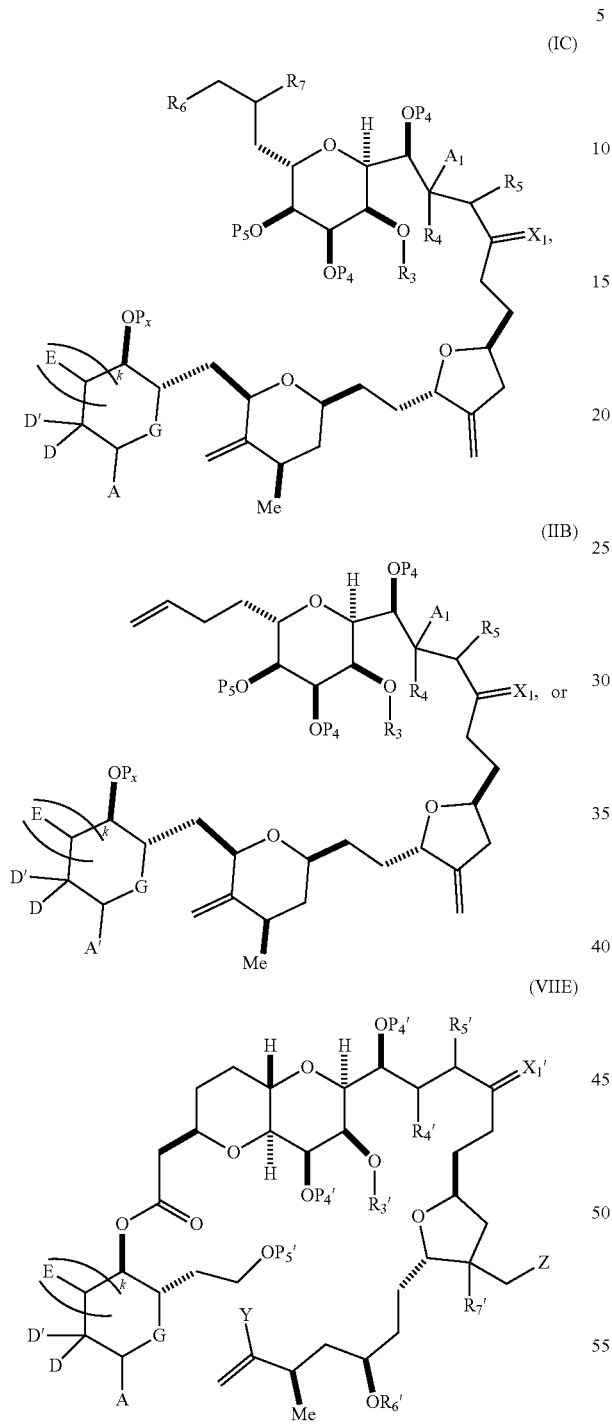

or a salt or a tautomer thereof,
where
each of D and D' is independently H, optionally substituted alkyl, or OP$_1$, provided that only one of D and D' is OP$_1$, where P$_1$ is H, alkyl, or a hydroxyl protecting group; A is a group of formula (1) or a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, the group of formula (1) having the structure:

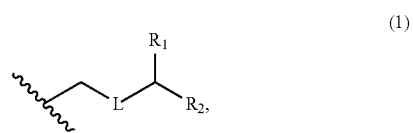

where
L is (CH(OP$_2$)), or —C(O)—;
R$_1$ is H, or R$_1$ and P$_1$ combine to form a bond;
R$_2$ is H or —(CH$_2$)$_n$OP$_3$, and each of P$_2$ and P$_3$ is independently optionally substituted alkyl or a hydroxyl protecting group, or P$_2$ and P$_3$, together with the atoms to which each is attached, combine to form a ketal, a cyclic carbonate, a dicarbonyl-dioxo, or silylene-dioxo; or R$_2$ and P$_2$ combine to form an optionally substituted ethylene or a structure selected from the group consisting of:

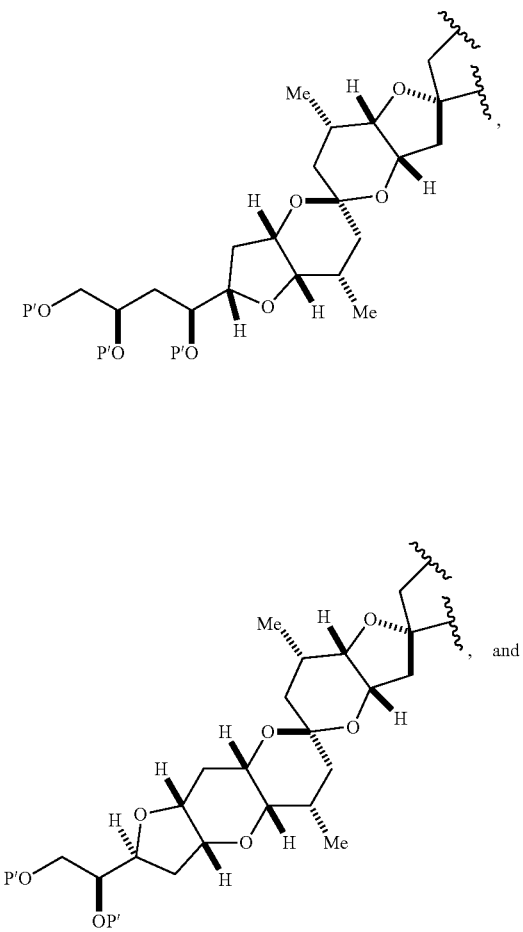

-continued

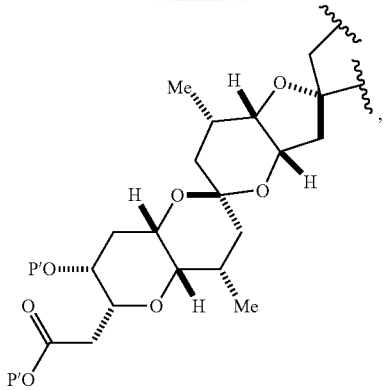

where each P' is independently a hydroxyl protecting group;
E is optionally substituted alkyl or optionally substituted alkoxy;
G is O, S, $CH_2$, or NRN, where RN is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
$P_X$ is H or a hydroxyl protecting group;
k is 0 or 1;
n is 0, 1, or 2;
  $A_1$ and $R_4$ combine to form oxo, $R_3$ is H or a hydroxyl protecting group, and $R_5$ is H;
  or
  $A_1$ is H or OP''', and:
    (i) $R_3$ is H or a hydroxyl protecting group, and $R_4$ and $R_5$ combine to form a double bond;
    or
    (ii) $R_3$ and $R_4$ combine to form a bond, and $R_5$ is H or OP''';
$R_6$ is OP''' and $R_7$ is H, or $R_6$ and $R_7$ combine to form a double bond;
each $P_4$ is independently a hydroxyl protecting group, and $X_1$ is O or $X_1$, together with the carbon atom to which it is attached, is —(CH(OP$_Y$))—, wherein $P_Y$ is H or a hydroxyl protecting group; or both $P_4$ groups and $X_1$, together with the atoms to which each is attached, combine to form ketal; and
$P_5$ is a hydroxyl protecting group;
each P''' is independently H or a hydroxyl protecting group;
A' is a group of formula (2) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (2) having the structure:

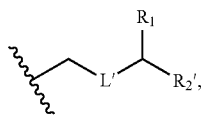

(2)

where
L' is —(CH(OP$_2$'))—, —(C(OH)(OP$_2$'))—, or —C(O)—;
$R_2$' is H or —(CH$_2$)$_n$OP$_3$, and each of $P_2$' and $P_3$' is independently H, optionally substituted alkyl, or a hydroxyl protecting group, or $P_2$' and $P_3$', together with the atoms to which each is attached, combine to form a ketal, a cyclic carbonate, a dicarbonyl-dioxo, or silylene-dioxo;
or $R_2$' and $P_2$' combine to form an optionally substituted ethylene or a structure selected from the group consisting of:

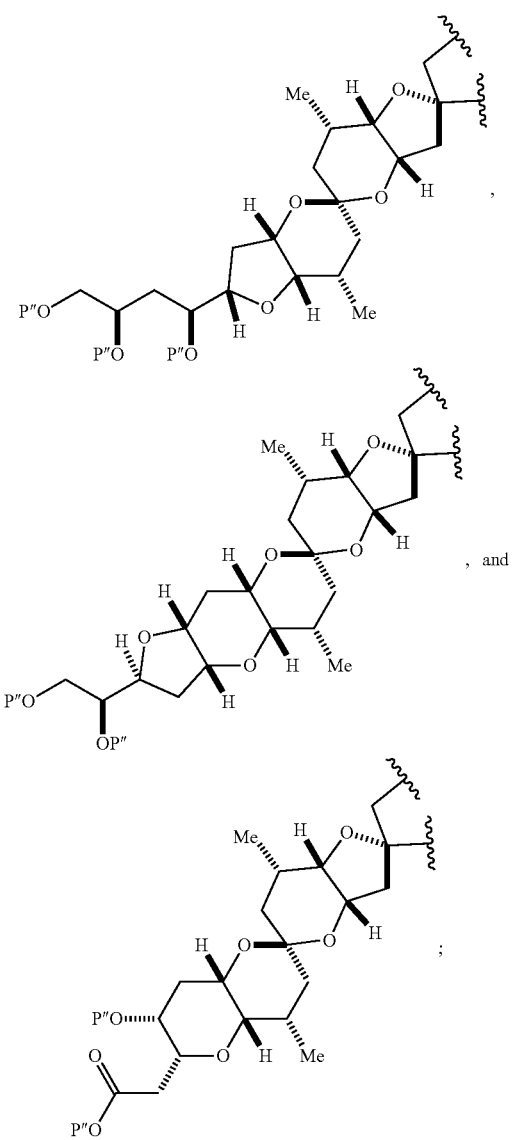

Y is iodide, bromide, or trifluoromethanesulfonate;
$P_5$' is H or a hydroxyl protecting group;
(a1) $R_3$' is H or a hydroxyl protecting group, $R_4$' and $R_5$' combine to form a double bond, each $P_4$' is independently H or a hydroxyl protecting group, and $X_1$', together with the carbon to which it is attached, forms a carbonyl or —(CH(OR$_8$))—, where $R_8$ is H or a hydroxyl protecting group;

or (a2) $R_3'$ and $R_4'$ combine to form a bond, $R_5'$ is H, and each $P_4'$ is independently H or a hydroxyl protecting group, and $X_1'$, together with the carbon to which it is attached, forms a carbonyl or —(CH(OR$_8$))—;

or both $P_4'$ groups and $X_1'$, together with the atoms to which each is attached, combine to form ketal; and (b1) Z is chloride, bromide, or iodide, and $R_6'$ and $R_7'$ combine to form a bond;

or (b2) Z and $R_7'$ combine to form a double bond, and $R_6'$ is H or a hydroxyl protecting group.

2. The compound of claim 1, of which the formula is (IC).

3. The compound of claim 1, of which the formula is:

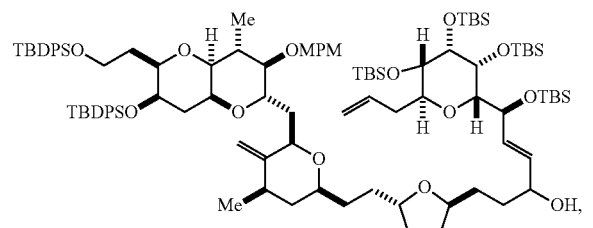

4. The compound of claim 1, of which the formula is (IIB).

5. The compound of claim 1, of which the formula is:

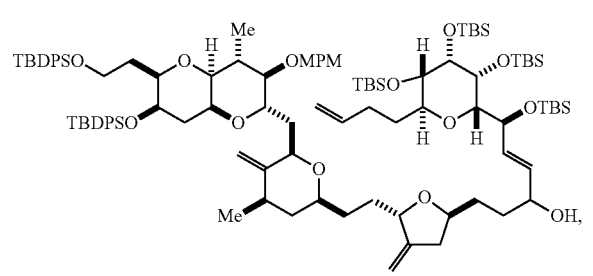

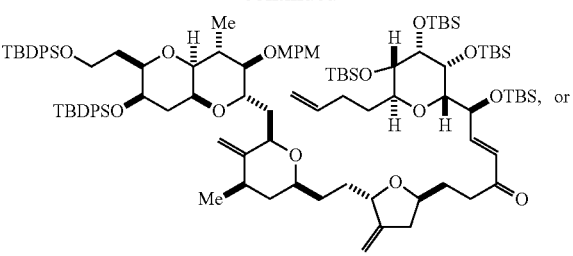

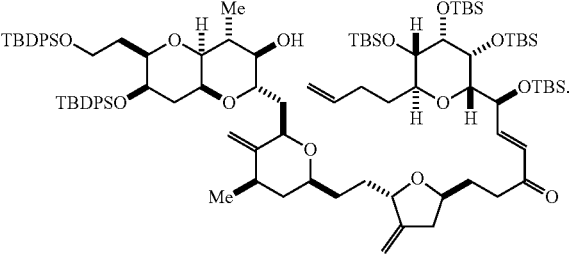

6. The compound of claim 1, of which the formula is (VIIE).

7. A compound of formula (IF), formula (IIC), formula (IICa), formula (IVD), or formula (VIC):

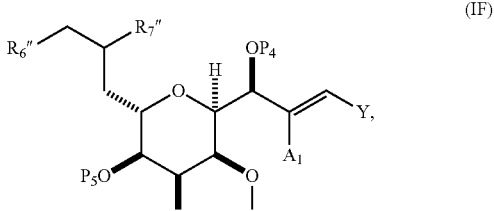
(IF)

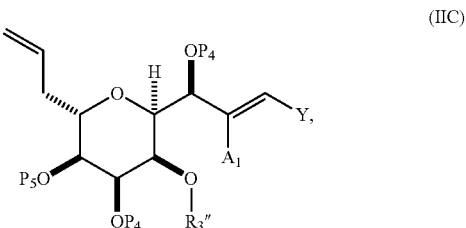
(IIC)

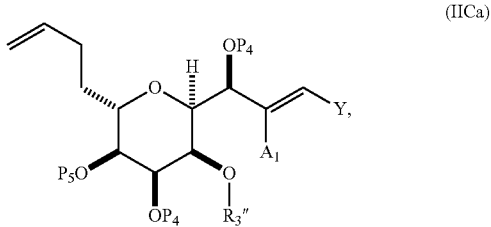
(IICa)

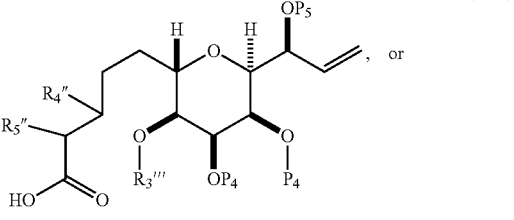
(IVD)

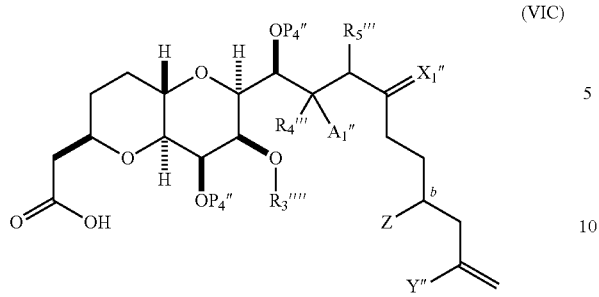

(VIC)

or a tautomer thereof,
where
each $R_3''$, $P_4$, and $P_5$ is independently a hydroxyl protecting group;
$A_1$ is H or $OP'$, where $P'$ is a hydroxyl protecting group;
$A_1'$ is H or $OP''$, where $P''$ is H or a hydroxyl protecting group;
$A_1''$ is H, $OP'''$, or combines with $R_4'''$ to form oxo;
$F_6''$ is $OP_5$, and $R_7''$ is H, or $R_6''$ and $R_7''$ combine to form a double bond;
Y is chloro, bromo, iodo, trifluoromethanesulfonate, or trialkylsilane;
Y' is chloro, bromo, iodo, or trifluoromethanesulfonate;
Y'' is iodo, bromo, or trifluoromethanesulfonate;
$R_3'''$, $R_4''$, and $R_5''$ are defined by the following terms:
  (i) $R_3'''$ is a hydroxyl protecting group, $R_4''$ is alkyl ether, and $R_5''$ is H;
  (ii) $R_3'''$ is a hydroxyl protecting group, and $R_4''$ and $R_5''$ combine to form a double bond;
  or
  (iii) $R_3'''$ and $R_4''$ combine to form a bond, and $R_5''$ is H;
$R_4''''$, $R_4'''$ and $R_5'''$ are defined by the following terms:
(i) $R_3''''$ is H or a hydroxyl protecting group, and $R_4'''$ and $R_5'''$ combine to form a double bond;
or
(ii) $R_3''''$ and $R_4'''$ combine to form a bond, and $R_5'''$ is H;
each $P_4''$ is independently a hydroxyl protecting group, and $X_1''$ is O or $X_1''$, together with the carbon atom to which it is attached, is —$(CH(OP_Y))$—, wherein $P_Y$ is H or a hydroxyl protecting group; or both $P_4''$ groups and $X_1''$, together with the atoms to which each is attached, combine to form ketal; and
b designates (R)-stereogenic center, and Z is a sulfonate, chloro, bromo, or iodo; or b designates (S)-stereogenic center, and Z is $OR_6'''$, where $R_6'''$ is a hydroxyl protecting group.

8. The compound of claim 7, of which the formula is (IF).

9. The compound of claim 7, of which the formula is:

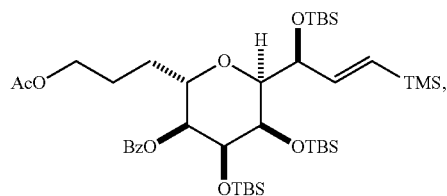

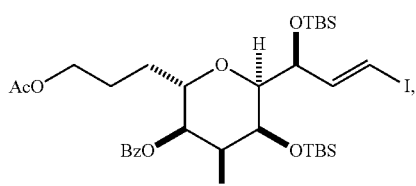

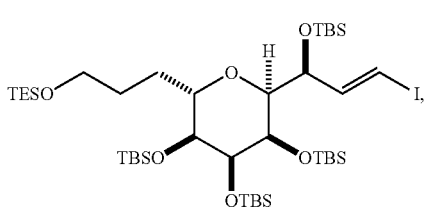

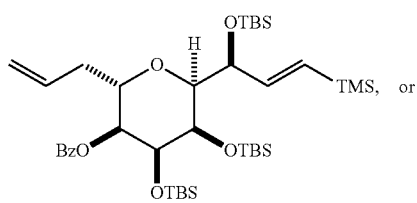

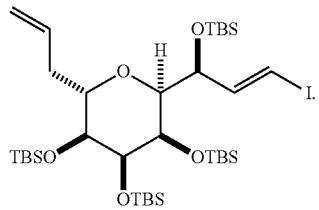

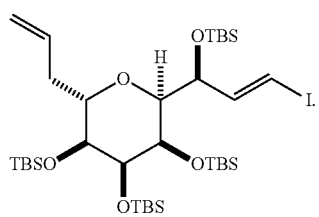

10. The compound of claim 7, of which the formula is (IIC).

11. The compound of claim 7, of which the formula is (IICa).

12. The compound of claim 7, of which the formula is:

13. The compound of claim 7, of which the formula is (IVD).

14. The compound of claim 7, of which the formula is (VIC).

15. A compound of formula (IE), formula (IVE), or formula (VIIID):

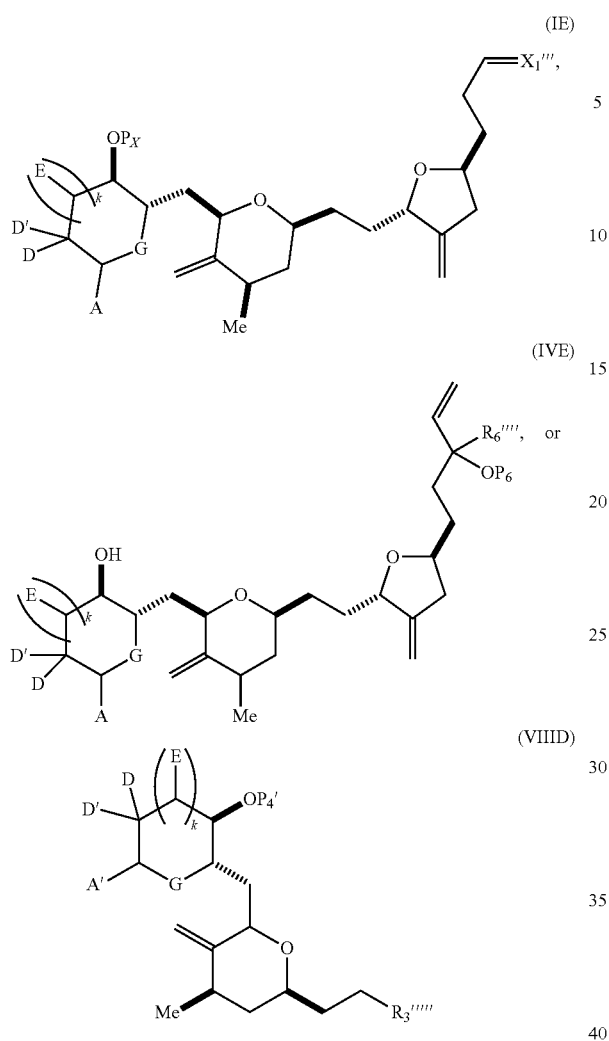

(IE)

(IVE)

(VIIID)

or a salt thereof,
where
each of D and D' is independently H, optionally substituted alkyl, or OP$_1$, provided that only one of D and D' is OP$_1$, where P$_1$ is H, alkyl, or a hydroxyl protecting group; A is a group of formula (1) or a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, the group of formula (1) having the structure:

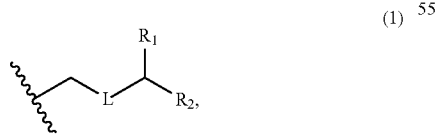

(1)

where
L is —(CH(OP$_2$))—, or —C(O)—;
R$_1$ is H, or R$_1$ and P$_1$ combine to form a bond;
R$_2$ is H or —(CH$_2$)$_n$OP$_3$, and each of P$_2$ and P$_3$ is independently optionally substituted alkyl or a hydroxyl protecting group, or P$_2$ and P$_3$, together with the atoms to which each is attached, combine to form a ketal, a cyclic carbonate, a dicarbonyl-dioxo, or silylene-dioxo; or R$_2$ and P$_2$ combine to form an optionally substituted ethylene or a structure selected from the group consisting of:

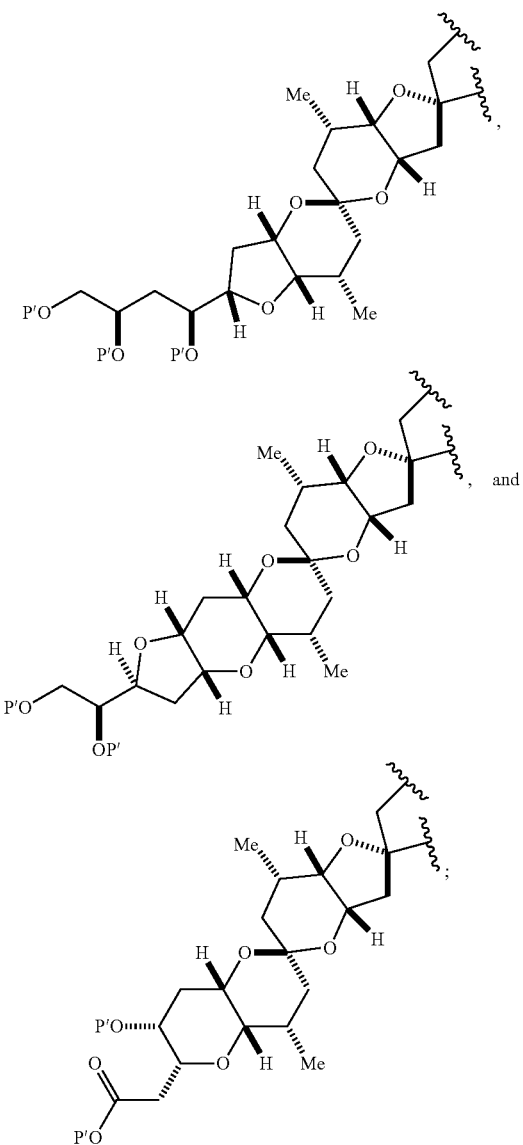

each P' is independently a hydroxyl protecting group;
E is optionally substituted alkyl or optionally substituted alkoxy;
G is O, S, CH$_2$, or NR$_N$, where R$_N$ is H, an N-protecting group, or optionally substituted alkyl;
each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_A$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
P$_X$ is a hydroxyl protecting group;

k is 0 or 1;

n is 0, 1, or 2; and $X_1'''$ is oxo;

$R_6''''$ is H, and $P_6$ is H or a hydroxyl protecting group; or $R_6''''$ and $P_6$ combine to form a double bond;

A' is a group of formula (2) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (2) having the structure:

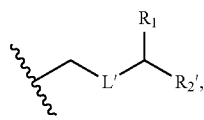

(2)

where

L' is —(CH(OP$_2$'))—, —(C(OH)(OP$_2$'))—, or —C(O)—;

$R_2'$ is H or —(CH$_2$)$_n$OP$_3'$, and each of $P_2'$ and $P_3'$ is independently H, optionally substituted alkyl, or a hydroxyl protecting group, or $P_2'$ and $P_3'$, together with the atoms to which each is attached, combine to form a ketal, a cyclic carbonate, a dicarbonyl-dioxo, or silylene-dioxo;

or $R_2'$ and $P_2'$ combine to form an optionally substituted ethylene or a structure selected from the group consisting of:

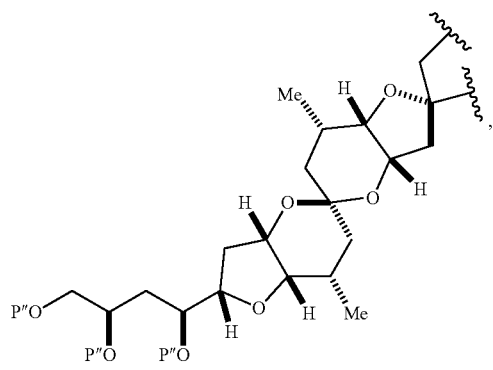

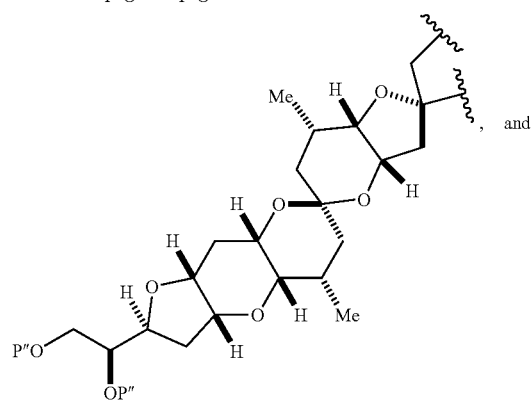

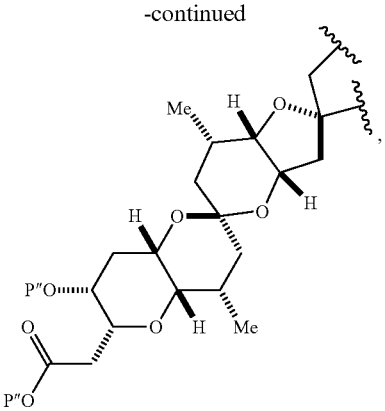

where each P'' is independently H or a hydroxyl protecting group;

$P_4'$ is H or a hydroxyl protecting group; and $R_3''''$ is —CH$_2$—OP$_5'$, —CH=CH$_2$,

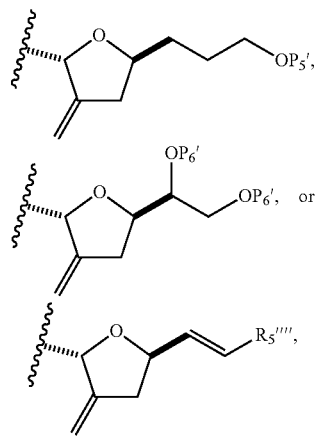

where $P_5'$ is H or a hydroxyl protecting group; each $P_6'$ is independently a hydroxyl protecting group, or both $P_6'$ groups, together with the atoms to which each is attached, combine to form a cyclic protected diol; and $R_5''''$ is H or —CH$_2$X$_1''''$CH$_2$CH=CH$_2$, where $X_1''''$ is O, —CH$_2$—, or NP$_7$, where $P_7$ is a sulfonyl.

16. The compound of claim 15, of which the formula is (IE).

17. The compound of claim 15, of which the formula is:

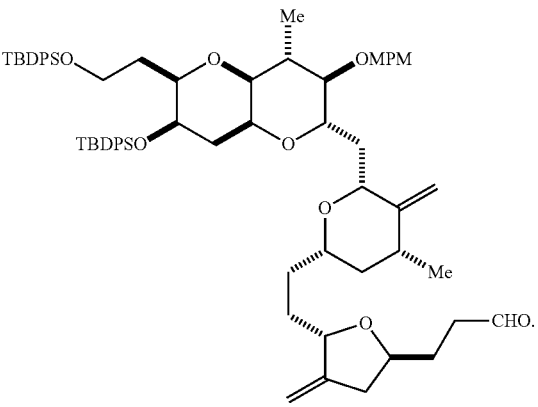

18. The compound of claim 15, of which the formula is (IVE).

19. The compound of claim 15, of which the formula is (VIIID).

20. The compound of claim 15, of which the formula is:

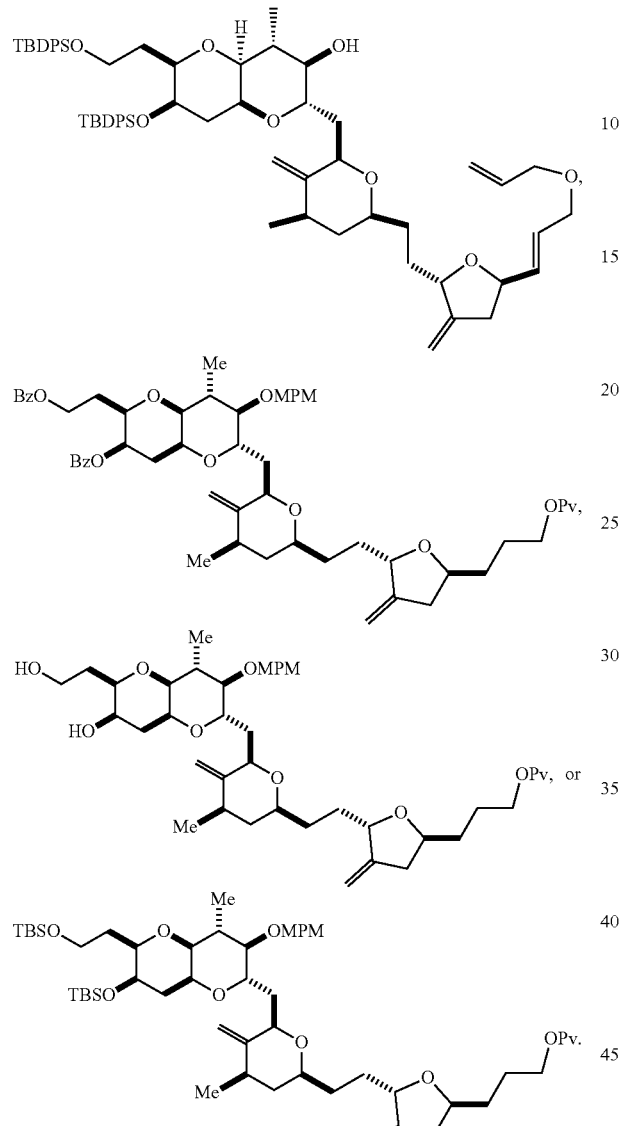

21. A compound of formula (VIIG):

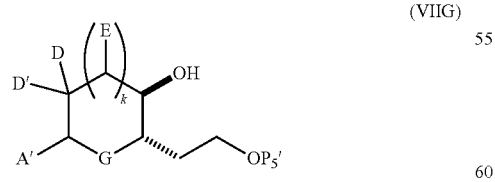

or a salt thereof,
each of D and D' is independently H, optionally substituted alkyl, or $OP_1$, provided that only one of D and D' is $OP_1$, where $P_1$ is H, alkyl, or a hydroxyl protecting group; A' is a group of formula (2) or a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, the group of formula (2) having the structure:

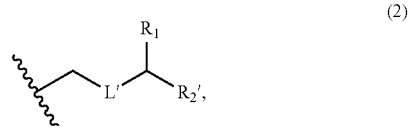

where
L' is —(CH($OP_2'$))—, —(C(OH)($OP_2'$))—, or —C(O)—;
$R_1$ is H, or $R_1$ and $P_1$ combine to form a bond;
$R_2'$ is H or —$(CH_2)_nOP_3'$, and each of $P_2'$ and $P_3'$ is independently H, optionally substituted alkyl, or a hydroxyl protecting group, or $P_2'$ and $P_3'$, together with the atoms to which each is attached, combine to form a ketal, a cyclic carbonate, a dicarbonyl-dioxo, or silylene-dioxo;
or $R_2'$ and $P_2'$ combine to form an optionally substituted ethylene or a structure selected from the group consisting of:

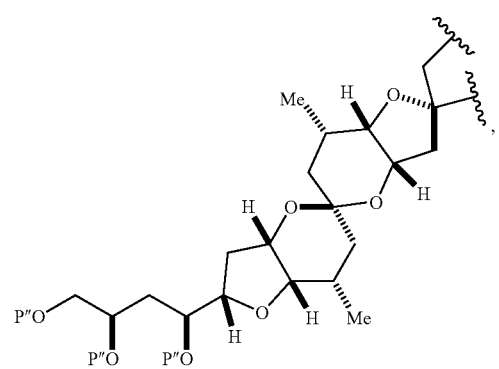

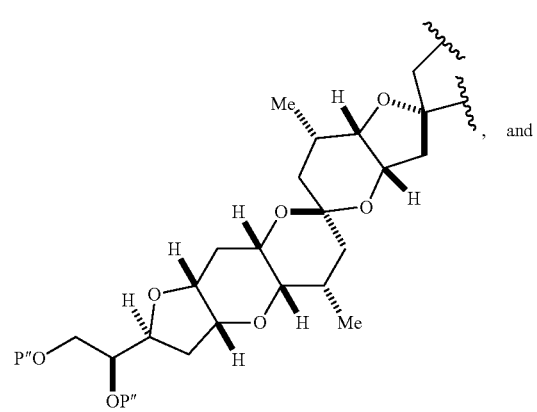

-continued

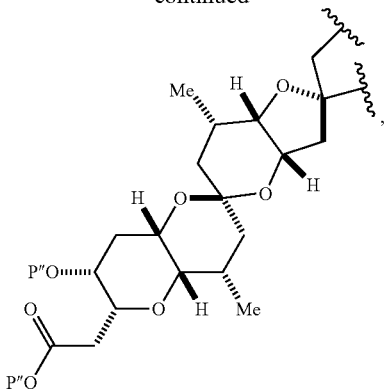

where each P″ is independently H or a hydroxyl protecting group;

E is optionally substituted alkyl or optionally substituted alkoxy;

G is O, S, $CH_2$, or $NR_N$, where $R_N$ is H, an N-protecting group, or optionally substituted alkyl;

each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_A(CO)NR_BR_A$, $NR_B(CO)OR_A$, (CO)$OR_A$, O(CO)$R_A$, (CO)$NR_BR_A$, or O(CO)$NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

k is 0 or 1;

n is 0, 1, or 2; and $P_5'$ is H or a hydroxyl protecting group.

* * * * *